United States Patent [19]

Bronson et al.

[11] Patent Number: 5,436,369
[45] Date of Patent: Jul. 25, 1995

[54] ALICYCLIC PHOSPHOLIPASE A$_2$ INHIBITORS

[75] Inventors: Joanne J. Bronson, Madison, Conn.; Katharine M. Greene, Eatontown, N.J.; Muzammil M. Mansuri, Cheshire; Stanley V. D'Andrea, Middletown, both of Conn.; F. Ivy Carroll, Durham; Anita Lewin, Chapel Hill, both of N.C.

[73] Assignee: Bristol-Myers Squibb Company, New York, N.Y.

[21] Appl. No.: 200,798

[22] Filed: Feb. 23, 1994

Related U.S. Application Data

[63] Continuation-in-part of Ser. No. 79,072, Jun. 16, 1993, abandoned.

[51] Int. Cl.$^6$ .............................................. C07C 63/64
[52] U.S. Cl. ................................ 562/495; 562/489; 562/442; 562/459; 562/429; 562/23; 560/51; 560/55; 560/76; 560/104
[58] Field of Search ................ 582/23, 495, 489, 442, 582/429, 459; 560/51, 55, 76, 104

[56] References Cited

PUBLICATIONS

Chem-Abs 88(7):50605 p 1978.

Primary Examiner—Paul J. Killos
Attorney, Agent, or Firm—Sandra M. Nolan

[57] ABSTRACT

Certain novel alicyclic compounds are effective phospholipase A$_2$ (PLA$_2$) inhibitors.

28 Claims, No Drawings

ALICYCLIC PHOSPHOLIPASE A2 INHIBITORS

CROSS-REFERENCE TO RELATED APPLICATION

This application is a continuation-in-part of application Ser. No. 08/079,072, filed Jun. 16, 1993, abandoned.

BACKGROUND

The invention deals with compounds having activity as phospholipase $A_2$ ($PLA_2$) inhibitors. $PLA_2$ is a calcium-dependent enzyme which cleaves the sn-2 acyl bond of phospholipids to yield arachidonic acid and a lysophospholipid (H. Van den Bosch et al. in *Biochim. Biophys. Acta* 1980, 604, 191). Both products of this reaction can serve as starting points for the biosynthesis of inflammatory mediators. Once released, arachidonic acid is rapidly metabolized by enzymes such as cyclooxygenase and lipoxygenases to give prostaglandins and leukotrienes, well-known mediators of inflammation (P. Davies and D. E. MacIntyre in "Inflammation: Basic Principles and Clinical Correlates," 2nd Ed., J. I. Gallin, I. M. Goldstein, and R. Snyderman, Eds., Raven Press, Ltd.: New York, 1992; Chapter 7; B. K. Lam and K. F. Austen in "Inflammation: Basic Principles and Clinical Correlates," 2nd Ed., J. I. Gallin, I. M. Goldstein; and R. Snyderman, Eds., Raven Press, Ltd.: New York, 1992; Chapter 8). Lysophospholipids can be utilized by certain cell types to produce platelet-activating factor (PAF), another potent inflammatory mediator (G. A. Zimmerman, S. M. Prescott, and T. M. Mcintyre in "Inflammation: Basic Principles and Clinical Correlates," 2nd Ed., J. I. Gallin, I. M. Goldstein, and R. Snyderman, Eds., Raven Press, Ltd.: New York, 1992; Chapter 9). The role of $PLA_2$ in inflammatory diseases has been described (P. Vadas and W. Pruzanski in *Laboratory Investigation*, 1986, 55, 391–404; W. Pruzanski, E. Bogoch, M. Wloch, and P. Vadas in Journal of Rheumatology, 1991, 18, 117–119; W. Pruzanski, K. Scott, G. Smith, I. Rajkovic, E. Stefanski, and P. Vadas in *Inflammation*, 1992, 16, 451–457; W. Pruzanski, D. W. Wilmore, A. Suffredini, G. D. Martich, A. G. D. Hoffman, J. L. Browning, E. Stefanski, B. Sternby, and P. Vadas in *Inflammation*, 1992, 16, 561–570; J. M. Gronroos and T. J. Nevalainen in Digestion, 1992, 52, 232–236). Since $PLA_2$ is the critical enzyme in the pathway leading to release of prostaglandins and leukotrienes and PAF, inhibition of this enzyme is a rational approach to prevention, elimination, or amelioration of inflammation.

Compounds having similar activity are disclosed in U.S. Pat. No. 5,141,959, the disclosure of which is hereby incorporated by reference. That patent discloses compounds of structure A:

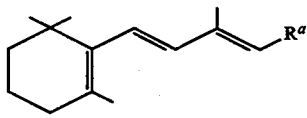

(A)

wherein $R^a$ is $CH=CY-C(CH_3)=CHX$, wherein X and Y are different and are selected from $COOR^b$ and

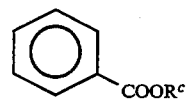

groups in which $R^b$ and $R^c$ independently are H or $C_{1-6}$ alkyl.

SUMMARY OF THE INVENTION

Applicants have discovered novel compounds of Formulas I:

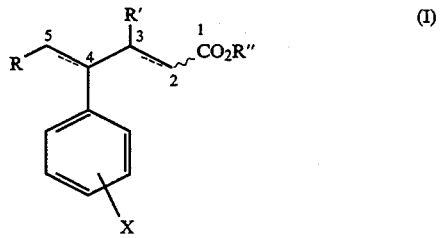

(I)

wherein the bonds between $C_2$ and $C_3$ and/or between $C_4$ and $C_5$ are unsaturated;

X=COOH, H, F, CI, Br, I, COOR", $CONH_2$, COR''', CHO, $CH_2OH$, $CH_2OR'''$, OH, OR''', $CF_3$, $C_{1-6}$ alkyl, $C_{1-6}$ alkenyl, $C_{1-6}$ haloalkyl, $NO_2$, $P(O)(OH)_2$, $SO_2H$, or $SO_3H$;

R=substituted or unsubstituted alkyl, aryl, arylalkyl, alkenyl, or arylalkenyl groups, with the proviso that each group have 6 or more carbons (preferable 6 to 30 carbons) and R cannot be

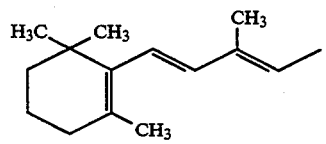

$R'$=H or $C_{1-6}$ alkyl;

$R''$=H, $C_{1-6}$ alkyl, $C(R^3)_2OC(O)R^4$, $CH_2CH_2NR^5R^6$, $CH_2CH_2CH_2NR^5R^6$, $CH_2C(O)N(R^6)_2$, or other groups yielding physiologically hydrolyzable esters;

$R'''$=$C_{1-6}$ alkyl;

$R^3$=H, $CH_3$, $C_2H_5$, $CH_3CH_2CH_2$ (with $R^3$'s being the same or different);

$R^4$=$C_{6-12}$ aryl, $C_{1-7}$ linear, branched or cyclic alkyl, or $C_{1-7}$ linear, branched or cyclic alkoxy;

$R^5$=$R^6$, or when linked with $R^6$, is a $C_3-C_6$ cycloalkyl or a —$CH_2CH_2OCH_2CH_2$-group; and $R^6$=$C_{1-3}$ alkyl.

These compounds, their geometric isomers and their pharmaceutical salts, exhibit $PLA_2$ inhibition with significant anti-inflammatory effects.

The novel compounds and isomers and derivatives thereof are useful in combination with pharmaceutical carriers and other excipients in formulations to be administered by, preferably, topical or oral routes.

DESCRIPTION OF THE INVENTION

The invention is concerned with novel compounds and the use of those compounds, their isomers or other pharmaceutically acceptable derivatives thereof, in processes and compositions to be used to treat inflammation.

Unless otherwise indicated, all percentages recited herein are weight percents, based upon total composition weight.

The compounds of the invention generally conform to Formula I:

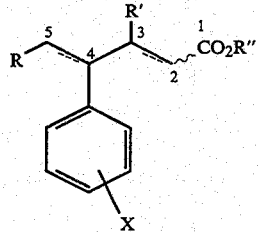

wherein the bonds between $C_2$ and $C_3$ and/or between $C_4$ and $C_5$ are unsaturated;

X=COOH, H, F, Cl, Br, I, COOR''', CONH$_2$, COR''', CHO, CH$_2$OH, CH$_2$OR''', OH, OR''', CF$_3$, C$_{1-6}$ alkyl, C$_{1-6}$ alkenyl, C$_{1-6}$ haloalkyl, NO$_2$, P(O)(OH)$_2$, SO$_2$H, or SO$_3$H;

R=substituted or unsubstituted alkyl, aryl, arylalkyl, alkenyl or arylalkenyl groups, with the proviso that each group must have 6 or more carbons (preferable 6 to 30 carbons) and R cannot be

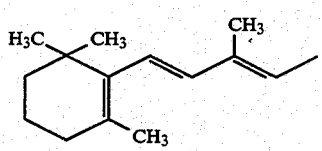

R'=H or C$_{1-6}$ alkyl;

R''=H, C$_{1-6}$ alkyl, C(R$^3$)$_2$OC(O)R$^4$, CH$_2$CH$_2$NR$^5$R$^6$, CH$_2$CH$_2$CH$_2$NR$^5$R$^6$, CH$_2$C(O)N(R$^6$)$_2$, or other groups yielding physiologically hydrolyzable esters;

R'''=C$_{1-6}$ alkyl;

R$^3$=H, CH$_3$, C$_2$H$_5$, CH$_3$CH$_2$CH$_2$ (with R$^3$'s being the same or different);

R$^4$=C$_{6-12}$ aryl, C$_{1-7}$ linear, branched or cyclic alkyl, or C$_{1-7}$ linear, branched or cyclic alkoxy;

R$^5$=R$^6$, or, when linked with R$^6$, is a C$_3$–C$_6$ cycloalkyl or a —CH$_2$CH$_2$OCH$_2$CH$_2$-group; and R$^6$=C$_{1-3}$ alkyl.

X is preferably H, COOH, F, CF$_3$, COOR'' or CONH$_2$.

In preferred embodiments, the phenyl ring at $C_4$ has an X substituent in the recta-position. R may be substituted or unsubstituted groups of the types recited. When the R group is substituted, the substituents may be OH, C$_{1-12}$ alkyloxy, C$_{1-12}$ alkenyloxy, C$_{1-12}$ cycloalkyl, C$_{1-12}$ halophenylalkyloxy, C$_{1-12}$ hydroxyalkyl or adamantyl. R may have from one to six substituents, with "substituents" meaning groups other than hydrogen. Preferred R groups are set out in Tables 1 and 2.

By "6 or more" carbons, applicants mean 6 to 30, and preferably 14 to 30.

R' may be H or C$_{1-6}$ alkyl, but is preferably H or CH$_3$.

R'' is preferably H.

By "halo" applicants mean Br, Cl, F, or I.

R$^3$, R$^5$ and R$^6$, when independent moieties (i.e., not linked to each other), may be the same or different.

Compounds of the invention preferably conform to formula types IA, IB, IC or ID, as follows:

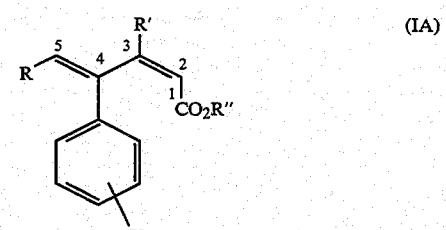

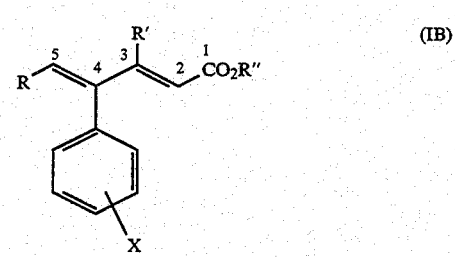

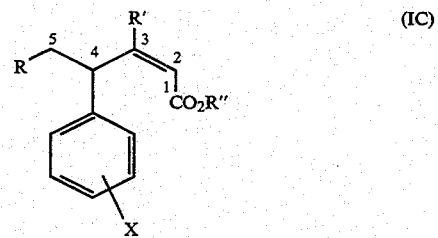

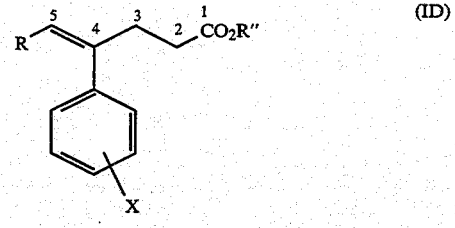

wherein the substitutents are as defined above.

When R'=H, compounds of structure types 11 and 14 conform to IA, types 18 and 20 conform to IB. When R'=CH$_3$, compounds of structure 11k conform to IA.

PREPARATION

The compounds of the invention are typically prepared using one or more of the steps shown below:

5,436,369
Scheme 1: Synthesis of Analogues of Type IA
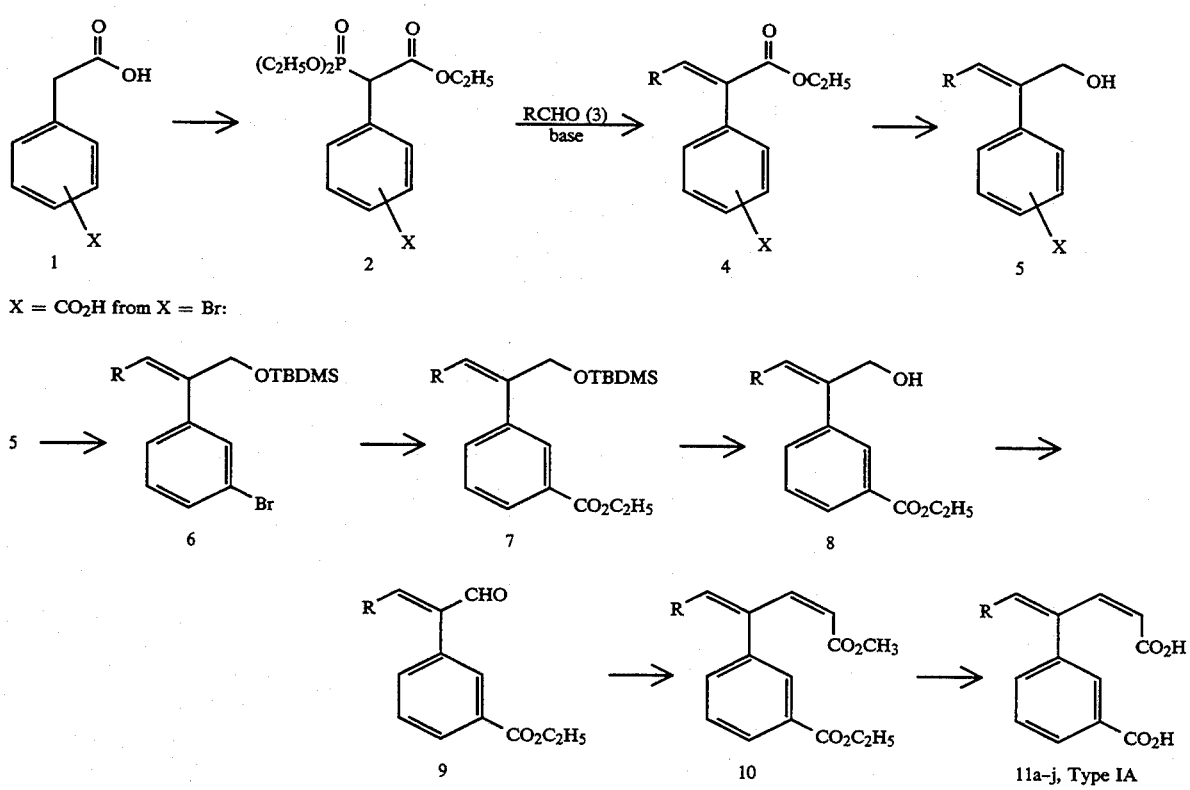
OTBDMS = TBDMSO = tertiary butyl dimethylsiloxy
Scheme 2: Synthesis of Analogues of Type IB
X = CO₂H:
-continued
Scheme 2: Synthesis of Analogues of Type IB
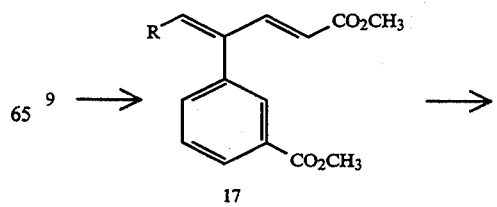

Scheme 2: Synthesis of Analogues of Type IB
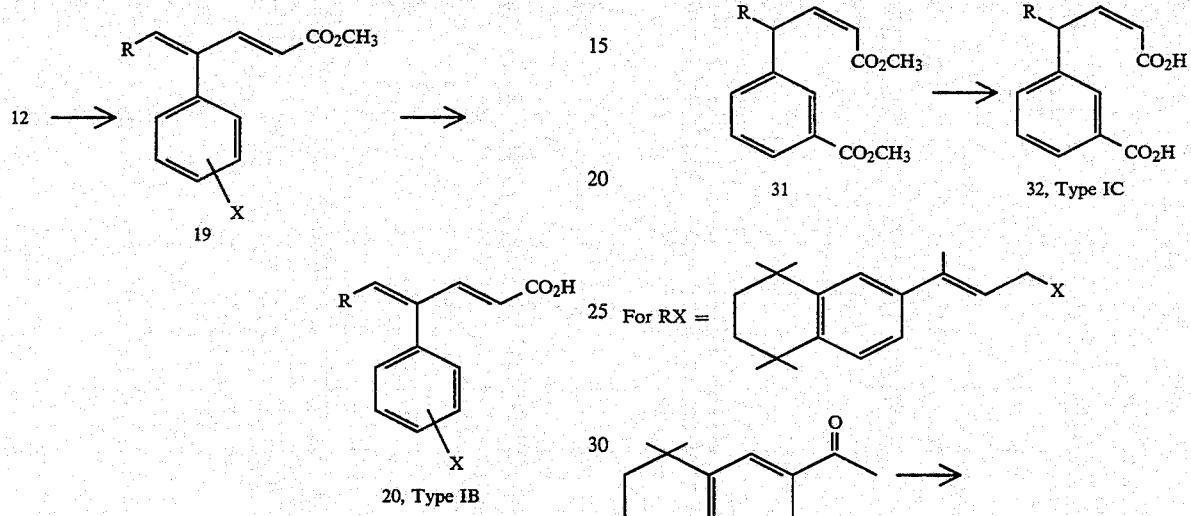
Scheme 3: Example of Type IC
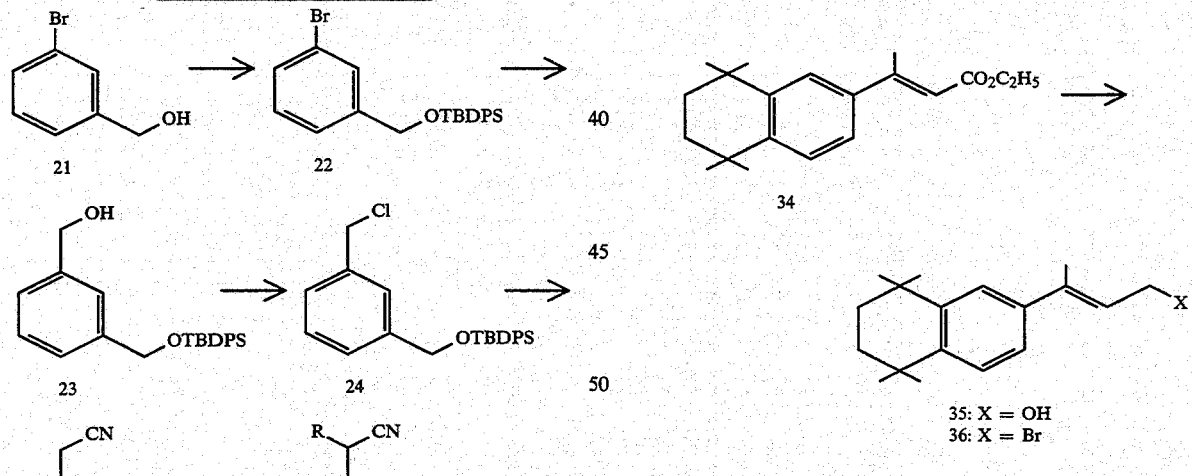
OTBDPS = tertiary butyl diphenylsiloxy
Scheme 4: Synthesis of Analogues of Type ID
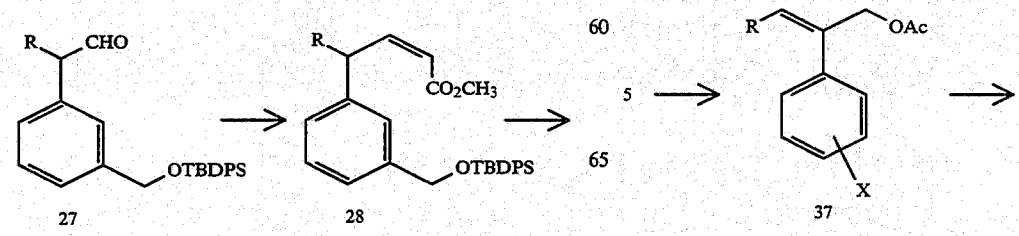

-continued
Scheme 4: Synthesis of Analogues of Type ID

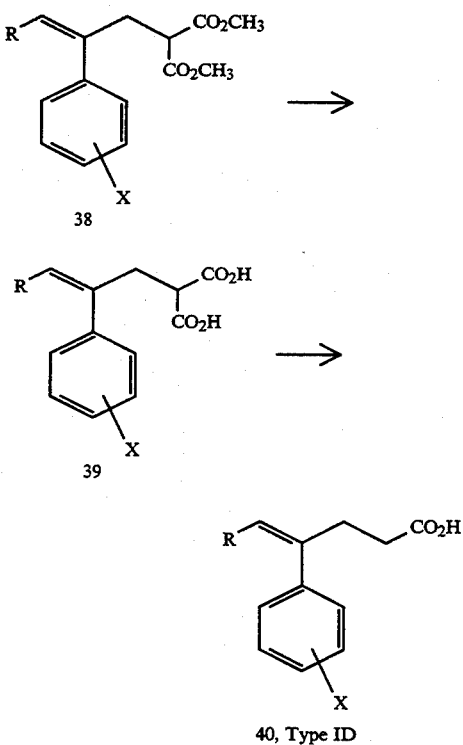

Ac = acetyl

Scheme 5: Synthesis of Aldehydes (3)

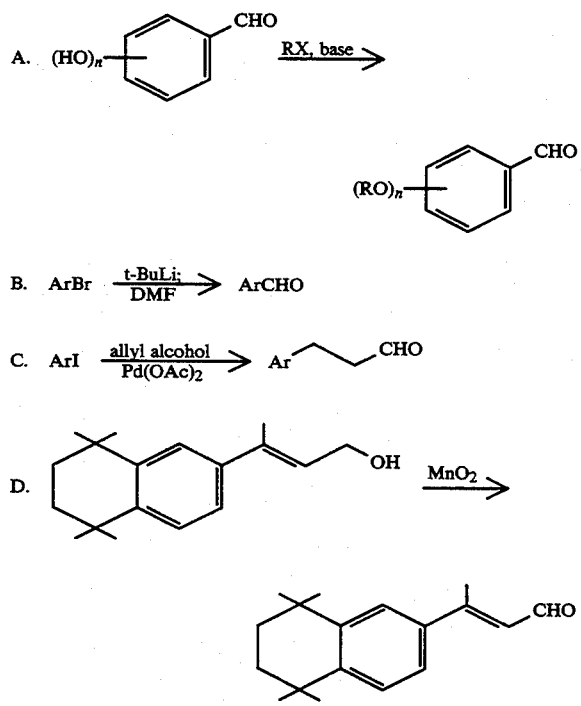

n = 1, 2
Ar = substituted phenyl, naphthyl, or anthracenyl

Scheme 6: Synthesis of 11k

-continued

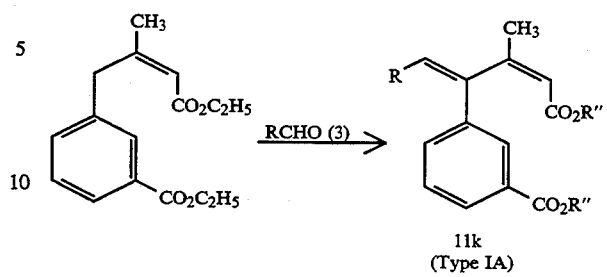

PLA$_2$ Inhibition Assay

The method used is similar to that reported by Franson, et al. [Jesse, R. L. and Franson R. C., Biochim. Biophys. Acta 575:467–470 (1979); Franson, R. C., Patriarca, P., and Elsback, P., J. Lipid Res. 15: 380–388 (1974)]. The enzyme is isolated from human platelets. The substrate used consists of $^{14}$C-oleate labeled Escherichia coli membranes. E. coli cells are grown in the presence of $^{14}$C-oleic acid and then autoclaved to prepare the membranes.

Various concentrations of test compounds are pre-incubated with PLA$_2$ (3.6 µg/mL in a buffer consisting of 25 mM HEPES (pH 7)), 150 mM NaCl, 5.0 mM CaCl$_2$, and 10% DMSO (v/v, test compound solvent) at 37° C. for 7 minutes. The E. coli membrane substrate is then added (0.1 mM phospholipid, 0.005 µCi $^{14}$C) and the reaction is then incubated at 37° C. for 30 minutes. The reaction is then terminated by the addition of 1.9 mL tetrahydrofuran (THF), and the entire solution is applied to a solid-phase extraction column (aminopropyl resin, Analytichem). The column is rinsed with an additional 1 mL of THF. The free fatty acid product of the reaction is then eluted from the column with 1 mL of 2% acetic acid in THF and collected in a scintillation vial. The amount of free fatty acid product is determined by liquid scintillation counting. The amount of inhibition produced by the test compound is calculated by comparing the counts obtained in the presence of the compound to those obtained in its absence (solvent only). Background counts were determined by performing incubations in the absence of enzyme.

Percent inhibition is determined by the equation:

$$\% \text{ Inhibition} = \left(1 - \frac{(\text{CPM with test compound}) - (\text{background})}{(\text{CPM without test compound}) - (\text{background})}\right) \times 100$$

The biological activities of compounds of Types IA through ID are given in Tables 1–6. The compounds are effective inhibitors of PLA$_2$.

TABLE 1

Biological Data for Compounds of Structure 11 (Type IA):

| R | Structure Number | % Inhibition of PLA$_2$ at 100 μM |
|---|---|---|
| phenyl | 11a | 6% |
| 5,5,8,8-tetramethyl-tetrahydronaphthyl | 11b | 44% |
| 1,1,4,4-tetramethyl-tetrahydroanthracenyl | 11c | 97% |
| 4-(C$_{10}$H$_{21}$O)phenyl | 11d | 100% |
| 3,4-bis(C$_{10}$H$_{21}$O)phenyl | 11e | 100% |
| phenethyl | 11f | 15% |
| 2-(5,5,8,8-tetramethyl-tetrahydronaphthyl)ethyl | 11g | 58% |
| 1-(5,5,8,8-tetramethyl-tetrahydronaphthyl)ethenyl | 11h | 97% |
| 3-methoxy-4-(1-adamantyl)phenyl | 11i | 100% |
| 4-methoxy-3-(1-adamantyl)phenyl | 11j | 98% |
| 1,1,4,4-tetramethyl-1,2,3,4-tetrahydronaphthyl (naphthalene) | 11k | 98% |

R' = H, except for 11k, where R' = CH$_3$

TABLE 2

Biological Data for Compounds of Structure 14 (Type IA):

| R | X | Structure Number | % Inhibition of PLA$_2$ at 100 μM |
|---|---|---|---|
| 4-(C$_{10}$H$_{21}$O)phenyl | m-CF$_3$ | 14a | 100% |

TABLE 2-continued

Biological Data for Compounds of Structure 14 (Type IA):

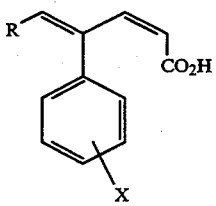

| R | X | Structure Number | % Inhibition of PLA$_2$ at 100 μM |
|---|---|---|---|
| C$_{10}$H$_{21}$O-phenyl (meta) | m-CF$_3$ | 14b | 100% |
| C$_{10}$H$_{21}$O-phenyl (ortho) | m-CF$_3$ | 14c | 92% |
| farnesyloxy-phenyl (para) | m-CF$_3$ | 14d | 98% |
| 3,4-bis(C$_{10}$H$_{21}$O)-phenyl | m-CF$_3$ | 14e | 99% |
| tetramethyltetrahydronaphthyl | m-CF$_3$ | 14f | 71% |
| tetramethyltetrahydronaphthyl-ethyl | m-CF$_3$ | 14g | 96% |
| tetramethyltetrahydronaphthyl-ethyl | p-F | 14h | 96% |
| tetramethyltetrahydronaphthyl-ethyl | m-F | 14i | 96% |
| tetramethyltetrahydronaphthyl-ethyl | H | 14j | 92% |

TABLE 2-continued
Biological Data for Compounds of Structure 14 (Type IA):

| R | X | Structure Number | % Inhibition of PLA$_2$ at 100 μM |
|---|---|---|---|
| 3-methoxy-4-adamantyl-phenethyl | m-CF$_3$ | 14k | 99% |
| 3-methoxy-4-adamantyl-phenethyl | H | 14l | 99% |
| 3-methoxy-4-adamantyl-phenethyl (isomer) | m-CF$_3$ | 14m | 99% |
| 3-methoxy-4-adamantyl-phenethyl (isomer) | H | 14n | 100% |
| 5-methoxy-2-adamantyl-phenethyl | m-CF$_3$ | 14o | 99% |
| 3-methoxy-4-adamantyl-phenethyl | m-CF$_3$ | 14p | 93% |
| 3-hydroxy-4-adamantyl-phenethyl | m-CF$_3$ | 14q | 100% |

TABLE 2-continued

Biological Data for Compounds of Structure 14 (Type IA):

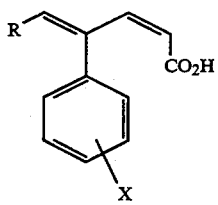

| R | X | Structure Number | % Inhibition of PLA$_2$ at 100 μM |
|---|---|---|---|
| CH$_3$(CH$_2$)$_4$O— [adamantyl-phenyl] | m-CF$_3$ | 14r | 95% |
| 3,5-F$_2$-benzyl-O— [adamantyl-phenyl] | m-CF | 14s | 100% |
| CH$_3$Cl-[4-chlorobenzyl]-O— [adamantyl-phenyl] | m-CF$_3$ | 14t | 100% |
| benzyl-O— [adamantyl-phenyl] | m-CF$_3$ | 14u | 100% |
| HOOC-CH$_2$-O-[phenyl]-CH$_2$-O— [adamantyl-phenyl] | m-CF$_3$ | 14v | 100% |

TABLE 3

Biological Data for compounds of Structure 18 (Type IB):

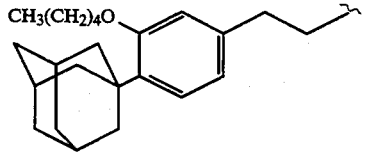

| R | Structure Number | % Inhibition of PLA$_2$ at 100 μM |
|---|---|---|
| 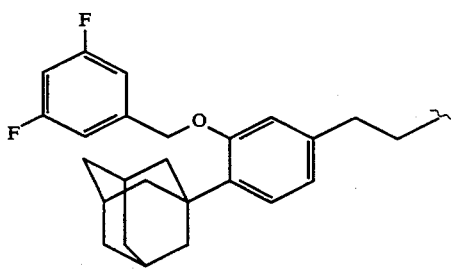 (tetramethyl-tetrahydronaphthyl) | 18a | 27% |
| (tetramethyl-tetrahydronaphthyl) | 18b | 100% |
| C$_5$H$_{11}$O— / C$_5$H$_{11}$O— phenyl | 18c | 70% |
| C$_{10}$H$_{21}$O— / C$_{10}$H$_{21}$O— phenyl | 18d | 91% |
| 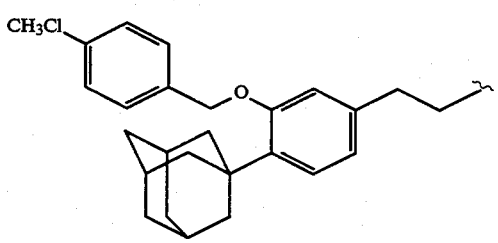 (tetramethyl-tetrahydronaphthyl-ethyl) | 18e | 55% |

TABLE 4
Biological Data for compounds of Structure 20 (Type IB).
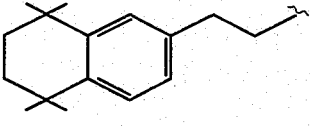
| R | X | Structure Number | % Inhibition of PLA$_2$ at 100 μM |
|---|---|---|---|
| 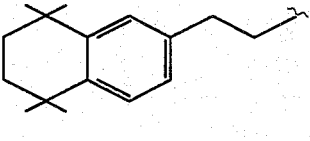 | m-CF$_3$ | 20a | 52% |
| 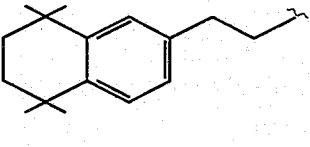 | p-F | 20b | 73% |
| 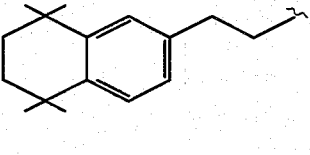 | m-F | 20c | 67% |
| 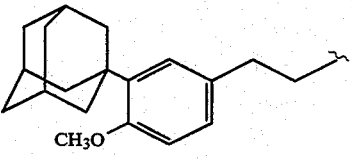 | H | 20d | 62% |
| 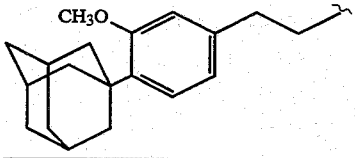 | m-CF$_3$ | 20e | 81% |
|  | m-CF$_3$ | 20f | 90% |

TABLE 5

Biological Data for Compounds of Structure 32 (Type IC):

| R | Structure Number | % Inhibition of $PLA_2$ at 100 μm |
|---|---|---|
| (phenethyl) | 32a | 1% |
| (tetramethyltetrahydronaphthyl-ethyl) | 32b | 56% |
| (tetramethyltetrahydronaphthyl-propenyl) | 32c | 67% |

TABLE 6

Biological Data for Compounds of Structure 40 (Type ID):

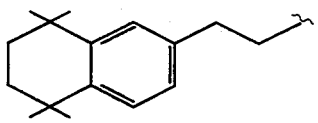

| R | X | Structure Number | % Inhibition of $PLA_2$ AT 100 μm |
|---|---|---|---|
| R⌒=⌒CO₂H (with phenyl-X) | m-CF₃ | 40 | 79% |

Formulations

Compositions or formulations may contain one or more of the compounds themselves. They may also contain isomers and/or pharmaceutically acceptable derivatives or analogs, such as hydrates, salts, e.g., succinates, acetates, hydrochlorides, alkali metal salts, ammonium salts, quaternary alkylammonium salts and the like. Examples of alkali metal salts are potassium and sodium salts. Ammonium and quaternary alkylammonium salts include salts derived from triethanolamine, N-methylglucamine, tris(hydroxymethyl)aminomethane, and L-lysine.

The concentration of active ingredient(s), or compound(s) of the invention, in such formulations will generally be from about 0.005 to about 10.0 wt %, with quantities of about 0.01 to about 5 wt % preferred.

Additives such as carriers, colorants, perfumes, vehicles, stabilizers, flow control agents and other pharmaceutically acceptable excipients can be used. Additionally, one or more other active ingredient(s) may be included.

The concentration of additives, i.e., ingredients other than the compound(s) of the invention, will generally be from about 90 to 99.995 wt %.

Administration

The compounds of the invention, their isomers and pharmaceutically acceptable derivatives or analogs thereof, may be administered to any subjects in need of treatment for inflammatory conditions, e.g., psoriasis, arthritis, and the like. While human subjects are preferred, the subjects may also be mice or other mammalian species.

The formulations discussed above may be adapted for administration via nasal, intravenous, intramuscular, opthalmic, buccal, oral or topical routes. Transdermal, i.e., topical, and oral administration are the preferred routes.

Suitable dosage forms for administration include pills, tablets, capsules, liquid compositions (administrable by injection, ingestion, or application to the surface of the skin or to other body parts), creams, gels, lotions, ointments and the like.

EXAMPLES

The following examples illustrate the preparation of various compounds conforming to Formula I.

In the following examples, all temperatures are given in degrees Centigrade. Melting points were determined on an electrothermal apparatus and are not corrected. Proton and carbon-13 nuclear magnetic resonance ($^1$H and $^{13}$C NMR) spectra were recorded on a Bruker AM-300 or a Varian Gemini 300 spectrometer. All spectra were determined in $CDCl_3$, DMSO-$d_6$, $CD_3OD$, or $D_{20}$ unless otherwise indicated. Chemical shifts are reported in δ units relative to tetramethylsilane (TMS) and interproton coupling constants are reported in Hertz (HZ). Splitting patterns are designated as follows: s, singlet; d, doublet; t, triplet; q, quartet; m, multipier; br, broad peak; dd, doublet of doublets and dt, doublet of triplets. Infrared spectra were determined on a Perkin-Elmer 1800 FT-IR spectrometer from 4000 cm$^{-1}$ to 400 cm$^{-1}$, calibrated to 1601 cm$^{-1}$ absorption of a polystyrene film, and are reported in reciprocal centimeters (cm$^{-1}$). Mass spectra were recorded on a Kratos MS-50 or a Finnegan 4500 instrument utilizing direct chemical ionization (DCI, isobutene) or fast atom bombardment (FAB). Ultraviolet spectra were determined on a Hewlett Packard 8452 diode array spectrophotometer in the solvent indicated.

Analytical thin-layer chromatography (TLC) was carried out on precoated silica gel plates (60F-254) and visualized using UV light, iodine vapors, and/or staining by heating with methanolic phosphomolybdic acid. Column chromatography, also referred to as flash chromatography, was performed in a glass column using finely divided silica gel at pressures somewhat above atmospheric pressure with the indicated solvents. Reversed-phase analytical thin-layer chromatography was carried out on precoated reverse phase plates and visualized using UV light or iodine vapors. Reversed-phase plates and visualized using UV light or iodine vapors. Reversed-phase column chromatography was performed in a glass column using Baker Octadecyl ($C_{18}$), 40 μm.

All evaporations of solvent were performed under reduced pressure. Celite is a registered trademark of the Johns-Manville Products Corporation for diatomaceous earth.

Example 1: General Procedure for Synthesis of 2

The route used to prepare phosphonates 2 was based on the following reference: Berry, J. P.; Isbell, A. F.; Hunt, G. E. J. Org. Chem. 1972, 37, 4396. The final product was purified by column chromatography on silica gel (10:1 ratio silica gel/crude compound, elution with 40 % ethyl acetate/hexane) or by distillation at 0.1 mm Hg.

For Ethyl 2-(3-bromophenyl)diethylphosphonoacetate: scale=68.0 mmol, purified by chromatography, yield=79%; scale=120 mmol, purified by distillation (bp 135°-140° C., 0.1 mm Hg), yield=75%; $^1$H NMR (300 MHz, CDCl$_3$) δ7.67 (d, J=2 Hz, 1 H, ArH), 7.44-7.48 (m, 2H, ArH), 7.22 (t, J=8 Hz, 1H, ArH), 4.00-4.31 (m, 7H, CO$_2$CH$_2$, 2×POCH$_2$, and CH), 1.21-1.36 (m, 9H, CO$_2$CH$_2$CH$_3$ and 2×POCH$_2$CH$_3$); $^{13}$C NMR (75 MHz, CDCl$_3$) δ166.50 (d, $J^2_{c,p}$=4 Hz, C=O), 133.23, 132.55 (d, $J^3_{c,p}$=7 Hz, ArC), 131.10 (d, $J^4_{c,p}$=3 Hz, ArC), 129.96, 128.33 (d, $J^3_{c,p}$=6 Hz, ArC), 122.36, 63.56 (d, $J^2_{c,p}$=7 Hz, POC), 63.29 (d, $J^2_{c,p}$=7 Hz, POC), 62.06 (CO$_2$CH$_2$), 51.76 (d, $J^1_{c,p}$=135 Hz, CHP(O)), 16.27 (d, $J^3_{c,p}$=5 Hz, POCH$_2$CH$_3$), and 14.04 (CO$_2$CH$_2$CH$_3$); IR (film) 2985, 2935, 2910, 1735 (C=O), 1595, 1570, 1475, 1370, 1320, 1300, 1260, 1210, 1150, 1095, 1050, 1025, and 690 cm$^{-1}$; MS (DCI) m/e 379 (MH+).

For Ethyl 2-(3-trifluoromethylphenyl)diethylphosphonoacetate: scale=34.3 mmol, purified by chromatography, yield=55%; scale=98.0 mmol, purified by distillation (bp 135°-140° C., 0.1 mm Hg), yield=69%; $^1$H NMR (300 MHz, CDCl$_3$) δ7.71-7.75 (m, 2 H, ArH), 7.55 (d, J=8 Hz, 1H, ArH), 7.45 (t, J=8Hz, 1H, ArH), 3.97-4.42 (m, 7 H, CO$_2$CH$_2$, 2×POCH$_2$, and CH), 1.03-1.33 (m, 9 H, CO$_2$CH$_2$CH$_3$ and 2×POCH$_2$CH$_3$); $^{13}$C NMR (75 MHz, CDCl$_3$) δ167.07 (d, $J^2_{c,p}$=4 Hz, C=O), 133.08 (d, $J^3_{c,p}$=6 Hz, ArC), 132.17 (d, $J^2_{c,f}$=8 Hz), 128.94, 126.52 (overlapping s and d, $J^3_{c,p}$=6 Hz, 2×ArC), 124.76 (d, $J^3_{c,f}$=3 Hz, ArC), 123.91 (d, $J^1_{c,f}$=272 Hz, CF$_3$), 63.54 (d, $J^2_{c,p}$=7 Hz, POC), 63.27 (d, $J^2_{c,p}$=7 Hz, POC), 62.10 (CO$_2$CH$_2$), 51.98 (d, $J^1_{c,p}$=135 Hz, CHP(O)), 16.23 (d, $J^3_{c,p}$=5 Hz, POCH$_2$CH$_3$), 16.16 (d, $J^3_{c,p}$=5 Hz, POCH$_2$CH$_3$), and 13.99 (CO$_2$CH$_2$CH$_3$); IR (film) 2985, 2935, 2910, 1740 (C=O), 1450, 1395, 1370, 1330, 1260, 1210, 1165, 1125, 1100, 1080, 1030, 970, 925, 805, and 700 cm$^{-1}$; MS (DCI) m/e 369 (MH+).

For Ethyl 2-(3-fluorophenyl)diethylphosphonoacetate: scale=31.4 mmol, purified by chromatography, yield=69%; $^1$H NMR (300 MHz, CDCl$_3$) δ7.21-7.32 (m, 3H, ArH), 6.95-7.01 (m, 1H, ArH), 3.93-4.29 (m, 7H, CO$_2$CH$_2$, 2×POCH$_2$, and CH), 0.98-1.33 (m, 9H, CO$_2$CH$_2$CH$_3$ and 2×POCH$_2$CH$_3$); $^{13}$C NMR (75 MHz, CDCl$_3$) δ167.50 (d, $J^2_{c,p}$=4 Hz, C=O), 162.58 (d, $J^1_{c,f}$=245 Hz, ArC), 133.20 (dd, $J^3_{c,p}$=8 Hz, $J^3_{c,f}$=8 Hz, ArC), 129.83 (d, $J^3_{c,f}$=8 Hz), 125.42 (d, $J^3_{c,p}$=4 Hz, ArC), 116.69 (dd, $J^2_{c,f}$=23 Hz, $J^3_{c,p}$=6 Hz, ArC), 114.94 (d, $J^2_{c,f}$=21 Hz, ArC), 63.50 (d, $J^2_{c,p}$=7 Hz, POC), 63.20 (d, $J^2_{c,p}$=7 Hz, POC), 61.99 (CO$_2$CH$_2$), 51.91 (d, $J^1_{c,p}$=135 Hz, CHP(O)), 16.30 (d, $J^3_{c,p}$=5 Hz, POCH$_2$CH$_3$), 16.23 (d, $J^3_{c,p}$=5 Hz, POCH$_2$CH$_3$), and 14.02 (CO$_2$CH$_2$CH$_3$); IR (film) 2985, 2935, 2910, 1735 (C=O), 1615, 1590, 1490, 1450, 1370, 1320, 1255, 1155, 1100, 1050, 1030, 970, 690, and 620 cm$^{-1}$; MS (DCI) m/e 319 (MH+).

For Ethyl 2-(4-fluorophenyl)diethylphosphonoacetate: scale=32.0 mmol, purified by chromatography, yield=85%; $^1$H NMR (300 MHz, CDCl$_3$) δ7.45-7.50 (m, 2H, ArH), 7.01 (apparent t, $J_{h,f}$=8.5 Hz, $J_{h,h}$=8.5 Hz, 2H, ArH), 3.88-4.25 (m, 7H, CO$_2$CH$_2$, 2×POCH$_2$, and CH), 0.99-1.45 (m, 9H, CO$_2$CH$_2$CH$_3$ and 2×POCH$_2$CH$_3$); $^{13}$C NMR (75 MHz, CDCl$_3$) δ167.50 (d, $J^2_{c,p}$=4 Hz, C=O), 162.55 (d, $J^1_{c,f}$=245 Hz, ArC), 131.31 (dd, $J^3_{c,p}$=8 Hz, $J^3_{c,f}$=8 Hz, ArC), 126.74 (d, $J^2_{c,p}$=6 Hz), 115.43 (d, $J^2_{c,f}$=20 Hz, ArC), 63.40 (d, $J^2_{c,p}$=7 Hz, POC), 63.12 (d, $J^2_{c,p}$=7 Hz, POC), 61.91 (CO$_2$CH$_2$), 51.36 (d, $J^1_{c,p}$=135 Hz, CHP(O)), 16.30 (d, $J^3_{c,p}$=5 Hz, POCH$_2$CH$_3$), 16.23 (d, $J^3_{c,p}$=5 Hz, POCH$_2$CH$_3$), and 14.02 (CO$_2$CH$_2$CH$_3$); IR (film) 2985, 2935, 2910, 1735 (C=O), 1605, 1510, 1475, 1445, 1390, 1370, 1325, 1300, 1260, 1225, 1150, 1100, 1050, 1030, 970, 900, 850, 815, 795, and 740 cm$^{-1}$; MS (DCI) m/e 319 (MH+).

For Ethyl 2-(phenyl)diethylphosphonoacetate: scale=46.5 mmol, purified by chromatography, yield=85%; $^1$H NMR (300 MHz, CDCl$_3$) δ7.47-7.51 (m, 2H, ArH), 7.25-7.35 (m, 3H, ArH), 3.88-4.25 (m, 7 H, CO$_2$CH$_2$, 2×POCH$_2$, and CH), 1.14-1.26 (m, 9H, CO$_2$CH$_2$CH$_3$ and 2×POCH$_2$CH$_3$); $^{13}$C NMR (75 MHz, CDCl$_3$) δ167.63 (d, $J^2_{c,p}$=4 Hz, C=O), 130.95 (d, $J^2_{c,p}$=8 Hz, ArC), 129.61 (d, $J^3_{c,p}$=6 Hz), 128.48, 127.91 (d, $J^4_{c,p}$=3 Hz, ArC), 63.38 (d, $J^2_{c,p}$=7 Hz, POC), 63.05 (d, $J^2_{c,p}$=7 Hz, POC), 61.79 (CO$_2$CH$_2$), 52.26 (d, $J^1_{c,p}$=135 Hz, CHP(O)), 16.29 (d, $J^3_{c,p}$=5 Hz, POCH$_2$CH$_3$), 16.23 (d, $J^3_{c,p}$=5 Hz, POCH$_2$CH$_3$), and 14.03 (CO$_2$CH$_2$CH$_3$); IR (film) 2985, 2935, 2910, 1735 (C=O), 1500, 1455, 1390, 1370, 1300, 1260, 1210, 1150, 1095, 1025, 970, 805, 730, and 700 cm$^{-1}$; MS (DCI) m/e 301 (MH+).

Example 2: Preparation of Aldehydes 3

Procedure A: Aryl aldehydes via transmetallation of aryl halides

A solution of the aryl halide (1 equivalent) in anhydrous THF (0.15-0.20M solution) was cooled to −78° C. under argon and treated with t-butyllithium solution (ca. 1.6M in pentane, 2.0-2.1 equivalents). The reaction mixture was stirred at −78° C. for 0.5–1 h and then treated with anhydrous N,N-dimethylformamide (2.0–3.0 equivalents). The reaction mixture was allowed to warm to room temperature, and then was poured into a separatory funnel containing diethyl ether and saturated ammonium chloride solution. The layers were agitated and separated, and the organic layer was washed with saturated sodium chloride solution, dried over anhydrous magnesium sulfate, filtered, and concentrated. The crude product was used without purification or was purified by column chromatography (20:1 ratio silica gel/crude product; elution with 1–10% ethyl acetate in hexanes).

For 5,6,7,8-Tetrahydro-5,5,8,8-tetramethyl-2-naphthaldehyde (3a): scale=10.2 mmol, yield=95%. The precursor aryl halide, 5,6,7,8-tetrahydro-5,5,8,8-tetramethyl-2-iodonaphthalene, was obtained from 5,6,7,8-tetrahydro-5,5,8,8-tetramethylnaphthalene (Maybridge Chemicals) via the method of W. W. Sy et al. *Synth. Commun.* 1990, 20, 877. For 3a: $^1$H NMR (300 MHz, CDCl$_3$) δ9.92 (s, 1H, CHO), 7.80 (d, J=2 Hz, 1H, ArH), 7.60 (dd, J=2, 8 Hz, 1H, ArH), 7.44 (d, J=8 Hz, 1H, ArH), 1.69 (br s, 4H, CH$_2$CH$_2$), 1.30 (s, 6H, 2×CH$_3$), and 1.29 (s, 6H, 2× CH$_3$); $^{13}$C NMR (75 MHz, CDCl$_3$) δ192.38 (C=O), 152.43, 145.92, 134.16, 128.61, 127.41, 126.60, 34.93, 34.73, 34.68, 34.41, 31.75 (CH$_3$), and 31.59 (CH$_3$); IR (film) 2960, 2930, 2860, 1695 (C=O), 1600, 1560, 1460, 1390, 1365, 1220, 1210, 1185, 1170, 1065, and 830 cm $^{-1}$; MS (DCI) m/e 217 (MH$^+$). Anal. Calcd. for C$_{15}$H$_{20}$O: C, 83.29; H, 9.32. Found: C, 83.21; H, 9.35.

For 5,6,7,8-Tetrahydro-5,5,8,8-tetramethyl-2-anthracenaldehyde (3b): scale=6.60 mmol, yield=77%. The precursor aryl halide, 5,6,7,8-tetrahydro-5,5,8,8-tetramethyl-2-bromoanthracene, was obtained via the method of M. Dawson et al. *J. Labelled Compounds and Radiopharmaceuticals* 1990, 28, 89. For 3b: $^1$H NMR (300 MHz, CDCl$_3$) δ10.09 (s, 1H, CHO), 8.23 (s, 1H, ArH), 7.93 (s, 1H, ArH), 7.78–7.84 (m, 3H, ArH), 1.77 (br s, 4 H, CH$_2$CH$_2$), and 1.39 (s, 12H, 4×CH$_3$); $^{13}$C NMR (75 MHz, CDCl$_3$) δ192.38 (C=O), 148.33, 145.83, 134.75, 134.57, 133.56, 130.97, 128.29, 126.83, 125.26, 121.67, 34.95, 34.85, 34.68, 32.47 (CH$_3$), and 32.40 (CH$_3$); IR (film) 2955, 2920, 2860, 1680 (C=O), 1630, 1470, 1460, 1385, 1365, 1310, 1165, 1125, 1110, 910, 895, and 810 cm$^{-1}$; MS (DCI) m/e 267 (MH$^+$). Anal. Calcd for C19H22O: C, 84.96; H, 8.27. Found: C, 84.82; H, 8.37.

For 4-(1-Adamantyl)-3-methoxybenzaldehyde (3c): scale=3.51 mmol, yield=43%: The precursor aryl halide, 2-adamantyl-5-iodoanisole, was obtained in two steps from 3-iodophenol via the following procedure. 3-Iodophenol was treated with 1-adamantanol and sulfuric acid in methylene chloride following the general procedure of Shreet et al. U.S. Pat. No. 4,717,720, January 1988. This gave, without recrystallization, pure 2-adamantyl-5-iodophenol: scale=114 mmol, yield=91%; mp 142°–44° C.; $^1$H NMR (300 MHz, DMSO-d$^6$) δ7.08 (d, J=2 Hz, 1H, ArH), 7.04 (dd, J=2, 8 Hz, 1H, ArH), 6.80 (d, J=8 Hz, 1H, ArH), 3.36 (s, 1H, OH), 1.99 (s, 9 H, adamantyl), and 1.68 (s, 6H, adamantyl); $^{13}$C NMR (75 MHz, CDCl$_3$) δ157.26, 135.66, 128.32, 127.54, 124.50, 91.23, 39.61, 36.56, 36.12, and 28.32; IR (KBr) 3480 (OH), 2900, 2845, 1490, 1395, 1210, and 875 cm$^{-1}$; MS (DCI) m/e 355 (MH$^+$), 354 (M$^+$), 353 (M—H)$^+$, 135 (C$_{10}$H$_{15}$$^+$). Anal. Calcd for C$_{16}$H$_{19}$OI: C, 54.25; H, 5.41. Found: C, 54.32; H, 5.37. A solution of 2-adamantyl-5-iodophenol (7.70 g, 21.7 mmol) in acetone (100 mL) was treated with dimethylsulfate (4.11 g, 32.6 mmol) and potassium carbonate (4.50 g, 32.6 mmol). The reaction mixture was stirred at reflux for 24 h, cooled, and concentrated in vacuo. The crude product was partitioned between methylene chloride and water. The organic phase was dried over anhydrous magnesium sulfate, filtered, and concentrated to provide 6.5 g (81%) of 2-adamantyl-5-iodoanisole; $^1$H NMR (300 MHz, CDCl$_3$) δ7.22 (dd, J=2, 8 Hz, 1H, ArH), 7.10 (d, J=2 Hz, 1H, ArH), 6.89 (d, J=8 Hz, 1H, ArH), 3.79 (s, 3H, OCH$_3$), 2.02 (s, 9H, adamantyl), and 1.73 (s, 6H, adamantyl); $^{13}$C NMR (75 MHz, CDCl$_3$) δ159.35, 138.43, 129.63, 128.25, 120.75, 91.20, 55.22 (OCH$_3$), 40.35, 37.02, 36.92, and 28.97; MS (DCI) m/e 369 (MH$^+$), 368 (M$^+$), 367 (M—H)$^+$, 135 (C$_{10}$H$_{15}$$^+$). Anal. Calcd for C$_{17}$H$_{21}$OI: C, 55.45; H, 5.75. Found: C, 55.51; H, 5.81. Reaction of 2-adamantyl-5-iodoanisole according to general procedure A gave 3c: $^1$H NMR (300 MHz, CDCl$_3$) δ9.92 (s, 1H, CHO), 7.35–7.41 (m, 3H, ArH), 3.88 (s, 3H, OCH$_3$), 2.08 (s, 9H, adamantyl), and 1.76 (s, 6H, adamantyl); $^{13}$C NMR (75 MHz, CDCl$_3$) δ192.04 (C=O), 159.38, 146.00, 135.36, 127.06, 124.45, 109.54, 55.09 (OCH$_3$), 40.15, 37.79, 36.95, and 28.90; IR (KBr) 2965, 2900, 2850, 1690 (C=O), 1250, 1160, 1135, 1035, and 1025 cm$^{-1}$; MS (DCI) m/e 271(MH$^+$), 135 (C$_{10}$H$_{15}$+). Anal. Calcd for C$_{18}$H$_{22}$O$_2$.0.02H$_2$O: C, 79.86; H, 8.21. Found: C, 79.48; H, 8.34.

Procedure B: Alkoxyarylaldehydes via alkylation of hydroxybenzaldehydes with alkyl halides Procedure B-1: Sodium hydride (1.1–2.1 equivalents, 80% dispersion in oil) was washed with pentane (3×) and suspended in anhydrous dimethyl sulfoxide (0.3–0.4M solution) at room temperature under argon. A solution of the hydroxybenzaldehyde (1 equivalent) in DMSO (0.2–0.25M final volume) was added via cannula and the solution was stirred at room temperature for 1 h. The alkyl halide (1.2–2.0 equivalents) was added next and the mixture was stirred for 12–20 h further. The mixture was then poured into a separatory funnel containing ethyl acetate and saturated ammonium chloride solution. The layers were agitated and separated, and the aqueous layer was extracted twice with ethyl acetate. The combined organic phases were washed with brine, dried over anhydrous magnesium sulfate, filtered, and concentrated. The residue was purified by column chromatography on silica gel (10:1 to 20:1, elution with hexanes to 5% to 10% ethyl acetate in hexanes).

Procedure B-2: A solution of the hydroxybenzaldehyde (1 equivalent) in acetone (0.5M) was treated with the alkyl halide (2–4 equivalents) and potassium carbonate (2–4 equivalents) at room temperature under argon. The resulting slurry was heated at reflux for 14–20 h, and then allowed to cool to room temperature. The mixture was partitioned between diethyl ether and water. The aqueous layer was extracted twice with diethyl ether, and the combined organic layers were washed with saturated sodium chloride solution, dried over anhydrous magnesium sulfate, filtered, and concentrated. Purification of the residue was achieved by column chromatography on silica gel (10:1 to 20:1, elution with hexanes to 5% to 10% ethyl acetate in hexanes).

4-Decyloxybenzaldehyde (3d): commercially available from Lancaster Chemicals.

For 3-decyloxybenzaldehyde (3e): from 3-hydroxybenzaldehyde (Aldrich Chemicals) via procedure B-1, scale=7.50 mmol, yield=72%; $^1$H NMR (300 MHz, CDCl$_3$) δ9.95 (s, 1H, CHO), 7.35-7.44 (m, 3H, ArH), 7.11-7.18 (m, 1H, ArH), 3.99 (t, J=7 Hz, 2H, ArOCH$_2$), 1.78 (quintet, J=7 Hz, 2H, ArOCH$_2$CH$_2$), 1.20-1.50 (m, 14 H, 7×CH$_2$), and 0.86 (t, J=7 Hz, 3H, CH$_3$); $^{13}$C NMR (75 MHz, CDCl$_3$) δ192.23 (C=O), 159.71, 137.57, 129.97, 123.28, 121.97, 112.75, 68.31 (ArOCH$_2$), 31.89, 29.55, 29.35, 29.31, 29.12, 25.99, 22.67, and 14.11; IR (film) 2925, 2855, 2725, 1700 (C=O), 1600, 1585, 1485, 1450, 1385, 1285, and 1260 cm$^{-1}$; MS (DCI) m/e 263 (MH+).

For 2-decyloxybenzaldehyde (3f): from 2-hydroxybenzaldehyde (Aldrich Chemicals) via procedure B-1, scale=7.50 mmol, yield=60%; $^1$H NMR (300 MHz, CDCl$_3$) δ10.49 (s, 1H, CHO), 7.80 (dd, J=2, 8 Hz, 1H, ArH), 7.50 (dt, J=2, 8 Hz, 1H, ArH), 6.94-7.01 (m, 2H, ArH), 4.05 (t, J=7 Hz, 2H, ArOCH$_2$), 1.81 (quintet, J=7 Hz, 2H, ArOCH$_2$CH$_2$), 1.20-1.51 (m, 14H, 7×CH$_2$), and 0.85 (t, J=7 Hz, 3H, CH$_3$); δ$^{13}$C NMR (75 MHz, CDCl$_3$) δ189.96 (C=O), 161.59, 135.90, 128.19, 124.89, 120.43, 112.47, 68.53 (ArOCH$_2$), 31.87, 29.54, 29.32, 29.30, 29.08, 26.05, 22.67, and 14.11; IR (film) 2925, 2855, 1690 (C=O), 1600, 1585, 1485, 1460, 1390, 1300, 1285, 1240, 1190, 1160, and 755 cm $^{-1}$; MS (DCI) m/e 263 (MH+).

For 4-[(2E),(6E)-3,7-dimethyl-2,6-octadienoxy}benzaldehyde (3 g): from 4-hydroxybenzaldehyde (Aldrich Chemicals) via procedure B-1, scale=11.3 mmol, yield=84%; $^1$H NMR (300 MHz, CDCl$_3$) δ9.85 (s, 1H, CHO), 7.80 (dt, J=2, 8 Hz, 2H, ArH), 6.98 (dr, J=2, 8 Hz, 2H, ArH), 5.43-5.48 (m, 1H, C=CHCH$_2$O), 5.04-5.09 (m, 1H, CH=C(CH$_3$)$_2$), 4.58 (d, J=7 Hz, 2H, ArOCH$_2$), 2.00-2.15 (m, 4H, C=CHCH$_2$CH$_2$), 1.73 (s, 3H, CH$_3$), 1.65 (s, 3H, CH$_3$), and 1.58 (s, 3H, CH$_3$); $^{13}$C NMR (75 MHz, CDCl$_3$) δ190.79 (C=O), 164.00, 142.13, 131.94, 129.80, 123.62, 118.59, 114.98, 65.24 (ArOCH$_2$), 39.50, 39.03, 37.26, 32.45, 26.52, 26.23, 25.67, 17.69, and 16.72; IR (film) 2970, 2925, 2855, 2735, 1695 (C=O), 1600, 1575, 1510, 1450, 1430, 1380, 1310, 1250, 1160, 1110, 990, and 830 cm$^{-1}$; MS (DCI) m/e 259 (MH+).

For 3,4-Bisdecyloxybenzaldehyde (3h): from 3,4-dihydroxybenzaldehyde (Aldrich Chemicals) via procedure B-2, scale=72.4 mmol, yield=53%; mp 59.5°-60° C.; UV$_{max}$(EtOH) 310 nm (ε=9,200), 276 nm (ε=11,000), 232 nm (ε=15,400); 1H NMR (300 MHz, CDCl$_3$) δ9.81 (s, 1H, CHO), 7.39 (d, J=8 Hz, 1H, ArH), 7.37 (s, 1H, ArH), 6.93 (d, J=8 Hz, 1H, ArH), 4.05 (t, J=7 Hz, 2H, ArOCH$_2$), 4.03 (t, J=7 Hz, 2H, ArOCH$_2$), 1.77-1.88 (m, 4 H, 2×ArOCH$_2$CH$_2$), 1.20-1.50 (m, 28 H, 14×CH$_2$), and 0.86 (t, J=7 Hz, 6H, 2×CH$_3$); $^{13}$C NMR (75 MHz, CDCl$_3$) δ190.98 (C=O), 154.68, 149.44, 129.87, 126.57, 111.76, 110.97, 69.13 (2×ArOCH$_2$), 31.90, 29.57, 29.34, 29.07, 28.98, 25.97, 25.94, and 14.10; IR (film) 2955, 2920, 2850, 1690 (C=O), 1675, 1595, 1585, 1510, 1470, 1440, 1395, 1275, 1235, 1135, and 810 cm$^{-1}$; MS (DCI) m/e 419 (MH+). Anal. Calcd for C$_{27}$H$_{46}$O$_3$: C, 77.46; H, 11.07. Found: C, 77.19; H, 10.99.

For 3,4-Bispentyloxybenzaldehyde (3i): from 3,4-dihydroxybenzaldehyde (Aldrich Chemicals) via procedure B-2, scale=109 mmol, yield=quantitative; mp 31°-32.5° C.; UV$_{max}$(EtOH) 310 nm (ε=9,000), 276 nm (ε=10,900), 232 nm (ε=15,500); $^1$H NMR (300 MHz, CDCl$_3$) δ9.79 (s, 1H, CHO), 7.38 (dd, J=2, 8 Hz, 1H, ArH), 7.36 (s, 1H, ArH), 6.91 (d, J=8 Hz, 1H, ArH), 4.04 (t, J=7 Hz, 2H, ArOCH$_2$), 4.02 (t, J=7 Hz, 2H, ArOCH$_2$), 1.77-1.88 (m, 4H, 2×ArOCH$_2$CH$_2$), 1.20-1.50 (m, 8 H, 4×CH$_2$), and 0.90 (t, J=7 Hz, 6H, 2×CH$_3$); $^{13}$C NMR (75 MHz, CDCl$_3$) δ190.99 (C=O), 154.65, 149.40, 129.84, 126.61, 111.68, 110.84, 69.08 (2×ArOCH$_2$), 28.74, 28.65, 28.16, 28.12, 22.42, and 14.02; IR (film) 2955, 2935, 2860, 1690 (C=O), 1675, 1595, 1585, 1510, 1465, 1440, 1395, 1275, 1240, 1165, 1135, 1050, 1025, 1000, 990, and 810 cm$^{-1}$; MS (DCI) m/e 279 (MH+). Anal. Calcd for C$_{17}$H$_{26}$O$_3$: C, 73.35; H, 9.41. Found: C, 73.61; H, 9.40.

Procedure C: 3-Arylpropionaldehydes via treatment of aryl iodides with allyl alcohol and palladium acetate 3-Arylpropionaldehydes were prepared according to the general procedure of T. Jeffery *J. Chem. Soc., Chem. Commun.* 1984, 1287. Upon consumption of all the aryl iodide as judged by $^1$H NMR analysis of a small aliquot, the reaction mixture was partitioned between water and 2:1 hexane/ethyl acetate. The organic phase was washed with water (5×), dried with anhydrous sodium sulfate, decanted, and concentrated to give the crude product.

For 3-(5,6,7,8-Tetrahydro-5,5,8,8-tetramethyl-2-naphthalenyl)propionaldehyde (3 j): scale=27.6 mmol, purified by column chromatography (40:1 silica gel/crude product), yield=82%. The precursor aryl iodide, 5,6,7,8-tetrahydro-5,5,8,8-tetramethyl-2-iodonaphthalene, was obtained from 5,6,7,8-tetrahydro-5,5,8,8-tetramethylnaphthalene (Maybridge Chemicals) via the method of W. W. Sy et al. *Synth. Commun.* 1990, 20, 877. 1H NMR (300 MHz, CDCl$_3$) δ7.59 (d, J=2 Hz, 1H, ArH), 7.42 (dd, J=2, 8 Hz, 1H, ArH), 7.03 (d, J=8 Hz, 1H, ArH), 1.65 (s, 4H, CH$_2$CH$_2$), 1.25 (s, 6H, 2×CH$_3$), 1.24 (s, 6H, 2×CH$_3$); $^{13}$C NMR (75 MHz, CDCl$_3$) δ147.68, 144.59, 135.58, 134.57, 128.74, 91.18, 34.83, 34.78, 34.33, 34.13, 31.75, 31.71; IR (KBr) 2955, 2920, 2860, 1580, 1480, 1455, 1385, 1360, 1065, 815 cm$^{-1}$; MS (DCI) m/e 315(MH+), 314 (M+), 299 (M—CH$_3$)+. Anal. Calcd for C$_{14}$H$_{19}$I: C, 53.51; H, 6.09; I, 40.39. Found: C, 53.82; H, 6.08; I, 40.33. For 3 j: $^1$H NMR (300 MHz, CDCl$_3$) δ9.84 (t, J=1.5 Hz, 1H, CHO), 7.25 (d, J=8 Hz, 1H, ArH), 7.13 (d, J=2 Hz, 1H, ArH), 6.97 (dd, J=2, 8 Hz, 1H, ArH), 2.89-2.95 (m, 2H, CH$_2$), 2.75-2.81 (m, 2H, CH$_2$), 1.69 (s, 4 H, CH$_2$CH$_2$), and 1.29 (s, 12 H, 4×CH$_3$); $^{13}$C NMR (75 MHz, CDCl$_3$) δ201.83 (C=O), 144.94, 142.73, 137.02, 126.63, 126.19, 125.40, 45.18, 35.02, 34.96, 34.10, 33.87, 31.77, and 27.77; IR (KBr) 2960, 2920, 2855, 1725 (C=O), 1455, 1385, 1360, and 820 cm$^{-1}$; MS (DCI) m/e 245(MH+), 227 (M—OH)+. Anal. Calcd for C$_{17}$H$_{24}$O: C, 83.55; H, 9.90. Found: C, 83.85; H, 9.93.

For 3-(3-(1-Adamantyl)-4-hydroxyphenyl)propionaldehyde (3k): scale=28.2 mmol, yield=98%. The precursor aryl iodide, 2-adamantyl-4-iodophenol was prepared from 4-oiodophenol and 1-adamantanol using the general procedure of Shreet et al. U.S. Pat. No. 4,717,720, January 1988. Scale=80 mmol, yield=58%; $^1$H NMR (300 MHz, CDCl$_3$) δ7.44 (d, J=2 Hz, 1H, ArH), 7.32 (dd, J=2, 8 Hz, 1H, ArH), 6.40 (d, J=8 Hz, 1H, ArH), 4.77 (s, 1H, OH), 2.06 (s, 9H, adamantyl), and 1.75 (s, 6H, adamantyl); $^{13}$C NMR (75 MHz, CDCl$_3$) δ154.18, 139.13, 136.05, 135.32, 118.87, 83.53, 40.16, 36.73, 36.80, and 28.80; IR (KBr) 3530 (OH),2910, 2885, 2850, 1480, 1390, 1245, 1120, 820, and 805cm$^{-1}$; MS (DCI) m/e 355 (MH+), 354 (M+), 135 (C$_{10}$H$_{15}$+). Anal. Calcd for C$_{16}$H$_{19}$OI: C, 54.25; H, 5.41. Found: C, 54.46; H, 5.44. Reaction of 2-adamantyl-4-iodophenol according to general procedure C gave 3k: $^1$H NMR (300 MHz, CDCl$_3$) δ9.80 (t, J=1 Hz, 1H, CHO), 7.00

(d, J=2 Hz, 1H, ArH), 6.86 (dd, J=2, 8 Hz, 1H, ArH), 6.56 (d, J=8 Hz, 1H, ArH), 4.71 (s, 1H, OH), 2.86 (t, J=7 Hz, 2H, $CH_2$), 2.73 (t, J=7 Hz, 2H, $CH_2$), 2.08 (br s, 9H, adamantyl), and 1.75 (s, 6H, adamantyl); $^{13}C$ NMR (75 MHz, $CDCl_3$) δ202.19 (C=O), 152.83, 136.51, 132.17, 127.04, 126.23, 116.82, 45.65, 40.50, 37.02, 36.64, 29.00, and 27.69; IR (KBr) 3340 (OH), 2910, 2890, 2850, 1710, 1510, 1425, 1370, and 1245 $cm^{-1}$; MS (DCI) m/e 285 (MH+), 284 (M+), 135 ($C_{10}H_{15}$+). Anal. Calcd for $C_{19}H_{24}O_2 \cdot 0.13\ H_2O$: C, 79.59; H, 8.53. Found: C, 79.23; H, 8.40.

For 3-(4-(1-Adamantyl)-3-hydroxyphenyl)propionaldehyde (3 l): scale=42.3 mmol, purified by column chromatography (40:1 silica gel/crude product; elution with methylene chloride followed by 5% methanol/methylene chloride), yield=44%. The precursor aryl iodide, 2-adamantyl-5-iodophenol was prepared from 3-iodophenol as described in the experimental for 3 c. For 3 l: $^1H$ NMR (300 MHz, DMSO-$d^6$) δ9.67 (s, 1H, CHO), 9.11 (s, 1, OH), 6.92 (d, 1=8 Hz, 1H, ArH), 6.53–6.55 (m, 2H, ArH), 2.68 (s, 4H, 2×$CH_2$), 2.01 (s, 9H, adamantyl), and 1.68 (s, 6H, adamantyl); $^{13}C$ NMR (75 MHz, $CDCl_3$) δ 202.88 (C=O), 155.91, 138.85, 133.25, 126.05, 118.57, 116.18, 44.23, 39.96, 36.66, 35.84, 28.41, and 26.87; IR (KBr) 3445 (OH), 2910, 2890, 2845, 1720 (C=O), 1430, and 1225 $cm^{-1}$; MS (DCI) m/e 285 (MH+), 284 (M+), 135 ($C_{10}H_{15}$+). Anal. Calcd for $C_{19}H_{24}O_2 \cdot 0.15\ H_2O$: C, 79.49; H, 8.53. Found: C, 79.62; H, 8.47.

For 3-[4-(1-Adamantyl)-3-t-butyldimethylsilyloxyphenyl)propionaldehyde (3m): scale=51.6 mmol, purified by column chromatography (40:1 silica gel/crude product; elution with 2:1 hexane/methylene chloride), yield=70%. The precursor aryl iodide, 2-adamantyl-5-iodo-1-(t-butyldimethylsiloxy)benzene, was prepared from 2-adamantyl-5-iodophenol (see 3c for preparation) via treatment with t-butyldimethylsilyl chloride for 24 h at 60° C. The procedure was taken from a similar conversion described by Shreet et al. U.S. Pat. No. 4,717,720, January 1988. Purification by column chromatography (10:1 silica gel/crude product; elution with hexane) gave 2-adamantyl-5-iodo-1-(t-butyldimethylsiloxy)benzene: scale=118 mmol, yield=97%; $^1H$ NMR (300 MHz, $CDCl_3$) δ7.19 (dd, J=2, 8 Hz, 1H, ArH), 7.09 (d, J=2 Hz, 1H, ArH), 6.90 (d, J=8 Hz, 1H, ArH), 2.04 (s, 9H, adamantyl), 1.74 (s, 6H, adamantyl), 1.03 (s, 9H, $SiC(CH_3)_3$), and 0.34 (s, 6H, $Si(CH_3)_2$); $^{13}C$ NMR (75 MHz, $CDCl_3$) δ155.39, 139.48, 129.58, 128.80, 127.86, 90.43, 40.18, 36.97, 36.78, 28.92, 26.39 ($SiC(CH_3)_3$), 19.00 ($SiC(CH_3)_3$), and −3.51 ($Si(CH_3)_2$); IR (film) 2930, 2910, 2875, 2855, 2845, 1575, 1480, 1390, 1265, 1250, 1240, 930, 850, 800, and 785 $cm^{-1}$; MS (DCI) m/e 469 (MH+), 135 ($C_{10}H_{15}$+). Anal. Calcd for $C_{22}H_{33}OISi$: C, 56.40; H, 7.10. Found: C, 56.66; H, 7.25. Reaction of 2-adamantyl-5-iodo-1-(t-butyldimethylsiloxy)benzene according to general procedure C gave 3m: $^1H$ NMR (300 MHz, $CDCl_3$) δ9.81 (s, 1H, CHO), 7.11 (d, J=8 Hz, 1H, ArH), 6.70 (dd, J=2, 8 Hz, 2H, ArH), 6.61 (d, J=2 Hz, 1H, ArH), 2.83–2.89 (m, 2H, $CH_2$), 2.71–2.76 (m, 2H, $CH_2$), 2.06 (s, 9H, adamantyl), 1.74 (s, 6H, adamantyl), 1.03 (s, 9H, $SiC(CH_3)_3$), and 0.33 (s, 6H, $Si(CH_3)_2$); $^{13}C$ NMR (75 MHz, $CDCl_3$) δ201.77 (C=O), 154.71,138.46, 137.53, 127.18, 120.14, 119.05, 45.03, 40.43, 37.05, 36.56, 29.02, 27.42, 26.43 ($SiC(CH_3)_3$), 18.96 ($SiC(CH_3)3$), and −3.34 ($Si(CH_3)_2$); IR (KBr) 2955, 2930, 2910, 2850, 1720 (C=O), 1415, 1250, 990, 855, and 780 $cm^{-1}$; MS (DCI) m/e 399 (MH+), 398 (M+), 135 ($C_{10}H_{15}$+). Anal. Calcd for $C_{25}H_{38}O_2Si$: C, 75.32; H, 9.61. Found: C, 75.62; H, 9.66.

For 3-[2-(1-Adamantyl)-4-methoxyphenyl]propionaldehyde (3n): Prepared by the following 5 step sequence. A solution of 2-(1-adamantyl)-1,4-hydroquinone (Miryan, N. I.; et al. Ukr. Khim. Zh. (Russ Ed.) 1990, 56, 183.) (1.88 g, 7.70 mmol) in acetone (100 mL) under a nitrogen atmosphere was treated with powdered potassium carbonate (1.06 g, 7.70 mmol) and dimethylsulfate (0.97 g, 7.70 mmol). After stirring for 48 h at reflux, the reaction mixture was cooled and concentrated in vacuo. The residue was partitioned between ether and a saturated ammonium chloride solution. The organic phase was washed with water (5×) and brine, dried with magnesium sulfate, treated with activated charcoal, filtered through celite, concentrated in vacuo to give an oil. Purification by column chromatography (20:1 silica gel/crude product; elution with methylene chloride) gave 1.0 g of an off-white solid. Trituration with ether gave 0.93 g (47%) of 2-(1-adamantyl)-4-methoxyphenol as a white solid. $^1H$ NMR (300 MHz, $CDCl_3$) δ8.75 (s, 1H, OH), 6.64 (d, J=8.5 Hz, 1H, ArH), 6.59 (d, J=3 Hz, 1H, ArH), 6.55 (dd, J=3, 8.5 Hz, 1H, ArH), 3.62 (s, 3H, $OCH_3$), 2.00–2.03 (m, 9H, adamantyl), and 1.70 (s, 6H, adamantyl); $^{13}C$ NMR (300 MHz, $CDCl_3$) δ151.98, 149.81, 136.51, 116.49, 112.75, 110.50, 55.14 ($OCH_3$), 39.72, 36.61, 36.17, and 28.39; IR (KBr) 3380, 2930, 2910, 2885, 2850, 1500, 1420, 1210, 1030, and 745 $cm^{-1}$; MS (DCI) m/e 259 (MH+), 258 (M+), 257 (M—H)+, 135 ($C_{10}H_{15}$+). Anal. Calcd for $C_{17}H_{22}O_2$: C, 79.03; H, 8.58. Found: C, 78.91; H, 8.51. A slurry of 2-(1-adamantyl)-4-methoxyphenol (0.93 g, 3.60 mmol) in methylene chloride (60 mL) cooled to −78° C. was treated with ethyldiisopropylamine (0.51 g, 3.96 mmol). Trifluoromethanesulfonic anhydride (1.12 g, 3.96 mmol) was added dropwise to the stirred solution. After the addition was complete, the reaction mixture was stirred at 0° C. for 5 h and at room temperature for 18 h. The solvent was removed in vacuo and the residue was partitioned between ethyl acetate and water. The organic phase was washed with water (5×), dried with anhydrous magnesium sulfate, filtered, and concentrated to give 1.36 g (96%) of 2-(1-adamantyl)-4-methoxyphenoxytrifluoromethanesulfonate. $^1H$ NMR (300 MHz, $CDCl_3$) δ7.22 (d, J=9 Hz, 1H, ArH), 6.92 (d, J=3 Hz, 1H, ArH), 6.71 (dd, J=3,9 Hz, 1H, ArH), 3.79 (s, 3H, $OCH_3$), 2.09 (s, 3H, adamantyl), 2.02–2.03 (m, 6H, adamantyl), and 1.74–1.76 (m, 6H, adamantyl); $^{13}C$ NMR (300 MHz, $CDCl_3$) δ158.34, 143.10, 142.88, 122.11, 118.36 (q, $J^1_{c,f}$=318 Hz, $CF_3$), 115.04, 110.84, 55.56 ($OCH_3$), 40.89, 37.13, 36.50, and 28.80; IR (KBr) 2910, 2855, 1580, 1480, 1415, 1270, 1245, 1220, 1210, 1195, 1140, 1035, 920, 890, 865, 800, and 580 $cm^{-1}$; MS (DCI) m/e 391 (MH+), 390 (M+), 389 (M—H)+, 255 (M—$C_{10}H_{15}$+2H)+, 135 ($C_{10}H_{15}$+). Anal. Calcd for $C_{18}H_{21}O_4SF_3$: C, 55.38; H, 5.42. Found: C, 55.48; H, 5.41. A solution of 2-(1-adamantyl)-4-methoxyphenoxytrifluoromethanesulfonate (1.51 g, 3.87 mmol), 3-tributylstannyl-(2E)-propenol (1.48 g, 4.25 mmol) (Jung, M. E.; Light, L. A. Tetrahedron Lett. 1982, 23, 3851), and bistriphenylphosphinepalladium dichloride (0.05 g, 0.08 mmol) in dimethylformamide was heated at 90° C. for 16 h according to the general procedure of A. Echavarren and J. K. Stille J. Am. Chem. Soc. 1987, 109, 5478. Purification by column chromatography (25:1 silica gel/crude product; elution with 20% ethyl acetate/hexane) gave 0.99g (86%) of 3-[2-(1-adamantyl)-4-methoxyphenyl]-(2E)-propenol. $^1H$ NMR (300 MHz, $CDCl_3$)

δ7.35 (d, J=15 Hz, 1H, ArCH=CH), 7.30 (d, J=8.5 Hz, 1H, ArH), 6.89 (d, J=3 Hz, 1H, ArH), 6.68 (dd, J=3, 8.5 Hz, 1H, ArH), 5.93 (dt, J=15, 6 Hz, 1H, ArCH=CH), 3.79 (s, 3H, OCH$_3$), 2.06–2.08 (m, 9H, adamantyl), and 1.75 (s, 6H, adamantyl); $^{13}$C NMR (300 MHz, CDCl$_3$) δ159.19, 149.10, 132.98, 130.76, 129.28, 127.76, 112.94, 109.80, 64.19 (OCH$_2$), 55.15 (OCH$_3$), 41.89, 37.95, 36.84, and 29.09; IR (KBr) 3345 (OH), 2905, 2850, 1600, 1570, 1475, 1450, 1300, 1260, 1235, 1030, and 760 cm$^{-1}$; MS (DCI) m/e 299 (MH+), 298 (M+), 281 (M-OH)+, 135 (C$_{10}$H$_{15}$+). Anal. Calcd for C$_{20}$H$_{26}$O$_2$: C, 80.50; H, 8.78. Found: C, 80.43; H, 8.87. Hydrogenation of 3-[2-(1-adamantyl)-4-methoxyphenyl]-(2E)-propenol (0.99 g, 3.30 mmol) was conducted at 60 psi in ethanol using catalytic 10% palladium on charcoal. After 48 h, the solution was filtered through celite and concentrated in vacuo to give the crude product. Purification by column chromatography (20:1 silica gel/crude product; elution with methylene chloride) gave 3-[2-(1-adamantyl)-4-methoxyphenyl]-propanol (0.74 g, 75%). $^1$H NMR (300 MHz, CDCl$_3$) δ7.09 (d, J=8.5 Hz, 1H, ArH), 6.87 (d, J=3 Hz, 1H, ArH), 6.69 (dd, J=3, 8.5 Hz, 1H, ArH), 3.73–3.77 (m, 5H, OCH$_2$ and OCH$_3$), 2.92–2.97 (m, 2H, ArCH$_2$), 2.04–2.09 (m, 9H, adamantyl), 1.81–1.91 (m, 2H, ArCH$_2$CH$_2$), and 1.75–1.77 (s, 6H, adamantyl); $^{13}$C NMR (300 MHz, CDCl$_3$) δ157.43, 149.02, 132.74, 132.69, 113.02, 109.98, 63.04 (OCH$_2$), 55.11 (OCH$_3$), 42.10, 37.93, 36.85, 36.39, 29.91, and 29.19; IR (KBr) 3355 (OH), 2905, 2850, 1605, 1575, 1450, 1290, 1255, 1235, 1055, 1035, and 755 cm$^{-1}$; MS (DCI) m/e 301 (MH+), 300 (M), 299 (M—H)+, 165 (M—C$_{10}$H$_{15}$)+, 135 (C$_{10}$H$_{15}$+). Anal. Calcd for C$_{20}$H$_{28}$O$_2$: C, 79.96; H, 9.39. Found: C, 79.63; H, 9.52. Oxidation of 3-[2-(1-Adamantyl)-4-methoxyphenyl]-propanol (0.62 g, 2.1 mmol) was carried out using catalytic tetrapropylammonium perruthenate using the general procedure of W. Griffith and S. Ley Aldrichimica Acta 1990, 23, 13. Purification by column chromatography (40:1 silica gel/crude product; elution with ethyl acetate/hexane) gave 3-[2-(1-adamantyl)-4-methoxyphenyl]propanal (3n) (0.42 g, 68%). $^1$H NMR (300 MHz, CDCl$_3$) δ9.87 (s, 1H, CHO), 7.04 (d, J=8 Hz, 1H, ArH), 6.90 (d, J=3 Hz, 1H, ArH), 6.71 (dd, J=3,8 Hz, 1H, ArH), 3.79 (s, 3H, OCH$_3$), 3.22 (m, 2H, CH$_2$), 2.77 (m, 2H, CH$_2$), 2.10 (s, 3H, adamantyl), 2.03 (m, 6H, adamantyl), and 1.77 (s, 6H, adamantyl).

Example 3: General Procedure for Synthesis of 4

A solution of the phosphonate 2 (1.2–1.6 equivalents) and aldehyde 3 (1 equivalent) in anhydrous toluene (0.10–0.25M) at room temperature under argon was treated dropwise with a solution of sodium ethoxide in ethanol (21 wt %, 1.1–1.5 equivalents). The reaction mixture was stirred at room temperature to 70° C. for 4–14 h. The mixture was then partitioned between diethyl ether and saturated ammonium chloride solution, and the organic layer was washed further with saturated sodium chloride solution, dried over anhydrous magnesium sulfate, filtered, and concentrated. The crude product was purified by column chromatography (40:1 ratio of silica gel/crude product; elution with 2-3% ethyl acetate in hexanes).

For Ethyl (E)-2-(3-bromophenyl)-3-phenyl-propenoate (4a): scale=2.46 mmol, yield=87% [3.5:1 ratio of (E)/(Z) isomers]; $^1$H NMR (300 MHz, CDCl$_3$) δ7.83 (s, 1H, C=CH from (E)-isomer), 7.62 (t, J=2 Hz, 1H, 2-ArH), 7.13–7.48 (m, 9H, ArH and C=CH from (Z)-isomer), 4.25 (q, J=7 Hz, 2H, CO$_2$CH$_2$), 1.28 (t, J=7 Hz, 3H, CO$_2$CH$_2$CH$_3$ from (E)-isomer), and 1.17 (t, J=7 Hz, 3H, CO$_2$CH$_2$CH$_3$ from (Z)-isomer); $^{13}$C NMR (75 MHz, CDCl$_3$) δ167.21 (C=O), 140.89, 138.01, 134.15, 132.70, 131.18, 130.85, 130.56, 130.07, 129.45, 129.30, 128.58, 128.46, 128.31, 125.12, 122.41, 61.50 (CO$_2$CH$_2$ from (Z)-isomer), 61.35 (CO$_2$CH$_2$ from (E)-isomer), 14.24 (CO$_2$CH$_2$CH$_3$ from (E)-isomer), and 13.81 (CO$_2$CH$_2$CH$_3$ from (Z)-isomer); IR (film) 2980, 1710 (C=O), 1560, 1475, 1450, 1370, 1245, 1210, 1180, 1075, 1040, and 690 cm$^{-1}$; MS (DCI) m/e 331/333 (MH+, 1:1).

For Ethyl (E)-2-(3-bromophenyl)-3-(5,6,7,8-tetrahydro-5,5,8,8-tetramethyl- 2-naphthalenyl)-propenoate (4b): scale=8.63 mmol, yield=63%; UV$_{max}$ (CH$_3$OH) 300 nm (68 =19,900); $^1$H NMR (300 MHz, CDCl$_3$) δ7.77 (s, 1H, C=CH), 7.47 (dt, J=2, 8 Hz, 1H, 2-ArH), 7.38 (t, J=2 Hz, 1H, 2-ArH), 7.13–7.28 (m, 3H, ArH), 6.92 (d, J=2 Hz, 1H, 3-ArH), 6.87 (dd, J=2, 8 Hz, 1H, 3-ArH), 4.23 (q, J=7 Hz, 2H, CO$_2$CH$_2$), 1.57 (br s, 4 H, CH$_2$CH$_2$), 1.27 (t, J=7 Hz, 3H, CO$_2$CH$_2$CH$_3$), 1.20 (s, 6H, 2×CH$_3$) and 0.98 (s, 6H, 2×CH$_3$); $^{13}$C NMR (75 MHz, CDCl$_3$) δ167.45 (C=O), 146.94, 144.85, 141.23, 138.82, 132.67, 131.12, 130.68, 130.25, 129.85, 129.11, 128.60, 128.41, 126.64, 122.61, 61.22 (CO$_2$CH$_2$), 34.79 (CH$_2$CH$_2$), 34.32, 33.96, 31.56 (CH$_3$), 31.42 (CH$_3$), and 14.29 (CO$_2$CH$_2$CH$_3$); IR (film) 2960, 2930, 2860, 1710 (C=O), 1620, 1605, 1560, 1490, 1470, 1460, 1365, 1280, 1245, 1215, 1175, 1070, 1040, and 830 cm$^{-1}$; MS (DCI) m/e 441/443 (MH+, 1:1).

For Ethyl (E)-2-(3-bromophenyl)-3-(5,6,7,8-tetrahydro-5,5,8,8-tetramethyl-2-anthracenyl)-propenoate (4c): scale=5.0 mmol, yield=64%; $^1$H NMR (300 MHz, CDCl$_3$) δ8.00 (s, 1H, 3-ArH), 7.66 (s, 3H, 3-ArH and C=CH), 7.41–7.51 (m, 3H, ArH), 7.15–7.21 (m, 2H, ArH), 6.81 (dd, J=1, 9 Hz, 1H, ArH), 4.29 (q, J=6 Hz, 2H, CO$_2$CH$_2$), 1.75 (s, 4H, CH$_2$CH$_2$), and 1.27–1.41 (m, 15 H, 4×CH$_3$ and CO$_2$CH$_2$CH$_3$); $^{13}$C NMR (75 MHz, CDCl$_3$) δ167.43 (C=O), 146.14, 145.06, 141.49, 138.27, 133.04, 131.81, 131.56, 131.39, 131.05, 130.85, 130.52, 130.00, 128.96, 126.94, 125.64, 125.60, 124.76, 122.40, 61.32 (CO$_2$CH$_2$), 34.97 (CH$_2$CH$_2$), 34.72, 34.58, 32.47 and 32.44 (4×CH$_3$), and 14.32 (CO$_2$CH$_2$CH$_3$); IR (film) 2960, 2930, 1710 (C=O), 1615, 1470, 1365, 1240, 1185, 1165, and 1150 cm$^{-1}$; MS (DCI) m/e 493/491 (MH+, 1:1).

For Ethyl (E)-2-(3-bromophenyl)-3-(4-decyloxyphenyl)propenoate (4d): scale=9.60 mmol, yield=79%; $^1$H NMR (300 MHz, CDCl$_3$) δ7.77 (s, 1H, C=CH), 7.36–7.48 (m, 2H, 2-ArH), 7.11–7.25 (m, 2H, 2-ArH), 6.96 (d, J=8 Hz, 2H, 3-ArH), 6.67 (d, J=8 Hz, 2H, 3-ArH), 4.22 (q, J=7 Hz, 2H, CO$_2$CH$_2$), 3.88 (t, J=7 Hz, 2H, ArOCH$_2$), 1.71 (quintet, J=7 Hz, 2H, ArOCH$_2$CH$_2$), 1.21–1.43 (m, 17H, 7×CH$_2$ and CO$_2$CH$_2$CH$_3$), and 0.85 (t, J=7 Hz, 3H, CH$_3$); $^{13}$C NMR (75 MHz, CDCl$_3$) δ167.52 (C=O), 160.12, 140.72, 138.59, 132.79, 132.43, 130.70, 130.17, 128.67, 128.50, 126.46, 122.50, 114.32, 68.01 (ArOCH$_2$), 61.16 (CO$_2$CH$_2$), 31.88, 29.54, 29.34, 29.11, 25.96, 22.67, 14.29, and 14.12; IR (film) 2925, 2855, 1710 (C=O), 1600, 1570, 1560, 1510, 1470, 1365, 1300, 1250, 1210, 1170, 1070, 1040, 830, and 690 cmA; MS (DCI) m/e 487/489 (MH+, 1:1).

For Ethyl (E)-2-(3-bromophenyl)-3-(3,4-bisdecyloxyphenyl)propenoate (4e): scale=3.2 mmol, yield=46%; $^1$H NMR (300 MHz, CDCl$_3$) δ7.75 (s, 1H, C=CH), 7.45 (dd, J=2, 6 Hz, 1H, 2-ArH), 7.41 (t, J=1 Hz, 1H, 2-ArH), 7.25 (t, J=8 Hz, 1H, 2-ArH), 7.16 (dt, J=1, 8 Hz, 1H 2-ArH), 6.77 (dd, J=2, 8 Hz, 1H, 3-ArH), 6.70 (d, J=8, 1 H, 3-ArH), 6.40 (d, J=2 Hz, 1H, 3-ArH), 4.23 (q, J=7 Hz, 2H, $CO_2CH_2$), 3.94 (t, J=7Hz, 2H, ArC-$^4OCH_2$), 3.48 (t, J=7 Hz, 2H, ArC$^3OCH_2$), 1.71–1.78 (m, 2H, ArC$^4OCH_2CH_2$), 1.60–1.65 (m, 2H, ArC-$^3OCH_2CH_2$), 1.17–1.29 (m, 31H, $CO_2CH_2CH_3$ and 14×$CH_2$), and 0.83–0.87 (m, 6H, 2×$CH_3$); $^{13}C$ NMR (75 MHz, CDCl$_3$) δ167.46 (C=O), 150.34 (3-ArC$^4$), 148.20 (3-ArC$^3$), 141.00, 138.90, 132.89, 130.59, 130.24, 128.76, 128.31, 126.65, 125.64, 114.15, 112.29, 68.87 (ArOCH$_2$), 68.46 (ArOCH$_2$), 61.14 (CO$_2$CH$_2$), 31.92, 31.89, 29.63, 29.57, 29.54, 29.37, 29.34, 29.03, 28.94, 25.93, 25.83, 22.69, 22.67, 14.29, and 14.13; IR (KBr) 2955, 2920, 2850, 1705 (C=O), 1515, 1465, 1275, 1250, 1225, 1190, and 1140 cm$^{-1}$; MS (DCI) m/e 645/643 (MH+, 1:1).

For Ethyl (E)-2-(3-bromophenyl)-5-phenyl-2-pentenoate (4f): scale=7.91 mmol, yield=48%; $^1H$ NMR (300 MHz, CDCl$_3$) δ7.42 (dt, J=2, 8 Hz, 1H, 2-ArH), 7.06–7.28 (m, 8 H, 3×2-ArH, 4×5-ArH, and C=CH), 6.91 (dt, J=2, 8 Hz, 1H, 5-ArH), 4.18 (q, J=7 Hz, 2H, CO$_2$CH$_2$), 2.72 (t, J=8 Hz, 2H, ArCH$_2$), 2.37 (q, J=8 Hz, 2H, ArCH$_2$CH$_2$), and 1.24 (t, J=7 Hz, 3H, CO$_2$CH$_2$CH$_3$); $^{13}C$ NMR (75 MHz, CDCl$_3$) δ166.44 (C=O), 144.41, 140.54, 137.21, 133.54, 130.43, 129.40, 128.34, 126.20, 121.80, 60.93 (CO$_2$CH$_2$), 34.81, 31.36, and 14.14 (CO$_2$CH$_2$CH$_3$); IR (film) 3060, 3025, 2980, 2935, 2860, 1710 (C=O), 1560, 1475, 1455, 1365, 1260, 1250, 1185, 1070, 1045, 790, 750, and 700 cm$^{-1}$; MS (DCI) m/e 359/361 (MH+, 1:1).

For Ethyl (E)-2-(3-bromophenyl)-5-(5,6,7,8-tetrahydro-5,5,8,8-tetramethyl-2-naphthalenyl)-2-pentenoate (4g): scale=14.7 mmol, yield=64%; $^1H$ NMR (300 MHz, CDCl$_3$) δ7.40–7.44 (m, 1H, 2-ArH), 7.10–7.26 (m, 4H, 3×2-ArH and C=CH), 7.04 (s, 1H, 5-ArH), 6.82–6.89 (m, 2H, 5-ArH), 4.21 (q, J=7 Hz, 2H, CO$_2$CH$_2$), 2.71 (t, 2H, J=8 Hz, ArCH$_2$), 2.37 (q, J=8 Hz, 2H, ArCH$_2$CH$_2$), 1.69 (m, 4H, CH$_2$CH$_2$), and 1.23–1.33 (m, 15H, 4×CH$_3$ and CO$_2$CH$_2$CH$_3$); $^{13}C$ NMR (75 MHz, CDCl$_3$) δ166.58 (C=O), 154.95, 144.90, 144.78, 142.73, 137.49, 137.37, 133.26, 132.55, 130.45, 60.99 (CO$_2$CH$_2$), 35.18, 35.14, 34.72, 34.20, 34.01, 31.96, 31.88, 31.62, and 14.29 (CO$_2$CH$_2$CH$_3$); IR (film) 2960, 2925, 2860, 1715 (C=O), and 1250 cm$^{-1}$; MS (DCI) m/e 469 (MH+); Exact mass spectrum (FAB) Calcd for C$_{27}$H$_{33}$BrO$_2$ (MH+): 469.1742. Found: 469.1745.

For Ethyl (2E),(4E)-2-(3-bromophenyl)-5-(5,6,7,8-tetrahydro-5,5,8,8-tetramethyl-2-naphthalenyl)-2,4-hexadienoate (4h): scale=8.19 mmol, yield=45%; $^1H$ NMR (300 MHz, CDCl$_3$) δ7.91 (d, J=12 Hz, 1H, C=CH), 7.42–7.46 (m, 2H, 2-ArH), 7.16–7.29 (m, 4 H, ArH), 7.10 (dd, J=2, 8 Hz, 1H, 5-ArH), 6.43 (dd, J=1.5, 12 Hz, 1H, C=CH), 4.25 (q, J=7 Hz, 2H, CO$_2$CH$_2$), 2.27 (d, J=1.5 Hz, 3H, C=CCH$_3$), 1.64 (br s, 4H, CH$_2$CH$_2$), 1.27 (t, J=7 Hz, 3H, CO$_2$CH$_2$CH$_3$), and 1.23 (s, 12H, 4×CH$_3$); $^{13}C$ NMR (75 MHz, CDCl$_3$) δ167.27 (C=O), 148.20, 146.20, 145.00, 139.00, 137.14, 133.32, 130.50, 129.36, 129.16, 126.64, 124.21, 123.32, 122.05, 61.01 (CO$_2$CH$_2$), 35.03, 34.88, 34.31, 34.20, 31.77, 31.69, 16.64 (C=CCH$_3$), and 14.33 (OCH$_2$CH$_3$); IR (film) 2960, 2930, 2860, 1705 (C=O), 1610, 1595, 1460, 1365, 1260, 1235, 1185, 1155, 1045, and 695 cm$^{-1}$; MS (DCI) m/e 481/483 (MH+, 1:1).

For Ethyl (E)-2-(3-bromophenyl)-5-[4-(1-adamantyl)-3-methoxyphenyl]-2-pentenoate (4i): scale=9.79 mmol, yield=55%; $^1H$ NMR (300 MHz, CDCl$_3$) δ7.37–7.41 (m, 1H, 2-ArH), 7.07–7.17 (m, 4H, 3×2-ArH and C=CH), 6.85 (dt, J=2, 8 Hz, 1H, 5-ArH), 6.61 (dd, J=2, 8 Hz, 1H, 5-ArH), 6.54 (d, J=1 Hz, 1H, 5-ArH), 4.18 (q, J=7 Hz, 2H, CO$_2$CH$_2$), 3.75 (s, 3H, OCH$_3$), 2.68 (t, J=8 Hz, 2H, ArCH$_2$), 2.35 (q, J=8 Hz, 2H, ArCH$_2$CH$_2$), 2.05 (br s, 9H, adamantyl), 1.74 (br s, 6H, adamantyl), and 1.22 (q, J=7 Hz, 3H, CO$_2$CH$_2$CH$_3$); $^{13}C$ NMR (75 MHz, CDCl$_3$) δ166.57 (C=O), 158.75, 144.70, 139.21, 137.29, 133.32, 132.48, 130.43, 129.41, 128.38, 126.49, 121.85, 120.25, 111.95, 60.99 (CO$_2$CH$_2$), 54.91 (OCH$_3$), 40.64, 37.13, 36.69, 34.60, 31.43, and 14.22 (CO$_2$CH$_2$CH$_3$); IR (film) 2905, 2850, 1715 (C=O), 1410, 1250, 1205, 1185, and 1040 cm$^{-1}$; MS (DCI) m/e 523/525 (MH+, 1:1).

For Ethyl (E)-2-(3-bromophenyl)-5-[3-(1-adamantyl)-4-hydroxyphenyl]-2-pentenoate (4j): scale =10.1 mmol, yield=76% (3:1 ratio of E:Z isomers); $^1H$ NMR (300 MHz, CDCl$_3$) δ(E-isomer) 7.43 (dd, J=1, 8 Hz, 1H, 2-ArH), 7.16–7.21 (m, 3H, C=CH and 2×2-ArH), 6.93–6.96 (m, 2H, 2-ArH and 5-ArH), 6.76 (dd, J=2, 8 Hz, 1H, 5-ArH), 6.55 (d, J=8 Hz, 1H, 5-ArH), 5.52 (br s, 1H, OH), 4.25 (q, J=7 Hz, 2H, CO$_2$CH$_2$), 2.68 (m, 2H, ArCH$_2$), 2.36 (m, 2H, ArCH$_2$CH$_2$), 2.13 (br s, 9H, adamantyl), 1.81 (s, 6H, adamantyl), and 1.30 (t, J=7 Hz, 3H, CO$_2$CH$_2$CH$_3$); (Z-isomer) 7.50 (m, 1H, 2-ArH), 7.43 (m, 1H, 2-ArH), 7.23 (m, 2H, 2-ArH), 7.06 (d, J=2 Hz, 1H, 5-ArH), 6.90 (dd, J=2, 8 Hz, 1H, 5-ArH), 6.59 (d, J=8 Hz, 1H, 5-ArH), 6.26 (m, 1H, C=CH), 5.52 (br s, 1H, OH), 4.32 (q, J=7 Hz, 2H, CO$_2$CH$_2$), 2.78 (m, 4 H, ArCH$_2$CH$_2$), 2.13 (m, 9H, adamantyl), 1.81 (s, 6H, adamantyl), and 1.34 (t, J=7 Hz, 3H, CO$_2$CH$_2$CH$_3$); $^{13}C$ NMR (75 MHz, CDCl$_3$) δ(E and Z isomers) 167.95 (C=O from Z-isomer), 167.13 (C=O from E-isomer), 153.21, 153.16, 145.55, 141.35, 140.11, 137.29, 136.29, 133.65, 133.15, 132.55, 132.14, 130.56, 130.51, 130.41, 129.76, 129.51, 128.43, 127.19, 126.38, 126.12, 122.37, 122.00, 116.83, 61.32 (CO$_2$CH$_2$ from E-isomer), 61.23 (CO$_2$CH$_2$ from Z-isomer), 40.54 (adamantyl CH$_2$), 37.17 (adamantyl CH$_2$), 36.67 (adamantyl quaternary), 34.93, 34.49 (CH$_2$), 32.20, 32.03 (CH$_2$), 29.13 (adamantyl CH), 15.23 (CO$_2$CH$_2$CH$_3$ from Z-isomer), and 14.29 (CO$_2$CH$_2$CH$_3$ from E-isomer); IR (film) 3440 (OH), 2905, 2850, 1700 (C=O), 1270, 1250, 1210, 1195, and 760 cm$^{-1}$; MS (DCI) m/e 509/511 (1:1, MH+); Exact mass spectrum (FAB) Calcd for C$_{29}$H$_{33}$BrO$_3$ (MH+): 531.1511. Found: 531.1492.

For Ethyl (E)-2-(3-bromophenyl)-3-(3,4-bispentyloxyphenyl)propenoate (4k): scale=5.39 mmol, yield=36%; $^1H$ NMR (300 MHz, CDCl$_3$) δ7.75 (s, 1H, C=CH), 7.40–7.47 (m, 2H, 2-ArH), 7.25 (t, J=8 Hz, 1H, 2-ArH), 7.16 (dt, J=2, 8 Hz, 1H, 2-ArH), 6.77 (dd, J=2, 8 Hz, 1H, 3-ArH) 6.70 (d, J=8 Hz, 1H, 3-ArH), 6.40 (d, J=2 Hz, 1H, 3-ArH), 4.23 (q, J=7 Hz, 2H, CO$_2$CH$_2$), 3.94 (t, J=6.5 Hz, 2H, ArOCH$_2$), 3.48 (t, J=6.5 Hz, 2H, ArOCH$_2$), 1.72–1.82 (m, 2H, ArOCH$_2$CH$_2$), 1.58–1.65 (m, 2H, ArOCH$_2$CH$_2$), 1.20–1.44 (m, 8H, 4×CH$_2$), 1.25 (t, J=7 Hz, 3H, CO$_2$CH$_2$CH$_3$), and 0.86–0.94 (m, 6H, 2×CH$_3$); $^{13}C$ NMR (75 MHz, CDCl$_3$) 15 167.46 (C=O), 150.37, 148.24, 140.99, 138.92, 132.92, 130.60, 130.24, 128.77, 128.35, 126.69, 125.65, 122.56, 114.21, 112.33, 68.88 (ArOCH$_2$), 68.46 (ArOCH$_2$), 61.22 (CO$_2$CH$_2$), 28.74, 28.64, 28.11, 28.01, 22.40, 14.30 (CO$_2$CH$_2$CH$_3$), 14.05, and 14.00; IR (film) 2955, 2935, 2870, 1710 (C=O), 1615, 1595, 1560, 1515, 1470, 1430, 1390, 1380, 1330, 1270, 1245, 1190, 1140, 1070, 1040, 1000, 805, and 690 cm$^{-1}$; MS (DCI) m/e 503/505 (MH+, 1:1).

For Ethyl (E)-2-(3-trifluoromethylphenyl)-3-(4-decyloxyphenyl)propenoate (4l): scale=11.9 mmol, yield=63%, 12:1 mixture of E:Z isomers. $^1$H NMR (300 MHz, CDCl$_3$) δ7.83 (s, 1H, C=CH), 7.58 (d, J=9 Hz, 1H, 2-ArH), 7.44–7.50 (m, 2H, 2-ArH), 7.39 (d, J=7 Hz, 1H, 2-ArH), 6.92 (d, J=9 Hz, 2H, 3-ArH), 6.66 (d, J=9 Hz, 2H, 3-ArH), 4.23 (q, J=7 Hz, 2H, CO$_2$CH$_2$), 3.95 (t, J=6 Hz, 2H, ArOCH$_2$ from minor isomer), 3.87 (t, J=6 Hz, 2H, ArOCH$_2$), 1.66–1.75 (m, 2H, ArOCH$_2$CH$_2$), 1.20–1.38 (m, 17H, 7×CH$_2$ and CO$_2$CH$_2$CH$_3$), and 0.85 (t, J=6 Hz, 3H, CH$_3$); $^{13}$C NMR (75 MHz, CDCl$_3$) δ167.41 (C=O), 160.16 (3-ArC4), 141.04, 137.23, 133.52, 132.32 (3-ArC), 130.75, 129.02, 128.39, 127.02 (q, J$^3_{c,f}$=4 Hz, 2-ArC), 126.33, 124.35 (q, J$^3_{c,f}$=4 Hz, 2-ArC), 114.33 (3-ArC), 68.03 (CO$_2$CH$_2$), 61.20 (ArOCH$_2$), 31.87, 29.52, 29.32, 29.08, 25.94, 22.66, 14.23, and 14.10; IR (KBr) 2925, 2855, 1710 (C=O), 1600, 1510, 1325, 1310, 1250, 1165, and 1130 cm$^{-1}$; MS (DCI) m/e 477 (MH+).

For Ethyl (E)-2-(3-trifluoromethylphenyl)-3-(3-decyloxyphenyl)propenoate (4m): scale=5.4 mmol, yield=50%; $^1$H NMR (300 MHz, CDCl$_3$) δ7.85 (s, 1H, C=CH), 7.57 (d, J=8 Hz, 1H, 2-ArH), 7.52 (s, 1H, 2-ArH), 7.47 (t, J=8 Hz, 1H, 2-ArH), 7.38 (d, J=8 Hz, 1H, 2-ArH), 7.08 (t, J=8 Hz, 1H, 3-ArH), 6.75 (dt, J=2, 8 Hz, 1H, 3-ArH), 6.65 (d, J=8 Hz, 1H, 3-ArH), 6.42 (t, J=2 Hz, 1H, 3-ArH), 4.26 (q, J=7 Hz, 2H, CO$_2$CH$_2$), 3.53 (t, J=7 Hz, 2H, ArOCH$_2$), 1.55–1.63 (m, 2H, ArOCH$_2$CH$_2$), 1.22–1.30 (m, 17H, 7×CH$_2$ and CO$_2$CH$_2$CH$_3$), and 0.87 (t, J=7 Hz, 3H, CH$_3$); $^{13}$C NMR (75 MHz, CDCl$_3$) δ167.07 (C=O), 158.76 (3-ArC$^3$), 141.30, 136.99, 135.16, 133.47, 131.20, 129.32, 129.04, 126.99 (q, J$^3_{c,f}$=4 Hz, 2-ArC), 124.44 (q, J$^3_{c,f}$=4 Hz, 2-ArC), 123.43, 117.01, 114.84, 67.65 (CO$_2$CH$_2$), 61.41 (ArOCH$_2$), 31.89, 29.41, 29.31, 29.02, 25.84, 22.68, 14.21, and 14.11; IR (film) 3585, 2925, 2855, 1710 (C=O), 1325, 1230, and 1165 cm$^{-1}$; MS (DCI) m/e 477 (MH+).

For Ethyl (E)-2-(3-trifluoromethylphenyl)-3-(2-decyloxyphenyl)propenoate (4n): scale=8.0 mmol, yield=72%, approx. 2:1 mixture of E:Z isomers. $^1$H NMR (300 MHz, CDCl$_3$) δ8.24 (s, 1H, C=CH), 7.13–7.74 (m, 4H, 2-ArH), 6.80–6.95 (m, 2H, 3-ArH), 6.53–6.62 (m, 2H, 3-ArH), 4.20–4.35 (m, 2H, CO$_2$CH$_2$ for both isomers), 4.01 (t, J=7 Hz, 2H, CO$_2$CH$_2$ for both isomers), 1.75–1.88 (m, 2H, OCH$_2$CH$_2$ for both isomers), 1.22–1.55 (m, 14H, 7×CH$_2$ for both isomers), 1.14 (t, J=7 Hz, 3H, CO$_2$CH$_2$CH$_3$ for both isomers), and 0.84–0.91 (m, 3H, CH$_3$ for both isomers).

For Ethyl (E)-2-(3-trifluoromethylphenyl)-3-[4-(2E),(6E)-3,7-dimethyl-octa-2,6-dienoxy]phenyl)-propenoate (4o): scale=2.73 mmol, yield=62%, 4:1 mixture of E:Z isomers. $^1$H NMR (300 MHz, CDCl$_3$) δ7.83 (s, 1H, C=CH), 7.31–7.60 (m, 4H, 2-ArH), 6.87–6.99 (m, 2H, 3-ArH), 6.68 (dt, J=2, 9 Hz, 2H, 3-ArH), 5.40 (t, J=6.5 Hz, 1H, C=CHCH$_2$OAr), 5.02–5.08 (m, 1H, CH=C(CH$_3$)$_2$), 4.55 (d, J=6.5 Hz, 2H, ArOCH$_2$ from minor isomer), 4.47 (d, J=6.5 Hz, 2H, ArOCH$_2$), 4.19–4.31 (m, 2H, CO$_2$CH$_2$), 1.96–2.08 (m, 4H, C=CHCH$_2$CH$_2$), 1.51–1.76 (m, 9H, 3×CH$_3$), 1.00–1.27 (m, 3H, CO$_2$CH$_2$CH$_3$); $^{13}$C NMR (75 MHz, CDCl$_3$) δ167.41 (C=O), 159.91 (3-ArC$^4$), 141.59, 141.01, 137.22, 133.53, 133.16, 132.30, 131.85, 130.76, 130.03, 129.68, 129.03, 128.57, 127.04 (q, J$^3_{c,f}$=4 Hz, 2-ArC), 126.45, 124.40 (q, J$^3_{c,f}$=4 Hz, 2-ArC), 123.70, 119.13, 118.96 (3-ArC), 114.68, 114.56 (3-ArC), 64.88 (ArOCH$_2$), 61.50, 61.21 (CO$_2$CH$_2$), 39.48, 29.71, 26.23, 25.67, 17.67, 16.64, 14.23 (CO$_2$CH$_2$CH$_3$), and 13.93; IR (film) 2980, 2930, 1710 (C=O), 1600, 1510, 1445, 1380, 1310, 1250, 1210, 1165, and 1130 cm$^{-1}$; MS (DCI) m/e 473 (MH+).

For Ethyl (E)-2-(3-trifluoromethylphenyl)-3-(3,4-bis-decyloxyphenyl)-propenoate (4p): scale=3.58 mmol, yield=69%; $^1$H NMR (300 MHz, CDCl$_3$) δ7.80 (s, 1H, C=CH), 7.40–7.59 (m, 4H, 2-ArH), 6.75 (dd, J=2, 8 Hz, 1H, 3-ArH), 6.69 (d, J=8 Hz, 1H, 3-ArH), 6.31 (d, J=2 Hz, 1H, 3-ArH), 4.23 (q, J=7 Hz, 2H, CO$_2$CH$_2$), 3.93 (t, J=7 Hz, 2H, ArOCH$_2$), 3.39 (t, J=7 Hz, 2H, ArOCH$_2$), 1.71–1.80 (m, 2H, CH$_2$CH$_2$O), 1.53–1.61 (m, 2H, CH$_2$CH$_2$O), 1.21–1.43 (m, 31H, 14×CH$_2$ and OCH$_2$CH$_3$), and 0.83–0.89 (m, 6H, 2×CH$_3$); $^{13}$C NMR (75 MHz, CDCl$_3$) δ167.35, 150.43, 148.31, 141.33, 137.85, 133.66, 129.15, 128.33, 136.80 (q, J$^2_{c,f}$=38 Hz, 2-ArC), 125.58, 124.25, 114.10, 112.40, 68.91 (CH$_2$O), 68.38 (CH$_2$O), 61.19 (CO$_2$CH$_2$), 31.91, 29.57, 29.35, 29.04, 28.93, 25.92, 25.76, 22.68, 14.25 (OCH$_2$CH$_3$), and 14.11; IR (film) 2925, 2855, 1710, 1595, 1515, 1470, 1430, 1390, 1325, 1310, 1270, 1250, 1165, 1130, 1095, 1075, 1045, and 700 cm$^{-1}$; MS (DCI) m/e 633 (MH+).

For Ethyl (E)-2-(3-trifluoromethylphenyl)-3-(5,6,7,8-tetrahydro-5,5,8,8-tetramethyl-2-anthracenyl)-propenoate (4q): scale=4.1 mmol, yield=approx. 50%, 3:1 mixture of product (A) to starting material (B). $^1$H NMR (300 MHz, CDCl$_3$) δ10.09 (s, 1H, CH=O, B), 8.24 (s, 1H, ArH, B), 8.05 (s, 1H, C=CH, A), 7.95 (s, 1H, ArH, B), 7.83–7.84 (m, 1H, ArH, A), 7.58–7.66 (m, 5H, ArH), 7.40–7.49 (m, 3H, ArH), 6.75 (dd, J=2, 9 Hz, 1H, ArH), 4.30 (q, J=7 Hz, 2H, CO$_2$CH$_2$), 1.79 (s, 4H, CH$_2$CH$_2$, B), 1.75 (s, 4H, CH$_2$CH$_2$, A), 1.41 (s, 12H, 4'CH$_3$, B), 1.36 (br s, 12H, 4'CH$_3$, A), and 1.32 (t, J=7 Hz, 3H, CO$_2$CH$_2$CH$_3$); $^{13}$C NMR (75 MHz, CDCl$_3$) δ192.44 (C=O, B), 168.80 (C=O, A), 146.22, 145.12, 141.80, 136.90, 134.64, 133.74, 131.79, 131.54, 131.34, 130.82, 130.41, 128.92, 128.31, 127.24, 126.96, 126.84, 125.62, 125.43, 125.27, 124.74, 124.51, 121.65, 61.38 (CO$_2$CH$_2$), 34.91, 34.83, 34.70, 34.56, 32.41 (4×CH$_3$), and 14.26 (CO$_2$CH$_2$CH$_3$); IR (KBr) 2960, 2930, 2860, 1710 (C=O, A), 1680 (C=O, B), 1470, 1320, 1310, 1240, and 1165 cm$^{-1}$; MS (DCI) m/e 481 (MH+, A) and 267 (MH+, B).

For Ethyl (E)-2-(3-trifluoromethylphenyl)-5-(5,6,7,8-tetrahydro-5,5,8,8-tetramethyl-2-naphthalenyl)-2-pentenoate (4r): scale=4.09 mmol, yield=56%; $^1$H NMR (300 MHz, CDCl$_3$) δ7.51 (br d, J=8 Hz, 1H, 2-ArH), 7.37 (t, J=8 Hz, 1H, 2-ArH), 7.30 (br s, 1H, 2-ArH), 7.17 (d, J=8 Hz, 1H, 2-ArH), 7.16 (t, J=8 Hz, 1H, C=CH), 7.03 (d, J=8 Hz, 5-ArH) 6.98 (d, J=2 Hz, 1H, 5-ArH), 6.81 (dd, J=2, 8 Hz, 1H, 5-ArH), 4.18 (q, J=7 Hz, 2H, CO$_2$CH$_2$), 2.68 (t, J=8 Hz, 2H, ArCH$_2$), 2.32 (q, J=8 Hz, 2H, ArCH$_2$CH$_2$), 1.64 (br s, 4H, CH$_2$CH$_2$), 1.25 (s, 6H, 2'CH$_3$), 1.24 (t, J=7 Hz, 3H, CO$_2$CH$_2$CH$_3$), and 1.21 (s, 6H, 2×CH$_3$); $^{13}$C NMR (75 MHz, CDCl$_3$) δ166.47 (C=O), 145.13, 144.80, 142.77, 137.37, 136.00, 133.22, 133.07, 130.26 (q, J$^2_{c,f}$=32 Hz, 2-ArC), 128.32, 126.65, 126.50 (q, J$^3_{c,f}$=4 Hz, 2-ArC), 125.65, 124.16 (q, J$^3_{c,f}$=4 Hz, 2-ArC), 61.01 (CO$_2$CH$_2$), 35.10, 34.64, 34.13, 33.95, 31.86, 31.77, 31.57, and 14.19 (CO$_2$CH$_2$CH$_3$); IR (film) 2960, 2930, 2860, 1715 (C=O), 1495, 1460, 1445, 1385, 1365, 1325, 1310, 1250, 1180, 1165, 1130, 1095, 1075, 1045, 810, and 700 cm$^{-1}$; MS (DCI) m/e 459 (MH+).

For Ethyl (E)-2-(4-fluorophenyl)-5-(5,6,7,8-tetrahydro-5,5,8,8-tetramethyl-2-naphthalenyl)-2-pentenoate (4s): scale=2.66 mmol, yield=58% $^1$H NMR (300 MHz, CDCl$_3$) δ7.17 (d, J=8 Hz, 1H, 5-ArH), 7.09 (t, J=8 Hz, 1H, C=CH), 6.80–6.98 (m, 6H, 4×2-ArH and 2×5-ArH), 4.17 (q, J=7 Hz, 2H, CO$_2$CH$_2$), 2.66 (t, J=8 Hz, 2H, ArCH$_2$), 2.32 (q, J=8 Hz, 2H, ArCH$_2$CH$_2$), 1.64 (br s, 4H, CH$_2$CH$_2$), 1.25 (s, 6H, 2×CH$_3$), 1.24 (t, J=7 Hz, 3H, CO$_2$CH$_2$CH$_3$), and 1.21 (s, 6H, 2'CH$_3$); $^{13}$C NMR (75 MHz, CDCl$_3$) δ166.97 (C=O), 162.02 (d, J$^1_{c,f}$=246 Hz, 2-ArC), 144.73, 144.31, 142.68, 137.58, 133.51, 131.26 (d, J$^3_{c,f}$=8 Hz, 2-ArC), 125.58, 125.74, 114.72 (J$^2_{c,f}$=21 Hz, 2-ArC), 60.86 (CO$_2$CH$_2$), 35.11, 35.07, 34.67, 34.14, 33.95, 31.89, 31.80, 31.55, and 14.24 (CO$_2$CH$_2$CH$_3$); IR (film) 2960, 2925, 2860, 1715 (C=O), 1640, 1605, 1510, 1495, 1460, 1410, 1385, 1365, 1250, 1220, 1205, 1185, 1160, 1095, 1070, 1045, 840, 825, and 765 cm$^{-1}$; MS (DCI) m/e 409 (MH+).

For Ethyl (E)-2-(3-fluorophenyl)-5-(5,6,7,8-tetrahydro-5,5,8,8-tetramethyl-2-naphthalenyl)-2-pentenoate (4t): scale=2.29 mmol, yield=57%; $^1$H NMR (300 MHz, CDCl$_3$) δ7.17–7.24 (m, 2H, 1×2-ArH and 1×5-ArH), 7.11 (t, J=8 Hz, 1H, C=CH), 6.98 (d, J=2 Hz, 1H, 5-ArH), 6.94 (apparent tt, J=2, 8 Hz, 1H, 2-ArH), 6.82 (dd, J=2, 8 Hz, 1H, 5-ArH), 6.67 (dt, J=2,8 Hz, 1H, 2-ArH), 6.58 (apparent dt, J=2, 8 Hz, 1H, 2-ArH), 4.17 (q, J=7 Hz, 2H, CO$_2$CH$_2$), 2-68 (t, J=8 Hz, 2H, ArCH$_2$), 2.33 (q, J=8 Hz, 2H, ArCH$_2$CH$_2$), 1.64 (br s, 4 H, CH$_2$CH$_2$), 1.25 (s, 6H, 2×CH$_3$), 1.24 (t, J=7 Hz, 3H, CO$_2$CH$_2$CH$_3$), and 1.21 (s, 6H, 2×CH$_3$); $^{13}$C NMR (75 MHz, CDCl$_3$) δ166.65 (C=O), 162.30 (d, J$^1_{c,f}$=246 Hz, 2-ArC), 144.77, 144.63, 142.73, 137.49, 137.36 (d, J$^3_{c,f}$=8 Hz, 2-ArC), 133.44, 129.25 (d, J$^3_{c,f}$=9 Hz, 2-ArC), 126.56, 125.72, 125.35 (d, J$^4_{c,f}$=3 Hz, 2-ArC), 116.64 (J$^2_{c,f}$=22 Hz, 2-ArC), 114.24 (J$^2_{c,f}$=22 Hz, 2-ArC), 60.92 (CO$_2$CH$_2$), 35.12, 35.08, 34.64, 34.14, 33.96, 31.87, 31.80, 31.55, and 14.23 (CO$_2$CH$_2$CH$_3$); IR (film) 2960, 2930, 2860, 1715 (C=O), 1640, 1610, 1585, 1490, 1460, 1440, 1410, 1385, 1365, 1260, 1230, 1190, 1175, 1135, 1070, 1045, 885, 825, and 790 cm$^{-1}$; MS (DCI) m/e 409 (MH+).

For Ethyl (E)-2-phenyl-5-(5,6,7,8-tetrahydro-5,5,8,8-tetramethyl-2-naphthalenyl)-2-pentenoate (4u): scale=2.66 mmol, yield=53%; $^1$H NMR (300 MHz, CDCl$_3$) δ7.23–7.30 (m, 3H, 2-ArH), 7.17 (d, J=8 Hz, 1H, 5-ArH), 7.08 (t, J=8 Hz, 1H, C=CH), 6.99 (d, J=2 Hz, 1H, 5-ArH), 6.92–6.95 (m, 2H, 2-ArH), 6.82 (dd, J=2, 8 Hz, 1H, 5-ArH), 4.17 (q, J=7 Hz, 2H, CO$_2$CH$_2$), 2.66 (t, J=8 Hz, 2H, ArCH$_2$), 2.34 (q, J=8 Hz, 2H, ArCH$_2$CH$_2$), 1.64 (br s, 4H, CH$_2$CH$_2$), 1.25 (s, 6H, 2×CH$_3$), 1.24 (t, J=7 Hz, 3H, CO$_2$CH$_2$CH$_3$), and 1.21 (s, 6H, 2×CH$_3$); $^{13}$C NMR (75 MHz, CDCl$_3$) δ167.18 (C=O), 144.59, 143.92, 142.58, 137.73, 135.25, 129.57, 127.82, 127.25, 126.53, 125.71, 60.76 (CO$_2$CH$_2$), 35.14, 35.09, 34.75, 34.15, 33.94, 31.88, 31.81, 31.47, and 14.25 (CO$_2$CH$_2$CH$_3$); IR (film) 2960, 2925, 2860, 1715 (C=O), 1495, 1460, 1445, 1385, 1365, 1250, 1205, 1185, 1070, 1045, 1030, 825, 775, and 700 cm$^{-1}$; MS (DCI) m/e 391 (MH+).

For Ethyl (E)-2-(3-trifluoromethylphenyl)-5-[3-(1-adamantyl)-4-hydroxyphenyl]-2-pentenoate (4v): scale=6.17 mmol, yield=32% (3:1 E:Z isomers); $^1$H NMR (300 MHz, CDCl$_3$) δ(E-isomer) 7.53 (d, J=8 Hz, 1H, 2-ArH), 7.41 (m, 1H, 2-ArH), 7.24 (s, 1H, 2-ArH), 7.17 (m, 2H, C=CH and 2-ArH), 6.89 (d, J=2 Hz, 1H, 5-ArH), 6.72 (dd, J=2, 8 Hz, 1H, 5-ArH), 6.51 (d, J=8 Hz, 1H, 5-ArH), 4.87 (s, 1H, OH), 4.20 (q, J=7 Hz, 2H, CO$_2$CH$_2$), 2.66 (t, J=7 Hz, 2H, ArCH$_2$), 2.31 (q, J=7 Hz, 2H, ArCH$_2$CH$_2$), 2.07 (m, 9H, adamantyl), 1.76 (s, 6H, adamantyl), and 1.25 (t, J=7 Hz, 3H, CO$_2$CH$_2$CH$_3$); (Z)-isomer, partially obscured: 7.03 (d, J=2 Hz, 1H, 5-ArH), 6.57 (d, J=8 Hz, 1H, 5-ArH), 6.26 (m, 1H, 5-ArH), 4.88 (s, 1H, OH), 4.27 (q, J=7 Hz, 2H, CO$_2$CH$_2$), 2.76 (m, 4H, ArCH$_2$CH$_2$), and 1.29 (t, J=7 Hz, 3H, CO$_2$CH$_2$CH$_3$); $^{13}$C NMR (75 MHz, CDCl$_3$) δ(E- and Z-isomers) δ166.64 (C=O), 152.88, 152.81, 145.32, 142.09, 138.93, 136.23, 135.99, 133.20, 133.12, 132.80, 132.34, 130.80, 130.26 (d, J$^2_{c,f}$=32 Hz, 2-ArC), 128.63, 128.34, 127.24, 127.18, 126.49 (d, J$^3_{c,f}$=4 Hz, 2-ArC), 126.31, 125.90, 124.19 (d, J$^3_{c,f}$=4 Hz, 2-ArC), 116.74, 61.13 (CO$_2$CH$_2$ from E-isomer), 61.05 (CO$_2$CH$_2$ from Z-isomer), 40.54 (adamantyl CH$_2$ from Z-isomer), 40.49 (adamantyl CH$_2$ from E-isomer), 37.05 (adamantyl CH$_2$), 36.59 (adamantyl quaternary), 34.84 (CH$_2$ from Z-isomer), 34.42 (CH$_2$ from E-isomer), 32.13 (CH$_2$ from Z-isomer), 31.91 (CH$_2$ from E-isomer), 29.01 (adamantyl CH), and 14.19 (CO$_2$CH$_2$CH$_3$); IR (film) 3450 (OH), 2905, 2850, 1695 (C=O), 1325, 1255, 1210, 1180, and 760 cm$^{-1}$; MS (DCI) m/e 499 (MH+), 488 (M+), 487 (M—H)+, 135 (C$_{10}$H$_{15}$+). Anal. Calcd for C$_{30}$H$_{33}$O$_3$F$_3$: C, 72.27; H, 6.67. Found: C, 72.70; H, 7.01.

For Ethyl (E)-2-(3-trifluoromethylphenyl)-5-[4-(1-adamantyl)-3-hydroxyphenyl]-2-pentenoate (4w): scale=6.17 mmol, yield=32%; $^1$H NMR (300 MHz, CDCl$_3$) δ7.53–7.55 (d, J=8 Hz, 1H, 2-ArH), 7.41 (t, J=8 Hz, 1H, 2-ArH), 7.33 (s, 1H, 2-ArH), 7.10–7.17 (m, 2H, C=CH and 2-ArH), 7.07 (d, J=8 Hz, 1H, 5-ArH), 6.60 (dd, J=2, 8 Hz, 1H, 5-ArH), 6.34 (d,J=2Hz, 1H, 5-ArH),4.83(s, 1H, OH),4.19(q, J=7Hz, 2H, CO$_2$CH$_2$), 2.63 (t, J=8 Hz, 2H, ArCH$_2$), 2.32 (q, 2H, ArCH$_2$CH$_2$), 2.08 (br s, 9H, adamantyl), 1.75 (s, 6H, adamantyl), and 1.24 (t, J=7 Hz, 3H, CO$_2$CH$_2$CH$_3$); $^{13}$C NMR (75 MHz, CDCl$_3$) δ166.60 (C=O), 154.40, 144.98, 139.21, 135.94, 134.40, 133.34, 133.13, 130.30 (d, J$^2_{c,f}$=32 Hz, 2-ArC), 128.40, 127.05, 126.47 (d, J$^3_{c,f}$=4 Hz, 2-ArC), 124.25 (d, J$^3_{c,f}$=4 Hz, 2-ArC), 124.08 (q, J$^1_{c,f}$=271 Hz, CF$_3$), 120.55, 116.73, 61.15 (CO$_2$CH$_2$), 40.59 (adamantyl CH$_2$), 37.04 (adamantyl CH$_2$), 36.40 (adamantyl quaternary), 34.00 (CH$_2$), 31.24 (CH$_2$), 29.01 (adamantyl CH), and 14.16 (CO$_2$CH$_2$CH$_3$); IR (KBr) 3460 (OH), 2905, 2850, 1695 (C=O), 1420, 1325, 1265, 1165, and 1125 cm$^{-1}$; MS (DCI) m/e 499 (MH+), 498 (M+), 497 (M—H)+, 135 (C$_{10}$H$_{15}$+). Anal. Calcd for C$_{30}$H$_{33}$O$_3$F$_3$: C, 72.27; H, 6.67. Found: C, 72.64; H, 6.60.

For Ethyl (E)-2-phenyl-5-[4-(1-adamantyl)-3-methoxyphenyl]-2-pentenoate (4x): scale=7.00 mmol, yield=59%; $^1$H NMR (300 MHz, CDCl$_3$) δ7.22–7.33 (m, 3H, 2-ArH), 7.08 (t, J=8 Hz, 1H, C=CH), 7.06 (d, J=8 Hz, 1H, 5-ArH), 6.96–7.01 (m, 2H, 2-ArH), 6.62 (dd, J=2, 8 Hz, 1H, 5-ArH), 6.54 (d, J=2 Hz, 1H, 5-ArH), 4.16 (q, J=7 Hz, 2H, CO$_2$CH$_2$), 374 (s, 3H, OCH$_3$), 2.67 (t, J=8 Hz, 2H, ArCH$_2$), 2.37 (q, J=8 Hz, 2H, ArCH$_2$CH$_2$), 2.03–2.08 (m, 9H, adamantyl), 1.74 (br s, 6H, adamantyl), and 1.24 (t, J=7 Hz, 3H, CO$_2$CH$_2$CH$_3$); $^{13}$C NMR (75 MHz, CDCl$_3$) δ167.17 (C=O), 158.72, 143.76, 139.50, 136.36, 135.24, 134.57, 129.62, 127.84, 127.29, 126.36, 120.25, 111.97, 60.80 (CO$_2$CH$_2$), 54.89 (OCH$_3$), 40.66, 37.14, 36.68, 34.67, 31.32, 29.11, and 14.24 (CO$_2$CH$_2$CH$_3$); IR (film) 2905, 2850, 1710 (C=O), 1610, 1465, 1450, 1415, 1250, 1205, 1185, 1165, 1140, 1100, 1045, 1030, 760, and 700 cm$^{-1}$; MS (DCI) m/e 445 (MH+).

For Ethyl (E)-2-(3-trifluoromethylphenyl)-5-[2-(1-adamantyl)-4-methoxyphenyl]-2-pentenoate (4y): scale=1.41 mmol, yield=41%; $^1$H NMR (300 MHz, CDCl$_3$) δ7.54 (d, J=8 Hz, 1H, 2-ArH), 7.43 (t, J=8 Hz, 1H, 2-ArH), 7.35 (s, 1H, 2-ArH), 7.18–7.28 (m, 2H, C=CH and 2-ArH), 6.90 (d, J=8 Hz, 1H, 5-ArH), 6.83 (d, J=3 Hz, 1H, 5-ArH), 6.63 (dd, J=3, 8 Hz, 1H, 5-ArH), 4.21 (q, J=7 Hz, 2H, CO$_2$CH$_2$), 3.74 (s, 3H, OCH$_3$), 2.97 (m, 2H, ArCH$_2$), 2.35 (m, 2H, ArCH$_2$CH$_2$), 2.03 (br s, 3H, adamantyl), 1.91 (m, 6H, adamantyl), 1.72 (m, 6H, adamantyl), and 1.26 (t, J=7 Hz, 3H, CO$_2$CH$_2$CH$_3$); $^{13}$C NMR (75 MHz, CDCl$_3$) δ166.54 (C=O), 157.69, 149.05, 144.95, 136.04, 133.06, 132.66, 131.34, 130.40 (d, J$^2$$_{c,f}$=32 Hz, 2-ArC), 128.41, 126.46 (d, J$^3$$_{c,f}$=4 Hz, 2-ArC), 124.30 (d, J$^3$c,f=4 Hz, 2-ArC), 113.17, 110.00, 61.12 (CO$_2$CH$_2$),55.09 (OCH$_3$), 42.10 (adamantyl CH$_2$), 37.85 (adamantyl quaternary), 36.74 (adamantyl CH$_2$), 33.31 (CH$_2$), 32.66 (CH$_2$), 29.07 (adamantyl CH), and 14.20 (CO$_2$CH$_2$CH$_3$); IR (film) 2910, 2850, 1715 (C=O), 1605, 1575, 1465, 1445, 1325, 1255, 1165, 1130, 1075, 760, 710, and 700 cm$^{-1}$; MS (DCI) m/e 513 (MH+), 135 (C$_{10}$H$_{15}$+). Exact mass spectrum (FAB) Calcd for C$_{31}$H$_{36}$O$_3$F$_3$ (MH+): 513.2617. Found: 513.2601.

For Ethyl (E)-2-(3-trifluorophenyl)-3-[4-(1-adamantyl)-3-methoxyphenyl]-propenoate (4z): scale=4.26 mmol, yield=65%; $^1$H NMR (300 MHz, CDCl$_3$) δ7.84 (s, 1H, C=CH), 7.42–7.61 (m, 4H, 2-ArH), 7.07 (d, J=8 Hz, 1H, 3-ArH), 6.74 (dd, J=2, 8 Hz, 1H, 3-ArH), 6.32 (d, J=2 Hz, 1H, 3-ArH), 4.25 (q, J=7 Hz, 2H, CO$_2$CH$_2$), 3.31 (s, 3H, OCH$_3$), 1.98 (br s, 9H, adamantyl), 1.71 (s, 6H, adamantyl), and 1.27 (t, J=7 Hz, 3H, CO$_2$CH$_2$CH$_3$); $^{13}$C NMR (75 MHz, CDCl$_3$) δ167.23 (C=O), 158.28, 141.14, 140.80, 137.50, 133.53, 132.40, 131.09 (d, J$^2$$_{c,f}$=32 Hz, 2-ArC), 130.07, 129.17, 126.99 (d, J$^3$$_{c,f}$=4 Hz, 2-ArC), 126.56, 124.38 (d, J$^3$$_{c,f}$=4 Hz, 2-ArC), 124.01 (d, J$^1$$_{c,f}$=271 Hz, CF$_3$), 112.59, 61.32 (CO$_2$CH$_2$), 54.17 (OCH$_3$), 40.26 (adamantyl CH$_2$), 37.14 (adamantyl quaternary), 36.99 (adamantyl CH$_2$), 28.92 (adamantyl CH), and 14.23 (CO$_2$CH$_2$CH$_3$); IR (film) 2905, 2850, 1710 (C=O), 1325, 1230, 1165, and 1130 cm$^{-1}$; MS (DCI) m/e 485 (MH+), 135 (C$_{10}$H$_{15}$+). Anal. Calcd for C$_{29}$H$_{31}$O$_3$F$_3$: C, 71.88; H, 6.45. Found: C, 70.46; H, 6.21.

For Ethyl (E)-2-(3-trifluoromethylphenyl)-5-[4-(1-adamantyl)-3-t-butyldimethylsilyloxyphenyl]-2-pentenoate (4aa): scale=4.94 mmol, yield=59%; $^1$H NMR (300 MHz, CDCl$_3$) δ7.53 (m, 1H, ArH), 7.39 (m, 1H, ArH), 7.33 (s, 1H, ArH), 7.15 (m, 1H, C=CH), 7.08 (m, 2H, ArH), 6.60 (dd, J=2, 8 Hz, 1H, 5-ArH), 6.47 (d, J=2 Hz, 1H, 5-ArH), 4.19 (q, J=7 Hz, 2H, CO$_2$CH$_2$), 2.63 (m, 2H, ArCH$_2$), 2.31 (m, 2H, ArCH$_2$CH$_2$), 2.06 (m, 9H, adamantyl), 1.74 (s, 6H, adamantyl), 1.24 (t, J=7 Hz, 3H, CO$_2$CH$_2$CH$_3$), 0.99 (s, 9H, SiC(CH$_3$)$_3$), and 0.25 (s, 6H, Si(CH$_3$)$_2$); $^{13}$C NMR (75 MHz, CDCl$_3$) δ166.41 (C=O), 154.58, 144.81, 138.73, 137.46, 135.97, 133.39, 133.05, 128.39, 127.09, 126.47 (d, J$^3$$_{c,f}$=4 Hz, 2-ArC), 124.23 (d, J$^3$$_{c,f}$=4 Hz, 2-ArC), 120.33, 119.06, 61.05 (CO$_2$CH$_2$), 40.43 (adamantyl CH$_2$), 37.05 (adamantyl CH$_2$), 36.55 (adamantyl quaternary), 34.25 (CH$_2$), 31.44 (CH$_2$), 29.03 (adamantyl CH), 26.38 (SiC(CH$_3$)$_3$), 18.89 (SiC(CH$_3$)$_3$), 14.19 (CO$_2$CH$_2$CH$_3$), and −3.43 (Si(CH$_3$)$_2$); IR (film) 2955, 2930, 2905, 2855, 1715 (C=O), 1415, 1325, 1265, 860, 840, 780, and 760 cm$^{-1}$; MS (DCI) m/e 613 (MH+), 135 (C$_{10}$H$_{15}$+). Anal. Calcd for C$_{36}$H$_{47}$O$_3$F$_3$Si: C, 70.56; H, 7.73. Found: C, 70.47; H, 7.66.

Example 4: General Procedure for Synthesis of 5

A solution of ester 4 (1 equivalent) in anhydrous THF (0.1–0.2M) was cooled to −78° C. under argon. A solution of diisobutylaluminum hydride (1M in hexanes, 2.5 equivalents) was added and the reaction mixture was allowed to warm to 0° C. to room temperature. The reaction was quenched by slow addition of methanol followed by treatment with saturated ammonium chloride. The resulting mixture was stirred for 15 min and then partitioned between diethyl ether and 1N HCl solution. The layers were agitated until all solid in the aqueous phase had dissolved. The organic layer was separated and washed with saturated sodium chloride solution, dried over anhydrous magnesium sulfate, filtered, and concentrated. Purification was achieved by column chromatography (30:1–40:1 ratio of silica gel/crude product; elution with 5% to 15% ethyl acetate in hexanes) to provide the target compound.

For (Z)-2-(3-Bromophenyl)-3-phenyl-2-propenol (5a): scale=2.14 mmol, yield=78%; $^1$H NMR (300 MHz, CDCl$_3$) δ7.38–7.43 (m, 2H, 2-ArH), 7.10–7.20 (m, 5H, ArH), 6.96–7.00 (m, 2H, ArH), 6.70 (br s, 1H, C=CH), and 4.41 (d, J=1.5 Hz, 2H, CH$_2$OH); $^{13}$C NMR (75 MHz, CDCl$_3$) δ140.81, 139.83, 135.86, 131.50, 130.63, 130.31, 129.22, 128.10, 127.70, 127.18, 122.76, and 68.35 (CH$_2$OH); IR (film) 3320 (OH), 3060, 3020, 1590, 1560, 1495, 1470, 1450, 1410, 1095, 1070, 1030, 1000, 920, 880, 790, 785, and 700 cm$^{-1}$; MS (DCI) m/e 288/290 (M+, 1:1), 271/273 (M+—OH, 1:1).

For (Z)-2-(3-Bromophenyl)-3-(5,6,7,8-tetrahydro-5,5,8,8-tetramethyl-2-naphthalenyl)-2-propenol (5b): scale=5.44 mmol, yield=99%; $^1$H NMR (300 MHz, CDCl$_3$) δ7.42–7.47 (m, 2H, 2-ArH), 7.18–7.28 (m, 2H, 2-ArH), 7.13 (d, J=8 Hz, 1H, 3-ArH), 6.88 (d, J=2 Hz, 1H, 3-ArH) 6.83 (dd, J=2, 8 Hz, 1H, 3-ArH), 6.63 (br s, 1H, C=CH), 4.42 (dd, J=1.5, 7 Hz, 2H, CH$_2$OH), 1.60 (br s, 4 H, CH$_2$CH$_2$), 1.20 (s, 6H, 2'CH$_3$) and 0.98 (s, 6H, 2×CH$_3$); IR (film) 3000–3300 (br, OH), 2950, 2920, 2860, 1555, 1500, 1470, 1460, 1415, 1360, 1350, 1035, 915, 820, and 700 cm$^{-1}$; MS (DCI) m/e 398/400 (M+, 1:1), 381/383 (M+—OH, 1:1).

For (Z)-2-(3-Bromophenyl)-3-(5,6,7,8-tetrahydro-5,5,8,8-tetramethyl-2-anthracenyl)-2-propenol (5c): scale=2.66 mmol, yield=87%; $^1$H NMR (300 MHz, CDCl$_3$) δ7.62 (d, J=9 Hz, 2H, ArH), 7.39–7.48 (m, 4 H, ArH), 7.13–7.15 (m, 2H, ArH), 6.83–6.87 (m, 2H, ArH and C=CH), 4.70 (dd, J=1, 6 Hz, 2H, CH$_2$OH), 1.73 (s, 4H, CH$_2$CH$_2$), and 1.34–1.37 (m, 12H, 4×CH$_3$); $^{13}$C NMR (75 MHz, CDCl$_3$) δ144.72, 144.60, 140.93, 139.29, 132.65, 131.53, 130.87, 130.66, 130.56, 128.34, 128.02, 126.60, 125.89, 125.02, 124.64, 122.76, 68.55 (CH$_2$OH), 35.04 (CH$_2$CH$_2$), 34.58, 34.53, and 32.47 (4×CH$_3$); IR (KBr) 3400 (br, OH), 2960, 2925, 2860, 1560, 1470, and 1360 cm$^{-1}$; MS (DCI) m/e 451/449 (MH+, 1:1), 433/431 (MH+—H$_2$O, 1:1).

For (Z)-2-(3-bromophenyl)-3-(4-decyloxyphenyl)-2-propenol (5d): scale=7.40 mmol, yield=78%; $^1$H NMR (300 MHz, CDCl$_3$) δ7.37–7.42 (m, 2H, 2-ArH), 7.12–7.24 (m, 2H, 2-ArH), 6.89 (d, J=8 Hz, 2H, 3-ArH), 6.61–6.67 (m, 3H, 2×3-ArH and C=CH), 4.39 (dd, J=1, 6 Hz, 2H, CH$_2$OH), 3.86 (t, J=7 Hz, 2H, ArOCH$_2$), 1.71 (quintet, J=7 Hz, 2H, ArOCH$_2$CH$_2$), 1.57 (t, J=6 Hz, 1H, OH), 1.18–1.43 (m, 14 H, 7×CH$_2$), and 0.86 (t, J=7 Hz, 3H, CH$_3$); $^{13}$C NMR (75 MHz, CDCl$_3$) δ158.33, 141.22, 137.61, 131.57, 130.48, 130.36, 128.11, 127.80, 127.62, 122.81, 114.09, 68.74 (CH$_2$OH), 67.91 (ArOCH$_2$), 31.89, 29.55, 29.37, 29.31, 29.21, 26.01, 22.68, and 14.12; IR (film) 3400 (br, OH), 2950, 2940, 2920, 2850, 1605, 1590, 1555, 1510, 1475, 1400, 1395, 1375, 1300, 1250, 1175, 1090, 1060, 1050, 1030, 995, 975, 880, 830, 790, 775, and 720 cm$^{-1}$; MS (DCI) m/e 444/446 (MH+, 1:1).

For (Z)-2-(3-Bromophenyl)-3-(3,4-bisdecyloxyphenyl)-2-propenol (5e): scale=0.84 mmol, yield=87%; $^1$H NMR (300 MHz, CDCl$_3$) δ7.39–7.43 (m, 2H, 2-ArH), 7.15–7.24 (m, 2H, 2-ArH), 6.67 (d, J=8 Hz, 1H, 3-ArH), 6.59 (dd, J=2, 8 Hz, 1H, 3-ArH), 6.58

(s, 1H, C=CH), 6.42 (d, J=2 Hz, 1H, 3-ArH), 4.39 (br s, 2H, CH$_2$OH), 3.91 (t, J=7 Hz, 2H, ArC$^4$OCH$_2$), 3.54 (t, J=7 Hz, 2H, ArC$^3$OCH$_2$), 1.75 (quint, J=7 Hz, 2H, ArC$^4$OCH$_2$CH$_2$), 1.59 (quint, J=7 Hz, 2H, ArC$^3$OCH$_2$CH$_2$), 1.24–1.40 (m, 28 H, 14×CH$_2$), and 0.83–0.89 (m, 6H, 2×CH$_3$); $^{13}$C NMR (75 MHz, CDCl$_3$) δ148.44 (3-ArC$^4$), 148.27 (3-ArC$^3$), 141.50, 137.70, 131.80, 130.42, 128.52, 127.78, 122.83, 122.68, 113.90, 112.96, 69.05, 68.75, 68.65, 31.93, 29.65, 29.60, 29.57, 29.37, 29.20, 29.04, 25.98, 25.89, 22.70, and 14.12; IR (KBr) 3100–3400 (br, OH), 2955, 2920, 2850, 1515, 1470, 1425, 1270, 1235, and 1140 cm$^{-1}$; MS (DCI) m/e 603/601 (MH+, 1:1), 585/583 (MH+—H$_2$O, 1:1).

For (Z)-2-(3-Bromophenyl)-5-phenyl-2-pentenol (5f): scale=5.80 mmol, yield=95%; $^1$H NMR (300 MHz, CDCl$_3$) δ7.39 (dt, J=2, 8 Hz, 1H, 2-ArH), 7.08–7.29 (m, 7H, 3×2-ArH and 4×5-ArH), 6.98 (dt, J=2, 8 Hz, 1H, 5-ArH), 5.77 (t, J=7.5 Hz, 1H, C=CH), 4.25 (s, 2H, CH$_2$OH), 2.67 (t, J=7.5 Hz, 2H, ArCH$_2$), and 2.30 (q, J=7.5 Hz, 2H, ArCH$_2$CH$_2$); $^{13}$C NMR (75 MHz, CDCl$_3$) δ141.17, 140.44, 139.72, 131.33, 130.10, 129.70, 128.78, 128.37, 128.22, 127.17, 125.85, 122.26, 67.70 (CH$_2$OH), 35.67, and 30.26; IR (film) 3350 (br, OH), 3085, 3060, 3025, 2920, 2860, 1590, 1560, 1495, 1475, 1455, 1410, 1365, 1100, 1080, 1070, 1030, 995, 790, 750, 700, and 670 cm$^{-1}$; MS (DCI) m/e 299/301 (M+—OH, 1:1).

For (Z)-2-(3-Bromophenyl)-5-(5,6,7,8-tetrahydro-5,5,8,8-tetramethyl-2-naphthalenyl)-2-pentenol (5g): scale=3.2 mmol, yield=87%; $^1$H NMR (300 MHz, CDCl$_3$) δ7.38 (ddd, J=1, 2, 8 Hz, 1H, 2-ArH), 7.27 (t, J=2 Hz, 1H, 2-ArH), 7.13–7.24 (m, 2H, 2-ArH), 7.01 (d, J=2 Hz, 1H, 5-ArH), 6.95 (dt, J=1, 8 Hz, 1H, 5-ArH), 6.86 (dd, J=2, 8 Hz, 1H, 5-ArH), 5.80 (m, 1H, C=CH), 4.26 (m, 2H, CH$_2$OH), 2.61 (t, J=7 Hz, 2H, ArCH$_2$), 2.28 (q, J=7 Hz, 2H, ArCH$_2$CH$_2$), 1.44 (m, 1H, OH), 1.25 (s, 6H, 2×CH$_3$), and 1.24 (s, 6H, 2×CH$_3$); $^{13}$C NMR (CDCl$_3$) δ144.66, 142.44, 140.63, 139.53, 138.19, 131.47, 130.18, 129.82, 129.42, 127.31, 126.47, 125.75, 122.34, 107.61, 67.88 (CH$_2$OH), 35.59, 35.18, 35.12, 34.16, 33.96, 31.93 (CH$_3$), 31.88, and 30.49; IR (film) 3335 (br, OH), 2960, 2925, 2860, 1470, 1460, 1360, 1070, 790, 760 cm$^{-1}$; MS (FAB) m/e 426/428 (MH+, 1:1). Anal. Calcd for C$_{25}$H$_{31}$BrO: C, 70.25; H, 7.31. Found: C, 70.15; H, 7.20.

For (2Z),(4E)-2-(3-Bromophenyl)-5-(5,6,7,8-tetrahydro-5,5,8,8-tetramethyl-2-naphthalenyl)-2,4-hexadienol (5h): scale=3.47 mmol, yield=93%; $^1$H NMR (300 MHz, CDCl$_3$) δ7.49 (d, J=2 Hz, 1H, 2-ArH), 7.41 (dt, J=2, 8 Hz, 1H, 2-ArH), 7.19–7.27 (m, 4H, 2×2-ArH and 2×5-ArH), 7.09 (dd, J=2, 8 Hz, 1H, 5-ArH), 6.74 (dt, J=1.5, 12 Hz, 1H, C=CH), 6.45 (br d, J=12 Hz, 1H, C=CH), 4.46 (d, J=1.5 Hz, 2H, CH$_2$OH), 2.22 (d, J=1.5 Hz, 3H, C=CCH$_3$), 1.65 (br s, 4H, CH$_2$CH$_2$), and 1.24 (s, 12H, 4×CH$_3$); $^{13}$C NMR (75 MHz, CDCl$_3$) δ139.99, 139.07, 131.87, 130.46, 129.86, 127.82, 126.46, 125.19, 123.83, 123.08, 122.47, 122.15, 67.87 (CH$_2$OH), 35.12, 34.97, 34.30, 34.10, 31.81, 31.75, and 16.11 (C=CCH$_3$); IR (film) 3335 (br, OH), 2960, 2930, 2860, 1590, 1555, 1495, 1470, 1460, 1385, 1360, 1215, 1085, 1070, 885, 825, 785, 760, 700, and 680 cm$^{-1}$; MS (DCI) m/e 438/440 (M+, 1:1), 421/423 (M+—OH).

For (Z)-2-(3-Bromophenyl)-5-[4-(1-adamantyl)-3-methoxyphenyl]-2-pentenol (5i): scale=5.4 mmol, yield=78%; $^1$H NMR (300 MHz, CDCl$_3$) δ 7.36–7.39 (m, 1H, 2-ArH), 7.23 (t, J=2 Hz, 1H, 2-ArH), 7.16 (t, J=8 Hz, 1H, 2-ArH), 7.07 (d, J=8 Hz, 1H, 3-ArH), 6.94 (dt, J=2, 8 Hz, 1H, 2-ArH), 6.63 (dd, J=2, 8 Hz, 1H, 3-ArH), 6.56 (d, J=2 Hz, 1H, 3-ArH), 5.77 (t, J=8 Hz, 1H, C=CH), 4.25 (d, J=5 Hz, 2H, CH$_2$OH), 3.75 (s, 3H, OCH$_3$), 2.62 (t, J=8 Hz, 2H, ArCH$_2$), 2.28 (q, J=8 Hz, 2H, ArCH$_2$CH$_2$), 2.05 (br s, 9H, adamantyl), and 1.74 (br s, 6H, adamantyl); $^{13}$C NMR (75 MHz, CDCl$_3$) δ158.71, 140.60, 139.93, 139.67, 136.21, 131.49, 130.18, 129.81, 129.22, 127.30, 126.30, 122.32, 120.31, 112.00, 67.85 (CH$_2$OH), 54.92 (OCH$_3$), 40.64, 37.14, 36.66, 35.48, 30.33, and 29.10; IR (film) 3355 (br, OH), 2900, 2850, 1560, 1450, 1410, and 1245 cm$^{-1}$; MS (DCI) m/e 483/481 (MH+, 1:1), 465/463 (MH+—H$_2$O, 1:1).

For (Z)-2-(3-Bromophenyl)-5-[3-(1-adamantyl)-4-hydroxyphenyl]-2-pentenol (5j): scale=2.6 mmol, yield=95% (3:1, Z:E); $^1$H NMR (300 MHz, CDCl$_3$) δ(Z-isomer) 7.37 (m, 1H, 2-ArH), 7.17 (m, 2H, 2-ArH), 6.99 (m, 1H, 2-ArH), 5.77 (t, J=7 Hz, 1H, C=CH), 5.09 (br s, 1H, ArOH), 4.26 (s, 2H, CH$_2$OH), 2.57 (t, J=7 Hz, 2H, ArCH$_2$), 2.25 (q, J=7 Hz, 2H, ArCH$_2$CH$_2$), 2.06 (m, 9H, adamantyl), and 1.76 (s, 6H, adamantyl); (E-isomer, partially obscured) 7.55 (m, 1H, 2-Ar), 5.91 (t, J=8 Hz, 1H, C=CH), 4.21 (s, 2H, CH$_2$OH), 2.71 (t, J=7 Hz, 2H, ArCH$_2$), and 2.53 (q, J=7 Hz, 2H, ArCH$_2$CH$_2$); $^{13}$C NMR (75 MHz, CDCl$_3$) δ153.11, 152.77, 143.39, 140.62, 139.43, 138.33, 136.19, 133.05, 132.64, 131.45, 130.16, 129.99, 129.82, 129.60, 129.38, 127.59, 127.36, 127.15, 126.67, 126.36, 124.86, 122.60, 122.37, 116.83, 116.61, 67.91, 59.45, 40.55, 40.45, 37.08, 36.60, 35.31, 35.08, 31.04, 30.78, 29.05, and 25.61; IR (KBr) 3520 (OH), 3345 (br, OH), 2900, 2850, 1450, 1420, 1240, 1100, 995, and 785 cm$^{-1}$; MS (DCI) m/e 466/468 (M+, 1:1), 241,135 (C$_{10}$H$_{15}$+). Anal. Calcd for C$_{27}$H$_{31}$BrO$_2$: C, 69.38; H, 6.68. Found: C, 69.06; H, 6.91.

For (Z)-2-(3-Bromophenyl)-3-(3,4-bispentyloxyphenyl)-2-propenol (5k): scale=1.67 mmol, yield=94%; $^1$H NMR (300 MHz, CDCl$_3$) δ7.39–7.44 (m, 2H, 2-ArH), 7.11–7.24 (m, 2H, 2-ArH), 6.67 (d, J=8 Hz, 1H, 3-ArH), 6.60 (dd, J=2, 8 Hz, 1H, 3-ArH), 6.58 (t, J=1.5 Hz, 1H, C=CH), 6.42 (d, J=2 Hz, 1H, 3-ArH), 4.39 (dd, J=1.5, 6 Hz, 2H, CH$_2$OH), 3.91 (t, J=6.5 Hz, 2H, 3-ArOCH$_2$), 3.54 (t, J=6.5 Hz, 2H, 3-ArOCH$_2$), 1.71–1.81 (m, 2H, 3-ArOCH$_2$CH$_2$), 1.55–1.65 (m, 2H, 3-ArOCH$_2$CH$_2$), 1.29–1.44 (m, 8H, 4×CH$_2$), and 0.86–0.92 (m, 6H, 2×CH$_3$); $^{13}$C NMR (75 MHz, CDCl$_3$) δ148.41, 148.23, 141.49, 137.69, 131.78, 130.43, 128.50, 127.79, 127.76, 122.83, 122.68, 113.81, 112.87, 69.00 (3-ArOCH$_2$), 68.75 (CH$_2$OH), 68.60 (3-ArOCH$_2$), 28.87, 28.70, 28.16, 28.05, 22.46, 22.40, 14.08 and 14.04; IR (film) 3355 (OH), 3265 (OH), 2955, 2930, 2870, 2855, 1515, 1465, 1430, 1270, 1235, 1170, 1140, 1085, 1070, 1035, 985, 800, and 785 cm$^{-1}$; MS (DCI) m/e 461/463 (MH+, 1:1), 443/445 (M+—OH).

For (Z)-2-(3-Trifluoromethylphenyl)-3-(4-decyloxyphenyl)-2-propenol (5l): scale=7.4 mmol, yield=80%; $^1$H NMR (300 MHz, CDCl$_3$) δ7.51–7.54 (m, 2H, 2-ArH), 7.39–7.42 (m, 2H, 2-ArH), 6.85 (dr, J=3, 8 Hz, 2H, 3-ArH), 6.61–6.67 (m, 3H, 2×3-ArH and C=CH), 4.44 (dd, J=1, 6 Hz, 2H, CH$_2$OH), 3.85 (t, J=6 Hz, ArOCH$_2$), 1.71 (quint, J=6 Hz, 2H, ArOCH$_2$CH$_2$), 1.24–1.41 (m, 14H, 7×CH$_2$), 0.85 (t, J=6 Hz, 3H, CH$_3$); $^{13}$C NMR (75 MHz, CDCl$_3$) δ158.40 (3-ArC4), 139.86, 137.59, 132.57, 130.42 (3-ArC), 129.20, 128.13, 127.99, 125.60 (q, J$^3$$_{c,f}$=4 Hz, 2-ArC), 124.16 (q, J$^3$$_{c,f}$=4 Hz, 2-ArC), 114.14 (3-ArC), 68.65, 67.93, 31.88, 29.54, 29.36, 29.30, 29.19, 25.99, 22.66, and 14.10; IR (KBr) 3550, 3400 (br, OH), 2960, 2940, 2920, 2850, 1605, 1510, 1475, 1420, 1390, 1325, 1310, 1255, 1180, and 1160 cm$^{-1}$; MS (DCI) m/e 434 (M+), 417 (MH+—H$_2$O).

For (Z)-2-(3-Trifluoromethylphenyl)-3-(3-decyloxyphenyl)-2-propenol (5m): scale=2.7 mmol, yield=68%; ¹H NMR (300 MHz, CDCl₃) δ7.52-7.54 (m, 2H, 2-ArH), 7.37-7.45 (m, 2H, 2-ArH), 7.02 (t, J=8 Hz, 1H, 3-ArH), 6.72 (br s, 1H, C=CH), 6.65 (dr, J=2, 8 Hz, 1H, 3-ArH), 6.54 (d, J=8 Hz, 1H, 3-ArH), 6.42 (t, J=2 Hz, 1H, 3-ArH), 4.46 (dd, J=1, 5 Hz, 2H, CH₂OH), 3.58 (t, J=7 Hz, 2H, ArOCH₂), 1.55-1.68 (m, 2H, ArOCH₂CH₂), 1.21-1.37 (m, 14H, 7×CH₂), and 0.87 (t, J=7 Hz, 3H, CH₃); ¹³C NMR (75 MHz, CDCl₃) δ158.74 (3-ArC), 139.90, 139.69, 136.94, 132.51, 129.24, 129.09, 128.17, 125.60 (q, J³$_{c,f}$=4 Hz, 2-ArC), 124.24 (q, J³$_{c,f}$=4 Hz, 2-ArC), 121.78, 114.48, 114.29, 68.31, 67.65, 31.89, 29.55, 29.31, 29.08, 25.88, 22.68, and 14.11; IR (film) 3330 (br, OH), 2925, 2855, 1600, 1570, 1470, 1435, 1325, 1265, 1165, and 1130 cm⁻¹; MS (DCI) m/e 435 (MH+), 417 (MH+—H₂O).

For (Z)-2-(3-Trifluoromethylphenyl)-3-(2-decyloxyphenyl)-2-propenol (5n): scale=5.7 mmol, yield=99%, ca. 5:3 mixture of Z:E isomers. A solution of the crude mixture (2.46 g, 5.5 mmol) in pyridine (23 mL) at room temperature was treated with acetic anhydride (0.73 g, 7.2 mmol) and 4,4-dimethylaminopyridine (10 mg). The solution was stirred for 1.5 h, and was then diluted with diethyl ether and poured into a separatory funnel containing 1N HCl solution. The layers were agitated and separated, and the organic layer was washed with saturated sodium chloride solution, dried over anhydrous magnesium sulfate, and concentrated in vacuo to yield 2.6 g of a yellow oil. The crude material was purified by column chromatography (40:1 ratio of silica gel/crude product; elution with 5% to 10% ethyl acetate in hexanes) to afford 1.1 g (42%) of the acetate target compound as a single isomer: ¹H NMR (300 MHz, CDCl₃) δ7.46-7.48 (m, 2H, 2-ArH), 7.31-7.39 (m, 2H, 2-ArH), 7.09 (dr, J=2, 8 Hz, 1H, 3-ArH), 6.98 (br s, 1H, C=CH), 6.80 (d, J=8 Hz, 1H, 3-ArH), 6.66 (dd, J=2, 8 Hz, 1H, 3-ArH), 6.56 (t, J=8 Hz, 1H, 3-Art1), 4.94 (d, J=1 Hz, 2H, CH₂OAc), 3.94 (t, J=7 Hz, 2H, ArOCH₂), 2.04 (s, 3H, COCH₃), 1.78 (quint, J=7 Hz, 2H, OCH₂CH₂), 1.13-1.50 (m, 14H, 7×CH₂), and 0.86 (t, J=7 Hz, 3H, CH₃); ¹³C NMR (75 MHz, CDCl₃) δ170.70 (C=O), 157.03 (3-ArC), 139.27, 134.33, 132.31, 130.09, 128.89, 128.80, 127.07, 125.64 (q, J³$_{c,f}$=4 Hz, 2-ArC), 124.59, 124.06 (q, J³$_{c,f}$=4 Hz, 2-ArC), 119.78, 111.62, 69.00, 68.30, 31.90, 29.62, 29.39, 29.33, 29.20, 26.09, 22.68, 20.92, 18.54, and 14.11; IR (film) 2925, 2855, 1740 (C=O), 1450, 1325, 1245, 1220, 1165, and 1125 cm⁻¹; MS (DCI) m/e 477 (MH+), 476 (M+). A solution of the acetate (1.04 g, 2.18 mmol) in methanol (10.9 mL) was treated with 2N NaOH solution (4.4 mL, 8.7 mmol) and was stirred at reflux for 2 h. The solution was allowed to cool to room temperature and was poured into water and extracted with diethyl ether. Sodium chloride was added to the aqueous layer, which was extracted a second time with diethyl ether. The organic layers were combined, washed sequentially with water and saturated sodium chloride solution, dried over anhydrous magnesium sulfate, filtered, and concentrated to afford 0.96 g of a colorless oil. Purification by column chromatography (20:1 silica gel/crude product; elution with 5% to 10% ethyl acetate in hexanes) afforded 0.87 g (92%) of the product (5n) as a clear, colorless oil: ¹H NMR (300 MHz, CDCl₃) δ7.45-7.51 (m, 2H, 2-ArH), 7.31-7.40 (m, 2H, 2ArH), 7.09 (dt, J=2, 8 Hz, 1H, 3-ArH), 6.95 (br s, 1H, C=CH), 6.80 (d, J=8 Hz, 1H, 3-ArH), 6.67 (dd, J=2, 8 Hz, 1H, 3-ArH), 6.56 (t, J=8 Hz, 1H, 3-ArH), 4.52 (dd, J=1, 6 Hz, 2H, CH₂OH), 3.94 (t, J=7 Hz, 2H, OCH₂), 1.78 (quint, J=7 Hz, 2H, OCH₂CH₂), 1.21-1.48 (m, 14 H, 7×CH₂), 0.87 (t, J=7 Hz, 3H, CH₃); ¹³C NMR (75 MHz, CDCl₃) δ157.05 (3-ArC), 139.66, 132.42, 130.19, 128.83, 128.59, 125.52 (q, J³$_{c,f}$=4 Hz, 2-ArC), 124.98, 124.49, 123.95 (q, J³$_{c,f}$=4 Hz, 2-ArC), 119.80, 111.63, 68.41, 68.34, 31.90, 29.62, 29.58, 29.39, 29.34, 29.20, 26.10, 22.68, and 14.11; IR (film) 3380 (br, OH), 2925, 2855, 1580, 1325, 1245, and 1125 cm⁻¹; MS (DCI) m/e 435 (MH+), 434 (M+), 417 (MH+—H₂O).

For (Z)-2-(3-Trifluoromethylphenyl)-3-[4-(2E),(6E)-3,7-dimethyl-octa-2,6-dienoxy]phenyl)-2-propenol (5o): scale=2.0 mmol, yield=67%; ¹H NMR (300 MHz, CDCl₃) δ7.52-7.54 (m, 2H, 2-ArH), 7.39-7.45 (m, 2H, 2-ArH), 6.86 (d, J=8 Hz, 2H, 3-ArH), 6.63-6.68 (m, 3H, 2×3-ArH and ArCH=C), 5.41 (dt, J=1, 6.5 Hz, 1H, C=CHCH₂O), 5.03-5.06 (m, 1H, CH=C(CH₃)2), 4.40-4.45 (m, 4 tt, ArOCH₂ and CH₂OH), 2.02-2.10 (m, 4H, C=CHCH₂CH₂), and 1.56-1.68 (m, 9H, 3×CH₃); ¹³C NMR (75 MHz, CDCl₃) δ158.14 (3-ArC), 141.22, 139.85, 137.67, 132.56, 131.81, 130.93, 130.41 (3-ArC), 129.20, 128.09, 125.61 (q, J³$_{c,f}$=4 Hz, 2-ArC), 124.15, 123.77, 119.31, 114.36 (3-ArC), 68.64 (CH₂OH), 64.81 (ArOCH₂), 39.50, 26.27, 25.66, 17.67, and 16.62; IR (film) 3360 (br, OH), 2970, 2920, 1605, 1510, 1325, 1305, 1245, 1175, and 1165 cm⁻¹; MS (DCI) m/e 431 (MH+), 413 (MH+—H₂O).

For (Z)-2-(3-Trifluoromethylphenyl)-3-(3,4-bis-decyloxyphenyl)-2-propenol (5p): scale=2.37 mmol, yield=93%; ¹H NMR (300 MHz, CDCl₃) δ7.40-7.55 (m, 4 H, 2-ArH), 6.66 (d, J=8 Hz, 1H, 3-ArH), 6.65 (d, J=2 Hz, 1H, 3-ArH), 6.57 (dd, J=2, 8 Hz, 1H, 3-ArH), 6.33 (t, J=2 Hz, 1H, C=CH), 4.43 (dt, J=2, 8 Hz, CH₂OH), 3.90 (t, J=7 Hz, 2H, CH₂OAr), 3.46 (t, J=7 Hz, 2H, CH₂OAr), 1.69-1.79 (m, 2H, CH₂CH₂O), 1.55-1.63 (m, 3H, CH₂CH₂O and OH), 1.24-1.45 (m, 28 H, 14×CH₂), 0.83-0.89 (m, 6H, 2×CH₃); ¹³C NMR (75 MHz, CDCl₃) δ148.47, 148.32, 140.22, 137.68, 132.69, 131.50 (q, J²$_{c,f}$=38 Hz, 2-ArC), 129.31, 128.40, 128.27, 125.73 (q, J³$_{c,f}$=4 Hz, 2-ArC), 124.07 (q, J³$_{c,f}$=4 Hz, 2-ArC), 122.65, 113.78, 113.00, 69.06 (CH₂O), 68.69 (CH₂O), 68.54 (CH₂O), 31.91, 29.59, 29.57, 29.33, 29.18, 29.01, 25.97, 25.82, 22.69, and 14.11; IR (KBr) 3400 (br, OH), 2960, 2920, 2850, 1515, 1475, 1430, 1330, 1270, 1235, 1170, 1140, 1125, 1100, 1070, and 1020 cm⁻¹; MS (DCI) m/e 590 (M+).

For (Z)-2-(3-trifluoromethylphenyl)-3-(5,6,7,8-tetrahydro-5,5,8,8-tetramethyl-2-anthracenyl)-2-propenol (5q): scale=3.0 mmol, obtained 1.14 g of a 2:1 mixture of target compound to impurity. Acetic anhydride (0.35 g, 3.5 mmol) and 4,4-dimethylaminopyridine (10 mg) were added to a stirred solution of the mixture (1.12 g) in pyridine (11.6 mL), and the solution was stirred at room temperature for 5 h. The solution was diluted with diethyl ether and poured into 1N HCl solution. The layers were agitated and separated, and the organic layer was washed with saturated sodium chloride solution, dried over anhydrous magnesium sulfate, and concentrated to yield 1.14 g of a pale yellow oil. Purification was accomplished by column chromatography (40:1 silica gel/crude product; gradient elution with 3% to 15% ethyl acetate in hexanes) to afford 0.80 g (20:1 mixture of Z:E isomers) of the acetate. ¹H NMR (300 MHz, CDCl₃) δ7.62 (s, 1H, ArH), 7.54-7.58 (m, 3H, ArH), 7.47 (s, 1H, ArH), 7.37-7.40 (m, 3H, ArH), 6.90 (br s, 1H, C=CH), 6.77 (dd, J=2, 9 Hz, 1H, 3-ArH), 4.94 (d, J=1 Hz, 2H, CH₂OAc), 2.05 (s, 3H, COCH₃), 1.72 (s, 4 H, CH₂CH₂), and 1.33 (br s, 12H, 4×CH₃);

$^{13}$C NMR (75 MHz, CDCl$_3$) δ170.72 (C=O), 145.04, 144.74, 139.17, 134.37, 132.70, 132.03, 131.81, 131.54, 131.01, 129.11, 128.70, 126.70, 125.56, 125.08, 124.64, 124.45, 69.28 (CH$_2$OAc), 34.99 (CH$_2$CH$_2$), 34.59, 34.52, 32.44 (4×CH$_3$), and 20.95 (COCH$_3$); IR (KBr) 2960, 2950, 2925, 1735 (C=O), 1325, 1255, 1230, 1160, and 1125 cm$^{-1}$; MS (DCI) m/e 481 (MH+), 480 (M+), 421 (M+—OAc). The acetate (0.77 g, 1.66 mmol) was dissolved in methanol (8.3 mL) and tetrahydrofuran (8.3 mL) and the stirred solution was treated with 2N NaOH (3.33 mL, 6.66 mmol). The mixture was heated at reflux for 2.5 h. The solution was then allowed to cool to room temperature and was poured into saturated ammonium chloride solution and extracted twice with diethyl ether. The organic layers were combined, washed sequentially with water and saturated sodium chloride solution, dried over anhydrous magnesium sulfate, and concentrated to give 0.74 g of a clear colorless oil. Purification by column chromatography (20:1 silica gel/crude product; elution with 10% to 15% ethyl acetate in hexanes) gave 0.69 g (56% overall yield from ester) of the propenol 5q as a pale yellow oil. $^1$H NMR (300 MHz, CDCl$_3$) δ7.63 (s, 1H, ArH), 7.54–7.59 (m, 3H, ArH), 7.47 (s, 1H, ArH), 7.35–7.42 (m, 3H, ArH), 6.89 (s, 1H, C=CH), 6.80 (dd, J=2, 9 Hz, 1H, 3-ArH), 4.52 (br s, 2H, CH$_2$OH), 1.72 (s, 4H, CH$_2$CH$_2$), and 1.34 (br s, 12 H, 4×CH$_3$); $^{13}$C NMR (75 MHz, CDCl$_3$) δ144.80, 144.67, 139.61, 139.21, 132.80, 132.46, 131.62, 131.30, 130.89, 129.16, 128.82, 128.36, 126.66, 125.75, 125.50 (q, J$^3_{c,f}$=4 Hz, 2-ArC), 125.01, 124.64, 124.36 (q, J$^3_{c,f}$=4 Hz, 2-ArC), 122.22, 68.52 (CH$_2$OH), 35.01 (CH$_2$CH$_2$), 34.58, 34.53, and 32.45 (4×CH$_3$); IR (film) 3320 (br, OH), 2960, 2930, 1325, 1165, and 1130 cm$^{-1}$; MS (DCI) m/e 439 (MH+), 421 (MH+—H$_2$O).

For (Z)-2-(3-Trifluoromethylphenyl)-5-(5,6,7,8-tetrahydro-5,5,8,8-tetramethyl-2-naphthalenyl)-2-pentenol (5r): scale=1.84 mmol, yield=87%; $^1$H NMR (300 MHz, CDCl$_3$) δ7.50 (br d, J=8 Hz, 1H, 2-ArH), 7.37–7.42 (m, 3H, 2-ArH), 7.17 (d, J=8 Hz, 5-ArH), 6.99 (d, J=2 Hz, 1H, 5-ArH), 6.83 (dd, J=2, 8 Hz, 1H, 5-ArH), 5.84 (t, J=8 Hz, 1H, C=CH), 4.29 (s, 2H, CH$_2$OH), 2.61 (t, J=8 Hz, 2H, ArCH$_2$), 2.25 (q, J=8 Hz, 2H, ArCH$_2$CH$_2$), 1.64 (br s, 4H, CH$_2$CH$_2$), 1.24 (s, 6H, 2×CH$_3$), and 1.22 (s, 6H, 2×CH$_3$); $^{13}$C NMR (75 MHz, CDCl$_3$) 15 144.68, 142.48, 139.56, 139.30, 138.08, 132.03, 130.50 (q, J$^2_{c,f}$=32 Hz, 2-ArC), 129.82, 128.71, 126.45, 125.69, 125.27 (q, J$^3_{c,f}$=4 Hz, 2-ArC), 123.91 (q, J$^3_{c,f}$=4 Hz, 2-ArC), 67.88 (OCH$_2$), 35.54, 35.14, 35.09, 34.13, 33.93, 31.87, 31.81, and 30.74; IR (film) 3320 (br, OH), 2960, 2925, 2860, 1460, 1365, 1325, 1310, 1165, 1130, 1110, 1070, 805, and 705 cm$^{-1}$; MS (DCI) m/e 399 (M+—OH).

For (Z)-2-(4-Fluorophenyl)-5-(5,6,7,8-tetrahydro-5,5,8,8-tetramethyl-2-naphthalenyl)-2-pentenol (5s): scale=2.91 mmol, yield=68%; $^1$H NMR (300 MHz, CDCl$_3$) δ7.17 (d, J=8 Hz, 1H, 5-ArH), 6.92–6.99 (m, 5H, 4×2-ArH and 1×5-ArH), 6.82 (dd, J=2, 8 Hz, 1H, 5-ArH), 5.76 (t, J=8 Hz, 1H, C=CH), 4.25 (d, J=5.5 Hz, 2H, CH$_2$OH), 2.59 (t, J=8 Hz, 2H, ArCH$_2$), 2.25 (q, J=8 Hz, 2H, ArCH$_2$CH$_2$), 1.64 (br s, 4H, CH$_2$CH$_2$), 1.36 (t, J=5.5 Hz, 1H, OH), 1.24 (s, 6H, 2×CH$_3$), and 1.22 (s, 6H, 2×CH$_3$); $^{13}$C NMR (75 MHz, CDCl$_3$) 15 161.90 (d, J$^1_{c,f}$=246 Hz, 2-ArC), 144.62, 144.40, 139.82, 138.28, 134.16, 130.16 (d, J$^3_{c,f}$=8 Hz, 2-ArC), 128.70, 126.49, 126.30, 125.78, 115.12 (J$^2_{c,f}$=21 Hz, 2-ArC), 68.12 (CH$_2$OH), 35.58, 35.15, 35.10, 34.13, 33.94, 31.90, 31.85, and 30.45; IR (film) 3300 (br, OH), 2960, 2925, 2860, 1600, 1510, 1455, 1385, 1360, 1220, and 835 cm$^{-1}$; MS (DCI) m/e 349 (M+—OH).

For (Z)-2-(3-Fluorophenyl)-5-(5,6,7,8-tetrahydro-5,5,8,8-tetramethyl-2-naphthalenyl)-2-pentenol (5t): scale=4.16 mmol, yield=65%; $^1$H NMR (300 MHz, CDCl$_3$) δ7.16–7.28 (m, 2H, 1×2-ArH and 1×5-ArH), 6.99 (d, J=2 Hz, 5-ArH), 6.94 (apparent tt, J=2, 8 Hz, 1H, 2-ArH), 6.79–6.86 (m, 2H, 1×5-ArH and 1×2-ArH), 6.71 (apparent dt, J=2, 8 Hz, 1H, 2-ArH), 5.78 (t, J=8 Hz, 1H, C=CH), 4.26 (d, J=5 Hz, 2H, CH$_2$OH), 2.61 (t, J=8 Hz, 2H, ArCH$_2$), 2.28 (q, J=8 Hz, 2H, ArCH$_2$CH$_2$), 1.65 (br s, 4H, CH$_2$CH$_2$), 1.40 (t, J=5 Hz, 1H, OH), 1.24 (s, 6H, 2×CH$_3$), and 1.23 (s, 6H, 2×CH$_3$); $^{13}$C NMR (75 MHz, CDCl$_3$) δ162.64 (d, J$^1_{c,f}$=246 Hz, 2-ArC), 144.66, 142.45, 140.67 (d, J$^3_{c,f}$=8 Hz, 2-ArC), 139.73, 138.21, 129.69 (d, J$^3_{c,f}$=8 Hz, 2-ArC), 129.13, 126.48, 126.41, 125.76, 124.29 (d, J$^4_{c,f}$=5 Hz, 2-ArC), 115.52 (J$^2_{c,f}$=21 Hz, 2-ArC), 113.98 (J$^2_{c,f}$=21 Hz, 2-ArC), 67.92 (CH$_2$OH), 35.55, 35.15, 35.10, 34.15, 33.95, 31.89, 31.84, and 30.48; IR (film) 3300 (br, OH), 3020, 2960, 2925, 2860, 1610, 1580, 1490, 1460, 1435, 1410, 1385, 1360, 1260, 1235, 1220, 1190, 1090, 1070, 1005, 890, 825, 785, 760, 720, and 700 cm$^{-1}$; MS (DCI) m/e 349 (M+—OH).

For (Z)-2-Phenyl-5-(5,6,7,8-tetrahydro-5,5,8,8-tetramethyl-2-naphthalenyl)-2-pentenol (5u): scale=1.10 mmol, yield=74%; $^1$H NMR (300 MHz, CDCl$_3$) δ7.23–7.32 (m, 3H, 2-ArH), 7.16 (d, J=8 Hz, 1H, 5-ArH), 7.00–7.07 (m, 3H, 1×5-ArH and 2×2-ArH), 6.84 (dd, J=2, 8 Hz, 1H, 5-ArH), 5.76 (t, J=8 Hz, 1H, C=CH), 4.29 (s, 2H, CH$_2$OH), 2.61 (t, J=8 Hz, 2H, ArCH$_2$), 2.28 (q, J=8 Hz, 2H, ArCH$_2$CH$_2$), 1.66 (br s, 4H, CH$_2$CH$_2$), 1.44 (br s, 1H, OH), 1.24 (s, 6H, 2'CH$_3$), and 1.22 (s, 6H, 2×CH$_3$); $^{13}$C NMR (75 MHz, CDCl$_3$) δ144.57, 142.31, 140.77, 138.44, 138.33, 128.56, 128.26, 128.19, 127.10, 126.47, 126.36, 125.76, 68.10 (CH$_2$OH), 35.70, 35.18, 35.12, 34.15, 33.93, 31.91, 31.86, and 30.43; IR (film) 3340 (br, OH), 2960, 2925, 2860, 1495, 1455, 1440, 1385, 1360, 1090, 1070, 1025, 1000, 825, 760, and 700 cm$^{-1}$; MS (DCI) m/e 331 (MH+—H$_2$O).

For (Z)-2-(3-Trifluoromethylphenyl)-5-[3-(1-adamantyl)-4-hydroxyphenyl]-2-pentenol (5v): scale=1.4 mmol, yield=81%; $^1$H NMR (300 MHz, CDCl$_3$) δ7.51 (d, J=8 Hz, 1H, 2-ArH), 7.42 (t, J=8 Hz, 1H, 2-ArH), 7.34 (s, 1H, 2-ArH), 7.23 (d, J=7 Hz, 1H, 2-ArH), 6.90 (d, J=2 Hz, 1H, 5-ArH), 6.73 (dd, J=2, 8 Hz, 1H, 5-ArH), 6.50 (d, J=8 Hz, 1H, 5-ArH), 5.82 (m, 1H, C=CH), 4.71 (s, 1H, ArOH), 4.30 (d, J=6 Hz, 2H, CH$_2$OH), 2.58 (t, J=7 Hz, 2H, ArCH$_2$), 2.23 (q, J=7 Hz, 2H, ArCH$_2$CH$_2$), 2.07 (br s, 9H, adamantyl), 1.75 (s, 6H, adamantyl), and 1.44 (t, J=6 Hz, 1H, OH); $^{13}$C NMR (75 MHz, CDCl$_3$) δ152.63, 139.56, 139.30, 136.15, 133.13, 132.08, 130.63 (d, J$^2_{c,f}$=32 Hz, 2-ArC), 129.89, 128.72, 127.18, 126.32, 125.26 (d, J$^3_{c,f}$=4 Hz, 2-ArC), 123.92 (d, J$^3_{c,f}$=4 Hz, 2-ArC), 116.61, 67.92 (CH$_2$OH), 40.55 (adamantyl CH$_2$), 37.05 (adamantyl CH$_2$), 36.58 (adamantyl quaternary), 35.27, 30.76, and 29.02 (adamantyl CH); IR (KBr)3430 (OH),3250 (br, OH), 2900, 1325, 1170, 1160, 1125, 1075, and 990 cm$^{-1}$; MS (DCI) m/e 456 (M+), 455 (M—H)+, 241, 135 (C$_{10}$H$_{15}$+). Anal. Calcd for C$_{28}$H$_{31}$F$_3$O$_2$: C, 73.66; H, 6.84. Found: C, 73.86; H, 6.87.

For (Z)-2-(3-Trifluoromethylphenyl)-5-[3-(1-adamantyl)-4-methoxyphenyl]-2-pentenol (5w): obtained from (Z)-2-(3-trifluoromethylphenyl)-5-[3-(1-adamantyl)-4-hydroxyphenyl]-2-pentenol (5v) via treatment with dimethyl sulfate (0.25 g, 2.0 mmol) and potassium carbonate (0.19 g, 1.3 mmol) in refluxing acetone (10 mL) for 6 h. Scale=0.87 mmol, yield=78%; $^1$H NMR (300 MHz, CDCl$_3$) δ7.51 (m, 1H, 2-ArH), 7.42 (t, J=8 Hz, 1H, 2-ArH), 7.35 (s, 1H, 2-ArH), 7.24 (m, 1H, 2-ArH), 6.92 (m, 1H, 5-ArH), 6.86 (dd, J=2, 8 Hz, 1H, 5-ArH), 6.74 (d, J=8 Hz, 1H, 5-Art t), 5.84 (m, 1H, C=CH), 4.30 (m, 2H, CH$_2$OH), 3.78 (s, 3H, OCH$_3$), 2.61 (t, J=7 Hz, 2H, ArCH$_2$), 2.25 (q, J=7 Hz, 2H, ArCH$_2$CH$_2$), 2.04 (br s, 9H, adamantyl), 1.75 (s, 6H, adamantyl), and 1.42 (t, J=6 Hz, 1H, OH); $^{13}$C NMR (75 MHz, CDCl$_3$) δ157.13, 139.57, 139.36, 138.28, 132.82, 132.08, 130.62 (d, $J^2_{c,f}$=32 Hz, 2-ArC), 129.91, 128.71, 126.82, 126.25, 125.91, 125.27 (d, $J^3_{c,f}$=4 Hz, 2-ArC), 123.90 (d, $J^3_{c,f}$=4 Hz, 2-ArC), 111.61, 67.92 (CH$_2$OH), 55.04 (OCH$_3$), 40.60 (adamantyl CH$_2$), 37.13 (adamantyl CH$_2$), 36.86 (adamantyl quaternary), 35.31, 30.77, and 29.10 (adamantyl CH); IR (film) 3345 (br, OH), 2905, 2850, 1325, 1235, 1165, and 1130 cm$^{-1}$; MS (DCI) m/e 470 (M+), 469 (M—H)+, 255, 135 (C$_{10}$H$_{15}$+). Anal. Calcd for C$_{29}$H$_{33}$F$_3$O$_2$: C, 74.02; H, 7.07. Found: C, 73.96; H, 7.05.

For (Z)-2-Phenyl-5-[3-(1-adamantyl)-4-methoxyphenyl]-2-pentenol (2.5:1, Z:E) (5×): obtained in three steps from (Z)-1-(t-butyldimethylsiloxy)-2-phenyl-5-[3-(1-adamantyl)-4-t-butyldimethylsiloxyphenyl]-2-pentene, a by-product in the synthesis of 7j. The bis-silyl ether (0.700 g, 1.14 mmol) was dissolved in 30 mL of 3:1:1 acetic acid/THF/H$_2$O, and stirred for 48 h. The solvent was removed in vacuo. A solution of the residue, 2-phenyl-5-[3-(1-adamantyl)-4-t-butyldimethylsiloxyphenyl]-2-pentenol (2.5:1, Z:E), in THF (10 mL) was treated with a 1.1M solution of tetrabutylammonium fluoride in THF (1.44 mL, 1.59 mmol). This mixture was stirred for 30 min at rt and then quenched by the addition of saturated ammonium chloride solution (10 mL). This solution was partitioned between ether and water. The organic phase was separated, dried over anhydrous magnesium sulfate, filtered, and concentrated to give 2-phenyl-5-[3-(1-adamantyl)-4-hydroxyphenyl]-2-pentenol (2.5:1, Z:E): $^1$H NMR (300 MHz, CDCl$_3$) a (Z-isomer) 7.25–7.34 (m, 3H, 2-ArH), 7.09–7.12 (m, 2H, 2-ArH), 6.91 (d, J=2 Hz, 1H, 5-ArH), 6.75 (dd, J=8,2 Hz, 1H, 5-ArH), 6.49 (d, J=8 Hz, 1H, 5-ArH), 5.75 (t, J=7 Hz, 1H, C=CH), 4.30 (m, 2H, CH$_2$OH), 2.58 (t, J=7 Hz, 2H, ArCH$_2$), 2.28 (q, J=7 Hz, 2H, ArCH$_2$CH$_2$), 2.08 (s, 9H, adamantyl), and 1.73 (s, 6H, adamantyl); (E-isomer, partially obscured) 7.40 (m, 1H, 2-ArH) 6.97 (d, J=2 Hz, 1H, 5-ArH), 6.86 (dd, J=2, 8 Hz, 1H, 5-ArH), 6.51 (d, J=8 Hz, 1 H, 5-ArH), 5.91 (t, J=8 Hz, 1H, C=CH), and 2.71 (t, J=8 Hz, 2H, ArCH$_2$); IR (KBr) 3520 (OH), 3345 (OH), 2900, 2850, 1240, and 700 cm$^{-1}$; MS (DCI) m/e 389 (MH+), 388 (M+), 371,241, 135 (C$_{10}$H$_{15}$+); Anal. Calcd for C$_{27}$H$_{32}$O$_2$.0.3 CH$_3$CO$_2$CH$_2$CH$_3$: C, 81.62; H, 8.36. Found: C, 81.62; H, 8.32. 2-Phenyl-5-[3-(1-adamantyl)-4-hydroxyphenyl]-2-pentenol (2.5:1, Z:E, 0.600 g, 1.55 mmol) was treated with dimethylsulfate (0.195 g, 1.55 mmol) and powdered potassium carbonate (0.214 g, 1.55 mmol) in refluxing acetone for 18 h. The cooled reaction mixture was concentrated in vacuo. The residue was purified by column chromatography on silica gel (elution with methylene chloride followed by 5% methanol/methylene chloride) to give 385 mg (84% overall yield) of 5× as a 3:1 mixture of Z:E isomers. $^1$H NMR (300 MHz, CDCl$_3$) δ(Z-isomer) 7.37–7.22 (m, 3H, 2-ArH), 7.12 (m, 2H, 2-ArH), 6.95 (d, J=2 Hz, 1H, 5-ArH), 6.88 (dd, J=8, 2 Hz, 1H, 5-ArH), 6.77 (d, J=8 Hz, 1H, 5-ArH), 5.78 (t, J=7 Hz, 1H, C=CH), 4.31 (m, 2H, CH$_2$OH), 3.79 (s, 3H, OCH$_3$), 2.58 (t, J=7 Hz, 2H, ArCH$_2$), 2.32 (q, J=7 Hz, 2H, ArCH$_2$CH$_2$), 2.02 (s, 9H, adamantyl), and 1.76 (s, 6H, adamantyl); (E-isomer, partially obscured) 7.41 (m, 1H, 2-ArH), 5.92 (t, J=8 Hz, 1H, C=CH), and 2.73 (t, J=8 Hz, 2H, ArCH$_2$).

For (Z)-2-(3-Trifluoromethylphenyl)-5-[4-(1-adamantyl)-3-hydroxyphenyl]-2-pentenol (5y): scale=1.8 mmol, yield=83%; $^1$H NMR (300 MHz, CDCl$_3$) δ7.51 (m, 1H, 2-ArH), 7.40 (m, 1H, 2-ArH), 7.35 (s, 1H, 2-ArH), 7.15 (d, J=8 Hz, 1H, 2-ArH), 7.06 (d, J=8 Hz, 1H, 5-ArH), 6.60 (dd, J=2, 8 Hz, 1H, 5-ArH), 6.36 (d, J=2 Hz, 1H, 5-ArH), 5.80 (m, 1H, C=CH), 5.00 (s, 1H, ArOH), 4.28 (m, 2H, CH$_2$OH), 2.56 (t, J=7 Hz, 2H, ArCH$_2$), 2.23 (q, J=7 Hz, 2H, ArCH$_2$CH$_2$), 2.08 (br s, 9H, adamantyl), and 1.75 (s, 6H, adamantyl); $^{13}$C NMR (75 MHz, CDCl$_3$) δ154.34, 139.88, 139.58, 139.23, 134.18, 132.09, 130.62 (d, $J^2_{c,f}$=32 Hz, 2-ArC), 129.59, 128.76, 126.87, 125.26 (d, $J^3_{c,f}$=3 Hz, 2-ArC), 124.09 (q, $J^1_{c,f}$=271 Hz, CF$_3$), 123.97 (d, $J^3_{c,f}$=3 Hz, 2-ArC), 120.63, 116.92, 67.79 (CH$_2$OH), 40.62 (adamantyl CH$_2$), 37.05 (adamantyl CH$_2$), 36.38 (adamantyl quaternary), 34.85, 30.11, and 29.03 (adamantyl CH); IR (film) 3500 (OH), 3280 (br, OH), 2910, 2870, 2850, 1420, 1320, 1310, 1165, 1125, 1085, and 1070 cm$^{-1}$; MS (DCI) m/e 455 (M—H)+, 135 (C$_{10}$H$_{15}$+). Anal. Calcd for C$_{28}$H$_{31}$F$_3$O$_2$: C, 73.66; H, 6.84. Found: C, 73.58; H, 6.84.

For (Z)-2-(3-Trifluoromethylphenyl)-5-[4-(1-adamantyl)-3-methoxyphenyl]-2-pentenol (5z): obtained from (Z)-2-(3-trifluoromethylphenyl)-5-[4-(1adamantyl)-3-hydroxyphenyl[-2-pentenol (5y) via treatment with dimethyl sulfate (0.25 g, 2.0 mmol) and potassium carbonate (0.19 g, 1.3 mmol) in refluxing acetone (10 mL) for 56 h. Scale=1.3 mmol, yield=82%; $^1$H NMR (300 MHz, CDCl$_3$) δ7.51 (m, 1H, 2-ArH), 7.40 (m, 2H, 2-ArH), 7.17 (d, J=8 Hz, 1H, 2-ArH), 7.07 (d, J=8 Hz, 1H, 5-ArH), 6.63 (dd, J=2, 8 Hz, 1H, 5-ArH), 6.55 (d, J=2 Hz, 5-ArH), 5.84 (m, 1H, C=CH), 4.29 (d, J=1 Hz, 2H, CH$_2$OH), 3.74 (s, 3H, OCH$_3$), 2.63 (t, J=7 Hz, 2H, ArCH$_2$), 2.27 (q, J=7 Hz, 2H, ArCH$_2$CH$_2$), 2.05 (br s, 9H, adamantyl), 1.74 (br s, 6H, adamantyl), and 1.47 (br s, 1H, OH); $^{13}$C NMR (75 MHz, CDCl$_3$) δ158.72, 139.85, 139.72, 139.30, 136.26, 132.08, 130.61 (d, $J^2_{c,f}$=32 Hz, 2-ArC), 129.62, 128.73, 126.31, 125.29 (d, $J^3_{c,f}$=4 Hz, 2-ArC), 124.10 (q, $J^1_{c,f}$=271Hz, CF$_3$), 123.93 (d, $J^3_{c,f}$=4Hz, 2-ArC), 120.29, 111.94, 67.83 (CH$_2$OH), 54.85 (OCH$_3$), 40.65 (adamantyl CH$_2$), 37.14 (adamantyl CH$_2$), 36.66 (adamantyl quaternary), 35.48, 33.31, and 29.10 (adamantyl CH); IR (film) 3355 (OH), 2905, 2850, 1325, 1250, 1165, 1130, 1100, and 1070 cm$^{-1}$; MS (DCI) m/e 470 (M+), 469 (M—H)+, 135 (C$_{10}$H$_{15}$+). Exact mass spectrum (FAB) Calcd for C$_{29}$H$_{34}$F$_3$O$_2$ (MH+) 471.2511. Found: 471.2496. Anal. Calcd for C$_{29}$H$_{33}$F$_3$O$_2$0.1 CH$_2$Cl$_2$: C, 72.96; H, 6.99. Found: C, 72.88; H, 7.10.

For (Z)-2-Phenyl-5-[4-(1-adamantyl)-3-methoxyphenyl]-2-pentenol (5aa): scale=3.82 mmol, yield=91%; $^1$H NMR (300 MHz, CDCl$_3$) δ7.20–7.33 (m, 3H, 2-ArH), 7.03–7.07 (m, 3H, 2×2-ArH and 1×5-ArH), 6.64 (dd, J=2, 8 Hz, 1H, 5-ArH), 6.55 (d, J=2 Hz, 1H, 5-ArH), 5.75 (t, J=8 Hz, 1H, C=CH), 4.29 (s, 2H, CH$_2$OH), 3.74 (s, 3H, OCH$_3$), 2.62 (t, J=8 Hz, 2H, ArCH$_2$), 2.30 (q, J=8 Hz, 2H, ArCH$_2$CH$_2$), 2.03–2.08 (m, 9H, adamantyl), and 1.74 (br s, 6H, adamantyl); $^{13}$C NMR (75 MHz, CDCl$_3$) δ158.68, 140.92, 140.22, 138.33, 136.10, 128.59, 128.26, 128.01, 127.11, 126.20, 120.32, 112.01, 68.06 (CH$_2$OH), 54.89 (OCH$_3$), 40.68, 37.14, 36.65, 35.62, 30.27, and 29.11; IR (film) 3350 (br, OH), 2904, 2848, 1610, 1494, 1452, 1412, 1246, 1162, 1138, 1102, 1090, 1042, 1026, 1002, 808, 760, and 702 cm$^{-1}$; MS (DCI) m/e 402 (M+), 385 (M+—OH).

For (Z)-2-(3-Trifluoromethylphenyl)-5-[2-(1-adamantyl)-4-hydroxyphenyl]-2-pentenol (5bb): scale=0.48 mmol, yield=88%; $^1$H NMR (300 MHz, CDCl$_3$) δ7.52 (m, 1H, 2-ArH), 7.43 (m, 2H, 2-ArH), 7.33 (m, 1H, 2-ArH), 6.93 (d, J=8 Hz, 1H, 5-ArH), 6.82 (d, J=3 Hz, 1H 5-ArH), 6.62 (dd, J=3, 8 Hz, 1H, 5-ArH), 5.90 (m, 1H, C=CH), 4.34 (m, 2H, CH$_2$OH), 3.74 (s, 3H, OCH$_3$), 2.90 (m, 2H, ArCH$_2$), 2.26 (m, 2H, ArCH$_2$CH$_2$), 2.02 (br s, 3H, adamantyl), 1.92 (m, 6H, adamantyl), 1.73 (m, 6H, adamantyl), and 1.51 (br s, 1H, OH); $^{13}$C NMR (75 MHz, CDCl$_3$) δ157.52, 148.97, 139.52, 139.33, 132.67, 132.08, 130.75 (d, $J^2_{c,f}$=32 Hz, 2-ArC), 129.59, 128.78, 125.17 (d, $J^3_{c,f}$=4 Hz, 2-ArC), 124.03 (d, $J^3_{c,f}$=4 Hz, 2-ArC), 113.02, 109.90, 67.83 (CH$_2$OH), 55.08 (OCH$_3$), 42.07 (adamantyl CH$_2$), 37.85 (adamantyl quaternary), 36.77 (adamantyl CH$_2$), 33.66, 32.35, and 29.10 (adamantyl CH); IR (film) 3390 (br, OH), 2910, 2850, 1325, 1165, 1125, and 1070 cm$^{-1}$; MS (DCI) m/e 471 (MH+), 470 (M+), 469 (M—H)+, 255, 135 (C$_{10}$H$_{15}$+).

For (Z)-2-(3-Trifluoromethylphenyl)-3-[-4-(1-adamantyl)-3-methoxyphenyl]-2-propenol (5cc): scale=2.48 mmol, yield=90%; $^1$H NMR (300 MHz, CDCl$_3$) δ7.55 (m, 2H, 2-Arid), 7.45 (m, 2H, 2-ArH), 7.01 (d, J=8 Hz, 1H, 3-ArH), 6.69 (s, 1 H, C=CH), 6.61 (dd, J=2, 8 Hz, 1H, 3-ArH), 6.32 (d, J=2 Hz, 1H, 3-ArH), 4.44 (d, J=5 Hz, 2H, CH$_2$OH), 3.34 (s, 3H, OCH$_3$), 1.98 (s, 9H, adamantyl), and 1.69 (m, 7H, 6×adamantyl and OH); $^{13}$C NMR (75 MHz, CDCl$_3$) δ158.22, 140.17, 139.08, 138.14, 134.07, 132.56, 131.23 (d, $J^2_{c,f}$=32 Hz, 2-ArC), 129.36, 127.99, 126.29, 125.75 (d, $J^3_{c,f}$=4 Hz, 2-ArC), 124.16 (d, $J^3_{c,f}$=4 Hz, 2-ArC), 122.11, 68.60 (CH$_2$OH), 54.25 (OCH$_3$), 40.42 (adamantyl CH$_2$), 37.06 (adamantyl CH$_2$), 36.83 (adamantyl quaternary), and 29.01 (adamantyl CH); IR (KBr) 3385 (br, OH), 2905, 2850, 1325, 1130, and 1070 cm$^{-1}$; MS (DCI) m/e 443 (MH+), 442 (M+), 441 (M—H)+, 135 (C$_{10}$H$_{15}$+). Anal. Calcd for C$_{27}$H$_{29}$F$_3$O$_2$.0.3CH$_3$CO$_2$CH$_2$CH$_3$: C, 72.23; H, 6.75. Found: C, 72.37; H, 6.59.

For (Z)-2-(3-Trifluoromethylphenyl)-5-[4-(1-adamantyl)-3-t-butyldimethylsilyloxyphenyl]-2-pentenol (5dd): scale=6.7 mmol, yield=82%; $^1$H NMR (300 MHz, CDCl$_3$) δ7.51 (m, 1H, 2-ArH), 7.40 (m, 2H, 2-ArH), 7.19 (d, J=8 Hz, 1H, 2-ArH), 7.07 (d, J=8 Hz, 1H, 5-ArH), 6.61 (dd, J=2, 8 Hz, 1H, 5-ArH), 6.48 (d, J=2 Hz, 1H, 5-ArH), 5.83 (m, 1H, C=CH), 4.29 (d, J=5 Hz, 2H, CH$_2$OH), 2.56 (t, J=7 Hz, 2H, ArCH$_2$), 2.23 (m, 2H, ArCH$_2$CH$_2$), 2.06 (br s, 9H, adamantyl), 1.74 (s, 6H, adamantyl), 1.43 (m, 1H, OH), 0.99 (s, 9H, SiC(CH$_3$)$_3$), and 0.26 (s, 6H, Si(CH$_3$)$_2$); $^{13}$C NMR (75 MHz, CDCl$_3$) δ154.50, 139.76, 139.43, 139.28, 137.17, 132.07, 130.88, 129.50, 128.75, 126.88, 125.24 (d, $J^3_{c,f}$=4 Hz, 2-ArC), 23.97 (d, $J^3_{c,f}$=4 Hz, 2-ArC), 120.38, 119.15, 67.85 (CH$_2$OH), 40.46 (adamantyl CH$_2$), 37.07 (adamantyl CH$_2$), 36.52 (adamantyl quaternary), 35.16, 30.32, 29.04 (adamantyl CH), 26.39 (SiC(CH$_3$)$_3$), 18.90 (SiC(CH$_3$)$_3$), and −3.42 (Si(CH$_3$)$_2$); IR (film) 3320 (br, OH), 2930, 2905, 2850, 1325, 1265, 1255, 1165, 1130, 855, and 835 cm$^{-1}$; MS (DCI) m/e 571 (MH+), 570 (M+), 569 (M—H)+, 135 (C$_{10}$H$_{15}$+). Exact mass spectrum (FAB) Calcd for C$_{34}$H$_{45}$F$_3$O$_2$Si (M+): 570.3141. Found 570.3122.

Example 5: General Procedure for Synthesis of 6

A solution of alcohol 5 (1 equivalent) in anhydrous methylene chloride (0.1–0.2M) was cooled to −10° to 0° C. under argon. The solution was treated with t-butyldimethylchlorosilane (1.3 equivalents) in one portion, followed by addition of 4-dimethylaminopyridine (0.05 equivalents). Triethylamine (1.4 equivalents) was added dropwise and the reaction mixture was stirred at 0°–25° C. for 2–5 h. The mixture was then partitioned between diethyl ether and saturated ammonium chloride solution, and the organic layer was washed with saturated sodium chloride solution, dried over anhydrous magnesium sulfate, filtered, and concentrated. Purification by column chromatography (20:1 ratio of silica gel/crude product; elution with hexanes to 2% to 4% ethyl acetate in hexanes) afforded the desired product.

For (Z)-1-(t-Butyldimethylsiloxy)-2-(3-bromophenyl)-3-Phenyl-2-propene (6a): scale=2.62 mmol, yield=96%; $^1$H NMR (300 MHz, CDCl$_3$) δ7.39 (dt, J=2, 8 Hz, 1H, 2-ArH), 7.35 (t, J=2 Hz, 1H, 2-ArH), 7.06–7.24 (m, 5H, ArH), 6.95–6.98 (m, 2H, ArH), 6.70 (t, J=2 Hz, 1H, C=CH), 4.37 (d, J=2 Hz, 2H, CH$_2$OSi), 0.92 (s, 9H, Si(C(CH$_3$)$_3$), and 0.07 (s, 6H, Si(CH$_3$)$_2$); $^{13}$C NMR (75 MHz, CDCl$_3$) δ139.87, 136.30, 131.58, 130.35, 130.14, 129.17, 128.01, 127.72, 126.78, 125.87, 122.52, 67.80 (CH$_2$O), 29.71 (SiC(CH$_3$)$_3$), 25.91 (SiC(CH$_3$)$_3$), and −5.34 (Si(CH$_3$)$_2$); IR (film) 2955, 2930, 2885, 2855, 1560, 1472, 1250, 1125, 1075, 1005, 880, 840, 780, 750, and 695 cm$^{-1}$; MS (DCI) m/e 401/403 (MH+, 1:1).

For (Z)-1-(t-Butyldimethylsiloxy)-2-(3-bromophenyl)-3-(5,6,7,8tetrahydro-5,5,8,8-tetramethyl-2-naphthalenyl)-2-propene (6b): scale=5.41 mmol, yield=98%; $^1$H NMR (300 MHz, CDCl$_3$) δ7.42 (dt, J=2, 8 Hz, 1H, 2-ArH), 7.38 (t, J=2 Hz, 1H, 2-ArH), 7.09–7.24 (m, 3H, ArH), 6.85 (d, J=2 Hz, 1H, 3-ArH), 6.83 (dd, J=2, 8 Hz, 1H, 3-ArH), 6.63 (s, 1H, C=CH), 4.38 (s, 2H, CH$_2$OSi), 1.60 (br s, 4 H, CH$_2$CH$_2$), 1.20 (s, 6H, 2×CH$_3$), 0.98 (s, 6H, 2'CH$_3$), 0.95 (s, 9H, Si(C(CH$_3$)$_3$), and 0.07 (s, 6H, Si(CH$_3$)$_2$).

For (Z)-1-(t-Butyldimethylsiloxy)-2-(3-bromophenyl)-3-(5,6,7,8-tetrahydro-5,5,8,8-tetramethyl-2-anthracenyl)-2-propene (6c): scale=2.3 mmol, yield=97%; $^1$H NMR (300 MHz, CDCl$_3$) δ7.61 (d, J=6 Hz, 2H, ArH), 7.37–7.60 (m, 4H, ArH), 7.08–7.15 (m, 2H, ArH), 6.83–6.87 (m, 2H, ArH and C=CH), 4.22 (d, J=1 Hz, 2H, CH$_2$OSi), 1.73 (s, 4H, CH$_2$CH$_2$), 1.27–1.30 (m, 12H, 4×CH$_3$), 0.95 (s, 9H, SiC(CH$_3$)$_3$), and 0.10 (s, 6H, Si(CH$_3$)$_2$); $^{13}$C NMR (75 MHz, CDCl$_3$) δ153.16, 144.42, 141.47, 139.34, 133.13, 131.68, 131.62, 130.71, 131.36, 130.08, 128.02, 126.44, 126.38, 126.10, 124.95, 124.58, 122.51, 67.86 (CH$_2$OSi), 35.07 (CH$_2$CH$_2$), 34.55, 34.53, 32.48 (4×CH$_3$), 29.72, 25.95 (SiC(CH$_3$)$_3$), 18.46 (SiC(CH$_3$)$_3$) and −5.29 (Si(CH$_3$)$_2$); IR (film) 2955, 2930, 2860, 1470, 1360, 1255, 1125, and 1110 cm$^{-1}$; MS (DCI) m/e 563/561 (MH+, 1:1), 433/431 (MH+—OTBDMS, 1:1).

For (Z)-1-(t-Butyldimethylsiloxy)-2-(3-bromophenyl)-3-(4-decyloxyphenyl)-2-propene (6d): scale=5.70 mmol, yield=97%; $^1$H NMR (300 MHz, CDCl$_3$) δ7.35–7.41 (m, 2H, 2-ArH), 7.16 (t, J=8 Hz, 1H, 2-ArH), 7.09 (dt, J=2, 8 Hz, 1H, 2-ArH), 6.88 (d, J=8 Hz, 2H, 3-ArH), 6.61–6.66 (m, 3H, 2×3-ArH and C=CH), 4.34 (d, J=1 Hz, 2H, CH$_2$OSi), 3.85 (t, J=7 Hz, 2H, ArOCH$_2$), 1.71 (quintet, J=7 Hz, 2H, ArOCH$_2$CH$_2$), 1.20–1.42 (m, 14H, 7×CH$_2$), 0.91 (s, 9H, Si(C(CH$_3$)$_3$), 0.85 (t, J=7 Hz, 3H, CH$_3$) and 0.06 (s, 6H, Si(CH$_3$)$_2$); $^{13}$C NMR (75 MHz, CDCl$_3$) δ158.02, 141.74, 137.65, 131.69, 130.35, 130.19, 130.17, 128.62, 127.83, 125.61, 122.54, 114.00, 68.08 (CH$_2$OSi), 67.88 (ArOCH$_2$), 31.89, 29.72, 29.56, 29.38, 29.32, 29.23, 26.02, 25.91 (SiC(CH$_3$)$_3$), 22.69, 18.43 (SiC(CH$_3$)$_3$), 14.13, and −5.40 (Si(CH$_3$)$_2$); IR (film) 2955, 2930, 2855, 1605, 1560, 1510, 1470, 1300, 1250, 1180, 1130, 1110, 1070, 1025, 1005, 885, 840, 780, and 695 cm$^{-1}$; MS (DCI) m/e 559/561 (MH$^+$, 1:1).

For (Z)-1-(t-Butyldimethylsiloxy)-2-(3-bromophenyl)-3-(3,4-bisdecyloxyphenyl)-2-propene (6e): scale=1.6 mmol, yield=100%; $^1$H NMR (300 MHz, CDCl$_3$) δ7.37–7.40 (m, 2H, 2-ArH), 7.21 (t, J=9 Hz, 1H, 2-ArH), 7.11 (dt, J=1, 9 Hz, 1H, 2-ArH), 6.66 (d, J=8 Hz, 1H, 3-ArH), 6.59 (dd, J=2, 9 Hz, 1H, 3-ArH$^6$), 6.58 (br s, 1H, C=CH), 6.40 (d, J=2 Hz, 1H, 3-ArH), 4.34 (d, J=2 Hz, 2H, CH$_2$OSi), 3.90 (t, J=7 Hz, 2H, ArC$^4$OCH$_2$), 3.53 (t, J=7 Hz, 2H, ArC$^3$OCH$_2$), 1.75 (quint, J=7 Hz, 2H, ArC$^4$OCH$_2$CH$_2$), 1.61 (quint, J=7 Hz, 2H, ArC$^3$OCH$_2$CH$_2$), 1.11–1.40 (m, 28H, 14'CH$_2$), 0.83–0.92 (m, 6H, 2×CH$_3$), 0.91 (s, 9H, SiC(C$_3$)$_3$), and 0.05 (s, 6H, Si(CH$_3$)$_2$); $^{13}$C NMR (75 MHz, CDCl$_3$) δ148.24 (3-ArC), 148.11 (3-ArC), 142.01, 137.80, 131.92, 130.19, 130.12, 129.07, 127.85, 125.86, 122.51, 113.90, 113.04, 69.09, 68.61, 68.16, 31.93, 31.91, 29.65, 29.60, 29.57, 29.37, 29.22, 29.05, 25.98, 25.91 (SiC(CH$_3$)$_3$), 22.69, 18.43 (SiC(CH$_3$)$_3$), 14.12, and −5.35 (Si(CH$_3$)$_2$); IR (film) 2955, 2925, 2855, 1515, 1470, 1270, 1260, 1240, 1140, 1085, and 1070 cm$^{-1}$; MS (FAB) m/e 717/715 (MH$^+$, 1:1).

For (Z)-1-(t-Butyldimethylsiloxy)-2-(3-bromophenyl)-5-phenyl-2-pentene (6f): scale=1.57 mmol, yield=98%; $^1$H NMR (300 MHz, CDCl$_3$) δ7.39 (dt, J=2, 8 Hz, 1H, 2-ArH), 7.07–7.27 (m, 7H, 3×2-ArH and 4×5-ArH), 6.98 (dt, J=2, 8 Hz, 1H, 5-ArH), 5.75 (tt, J=1.5, 7.5 Hz, 1H, C=CH), 4.25 (d, J=1.5 Hz, 2H, CH$_2$OSi), 2.65 (t, J=7.5 Hz, 2H, ArCH$_2$), 2.26 (q, J=7.5 Hz, 2H, ArCH$_2$CH$_2$), 0.87 (s, 9H, Si(C(CH$_3$)$_3$), and 0.00 (s, 6H, Si(CH$_3$)$_2$); $^{13}$C NMR (75 MHz, CDCl$_3$) δ141.43, 141.01, 139.35, 131.47, 129.77, 129.42, 128.15, 127.29, 126.51, 125.72, 121.94, 67.09 (CH$_2$OSi), 35.82, 30.16, 25.77 (SiC(CH$_3$)$_3$), 18.27 (SiC(CH$_3$)$_3$), and −5.52 (Si(CH$_3$)$_2$); IR (film) 3085, 3060, 3025, 3030, 2955, 2930, 2895, 2855, 1590, 1560, 1495, 1470, 1460, 1455, 1360, 1255, 1125, 1090, 1070, 1050, 1005, 840, 815, 775, 750, 700, and 675 cm$^{-1}$; MS (FAB) m/e 429/431 (M$^+$, 1:1), 373/375 (M$^+$—t-Bu).

For (Z)-1-(t-Butyldimethylsiloxy)-2-(3-bromophenyl)-5-(5,6,7,8tetrahydro-5,5,8,8-tetramethyl-2-naphthalenyl)-2-pentene (6g): scale=2.4 mmol, yield=94%; $^1$H NMR (300 MHz, CDCl$_3$) δ7.35 (ddd, J=1, 2, 8 Hz, 1H, 2-ArH), 7.23 (t, J=2 Hz, 1H, 2-ArH), 7.18 (d, J=8 Hz, 1H, 2 -ArH), 7.13 (t, J=8 Hz, 1H, 2-ArH), 7.01 (d, J=2 Hz, 1H, 5-ArH), 6.84–6.91 (m, 2H, 5-ArH), 5.77 (t, J=7 Hz, 1H, C=CH), 4.22 (d, J=1Hz, 2H, CH$_2$OSi), 2.60 (t, J=7 Hz, 2H, ArCH$_2$), 2.25 (q, J=7 Hz, 2H, ArCH$_2$CH$_2$), 1.65 (s, 4 H, CH$_2$CH$_2$), 1.25 (s, 6H, 2×CH$_3$), 1.23 (s, 6H, 2×CH$_3$), 0.87 (s, 9H, SiC(CH$_3$)$_3$), and 0.00 (s, 6H, Si(CH$_3$)$_2$); $^{13}$C NMR (75 MHz, CDCl$_3$) δ144.58, 142.27, 141.22, 139.19, 138.43, 131.63, 129.84, 129.55, 127.44, 127.13, 126.45, 126.37, 125.80, 122.03, 67.27 (CH$_2$OSi), 35.70, 35.21, 35.14, 34.15, 33.94, 31.93, 31.87, 30.32, 25.91 (SiC(CH$_3$)$_3$), and 18.39 (SiC(CH$_3$)$_3$); IR (film) 2955, 2930, 2855 1470, 1460, 1125, 840, and 775 cm$^{-1}$; MS (DCI) m/e 539/541 (M—H)$^+$, 1:1). Anal. Calcd for C$_{31}$H$_{45}$OSiBr: C, 68.74; H, 8.37. Found: C, 69.02; H, 8.34.

For (2Z),(4E)-1-(t-Butyldimethylsiloxy)-2-(3-bromophenyl)-5-(5,6,7,8-tetrahydro-5,5,8,8-tetramethyl-2-naphthalenyl)-2,4-hexadiene (6h): scale=3.20 mmol, yield=92%; $^1$H NMR (300 MHz, CDCl$_3$) δ7.45 (d, J=2 Hz, 1H, 2-ArH), 7.39–7.43 (m, 1H, 2-ArH), 7.19–7.28 (m, 4H, 2×2-ArH and 2×5-ArH), 7.09 (dd, J=2, 8 Hz, 1H, 5-ArH), 6.80 (dt, J=1.5, 12 Hz, 1H, C=CH), 6.45 (br d, J=12 Hz, 1H, C=CH), 4.46 (d, J=1.5 Hz, 2H, CH$_2$OSi), 2.20 (d, J=1.5 Hz, 3H, C—CCH$_3$), 1.67 (br s, 4H, CH$_2$CH$_2$), 1.24 (s, 12H, 4×CH$_3$), 0.93 (s, 9H, Si(C(CH$_3$)$_3$), and 0.09 (s, 6H, Si(CH$_3$)$_2$); IR (film) 2955, 2930, 2860, 1555, 1495, 1470, 1460, 1405, 1390, 1360, 1255, 1215, 1190, 1125, 1070, 1050, 1030, 885, 840, 780, 700, and 680 cm$^{-1}$; MS (DCI) m/e 552/554 (M$^+$, 1:1), 421/423 (M$^+$—OSi[C(CH$_3$)$_3$](CH$_3$)$_2$).

For (Z)-1-(t-Butyldimethylsiloxy)-2-(3-bromophenyl)-5-[4-(1-adamantyl)-3-methoxyphenyl]-2-pentene (6i): scale - 4.36 mmol, yield=87%; $^1$H NMR (300 MHz, CDCl$_3$) δ7.33–7.36 (m, 1H, 2-ArH), 7.18 (t, J=2 Hz, 1H, 2-ArH), 7.12 (t, J=8 Hz, 1H, 2-ArH), 7.07 (d, J=8 Hz, 1H, 3-ArH), 6.88 (dt, J=2, 8 Hz, 1H, 2-ArH), 6.63 (d, J=8 Hz, 1H, 3-ArH), 6.56 (d, J=1 Hz, 1 H, 3-ArH), 5.75 (t, J=8 Hz, 1H, C=CH), 4.20 (br s, 2H, CH$_2$OSi), 3.76 (s, 3H, OCH$_3$), 2.60 (t, J=8 Hz, 2H, ArCH$_2$), 2.24 (q, J=8 Hz, 2H, ArCH$_2$CH$_2$), 2.05 (br s, 9H, adamantyl), 1.74 (br s, 6H, adamantyl), 0.86 (s, 9H, SiC(CH$_3$)$_3$), and −0.10 (s, 6H, Si(CH$_3$)$_2$); $^{13}$C NMR (75 MHz, CDCl$_3$) δ158.66, 141.72, 140.19, 139.33, 136.04, 131.63, 129.85, 129.54, 127.45, 126.88, 126.24, 122.00, 120.38, 112.03, 67.23 (CH$_2$OSi), 54.89 (OCH$_3$), 37.16, 36.64, 35.63, 30.22, 29.12, 25.89 (SiC(CH$_3$)$_3$), 18.38 (SiC(CH$_3$)$_3$), and −5.39 (Si(CH$_3$)$_2$); IR (film) 2950, 2930, 2905, 2850, 1470, 1460, 1455, 1410, 1250, and 1125 cm$^{-1}$; MS (DCI) m/e 595 (MH$^+$), 465/463 (MH$^+$—OTBDMS, 1:1).

For (Z)-1-(t-Butyldimethylsiloxy)-2-(3-bromophenyl)-5-[3-(1-adamantyl)-4-t-butyldimethylsiloxyphenyl]-2-pentene (6j): scale=6.9 mmol, yield=80%, ca. 3:1 mixture of Z:E isomers. This compound was prepared using a modified procedure of Shreet, B. et al, U.S. Pat. No. 4,717,720, January 1988. 1H NMR (300 MHz, CDCl$_3$) δ(Z-isomer) 7.36 (dt, J=8, 2 Hz, 1H, 2-ArH), 7.24 (t, J=2 Hz, 1H, 2-ArH), 7.15 (t, J=8 Hz, 1H, 2-ArH), 6.92–6.95 (m, 2H, 2-ArH and 5-ArH), 6.77 (dd, J=8, 2 Hz, 1H, 5-ArH), 6.64 (d, J=8 Hz, 1H, 5-ArH), 5.78 (t, J=7 Hz, 1H, C=CH), 4.22 (d, J=1H, 2H, CH$_2$OSi), 2.58 (t, J=7 Hz, 2H, ArCH$_2$), 2.22 (q, J=7 Hz, 2H, ArCH$_2$CH$_2$), 2.05 (m, 9H, adamantyl), 1.76 (s, 6H, adamantyl), 1.01 (s, 9H, SiC(CH$_3$)$_3$), 0.88 (s, 9H, SiC(CH$_3$)$_3$), 0.31 (s, 6H, Si(CH$_3$)$_2$), and 0.00 (s 6H, Si(CH$_3$)$_2$); (E-isomer) 7.55 (t, J=2 Hz, 1H, 2-ArH), 7.31 (m, 2H, 2-ArH), 7.14 (t, J=8 Hz, 1H, 2-ArH), 7.01 (d, J=2 Hz, 1H, 5-ArH), 6.86 (dd, J=8, 2 Hz, 1H, 5-ArH), 6.72 (d, ]=8 Hz, 1H, 5-ArH), 5.82 (t, J=7 Hz, 1H, C=CH), 4.34 (s, 2H, CH$_2$OSi), 2.68 (t, J=7 Hz, 2H, ArCH$_2$), 2.52 (q, J=7 Hz, 2H, ArCH$_2$CH$_2$), 1.12 (s, 9H, SiC(CH$_3$)$_3$), 0.82 (s, 9H, SiC(CH$_3$)$_3$), 0.32 (s, 6H, Si(CH$_3$)$_2$), and 0.01 (s, 6H, Si(CH$_3$)$_2$).

For (Z)-1-(t-Butyldimethylsiloxy)-2-(3-bromophenyl)-3-(3,4-bispentyloxyphenyl)-2-propene (6k): scale=1.52 mmol, yield=90%; $^1$H NMR (300 MHz, CDCl$_3$) δ7.37–7.41 (m, 2H, 2-ArH), 7.10–7.24 (m, 2H, 2-ArH), 6.67 (d, J=8 Hz, 1H, 3-ArH), 6.59 (dd, J=2, 8 Hz, 1H, 3-ArH), 6.58 (t, J=1.5 Hz, 1H, C—CH), 6.41 (d, J=2 Hz, 1H, 3-ArH), 4.35 (d, J=1.5 Hz, 2H, CH$_2$OSi), 3.91 (t, J=6.5 Hz, 2H, 3-ArOCH$_2$), 3.53 (t, J=6.5 Hz, 2H, 3-ArOCH$_2$), 1.71–1.78 (m, 2H, 3-

ArOCH$_2$CH$_2$), 1.57–1.65 (m, 2H, 3-ArOCH$_2$CH$_2$), 1.27–1.41 (m, 8 H), 0.86–0.93 (m, 15 H, 2×CH$_3$ and Si(C(CH$_3$)$_3$) and 0.06 (Si(CH$_3$)$_2$); $^{13}$C NMR (75 MHz, CDCl$_3$) δ148.22, 148.09, 142.00, 137.80, 131.91, 130.21,130.12, 129.07, 127.86, 125.85, 122.51, 113.86, 113.00, 69.06 (3-ArOCH$_2$), 68.57 (3-ArOCH$_2$), 68.15 (CH$_2$OSi), 29.70, 28.90, 28.71, 28.05, 25.91 (SiC(CH$_3$)$_3$), 22.45, 22.40, 18.43 (SiC(CH$_3$)$_3$), 14.06, 14.03, and −5.35 (Si(CH$_3$)$_2$); IR (film) 2955, 2930, 2860, 1590, 1560, 1515, 1470, 1430, 1390, 1270, 1240, 1170, 1140, 1085, 1070, 1050, 1030, 1005, 890, 840, 810, 780, and 700 cm$^{-1}$; MS (DCI) m/e 575/577 (MH$^+$, 1:1), 43/445 (M$^+$—O—Si[C(CH$_3$)$_3$](CH$_3$)$_2$).

Example 6: General Procedure for Synthesis of 7

Procedure A: A solution of aryl bromide 6 (1 equivalent) in anhydrous tetrahydrofuran (0.1–0.15M) was cooled to −78° C. under argon and treated with t-butyllithium solution (1.4–1.8M in pentane, 2.1 equivalents). The pale yellow reaction mixture was stirred at −78° C. for 30 min, and then added via cannula to a precooled solution of ethyl chloroformate (1.5–3 equivalents) in anhydrous THF at −78° C. The resulting mixture was allowed to warm to room temperature, and then was poured into a separatory funnel containing diethyl ether and saturated ammonium chloride solution. The layers were agitated and separated, and the organic phase was washed with saturated sodium chloride solution, dried over anhydrous magnesium sulfate, filtered, and concentrated. Purification by column chromatography (20:1 ratio of silica gel/crude product; elution with 1% to 2% ethyl acetate in hexanes) gave the desired product.

Procedure B: A solution of aryl bromide 6 (1 equivalent) in anhydrous tetrahydrofuran (0.1M) was cooled to −78° C. under argon and treated with t-butyllithium solution (1.4–1.8M in pentane, 2 equivalents). The pale yellow reaction mixture was stirred at −78° C. for 30 min, and then treated with anhydrous dimethylformamide (2 equivalents). The resulting mixture was allowed to warm to room temperature, and then was poured into a separatory funnel containing diethyl ether and saturated ammonium chloride solution. The layers were agitated and separated, and the organic phase was washed with saturated sodium chloride solution, dried over anhydrous magnesium sulfate, filtered, and concentrated. The crude aldehyde (1 equivalent) was dissolved in methanol (0.1M solution) and treated with sodium cyanide (5.4 equivalents), acetic acid (a few drops), and manganese dioxide (5:1 weight ratio of MnO$_2$/crude aldehyde). The mixture was stirred at room temperature for 2–14 h and then diluted with methylene chloride and filtered through a one-inch pad of Celite. The filtrate was washed with water and saturated sodium chloride solution, dried over anhydrous magnesium sulfate, filtered, and concentrated. Purification by column chromatography (20–40:1 ratio of silica gel/crude product; elution with 1% to 2% ethyl acetate in hexanes) gave the desired product.

For (Z)-1-(t-Butyldimethylsiloxy)-2-(3-carboethoxyphenyl)-3-phenyl-2-propene (7a): via procedure A, scale=2.48 mmol, yield=46%; $^1$H NMR (300 MHz, CDCl$_3$) δ7.93–7.96 (m, 1H, 2-ArH), 7.90 (t, J=2 Hz, 1H, 2-ArH), 7.30–7.36 (m, 2H, 2-ArH), 7.04–7.10 (m, 3H, 3-ArH), 6.92–6.95 (m, 2H, 3-ArH), 6.73 (t, J=2 Hz, 1H, C=CH), 4.41 (d, J=2 Hz, 2H, CH$_2$OSi), 4.34 (q, J=7 Hz, 2H, CO$_2$CH$_2$), 1.35 (t, J=7 Hz, 3H, CO$_2$CH$_2$CH$_3$), 0.91 (s, 9H, Si(C(CH$_3$)$_3$), and 0.07 (s, 6H, Si(CH$_3$)$_2$; $^{13}$C NMR (75 MHz, CDCl$_3$) δ 166.50 (C=O), 140.44, 139.41, 136.46, 133.73, 130.84, 129.70, 129.17, 128.62, 128.49, 127.97, 126.66, 125.81, 67.89 (CH$_2$OSi), 61.02 (CO$_2$CH$_2$), 25.91 (SiC(CH$_3$)$_3$), 18.42 (SiC(CH$_3$)$_3$), 14.30 (CO$_2$CH$_2$CH$_3$) and −5.34 (Si(CH$_3$)$_2$); IR (film) 2955, 2930, 2895, 2855, 1720 (C=O), 1470, 1465, 1370, 1265, 1195, 1125, 1110, 1080, 1020, 880, 840, 780, and 695 cm$^{-1}$; MS (FAB) m/e 395 (M—H$^+$).

For (Z)-1-(t-Butyldimethylsiloxy)-2-(3-carboethoxyphenyl)-3-(5,6,7,8-tetrahydro-5,5,8,8-tetramethyl-2-naphthalenyl)-2-propene (7b): via procedure A, scale=4.77 mmol, yield=73 %; $^1$H NMR (300 MHz, CDCl$_3$) δ7.94–7.97 (m, 2H, 2-ArH), 7.36–7.38 (m, 2H, ArH), 7.05 (d, J=8 Hz, 1H, 3-ArH), 6.75–6.83 (m, 2H, 3-ArH), 6.64 (br s, 1H, C=CH), 4.42 (d, J=1.5 Hz, 2H, CH$_2$OSi), 4.33 (q, J=7 Hz, 2H, CO$_2$CH$_2$), 1.54 (br s, 4H, CH$_2$CH$_2$), 1.34 (t, J=7 Hz, 3H, CO$_2$CH$_2$CH$_3$), 1.19 (s, 3H, CH$_3$), 1.18 (s, 3H, CH$_3$), 0.98 (s, 6H, 2×CH$_3$), 0.95 (s, 9H, Si(C(CH$_3$)$_3$), and 0.06 (s, 6H, Si(CH$_3$)$_2$); $^{13}$C NMR (75 MHz, CDCl$_3$) δ 166.54 (C=O), 144.20, 143.57, 140.00, 139.30, 133.79, 133.26, 130.87, 129.94, 128.67, 128.34, 127.30, 126.67, 126.16, 126.10, 68.28 (CH$_2$OSi), 60.94 (CO$_2$CH$_2$), 34.96, 33.98, 33.86, 31.67, 31.42, 27.93, 25.91 (SiC(CH$_3$)$_3$), 18.42 (SiC(CH$_3$)$_3$), 14.31 (CO$_2$CH$_2$CH$_3$) and −5.33 (Si(CH$_3$)$_2$); IR (film) 2960, 2930, 2860, 1720 (C=O), 1470, 1460, 1280, 1260, 1195, 840, and 775 cm$^{-1}$; MS (DCI) m/e 506 (M$^+$).

For (Z)-1-(t-Butyldimethylsiloxy)-2-(3-carboethoxyphenyl)-3-(5,6,7,8-tetrahydro-5,5,8,8-tetramethyl-2-anthracenyl)-2-Propene (7c): via procedure A, scale=2.21 mmol, yield=43%; $^1$H NMR (300 MHz, CDCl$_3$) δ7.94–7.98 (m, 2H, ArH), 7.58 (d, J=9 Hz, 2H, ArH), 7.45 (s, 1H, ArH), 7.27–7.36 (m, 3H, ArH), 6.88 (s, 1H, C=CH), 6.80 (dd, J=2, 9 Hz, 1H, ArH), 4.47 (d, J=1 Hz, 2H, CH$_2$OSi), 4.34 (q, J=7 Hz, 2H, CO$_2$CH$_2$), 1.72 (s, 4H, CH$_2$CH$_2$), 1.29–1.38 (m, 15H, 4×CH$_3$ and CO$_2$CH$_2$CH$_3$), 0.94 (s, 9H, Si(CH$_3$)$_3$), and 0.10 (s, 6H, Si(CH$_3$)$_2$); $^{13}$C NMR (75 MHz, CDCl$_3$) δ166.58 (C=O), 144.38, 144.32, 139.95, 139.51,134.07, 133.29, 131.66, 130.80, 130.64, 129.67, 128.56, 128.52, 127.93, 126.42, 126.31, 126.18, 124.92, 124.55, 67.95 (CH$_2$OSi), 61.02 (CO$_2$CH$_2$), 35.05, 34.51, 32.46, 25.95 (SiC(CH$_3$)$_3$), 18.45 (SiC(CH$_3$)$_3$), and 14.28; IR (film) 2960, 2930, 2860, 1720 (C=O), 1470, 1460, 1365, 1265, 1190, 1125, and 1110 cm$^{-1}$; MS (DCI) m/e 556 (MH$^+$), 425 (MH$^+$—OTBDMS).

For (Z)-1-(t-Butyldimethylsiloxy)-2-(3-carbomethoxyphenyl)-3-(4-decyloxyphenyl)-2-propene (7d): scale=2.11 mmol, yield=89%; $^1$H NMR (300 MHz, CDCl$_3$) δ7.92–8.01 (m, 2H, 2-ArH), 7.34–7.44 (m, 2H, 2-ArH), 6.87 (d, J=8 Hz, 2H, 3-ArH), 6.60–6.67 (m, 3H, 2×3-ArH and C=CH), 4.41 (d, J=1 Hz, 2H, CH$_2$OSi), 3.92 (s, 3H, CO$_2$CH$_3$), 3.86 (t, J=7 Hz, 2H, ArOCH$_2$), 1.72 (quintet, J=7 Hz, 2H, ArOCH$_2$CH$_2$), 1.20–1.42 (m, 14H, 7×CH$_2$), 0.92 (s, 9H, Si(C(CH$_3$)$_3$), 0.85 (t, J=7 Hz, 3H, CH$_3$ and 0.08 (s, 6H, Si(CH$_3$)$_2$); $^{13}$C NMR (75 MHz, CDCl$_3$) δ166.92 (C=O), 157.78, 139.75, 138.05, 134.33, 133.89, 131.38, 130.84, 130.33, 130.20, 129.71, 128.56, 128.26, 125.40, 113.95, 68.01 (CH$_2$OSi), 67.72 (ArOCH$_2$), 52.00 (CO$_2$CH$_3$), 31.75, 29.42, 29.24, 29.18, 29.09, 25.88, 25.78 (SiC(CH$_3$)$_3$), 25.58, 22.55, 18.29 (SiC(CH$_3$)$_3$), 14.00, and −4.72 (Si(CH$_3$)$_2$); IR (film) 2950, 2930, 2855, 1730 (C=O), 1605, 1510, 1470, 1440, 1390, 1360, 1290, 1250, 1200, 1175, 1110, 1005, 985, 840, 780, 755, 730, and 695 cm$^{-1}$; MS (DCI) m/e 538 (M$^+$).

For (Z)-1-(t-Butyldimethylsiloxy)-2-(3-carboethoxyphenyl)-3-(3,4-bisdecyloxyphenyl)-2-propene (7e): via procedure A, scale=1.29 mmol, yield=44%; $^1$H NMR (300 MHz, CDCl₃) δ7.92–7.96 (m, 2H, 2-ArH), 7.36–7.37 (m, 2H, 2-ArH), 6.63 (d, J=8 Hz, 1 lt, 3-ArH), 6.57 (br s, 1H, C=CH), 6.55 (dd, J=2, 8 Hz, 1H, 3-ArH), 6.38 (d, J=2 Hz, 1H, 3-ArH), 4.39 (d, J=2 Hz, 2H, CH₂OSi), 4.34 (q, J=6 Hz, 2H, CO₂CH₂), 3.89 (t, J=7 Hz, 2H, ArC⁴OCH₂), 3.48 (t, J=7 Hz, 2H, ArC³OCH₂), 1.73 (quint, J=7 Hz, 2H, ArC⁴OCH₂CH₂), 1.54–1.59 (m, 2H, ArC³OCH₂CH₂), 1.36 (t, J=6 Hz, 3H, CO₂CH₂CH₃), 1.19–1.38 (m, 28H, 14×CH₂), 0.83–0.96 (m, 15H, 2×CH₃ and SiC(CH₃)₃) and 0.06 (s, 6H, Si(CH₃)₂); ¹³C NMR (75 MHz, CDCl₃) δ166.42 (C=O), 148.15 (3-ArC), 148.00 (3-ArC), 140.01, 138.39, 133.93, 130.90, 129.97, 129.22, 128.63, 128.30, 125.81, 122.40, 114.06, 112.99, 69.04, 68.57, 68.25, 61.00 (CH₂OSi), 31.90, 29.60, 29.40, 29.36, 29.22, 29.01, 25.98, 25.91 (SiC(CH₃)₃), 25.85, 24.14, 24.03, 22.68, 18.42 (SiC(CH₃)₃), 14.30, 14.12, and −5.34 (Si(CH₃)₂); IR (film) 2955, 2925, 2855, 1720 (C=O), 1515, 1470, 1265, 1240, 1140, 1085, and 1020 cm⁻¹; MS (FAB) m/e 709 (MH⁺).

For (Z)-1-(t-Butyldimethylsiloxy)-2-(3-carboethoxyphenyl)-5-phenyl-2-pentene (7f): via procedure A, scale=1.51 mmol, yield=52%; ¹H NMR (300 MHz, CDCl₃) δ7.94 (dr, J=2, 8 Hz, 1H, 2-ArH), 7.82 (t, J=2 Hz, 1H, 2-ArH), 7.34 (t, J=8 Hz, 1H, 2-ArH), 7.08–7.26 (m, 6H, 1×2-ArH and 5×5-ArH), 5.80 (tt, J=1.5, 7.5 Hz, 1H, C=CH), 4.38 (q, J=7 Hz, 2H, CO₂CH₂), 4.28 (d, J=1.5 Hz, 2 H, CH₂OSi), 2.67 (t, J=7.5 Hz, 2H, ArCH₂), 2.26 (q, J=7.5 Hz, 2H, ArCH₂CH₂), 1.40 (t, J=7 Hz, 3H, CO₂CH₂CH₃), 0.88 (s, 9H, SiC(CH₃)₃), and 0.02 (s, 6H, Si(CH₃)₂); ¹³C NMR (75 MHz, CDCl₃) δ166.50 (C=O), 141.53, 139.75, 139.09, 133.17, 130.21, 129.60, 128.36, 128.10, 127.95, 126.51, 125.66, 67.21 (CH₂OSi), 60.83 (CO₂CH₂), 35.87, 30.17, 25.78 (SiC(CH₃)₃), 18.26 (SiC(CH₃)₃), 14.22 (CO₂CH₂CH₃), and −5.52 (Si(CH₃)₂); IR (film) 3085, 3065, 3030, 2955, 2930, 2895, 2855, 1720 (C=O), 1470, 1460, 1455, 1365, 1270, 1170, 1125, 1110, 1085, 1050, 1030, 840, 815, 775, 755, 700, and 675 cm⁻¹; MS (DCI) m/e 425 (MH⁺), 293 (M⁺—OSi[(C(CH₃)₃](CH₃)₂).

For (Z)-1-(t-Butyldimethylsiloxy)-2-(3-carbomethoxyphenyl)-5-(5,6,7,8-tetrahydro-5,5,8,8-tetramethyl-2-naphthalenyl)-2-pentene (7g): scale=1.40 mmol, yield=100%; ¹H NMR (300 MHz, CDCl₃) δ7.92 (dt, J=1, 8 Hz, 1H, 2-ArH), 7.85 (t, J=1 Hz, 1H, 2-ArH), 7.33 (t, J=8 Hz, 1H, 2-ArH), 7.12–7.17 (m, 2H, 2-ArH and 5-ArH), 7.01 (d, J=2 Hz, 1H, 5-ArH), 6.84 (dd, J=2, 8 Hz, 1H, 5-ArH), 5.81 (br t, J=7 Hz, 1H, C=CH), 4.36 (q, J=7 Hz, 2H, CO₂CH₂), 4.28 (d, J=1 Hz, 2H, CH₂OSi), 2.60 (t, J=8 Hz, 2H, ArCH₂), 2.24 (q, J=8 Hz, 2H, ArCH₂CH₂), 1.64 (s, 4H, CH₂CH₂), 1.38 (t, J=7 Hz, 3H, CO₂CH₂CH₃), 1.24 (s, 6H, 2×CH₃), 122 (s, 6H, 2'CH₃), 0.87 (s, 9H, SiC(CH₃)₃), and 0.00 (s, 6H, Si(CH₃)₂); ¹³C NMR (75 MHz, CDCl₃) δ166.64 (C=O), 144.56, 142.23, 139.63, 139.28, 138.54, 133.35, 130.28, 129.75, 128.04, 127.06, 126.40, 126.33, 125.76, 67.39 (CH₂OSi), 60.94 (CO₂CH₂), 35.74, 35.20, 35.13, 34.13, 33.92, 31.91, 31.85, 30.34, 25.91 (SiC(CH₃)₃), 18.39 (SiC(CH₃)₃), 14.35 (CO₂CH₂CH₃), and −5.36 (Si(CH₃)₂); IR (film) 2955, 2930, 2860, 1720 (C=O), 1270, 1120, 1110, and 840 cm⁻¹; MS (FAB) m/e 534 (M⁺), 533 (M—H)⁺. Anal. Calcd for C₃₄H₅₀O₃Si: C, 76.35; H, 9.42. Found: C, 76.78; H, 9.40.

For (2Z),(4E)-1-(t-Butyldimethylsiloxy)-2-(3-carboethoxyphenyl)-5-(5,6,7,8-tetrahydro-5,5,8,8-tetramethyl-2-naphthalenyl)-2,4-hexadiene (7h): via procedure A, scale=2.04 mmol, yield=34%; ¹H NMR (300 MHz, CDCl₃) δ7.95 (d, J=2 Hz, 1H, 2-ArH), 7.94 (dt, J=2, 8 Hz, 1H, 2-ArH), 7.36–7.45 (m, 2H, 2-ArH), 7.22 (d, J=2 Hz, 1H, 5-ArH), 7.15 (d, J=8 Hz, 1H, 5-ArH), 7.04 (dd, J=2, 8 Hz, 1H, 5-ArH), 6.80 (br d, J=12 Hz, 1H, C=CH), 6.37 (br d, J=12 Hz, 1H, C=CH), 4.46 (s, 2H, CH2OSi), 4.35 (q, J=7 Hz, 2H, CO₂CH₂), 2.20 (s, 3H, C=CCH₃), 1.62 (br s, 4H, CH₂CH₂), 1.36 (t, J=7 Hz, 3H, CO₂CH₂CH₃), 1.20 (s, 6H, 2×CH₃), 119 (s, 6H, 2×CH₃), 0.91 (s, 9H, Si(C(CH₃)₃), and 0.07 (s, 6H, Si(CH₃)₂); ¹³C NMR (75 MHz, CDCl₃) δ166.56 (C=O), 144.48, 143.88, 140.48, 140.42, 139.07, 137.49, 133.76, 130.42, 129.92, 128.35, 128.11, 126.31, 123.77, 123.06, 123.00, 122.60, 67.14 (CH₂OSi), 60.98 (CO₂CH₂), 35.12, 35.00, 34.24, 34.04, 31.74, 25.90 (SiC(CH₃)₃), 18.36 (SiC(CH₃)₃), 16.00 (C=CCH₃), 14.32 (CO₂CH₂CH₃), and −5.32 (Si(CH₃)₂); IR (film) 2960, 2930, 2860, 1720 (C=O), 1470, 1460, 1390, 1365, 1260, 1215, 1110, 1085,840, 780, and 755 cm⁻¹; MS (DCI) m/e 546 (M⁺), 415 (M⁺—OSi[(C(CH₃)₃](CH₃)₂).

For (Z)-1-(t-Butyldimethylsiloxy)-2-(3-carbomethoxyphenyl)-5-[4-(1-adamantyl)-3-methoxyphenyl]-2-pentene (7i): via procedure B, scale=3.81 mmol, yield=25%; ¹H NMR (300 MHz, CDCl₃) δ7.91 (dr, J=2, 8 Hz, 1H, 2-ArH), 7.83 (t, J=2 Hz, 1H, 2-ArH), 7.31 (t, J=8 Hz, 1H, 2-ArH 7.14 (dt, J=2, 8 Hz, 1H, 2-ArH), 7.04 (d, J=8 Hz, 1H, 3-ArH), 6.63 (dd, J=2, 8 Hz, 1H, 3-ArH), 6.55 (d, J=2 Hz, 1H, 3-ArH), 5.79 (br t, J=8 Hz, 1H, C=CH), 4.26 (d, J=2 Hz, 2H, CH₂OSi), 3.90 (s, 3H, CO₂CH₃), 3.73 (s, 3H, OCH₃), 2.60 (t, J=8 Hz, 2H, ArCH₂), 2.24 (q, J=8 Hz, 2H, ArCH₂CH₂), 2.04 (br s, 9H, adamantyl), 1.74 (br s, 6H, adamantyl), 0.86 (s, 9H, SiC(CH₃)₃), and −0.01 (s, 6H, Si(CH₃)₂); ¹³C NMR (75 MHz, CDCl₃) δ137.11 (C=O), 158.64, 140.29, 139.67, 139.30, 136.01, 133.50, 129.92, 129.78, 128.08, 126.87, 126.20, 120.34, 112.00, 67.32 (CH₂OSi), 54.86 (OCH₃), 52.09 (CO₂CH₃), 40.67, 37.15, 36.62, 35.65, 30.20, 29.11, 25.88 (SiC(CH₃)₃), and 18.38 (SiC(CH₃)₃); IR (film) 2950, 2930, 2905, 2850, 1725 (C=O), 1460, 1455, 1440, 1410, 1280, 1260, 1160, and 1120 cm⁻¹; MS (DCI) m/e 575 (MH⁺), 574 (M⁺), 573 (M—H)⁺, and 443 (MH⁺—OSi[(C(CH₃)₃](CH₃)₂).

For (Z)-1-(t-Butyldimethylsiloxy)-2-(3-carboethoxyphenyl)-5-[3-(1-adamantyl)-4-t-butyldimethylsiloxyphenyl]-2-pentene (7j): via procedure A, scale=3.6 mmol. Column chromatography on silica gel afforded 1.6 g of a ca. 1:1 mixture of 7j (3:1, Z:E) and 1-(t-butyldimethylsiloxy)-2-phenyl-5-[3-(1-adamantyl)-4-t-butyldimethylsiloxyphenyl]-2-pentene (3:1, Z:E). Separate fractions were pooled and concentrated to give 0.800 g (36%) of the latter compound, 1-(t-butyldimethylsiloxy)-2-phenyl-5-[3-(1-adamantyl)-4-t-butyldimethylsiloxyphenyl]-2-pentene (3:1, Z:E): ¹H NMR (300 MHz, CDCl₃) δ(Z-isomer) 7.20–7.32 (m, 3H, 2-ArH), 7.04–7.07 (m, 2H, 2-ArH), 6.94 (d, J=2 Hz, 1H, 5-ArH), 6.77 (dd, J=2, 8 Hz, 1H, 5-ArH), 6.66 (d, J=8 Hz, 1H, 5-ArH), 5.77 (t, J=7 Hz, 1H, C=CH), 4.28 (d, J=1H, 2H, CH₂OSi), 2.58 (t, J=7 Hz, 2H, ArCH₂), 2.26 (q, J=7 Hz, 2H, ArCH₂CH₂), 2.08 (m, 9H, adamantyl), 1.76 (s, 6H, adamantyl), 1.03 (s, 9H, SiC(CH₃)₃), 0.89 (s, 9H, SiC(CH₃)₃), 0.32 (s, 6H, Si(CH₃)₂), and 0.02 (s, 6H, Si(CH₃)2); (E-isomer, partially obscured) 7.40 (m, 1H, 2-ArH), 6.90 (dd, J=2, 8 Hz, 1H, 5-ArH), 6.72 (d, J=8 Hz, 1H, 5-ArH), 5.88 (t, J=7 Hz, 1H, C=CH), 4.41 (s, 2H, CH₂OSi), 2.69 (t, J=7 Hz, 2H, ArCH₂), 1.04 (s, 9H, SiC(CH₃)₃), 0.84 (s, 9H, SiC(CH₃)₃), 0.34 (s, 6H, Si(CH₃)₂), and 0.02 (s, 6H, Si(CH₃)₂); IR (film) 2955, 2930, 2905, 2855, 1490, 1255, and 840 cm⁻¹; MS (FAB)

m/e 617 (MH+), 616 (M+). Anal. Calcd for C$_{39}$H$_{60}$O$_2$-Si$_2$: C, 75.91; H, 9.80. Found: C, 75.62; H, 9.77.

For (Z)-1-(t-Butyldimethylsiloxy)-2-(3-carbomethoxyphenyl)-3-(3,4-bispentyloxyphenyl)-2-propene (7k): via procedure B, scale=1.33 mmol, yield=84%; $^1$H NMR (300 MHz, CDCl$_3$) δ7.91–7.95 (m, 2H, 2-ArH), 7.36–7.38 (m, 2H, 2-ArH), 6.63 (d, J=8 Hz, 1H, 3-ArH), 6.62 (br s, J=1.5 Hz, 1H, C=CH), 6.56 (dd, J=2, 8 Hz, 1H, 3-ArH), 6.37 (d, J=2 Hz, 1H, 3-ArH), 4.35 (d, J=1.5 Hz, 2H, CH$_2$OSi), 3.89 (t, J=6.5 Hz, 2H, ArOCH$_2$), 3.88 (s, 3H, CO$_2$CH$_3$), 3.47 (t, J=6.5 Hz, 2H, ArOCH$_2$), 1.70–1.79 (m, 2H, ArOCH$_2$CH$_2$), 1.55–1.60 (m, 2H, ArOCH$_2$CH$_2$), 1.24–1.41 (m, 8 H, 2×CH$_2$), 0.85–0.91 (m, 15H, 2×CH$_3$ and Si(C(CH$_3$)$_3$), and 0.05 (Si(CH$_3$)$_2$); $^{13}$C NMR (75 MHz, CDCl$_3$) δ166.89 (C=O), 148.15, 148.00, 140.09, 138.34, 134.08, 130.57, 130.01, 129.20, 128.69, 128.33, 125.81, 122.42, 114.03, 112.97, 69.01 (ArOCH$_2$), 68.53 (CH$_2$OSi), 68.19 (ArOCH$_2$), 52.11 (CO$_2$CH$_3$), 28.89, 28.66, 28.15, 28.01, 25.91 (SiC(CH$_3$)$_3$), 22.44, 22.36, 18.42 (SiC(CH$_3$)$_3$), 14.02 and −5.34 (Si(CH$_3$)$_2$); IR (film) 2955, 2930, 2860, 1725 (C=O), 1515, 1470, 1435, 1265, 1205, 1170, 1140, 1080, 1050, 1005, 840, and 780 cm$^{-1}$; MS (DCI) m/e 554 (MH+), 423 (M+—OSi[C(CH$_3$)$_3$](CH$_3$)$_2$).

Example 7: General Procedure for Synthesis of 8

Ester 7 was dissolved in a mixture of acetic acid/tetrahydrofuran/water (3:2:1, 0.03M) and stirred at room temperature for 12–40 h. The mixture was then concentrated in vacuo and the residue was purified by column chromatography (20:1 to 30:1 ratio of silica gel/crude product; elution with 10% to 20% ethyl acetate in hexanes).

For (Z)-2-(3-Carboethoxyphenyl)-3-phenyl-2-propenol (8a): scale=1.09 mmol, yield=94%; $^1$H NMR (300 MHz, CDCl$_3$) δ7.93–7.98 (m, 2H, 2-ArH), 7.34–7.38 (m, 2H, 2-ArH), 7.07–7.10 (m, 3H, 3-ArH), 6.93–6.98 (m, 2H, 3-ArH), 6.73 (s, 1H, C=CH), 4.47 (d, J=5 Hz, 2H, CH$_2$OH), 4.34 (q, J=7 Hz, 2H, CO$_2$CH$_2$), 1.73 (t, J=5 Hz, 1H, OH, exch), and 1.35 (t, J=7 Hz, 3H, CO$_2$CH$_2$CH$_3$); $^{13}$C NMR (75 MHz, CDCl$_3$) δ166.42 (C=O), 140.45, 138.90, 136.03, 133.74, 131.06, 129.55, 129.22, 128.83, 128.73, 128.07, 127.42, 127.04, 68.37 (CH$_2$OH), 61.09 (CO$_2$CH$_2$), and 14.30 (CO$_2$CH$_2$CH$_3$); IR (film) 3400 (br, OH), 2980, 1720, 1370, 1265, 1195, 1110, 1090, 1022, 760, and 700 cm$^{-1}$; MS (DCI) m/e 282 (MH+).

For (Z)-2-(3-Carboethoxyphenyl)-3-(5,6,7,8-tetrahydro-5,5,8,8-tetramethyl-2-naphthalenyl)-2-propenol (8b): scale=3.35 mmol, yield=91%; $^1$H NMR (300 MHz, CDCl$_3$) δ7.94–7.99 (m, 2H, 2-ArH), 7.37–7.44 (m, 2H, ArH), 7.05 (d, J=8 Hz, 1H, 3-ArH), 6.86 (d, J=2 Hz, 1H, 3-ArH), 6.76 (dd, J=2, 8 Hz, 1H, 3-ArH), 6.65 (s, 1H, C=CH), 4.45 (s, 2H, CH$_2$OH), 4.33 (q, J=7 Hz, 2H, CO$_2$CH$_2$), 1.51–1.59 (m, 5H, CH$_2$CH$_2$ and OH, exch), 1.32 (t, J=7 Hz, 3H, CO$_2$CH$_2$CH$_3$), 1.17 (s, 6H, 2×CH$_3$), and 0.93 (s, 6H, 2×CH$_3$); $^{13}$C NMR (75 MHz, CDCl$_3$) δ166.42 (C=O), 144.35, 144.05, 139.47, 139.26, 133.71, 132.83, 131.13, 129.76, 128.92, 128.58, 127.76, 127.47, 126.63, 126.28, 68.78 (CH$_2$OH), 61.02 (CO$_2$CH$_2$), 34.92, 34.03, 33.88, 31.65, 31.44, 27.92, and 14.32 (CO$_2$CH$_2$CH$_3$); IR (film) 3100–3400 (br, OH), 2960, 2925, 2860, 1720 (C=O), 1460, 1365, 1285, 1265, 1200, 1110, 1085, 755, and 750 cm$^{-1}$; MS (DCI) m/e 392 (M+), 375 (M+—OH).

For (Z)-2-(3-Carboethoxyphenyl)-3-(5,6,7,8-tetrahydro-5,5,8,8-tetramethyl-2-anthracenyl)-2-propenol (8c): scale=0.95 mmol, yield=97%; $^1$H NMR (300 MHz, CDCl$_3$) δ7.95–7.99 (m, 2H, ArH), 7.59 (d, J=12 Hz, 2H, ArH), 7.47 (s, 1H, ArH), 7.29–7.40 (m, 3H, ArH), 6.88 (br s, 1H, C=CH), 6.82 (dd, J=1, 9 Hz, 1H, ArH), 4.53 (dd, J=1, 6 Hz, 2H, CH$_2$OH), 4.34 (q, J=7 Hz, 2H, CO$_2$CH$_2$), 1.72 (s, 4H, CH$_2$CH$_2$), and 1.31–1.36 (m, 15 H, 4×CH$_3$ and CO$_2$CH$_2$CH$_3$); $^{13}$C NMR (75 MHz, CDCl$_3$) δ166.47 (C=O), 144.62, 144.55, 139.96, 138.98, 134.08, 132.84, 131.64, 131.08, 130.81, 129.53, 128.76, 128.22, 128.08, 126.58, 125.98, 124.98, 124.56, 68.52 (CH$_2$OH), 61.07 (CO$_2$CH$_2$), 35.04 (CH$_2$CH$_2$), 34.56, 34.52, 32.46 (4×CH$_3$), and 14.27 (CO$_2$CH$_2$CH$_3$); IR (KBr) 3400 (br, OH), 2960, 2930, 2860, 1720 (C=O), 1465, 1385, 1365, 1270, 1210, 1190, 1110, 1085, and 1020 cm$^{-1}$; MS (DCI) m/e 443 (MH+), 425 (MH+—OH).

For (Z)-2-(3-Carboethoxyphenyl)-3-(4-decyloxyphenyl)-2-propenol (8d): scale=1.86 mmol, yield=94%; $^1$H NMR (300 MHz, CDCl$_3$) δ7.96–8.00 (m, 2H, 2-ArH), 7.34–7.43 (m, 2H, 2-ArH), 6.88 (d, J=8 Hz, 2H, 3-ArH), 6.67 (s, 1H, C=CH), 6.63 (d, J=8 Hz, 2H, 3-ArH), 4.46 (br s, 2H, CH$_2$OH), 3.90 (s, 3H, CO$_2$CH$_3$), 3.86 (t, J=7 Hz, 2H, ArOCH$_2$), 1.72 (quintet, J=7 Hz, 2H, ArOCH$_2$CH$_2$), 1.20–1.45 (m, 14H, 7×CH$_2$), and 0.87 (t, J=7 Hz, 3H, CH$_3$); $^{13}$C NMR (75 MHz, CDCl$_3$) δ166.96 (C=O), 158.22, 139.39, 138.19, 133.98, 130.78, 130.45, 129.69, 128.92, 128.64, 128.25, 127.39, 114.05, 68.74 (CH$_2$OH), 67.88 (ArOCH$_2$), 52.19 (CO$_2$CH$_3$), 31.89, 29.56, 29.37, 29.31, 29.21, 26.01, 22.69, and 14.14; IR (film) 3400 (br, OH), 2925, 2855, 1725 (C=O), 1605, 1510, 1470, 1440, 1390, 1290, 1270, 1250, 1200, 1180, 1110, 1090, 1020, 980, 885, 825, 755, 710, and 700 cm$^{-1}$; MS (DCI) m/e 424 (M+), 407 (M+—OH).

For (Z)-2-(3-Carboethoxyphenyl)-3-(3,4-bisdecyloxyphenyl)-2-propenol (8e): scale=0.53 mmol, yield=96%; $^1$H NMR (300 MHz, CDCl$_3$) δ7.94–7.97 (m, 2H, 2-ArH), 7.33–7.43 (m, 2H, 2-ArH), 6.63 (d, J=8 Hz, 1H, 3-ArH), 6.62 (s, 1H, C=CH), 6.56 (dd, J=2, 8 Hz, 1H, 3-ArH), 6.40 (d, J=2 Hz, 1H, 3-ArH), 4.44 (d, J=6 Hz, 2H, CH$_2$OH), 4.34 (q, J=7 Hz, 2H, CO$_2$CH$_2$), 3.89 (t, J=7 Hz, 2H, ArC$^4$OCH$_2$), 3.49 (t, J=7 Hz, 2H, ArC$^3$OCH$_2$), 1.74 (quint, J=7 Hz, 2H, ArC$^4$OCH$_2$CH$_2$), 1.55–1.61 (m, 2H, ArC$^3$OCH$_2$CH$_2$), 1.36 (t, J=7 Hz, 3H, CO$_2$CH$_2$CH$_3$), 1.21–1.38 (m, 28H, 14×CH$_2$), and 0.83–0.89 (m, 6H, 2×CH$_3$); $^{13}$C NMR (75 MHz, CDCl$_3$) δ166.32 (C=O), 148.32 (3-ArC), 148.20 (3-ArC), 139.50, 138.32, 133.87, 131.17, 129.79, 128.87, 128.68, 128.54, 127.54, 122.53, 114.06, 112.93, 69.01, 68.76, 68.61, 61.07 (CO$_2$CH$_2$), 31.91, 29.60, 29.34, 29.19, 28.99, 25.97, 25.85, 22.68, 14.30, and 14.12; IR (KBr) 3500 (br, OH), 2960, 2920, 2850, 1720 (C=O), 1705 (C=O), 1515, 1295, 1265, 1235, and 1140 cm$^{-1}$; MS (FAB) m/e 595 (MH+).

For (Z)-2-(3-Carboethoxyphenyl)-5-phenyl-2-pentenol (8f): scale=0.78 mmol, yield=99%; $^1$H NMR (300 MHz, CDCl$_3$) δ7.95 (dt, J=2, 8 Hz, 1H, 2-ArH), 7.83 (t, J=2 Hz, 1H, 2-ArH), 7.39 (t, J=8 Hz, 1H, 2-ArH 7.07–7.27 (m, 6H, 1×2-ArH and 5×5-ArH), 5.81 (t, J=7.5 Hz, 1H, C=CH), 4.37 (q, J=7 Hz, 2H, CO$_2$CH$_2$), 4.28 (s, 2H, CH$_2$OH), 2.67 (t, J=7.5 Hz, 2H, ArCH$_2$), 2.31 (q, J=7.5 Hz, 2H, ArCH$_2$CH$_2$), and 1.39 (t, J=7 Hz, 3H, CO$_2$CH$_2$CH$_3$); $^{13}$C NMR (75 MHz, CDCl$_3$) δ166.40 (C=O), 141.27, 140.12, 138.53, 133.01, 130.48, 129.43, 128.57, 128.31, 128.24, 128.17, 125.78, 67.73 (CH$_2$OH), 60.93 (CO$_2$CH$_2$), 35.73, 30.26, and 14.22 (CO$_2$CH$_2$CH$_3$); IR (film) 3420 (br, OH), 3085, 3060, 3025, 2980, 2930, 2860, 1720 (C=O), 1495, 1455, 1390, 1370, 1280, 1225, 1170, 1110, 1085, 1020, 1000, 755, 700, and 675 cm$^{-1}$; MS (DCI) m/e 311 (MH+), 293 (M+—OH).

For (Z)-2-(3-Carbethoxyphenyl)-5-(5,6,7,8-tetrahydro-5,5,8,8-tetramethyl-2-naphthalenyl)-2-pentenol (8g): scale=1.3 mmol, yield=84%; $^1$H NMR (300 MHz, CDCl$_3$) δ7.94 (d, J=8 Hz, 1H, 2-ArH), 7.88 (s, 1H, 2-ArH), 7.36 (t, J=8 Hz, 1H, 2-ArH), 7.15–7.28 (m, 2H, 2-ArH and 5-ArH), 7.00 (s, 1H, 5-ArH), 6.84 (d, J=8 Hz, 1H, 5-ArH), 5.83 (t, J=7 Hz, 1H, C=CH), 4.32–4.40 (m, 4H, CO$_2$CH$_2$CH$_3$ and CH$_2$OH), 2.64 (t, J=7 Hz, 2H, ArCH$_2$), 2.27 (q, J=7 Hz, ArCH$_2$CH$_2$), 1.65 (s, 4H, CH$_2$CH$_2$), 1.38 (t, J=7 Hz, 3H, CO$_2$CH$_2$CH$_3$), 1.24 (s, 6H, 2×CH$_3$), and 1.22 (s, 6H, 2×CH$_3$); $^{13}$C NMR (75 MHz, CDCl$_3$) δ166.54 (C=O), 144.63, 142.38, 139.99, 138.76, 138.31, 133.20, 130.55, 129.58, 129.35, 129.08, 128.33, 126.42, 125.72, 67.85 (CH$_2$OH), 61.03 (CO$_2$CH$_2$CH$_3$), 35.66, 35.18, 35.12, 34.14, 33.94, 31.91, 31.86, 30.51, and 14.36 (CO$_2$CH$_2$CH$_3$); IR (film) 3410 (OH), 2960, 2925, 2860, 1720 (C=O), 1270, 1025, and 755 cm$^{-1}$; MS (DCI) m/e 421 (MH$^+$), 403, 201; Exact mass spectrum (FAB) Calcd for C$_{28}$H$_{36}$O$_3$Na (MNa$^+$): 443.2562. Found: 443.2544.

For (2Z),(4E)-2-(3-Carbethoxyphenyl)-5-(5,6,7,8-tetrahydro-5,5,8,8-tetramethyl-2-naphthalenyl)-2,4-hexadienol (8h): scale=0.64 mmol, yield=93%; $^1$H NMR (300 MHz, CDCl$_3$) δ8.04 (d, J=2 Hz, 1H, 2-ArH), 7.99 (dt, J=2, 8 Hz, 1H, 2-ArH), 7.52 (dt, J=2, 8 Hz, 1H, 2-ArH), 7.44 (t, J=8 Hz, 1H, 2-ArH), 7.25 (d, J=2 Hz, 1H, 5-ArH), 7.20 (d, J=8 Hz, 1H, 5-ArH), 7.10 (dd, J=2, 8 Hz, 1H, 5-ArH), 6.80 (br d, J=12 Hz, 1H, C=CH), 6.37 (br d, J=12 Hz, 1H, C=CH), 4.46 (br d, J=6 Hz, 2H, CH$_2$OH), 4.39 (q, J=7 Hz, 2H, CO$_2$CH$_2$), 2.23 (s, 3H, C=CCH$_3$), 1.65 (br s, 4H, CH$_2$CH$_2$), 1.39 (t, J=7 Hz, 3H, CO$_2$CH$_2$CH$_3$), 1.25 (t, J=6 Hz, 1H, OH), 1.23 (s, 6H, 2×CH$_3$), and 1.21 (s, 6H, 2×CH$_3$).

For (Z)-2-(3-Carbomethoxyphenyl)-5-[4-(1-adamantyl)-3-methoxyphenyl]-2-pentenol (8i): scale=0.96 mmol, yield=98%; $^1$H NMR (300 MHz, CDCl$_3$) δ 7.93 (dt, J=2, 8 Hz, 1H, 2-ArH), 7.86 (t, J=2 Hz, 1H, 2-ArH), 7.37 (t, J=8 Hz, 1H, 2-ArH), 7.19 (dt, J=2, 8 Hz, 1H, 2-(ArH), 7.05 (d, J=8 Hz, 1H, 3-ArH), 6.62 (dd, J=2, 8 Hz, 1H, 3-ArH), 6.54 (d, J=2 Hz, 1H, 3-ArH), 5.81 (t, J=8 Hz, 1H, C=CH), 4.30 (br s, 2H, CH$_2$OH), 3.90 (s, 3H, CO$_2$CH$_3$), 3.73 (s, 3H, OCH$_3$), 2.61 (t, J=8 Hz, 2H, ArCH$_2$), 2.28 (q, J=8 Hz, 2H, ArCH$_2$CH$_2$), 2.04 (br s, 9H, adamantyl), and 1.73 (br s, 6H, adamantyl); $^{13}$C NMR (75 MHz, CDCl$_3$) δ166.00 (C=O), 158.66, 140.03, 138.74, 136.17, 133.31, 130.20, 129.64, 129.07, 128.40, 128.35, 126.25, 120.28, 111.95, 67.89 (CH$_2$OH), 54.89 (OCH$_3$), 52.17 (CO$_2$CH$_3$), 40.65, 37.13, 36.65, 35.52, 30.31, 29.70, and 29.08; IR (film) 3400 (br, OH), 2905, 2850, 1725 (C=O), 1450, 1440, 1410, 1285, 1270, 1245, and 1110 cm$^{-1}$; MS (DCI) m/e 461 (MH$^+$), 460 (M$^+$), 459 (M—H)$^+$, and 443 (MH$^+$—H$_2$O).

For (Z)-2-(3-Carbethoxyphenyl)-5-[3-(1-adamantyl)-4-methoxyphenyl]-2-pentenol (8j). A ~1:1 mixture of 7j (3:1, Z:E) and 1-(t-butyldimethylsiloxy)-2-phenyl-5-[3-(1-adamantyl)-4-t-butyldimethylsiloxyphenyl]-2-pentene (3:1, Z:E) (1.6 g) was dissolved in 30 mL of 3:1:1 acetic acid/THF/H$_2$O, and stirred for 48 h. The solvent was removed in vacuo. The residue was purified by column chromatography on silica gel (elution with methylene chloride to 5% methanol/methylene chloride) to give 0.490 g of pure (Z)-2-(3-carboethoxyphenyl)-5-[3-(1-adamantyl)-4-t-butyldimethylsiloxyphenyl]-2-pentenol (74% based on ca. 800 mg of 7j in the starting mixture): $^1$H NMR (300 MHz, CDCl$_3$) δ7.96 (dt, J=8, 1 Hz, 1H, 2-ArH), 7.89 (t, J=1 Hz, 1H, 2-ArH), 7.38 (t, J=8 Hz, 1H, 2-ArH), 7.22 (m, 1H, 2-ArH), 6.91 (d, J=2 Hz, 1H, 5-ArH), 6.77 (dd, J=2, 8 Hz, 1H, 5-ArH), 6.63 (d, J=8 Hz, 1H, 5-ArH), 5.82 (t, J=8 Hz, 1H, C=CH), 4.23–4.40 (m, 4H, CH$_2$OH and CO$_2$CH$_2$CH$_3$), 2.59 (t, J=8 Hz, 2H, ArCH$_2$), 2.26 (q, J=8 Hz, 2H, ArCH$_2$CH$_2$), 2.08 (s, 9H, adamantyl), 1.76 (s, 6H, adamantyl), 1.39 (t, J=8 Hz, 3H, CO$_2$CH$_2$CH$_3$), 1.01 (s, 9H, SiC(CH$_3$)$_3$), and 0.31 (s, 6H, Si(CH$_3$)$_2$). (Z)-2-(3-Carboethoxyphenyl)-5-[3-(1-adamantyl)-4-t-butyldimethylsiloxyphenyl]-2-pentenol (490 mg) was converted in two steps to 8j via treatment with tetrabutylammonium fluoride and then alkylation with dimethyl sulfate as described in the synthesis of 5X. Purification of 8j by column chromatography on silica gel (elution with 30% ethyl acetate/hexane) gave 0.150 g of pure 8j (37% for two steps): $^1$H NMR (300 MHz, CDCl$_3$) δ7.96 (dt, J=1, 8 Hz, 1H, 2-ArH), 7.89 (t, J=1 Hz, 1H, 2-ArH), 7.39 (t, J=8 Hz, 1H, 2-ArH), 7.28 (m, 1H, 2-ArH), 6.92 (d, J=2 Hz, 1H, 5-ArH), 6.89 (dd, J=2, 8 Hz, 1H, 5- ArH), 6.76 (d, J=8 Hz, 1H, 5-ArH), 5.83 (t, J=8 Hz, 1H, C=CH), 4.33–4.42 (m, 4H, CH$_2$OH and CO$_2$CH$_2$CH$_3$), 3.80 (s, 3H, OCH$_3$), 2.61 (t, J=8 Hz, 2H, ArCH$_2$), 2.29 (q, J=8 Hz, 2H, ArCH$_2$CH$_2$), 2.06 (s, 9H, adamantyl), 1.76 (s, 6H, adamantyl), and 1.40 (t, J=8 Hz, 3H, CO$_2$CH$_2$CH$_3$).

For (Z)-2-(3-Carbomethoxyphenyl)-3-(3,4-bispentyloxyphenyl)-2-propenol (8k): scale=1.08 mmol, yield=96%; $^1$H NMR (300 MHz, CDCl$_3$) δ7.94–7.97 (m, 2H, 2-ArH), 7.36–7.44 (m, 2H, 2-ArH), 6.64 (d, J=8 Hz, 1H, 3-ArH), 6.63 (br s, 1H, C=CH), 6.57 (dd, J=2, 8 Hz, 1H, 3-ArH), 6.39 (d, J=2 Hz, 1H, 3-ArH), 4.35 (dd, J=1.5, 6 Hz, 2H, CH$_2$OH), 3.90 (t, J=6.5 Hz, 2H, ArOCH$_2$), 3.87 (s, 3H, CO$_2$CH$_3$), 3.48 (t, J=6.5 Hz, 2H, ArOCH$_2$), 1.70–1.79 (m, 2H, ArOCH$_2$CH$_2$), 1.63 (t, J=6 Hz, 1H, OH), 1.55–1.65 (m, 2H, ArOCH$_2$CH$_2$), 1.22–1.44 (m, 8H, 4×CH$_2$), and 0.88 (t, J=7 Hz, 6H, 2×CH$_3$); $^{13}$C NMR (75 MHz, CDCl$_3$) δ166.80 (C=O), 148.33, 148.20, 139.61, 138.28, 134.00, 130.82, 129.85, 128.92, 128.67, 128.57, 127.59, 122.57, 114.04, 112.93, 68.99, 68.74, 68.58, 52.17 (CO$_2$CH$_3$), 28.88, 28.66, 28.15, 28.01, 22.44, 22.36, and 14.02; IR (film) 3430 (br, OH), 2955, 2935, 2870, 1725 (C=O), 1510, 1470, 1440, 1265, 1235, 1205, 1170, 1140, 1110, 1090, 1020, and 760 cm$^{-1}$; MS (DCI) m/e 441 (MH$^+$), 423 (M$^+$—OH).

Example 8: General Procedure for Synthesis of 9

Manganese dioxide (5:1 weight ratio MnO$_2$/alcohol) was added in one portion to a solution of alcohol 8 in methylene chloride (0.1M). The reaction mixture was stirred in a stoppered flask at room temperature for 4–18 h. Additional MnO$_2$ was added if necessary to take the reaction to completion. The brown slurry was filtered through a one-inch pad of Celite and the collected solid was washed with methylene chloride. The filtrate was concentrated in vacuo, and the aldehyde product was used without purification.

For (Z)-2-(3-Carboethoxyphenyl)-3-phenyl-2-propenal (9a): scale=0.96 mmol, yield=85%; $^1$H NMR (300 MHz, CDCl$_3$) δ9.80 (s, 1H, CHO), 8.07–8.11 (dt, J=2, 8 Hz, 1H, 2-ArH), 7.88 (t, J=2 Hz, 1H, 2-ArH), 7.15–7.50 (m, 8H, ArH), 4.35 (q, J=7 Hz, 2H, CO$_2$CH$_2$), and 1.35 (t, J=7 Hz, 3H, CO$_2$CH$_2$CH$_3$).

For (Z)-2-(3-Carboethoxyphenyl)-3-(5,6,7,8-tetrahydro-5,5,8,8-tetramethyl-2-naphthalenyl)-2-propenal (9b): scale=2.13 mmol, yield=90%; $^1$H NMR (300 MHz, CDCl$_3$) δ9.78 (s, 1H, CHO), 8.09 (dt, J=2, 8 Hz, 1H, 2-ArH), 7.92 (t, J=2 Hz, 1H, 2-ArH), 7.55 (t, J=8 Hz, 1H, 2-ArH), 7.38–7.43 (m, 2H, ArH and C=CH), 7.20 (d, J=8 Hz, 1H, 3-ArH), 7.12 (d, J=2 Hz, 1H, 3-ArH), 6.97 (dd, J=2, 8 Hz, 1H, 3-ArH), 4.36 (q, J=7 Hz, 2H, CO$_2$CH$_2$), 1.60 (br s, 4H, CH$_2$CH$_2$), 1.35 (t, J=7 Hz, 3H, CO$_2$CH$_2$CH$_3$), 1.22 (s, 6H, 2×CH$_3$), and 0.98 (s, 6H, 2×CH$_3$).

For (Z)-2-(3-Carboethoxyphenyl)-3-(5,6,7,8-tetrahydro-5,5,8,8-tetramethyl-2-anthracenyl)-2-propenal (9c): scale=0.89 mmol, yield=88%; $^1$H NMR (300 MHz, CDCl$_3$) δ9.80 (s, 1H, CHO), 8.08 (dr, J=2, 8 Hz, 1H, 2-ArH), 7.93 (t, J=2 Hz, 1H, 2-ArH), 7.74 (s, 1H, ArH or C=H), 7.66 (s, 2H, ArH), 7.57 (s, 1H, ArH or C=CH), 7.36–7.49 (m, 3H, ArH), 6.92 (dd, J=2, 9 Hz, 1H, ArH), 4.33 (q, J=7 Hz, 2H, CO$_2$CH$_2$), 1.73 (s, 4H, CH$_2$CH$_2$), and 1.31–1.41 (m, 15H, 4×CH$_3$ and OCH$_2$CH$_3$); $^{13}$C NMR (75 MHz, CDCl$_3$) δ193.57 (CH=O), 166.32 (C=O), 151.49, 146.93, 145.45, 140.18, 134.18, 133.89, 132.32, 132.11, 131.33, 131.15, 130.79, 130.55, 129.51, 128.86, 127.35, 125.90, 125.33, 124.88, 61.09 (CO$_2$CH$_2$), 34.88 (CH$_2$CH$_2$), 34.78, 34.60, 32.43 and 32.39 (4×CH$_3$), and 14.28 (CO$_2$CH$_2$CH$_3$); IR (KBr) 2960, 2930, 1720 (ester C=O), 1685 (CH=O), 1470, 1365, 1270, 1210, 1190, 1110, and 1090 cmA; MS (DCI) m/e 441 (MH+).

For (Z)-2-(3-Carboethoxyphenyl)-3-(4-decyloxyphenyl)-2-propenal (9d): scale=1.70 mmol, yield=80%; $^1$H NMR (300 MHz, CDCl$_3$) δ9.72 (s, 1H, CHO), 8.08 (dt, J=2, 8 Hz, 1H, 2-ArH), 7.91 (t, J=2 Hz, 1H, 2-ArH), 7.51 (t, J=8 Hz, 1H, 2-ArH), 7.39 (dr, J=2, 8 Hz, 1H, 2-ArH), 7.37 (s, 1H, C=CH), 7.12 (d, J=8 Hz, 2H, 3-ArH), 6.72 (d, J=8 Hz, 2H, 3-ArH), 3.92 (t, J=7 Hz, 2H, ArOCH$_2$), 3.90 (s, 3H, CO$_2$CH$_3$), 1.75 (quintet, J=7 Hz, 2H, ArOCH$_2$CH$_2$), 1.20–1.46 (m, 14H, 7×CH$_2$), and 0.87 (t, J=7 Hz, 3H, CH$_3$).

For (Z)-2-(3-Carboethoxyphenyl)-3-(3,4-bisdecyloxyphenyl)-2-propenal (9e): scale=0.46 mmol, yield=93%; $^1$H NMR (300 MHz, CDCl$_3$) δ9.70 (s, 1H, CHO), 8.05 (dt, J=2, 8 Hz, 1H, 2-ArH), 8.03 (t, J=2 Hz, 1H, 2-ArH), 7.50 (t, J=8 Hz, 1H, 2-ArH), 7.39 (dt, J=2, 8 Hz, 1H, 2-ArH), 7.33 (s, 1H, C—CH), 6.87 (dd, J=2, 8 Hz, 1H, 3-ArH), 6.73 (d, J=8 Hz, 1H, 3-ArH), 6.55 (d, J=2 Hz, 1H, 3-ArH), 4.33 (q, J=6 Hz, 2H, CO$_2$CH$_2$), 3.95 (t, J=7 Hz, 2H, ArC$^4$OCH$_2$), 3.45 (t, J=7 Hz, 2H, ArC$^3$OCH$_2$), 1.77 (quint, J=7 Hz, 2H, ArC$^4$OCH$_2$CH$_2$), 1.55–1.60 (m, 2 H, ArC$^3$OCH$_2$CH$_2$), 1.35 (t, J=6 Hz, 3H, CO$_2$CH$_2$CH$_3$), 1.19–1.40 (m, 28H, 14×CH$_2$), and 0.83–0.88 (m, 6H, 2×CH$_3$); $^{13}$C NMR (75 MHz, CDCl$_3$) δ193.45 (CH=O), 166.14 (C=O), 151.46, 151.17, 148.36, 139.63, 134.55, 134.15, 131.28, 130.79, 129.24, 129.00, 126.27, 126.01, 114.42, 112.32, 68.91, 68.57, 61.09 (CO$_2$CH$_2$), 31.91, 29.57, 29.33, 28.98, 28.85, 25.91, 25.78, 22.68, 14.30, and 14.12; IR (KBr) 2960, 2920, 2875, 2850, 1715 (ester C=O), 1675 (CH=O), 1665, 1615, 1595, 1570, 1515, 1475, 1430, 1285, 1270, 1245, 1210, 1145, and 1120 cm$^{-1}$; MS (FAB) m/e 593 (MH+).

For (Z)-2-(3-Carboethoxyphenyl)-5-phenyl-2-pentenal (9f): scale=0.76 mmol, yield=88%; 1H NMR (300 MHz, CDCl$_3$) δ9.62 (s, 1H, CHO), 8.04 (dr, J=2, 8 Hz, 1H, 2-ArH), 7.80 (t, J=2 11z, 1H, 2-Ar11), 7.45 (t, J=8 Hz, 1H, 2-ArH), 7.11–7.31 (m, 6H, 1×2-ArH and 5×5-ArH), 6.79 (t, J=7.5 Hz, 1H, C=CH), 4.40 (q, J=7 Hz, 2H, CO$_2$CH$_2$), 2.85 (t, J=7.5 Hz, 2H, ArCH$_2$), 2.68 (q, J=7.5 Hz, 2H, ArCH$_2$CH$_2$), and 1.40 (t, J=7 Hz, 3H, CO$_2$CH$_2$CH$_3$); MS (DCI) m/e 309 (MH+).

For (Z)-2-(3-Carbomethoxyphenyl)-5-(5,6,7,8-tetrahydro-5,5,8,8-tetramethyl-2-naphthalenyl)-2-pentenal (9g): scale=0.62 mmol, yield=100%; $^1$H NMR (300 MHz, CDCl$_3$) δ9.62 (s, 1H, CHO), 8.01 (d, J=8 Hz, 1H, 2-ArH), 7.82 (s, 1H, 2-ArH), 7.41 (t, J=8 Hz, 1H, 2-ArH), 7.21 (d, J=8 Hz, 1H, 2-ArH), 7.09 (d, J=7 Hz, 1H, 5-ArH), 7.03 (s, 1H, 5-ArH) 6.88 (d, J=8 Hz, 1H, 5-ArH), 6.82 (t, J=7 Hz, 1H, C=CH), 4.38 (q, J=7 Hz, 2H, CO$_2$CH$_2$), 2.78 (m, 2H, ArCH$_2$), 2.64 (q, J=7 Hz, 2H, ArCH$_2$CH$_2$), 1.66 (s, 4H, CH$_2$CH$_2$), 1.39 (t, J=7 Hz, 3H, CO$_2$CH$_2$CH$_3$) 1.26 (s, 6H, 2×CH$_3$), and 1.23 (s, 6H, 2×CH$_3$).

For (2Z),(4E)-2-(3-Carboethoxyphenyl)-5-(5,6,7,8-tetrahydro-5,5,8,8-tetramethyl-2-naphthalenyl)-2,4-hexadienal (9h): scale=0.54 mmol, yield=89%; $^1$H NMR (300 MHz, CDCl$_3$) δ9.72 (s, 1H, CHO), 8.02 (dt, J=2, 8 Hz, 1H, 2-ArH), 7.94 (d, J=2 Hz, 1H, 2-ArH), 7.79 (br d, J=12 Hz, 1H, C=CH), 7.48–7.59 (m, 2H, 2-ArH), 7.35 (d, J=2 Hz, 1H, 5-ArH) 7.27 (d, J=8 Hz, 1H, 5-ArH), 7.17 (dd, J=2, 8 Hz, 1H, 5-ArH), 6.74 (br d, J=12 Hz, 1H, C=CH), 4.36 (q, J=7 Hz, 2H, CO$_2$CH$_2$), 2.43 (d, J=1.5 Hz, 3H, C=CCH$_3$), 1.66 (br s, 4H, CH$_2$CH$_2$), 1.36 (t, J=7 Hz, 3H, CO$_2$CH$_2$CH$_3$), 1.23 (s, 6H, 2×CH$_3$), and 1.21 (s, 6H, 2×CH$_3$).

For (Z)-2-(3-Carbomethoxyphenyl)-5-[4-(1-adamantyl)-3-methoxyphenyl]]-2-pentenal (9i): scale=0.93 mmol, yield=88%; $^1$H NMR (300 MHz, CDCl$_3$) 8 9.59 (s, 1H, CHO), 7.99 (dt, J=2, 8 Hz, 1H, 2-ArH), 7.79 (t, J=2 Hz, 1H, 2-ArH), 7.41 (t, J=8 Hz, 1H, 2-ArH), 7.10 (dt, J=2, 8 Hz, 1H, 2-ArH), 7.08 (d, J=8 Hz, 1H, 3-ArH), 6.79 (t, J=7 Hz, 1H, C=CH), 6.65 (dd, J=2, 8 Hz, 1H, 3-ArH), 6.56 (d, J=2 Hz, 1H, 3-ArH), 3.89 (s, 3H, CO$_2$CH$_3$), 3.74 (s, 3H, OCH$_3$), 2.78 (t, J=7 Hz, 2H, ArCH$_2$), 2.64 (q, J=7 Hz, 2H, ArCH$_2$CH$_2$), 2.08 (br s, 9H, adamantyl), and 1.74 (br s, 6H, adamantyl); $^{13}$C NMR (75 MHz, CDCl$_3$) 8 193.08 (CH=O), 166.76 (ester C=O), 158.88, 155.58, 143.64, 138.64, 136.75, 133.98, 132.77, 130.49, 130.22, 129.16, 128.34, 126.55, 120.23, 111.82, 54.91 (OCH$_3$),52.16 (CO$_2$CH$_3$), 40.64, 37.50, 37.11, 36.72, 34.40, 31.38, and 29.09.

For (Z)-2-(3-Carboethoxyphenyl)-5-[3-(1-adamantyl)-4-methoxyphenyl]-2-pentenal (9j): scale=0.32 mmol, yield=93%; $^1$H NMR (300 MHz, CDCl$_3$) δ9.61 (s, 1H, CHO), 8.02 (dt, J=8, 1 Hz, 1H, 2-ArH), 7.81 (t, J=1 Hz, 1H, 2-ArH), 7.44 (t, J=8 Hz, 1H, 2-ArH), 7.19 (dt, J=8, 1 Hz, 1H, 2-ArH), 6.89–6.95 (m, 2H, 5-ArH and C=CH), 6.75–6.83 (m, 2H, 5-ArH), 4.37 (q, J=7 Hz, 2H, CO$_2$CH$_2$), 3.80 (s, 3H, OCH$_3$), 2.76 (t, J=7 Hz, 2H, ArCH$_2$), 2.64 (q, J=7 Hz, 2H, ArCH$_2$CH$_2$), 2.04 (s, 9H, adamantyl), 1.76 (s, 6H, adamantyl), and 1.39 (t, J=7 Hz, 3H, CO$_2$CH$_2$CH$_3$).

For (Z)-2-(3-Carbomethoxyphenyl)-3-(3,4-bispentyloxyphenyl)-2-propenal (9k): scale=0.99 mmol, yield=96%; $^1$H NMR (300 MHz, CDCl$_3$) δ9.72 (s, 1H, CHO), 8.07 (dt, J=2, 8 Hz, 1H, 2-ArH), 7.93 (t, J=2 Hz, 1H, 2-ArH), 7.53 (t, J=8 Hz, 1H, 2-ArH), 7.42 (dt, J=2, 8 Hz, 1H, 2-ArH), 7.35 (s, 1H, C=CH), 6.90 (dd, J=2, 8 Hz, 1H, 3-ArH), 6.75 (d, J=8 Hz, 1H, 3-ArH), 6.39 (d, J=2 Hz, 1H, 3-ArH), 3.98 (t, J=6.5 Hz, 2H, 3-ArOCH$_2$), 3.89 (s, 3H, CO$_2$CH$_3$), 3.47 (t, J=6.5 Hz, 2H, 3-ArOCH$_2$), 1.75–1.86 (m, 2H, 3-ArOCH$_2$CH$_2$), 1.56–1.66 (m, 2H, 3-ArOCH$_2$CH$_2$), 1.25–1.49 (m, 8 H), and 1.86–1.96 (m, 6H, 2×CH$_3$).

Example 9: General Procedure for Synthesis of 10

A solution of 18-crown-6 (5 equivalents) and bis(2,2,2-trifluoroethyl) (methoxycarbonylmethyl)phosphonate (1.1 equivalents) in anhydrous tetrahydrofuran was cooled to −78° C. under argon. A solution of potassium bistrimethylsilylamide (0.5M in toluene, 1.1 equivalents) was added, followed by addition of a solution of the aldehyde 9 (1 equivalent) in tetrahydrofuran (0.05M final concentration). The reaction mixture was allowed to warm to room temperature and then was poured into a separatory funnel containing diethyl ether and saturated ammonium chloride solution. The layers were agitated and separated. The ether layer was washed further with saturated sodium chloride solution, dried over anhydrous magnesium sulfate, filtered, and concentrated. Purification was accomplished by column chromatography (30:1 to 40:1 ratio of silica gel/crude product; elution with 5% ethyl acetate/hexanes) to provide the target compound.

For Methyl (2Z),(4Z)-4-(3-carboethoxyphenyl)-5-phenyl-2,4-pentadienoate (10a): scale=0.82 mmol, yield=93%; $^1$H NMR (300 MHz, CDCl$_3$) δ7.94 (dt, J=2, 8 Hz, 1H, 4-ArH), 7.86 (t, J=2 Hz, 1H, 4-ArH), 7.30–7.37 (m, 2H, 4-ArH), 7.08–7.11 (m, 3H, 5-ArH), 6.91–6.94 (m, 2H, 5-ArH), 6.86 (s, 1H, C=CH), 6.67 (d, J=12 Hz, 1H, CH=CHCO$_2$), 5.87 (d, J=12 Hz, 1H, CH=CHCO$_2$), 4.32 (q, J=7 Hz, 2H, CO$_2$CH$_2$), 3.31 (s, 3H, CO$_2$CH$_3$), and 1.34 (t, J=7 Hz, 3H, CO$_2$CH$_2$CH$_3$); $^{13}$C NMR (75 MHz, CDCl$_3$) δ166.72 (C=O), 166.35 (C=O), 142.77, 138.38, 136.95, 135.77, 135.09, 134.24, 130.82, 130.47, 129.58, 128.72, 128.52, 128.10, 127.70, 120.58, 61.01 (CO$_2$CH$_2$), 51.27 (CO$_2$CH$_3$) and 14.28 (CO$_2$CH$_2$CH$_3$); IR (film) 2980, 2950, 1720 (C=O), 1435, 1265, 1195, 1175, 1110, 1085, 1020, 760, and 700 cm$^{-1}$; MS (DCI) m/e 336 (M+).

For Methyl (2Z),(4Z)-4-(3-carboethoxyphenyl)-5-(5,6,7,8-tetrahydro-5,5,8,8-tetramethyl-2-naphthalenyl)-2,4-pentadienoate (10b): scale=1.05 mmol, yield=83%; UV$_{max}$ (CH$_3$OH) 308 nm (ε=20,100), 228 nm (ε=22,700); $^1$H NMR (300 MHz, CDCl$_3$) δ7.94–7.98 (m, 1H, 4-ArH), 7.90 (t, J=2 Hz, 1H, 4-ArH), 7.37–7.43 (m, 2H, 4-ArH), 7.06 (d, J=8 Hz, 1H, 5-ArH), 6.80 (s, 2H, 5-ArH and C=CH), 6.73 (dd, J=2, 8 Hz, 1H, 5-ArH), 6.64 (d, J=12 Hz, 1H, CH=CHCO$_2$), 5.80 (d, J=12 Hz, 1H, CH=CHCO$_2$), 4.32 (q, J=7 Hz, 2H, CO$_2$CH$_2$), 3.25 (s, 3H, CO$_2$CH$_3$), 1.50–1.58 (m, 4H, CH$_2$CH$_2$), 1.33 (t, J=7 Hz, 3H, CO$_2$CH$_2$CH$_3$), 1.17 (s, 6H, 2×CH$_3$), and 0.92 (s, 6H, 2×CH$_3$); $^{13}$C NMR (75 MHz, CDCl$_3$) δ166.90 (C=O), 166.38 (C=O), 145.04, 144.45, 142.72, 138.85, 136.23, 136.03, 134.26, 132.64, 130.88, 130.70, 128.67, 128.60, 127.81, 127.30, 126.39, 119.65, 60.95 (CO$_2$CH$_2$), 51.24 (OCH$_3$), 34.88, 34.13, 33.89, 31.61, 31.38, and 14.31 (CO$_2$CH$_2$CH$_3$); IR (film) 2960, 2930, 2860, 1720 (C=O), 1460, 1440, 1280, 1265, 1195, 1170, 1110, 1085, and 755 cm$^{-1}$; MS (DCI) m/e 447 (MH+), 415 (M+—OCH$_3$).

For Methyl (2Z),(4Z)-4-(3-carboethoxyphenyl)-5-(5,6,7,8-tetrahydro-5,5,8,8-tetramethyl-2-anthracenyl)-2,4-pentadienoate (10c): scale=0.76 mmol, yield=94%; $^1$H NMR (300 MHz, CDCl$_3$) δ7.96 (dr, J=2, 8 Hz, 1H, 4-ArH), 7.91 (t, J=2H, 1H, 4-ArH), 7.58 (d, J=12 Hz,2H, ArH), 7.47 (s, 1H, ArH), 7.29–7.40 (m, 3H, ArH), 7.01 (br s, 1H, C=CH), 6.75 (dd, J=2, 9 Hz, 1H, ArH), 6.72 (dd, J=1, 12 Hz, 1H, CH=CHCO$_2$), 5.88 (d, J=12 Hz, 1H, CH=CHCO$_2$), 4.32 (q, J=7 Hz, 2H, CO$_2$CH$_2$), 3.30 (s, 3H, CO$_2$CH$_3$), 1.72 (s, 4H, CH$_2$CH$_2$), and 1.29–1.36 (m 15H, 4×CH$_3$ and CO$_2$CH$_2$CH$_3$); $^{13}$C NMR (75 MHz, CDCl$_3$) δ166.89 (C=O), 166.41 (C=O), 145.12, 144.69, 142.97, 138.61, 136.51, 135.74, 134.51, 132.58, 131.54, 131.10, 130.82, 130.50, 129.22, 128.76, 128.49, 126.62, 125.82, 125.21, 124.62, 120.37, 61.01 (CO$_2$CH$_3$), 51.28 (CO$_2$CH$_2$), 35.00, 34.60, 34.52, 32.44, and 14.24 (CO$_2$CH$_2$CH$_3$); IR (film) 2960, 2860, 1720 (C=O), 1365, 1270, 1195, 1175, and 1110 cm$^{-1}$; MS (DCI) m/e 497 (MH+), 465 (MH+—CH$_3$OH).

For Methyl (2Z),(4Z)-4-(3-carboethoxyphenyl)-5-(4decyloxyphenyl)-2,4-pentadienoate (10d): scale=1.37 mmol, yield=98%; $^1$H NMR (300 MHz, CDCl$_3$) δ7.95 (dt, J=2, 8 Hz, 1H, 4-ArH), 7.88 (t, J=2 Hz, 1H, 4-ArH), 7.34–7.41 (m, 2H, 4-ArH), 6.82 (d, J=8 Hz, 2H, 5-ArH), 6.81 (s, 1H, C=CH), 6.63 (d, J=12 Hz, 1H, CH=CHCO$_2$), 6.61 (d, J=8 Hz, 2H, 5-ArH), 5.79 (d, J=12 Hz, 1H, CH=CHCO$_2$), 3.88 (s, 3H, CO$_2$CH$_3$), 3.85 (t, J=7 Hz, 2H, ArOCH$_2$), 3.26 (s, 3H, CO$_2$CH$_3$), 1.70 (quintet, J=7 Hz, 2H, ArOCH$_2$CH$_2$), 1.17–1.42 (m, 14H, 7×CH$_2$), and 0.85 (t, J=7 Hz, 3H, CH$_3$); $^{13}$C NMR (75 MHz, CDCl$_3$) δ166.90 (C=O), 158.86, 142.94, 138.88, 135.64, 134.91, 134.48, 131.09, 130.58, 128.66, 128.00, 119.42, 114.11, 67.91 (ArOCH$_2$), 52.17 (CO$_2$CH$_3$), 51.24 (CO$_2$CH$_3$), 31.88, 29.54, 29.36, 29.31, 29.16, 25.98, 22.68, and 14.12; IR (film) 2925, 2855, 1725 (C=O), 1600, 1510, 1470, 1435, 1280, 1270, 1250, 1195, 1175, 1110, 1085, 1070, 1000, 825, 755, and 710 cm$^{-1}$; MS (DCI) m/e 479 (MH+), 447 (M+—OCH$_3$).

For Methyl (2Z),(4Z)-4-(3-carboethoxyphenyl)-5-(3,4-bisdecyloxyphenyl)-2,4-pentadienoate (10e): scale=0.41 mmol, yield=86%; $^1$H NMR (300 MHz, CDCl$_3$) δ7.90–7.96 (m, 2H, 4-ArH), 7.38–7.48 (m, 2H, 4-ArH), 6.79 (s, 1H, C=CH), 6.56–6.65 (m, 3H, 2×5-ArH and CH=CHCO$_2$), 6.32 (d, J=2 Hz, 1H, 5-ArH), 4.78 (d, J=12 Hz, 1H, CH=CHCO$_2$), 4.33 (q, J=7 Hz, 2H, CO$_2$CH$_2$), 3.90 (t, J=7 Hz, 2H, ArC$^4$OCH$_2$), 3.45 (t, J=7 Hz, 2H, ArC$^3$OCH$_2$), 3.25 (s, 3H, CO$_2$CH$_3$), 1.74 (quint, J=7 Hz, 2H, ArC$^4$OCH$_2$CH$_2$), 1.54–1.60 (m, 2H, ArC$^3$OCH$_2$CH$_2$), 1.35 (t, J=7 Hz, 3H, CO$_2$CH$_2$CH$_3$), 1.19–1.40 (m, 28H, 14×CH$_2$), and 0.83–0.88 (m, 6H, 2×CH$_3$); $^{13}$C NMR (75 MHz, CDCl$_3$) δ166.93 (C=O), 166.27 (C=O), 149.06, 148.17, 142.78, 135.03, 134.97, 134.45, 130.93, 130.75, 128.62, 128.54, 128.37, 123.68, 119.28, 114.05, 112.67, 68.93, 68.57, 61.03 (CO$_2$CH$_2$), 51.22 (CO$_2$CH$_3$), 31.91, 29.58, 29.37, 29.34, 29.13, 28.98, 25.95, 25.83, 22.68, 14.30, and 14.12; IR (film) 2925, 2855, 1720 (C=O), 1510, 1470, 1265, 1200, 1170, and 1140 cm$^{-1}$; MS (DCI) m/e 649 (MH+).

For Methyl (2Z),(4Z)-4-(3-carboethoxyphenyl)-7-phenyl-2,4-heptadienoate (10f): scale=0.65 mmol, yield=77%; UV$_{max}$ (CH$_3$OH) 262 nm (ε=10,600); $^1$H NMR (300 MHz, CD$_3$OD) δ7.89 (dt, J=2, 8 Hz, 1H, 4-ArH), 7.70 (t, J=2 Hz, 1H, 4-ArH), 7.39 (t, J=8 Hz, 1H, 4-ArH), 7.04–7.22 (m, 6H, 1×4-ArH and 5×7-ArH), 6.60 (d, J=12 Hz, 1H, CH=CHCO$_2$), 6.06 (t, J=7.5 Hz, 1H, C=CH), 5.74 (d, J=12 Hz, 1H, CH=CHCO$_2$), 4.35 (q, J=7 Hz, 2H, CO$_2$CH$_2$), 3.14 (s, 3H, CO$_2$CH$_3$), 2.68 (t, J=7.5 Hz, 2H, ArCH$_2$), 2.32 (q, J=7.5 Hz, 2H, ArCH$_2$CH$_2$), and 1.38 (t, J=7 Hz, 3H, CO$_2$CH$_2$CH$_3$); $^{13}$C NMR (75 MHz, CD$_3$OD) δ168.28 (C=O), 167.89 (C=O), 142.98, 142.46, 139.60, 139.43, 139.33, 135.01, 131.44, 131.26, 129.47, 129.35, 129.30, 129.10, 127.02, 120.01, 62.21 (CO$_2$CH$_2$), 51.61 (CO$_2$CH$_3$), 36.37, 32.30, and 14.63 (CO$_2$CH$_2$CH$_3$); IR (film) 3060, 3025, 2980, 2950, 2855, 1720 (C=O), 1455, 1435, 1370, 1270, 1195, 1170, 1110, 1085, 1020, 760, and 700 cm$^{-1}$; MS (DCI) m/e 365 (MH+), 333 (M+—OCH$_3$).

For Methyl (2Z),(4Z)-4-(3-carbomethoxyphenyl)-7-(5,6,7,8-tetrahydro-5,5,8,8-tetramethyl-2-naphthalenyl)-2,4-heptadienoate (10g): scale=0.62 mmol, yield=85%; $^1$H NMR (300 MHz, CDCl$_3$) δ7.92 (d, J=8 Hz, 1H, 4-ArH), 7.85 (s, 1H, 4-ArH), 7.36 (t, J=8 Hz, 1H, 4-ArH), 7.15–7.24 (m, 2H, 4-ArH and 7-ArH), 7.00 (d, J=2 Hz, 1H, 7-ArH), 6.84 (dd, J=2, 8 Hz, 1H, 7-ArH), 6.57 (d, J=12 Hz, 1H, CH=CHCO$_2$), 6.07 (t, J=7 Hz, 1H, C=CH), 5.73 (d, J=12 Hz, 1H, CH=CHCO$_2$), 4.36 (q, J=7 Hz, 2H, CO$_2$CH$_2$), 3.21 (s, 3H, OCH₃), 2.63 (t, J=8 Hz, 2H, ArCH₂), 2.35 (q, J=8 Hz, 2H, ArCH₂CH₂), 1.64 (s, 4H, CH₂CH₂), 1.38 (t, J=7 Hz, 3H, CO₂CH₂CH₃), 1.24 (s, 6H, 2×CH₃), and 1.22 (s, 6H, 2'CH₃); $^{13}$C NMR (75 MHz, CDCl₃) δ166.80 (C=O), 166.47 (C=O), 144.71, 142.48, 142.26, 138.53, 138.20, 137.98, 137.28, 133.51, 130.29, 130.12, 128.21, 128.06, 126.46, 126.39, 125.64, 119.07, 61.01 (CO₂CH₂), 51.09 (OCH₃), 35.22, 35.15, 35.09, 34.15, 33.94, 31.89, 31.84, 31.13, and 14.35 (CO₂CH₂CH₃); IR (film) 2960, 2925, 1720 (C=O), 1270, and 1170 cm⁻¹; MS (DCI) m/e 475 (MH+), 474 (M+); Exact mass spectrum (FAB) Calcd for C₃₁H₃₈O₄Na: 497.2668 (MNa+). Found: 497.2652.

For Methyl (2Z),(4Z),(6E)-4-(3-carboethoxyphenyl)-7-(5,6,7,8tetrahydro-5,5,8,8-tetramethyl-2-naphthalenyl)-2,4,6-octatrienoate (10h): scale=0.47 mmol, yield=74%; UV$_{max}$ (CH₃OH) 348 nm (ε=14,300); $^1$H NMR (300 MHz, CD₃OD) δ7.95 (dt, J=2, 8 Hz, 1H, 4-ArH), 7.91 (d, J=2 Hz, 1H, 4-ArH), 7.41-7.51 (m, 2H, 4-ArH), 7.04-7.22 (m, 4H, 3×7-ArH and C=CH), 6.81 (d, J=12 Hz, 1H, CH=CHCO₂), 6.41 (br d, J=12Hz, 1H, C=CH),5.82(d,J=12Hz, 1H, CH=CHCO₂),4.35(q,J=7Hz, 2H, CO₂CH₂), 3.15 (s, 3H, CO₂CH₃), 2.25 (d, J=1.5 Hz, 3H, C=CCH₃), 1.63 (s, 4H, CH₂CH₂), 1.35 (t, J=7 Hz, 3H, CO₂CH₂CH₃), 1.21 (s, 6H, 2×CH₃), and 1.16 (s, 6H, 2×CH₃); $^{13}$C NMR (75 MHz, CD₃OD) δ168.50 (C=O), 167.90 (C=O), 145.89, 145.69, 143.19, 140.96, 140.17, 138.62, 135.27, 134.69, 132.02, 131.50, 129.44, 129.26, 127.62, 124.73, 124.09, 123.55, 120.03, 62.29 (CO₂CH₂), 51.64 (OCH₃), 36.18, 36.09, 35.18, 35.04, 32.21, 32.08, 16.20 (C=CCH₃), and 14.62 (CO₂CH₂CH₃); IR (film) 2960, 2930, 2860, 1720 (C=O), 1460, 1440, 1365, 1265, 1205, 1170, 1110, 1085, and 760 cm⁻¹; MS (DCI) m/e 487 (MH+), 455 (M+—OCH₃).

For Methyl (2Z),(4Z)-4-(3-carbomethoxyphenyl)-7-[4-(1-adamantyl)-3-methoxyphenyl]-2,4-heptadienoate (10i): scale=0.81 mmol, yield=69%; $^1$H NMR (300 MHz, CDCl₃) δ7.91 (dt, J=2, 8 Hz, 1H, 4-ArH), 7.84 (t, J=2 Hz, 1H, 4-ArH), 7.36 (t, J=8 Hz, 1H, 4-ArH), 7.21 (dt, J=2, 8 Hz, 1H, 4-ArH), 7.05 (d, J=8 Hz, 1H, 7-ArH), 6.62 (dd, J=2, 8 Hz, 1H, 7-ArH), 6.54-6.58 (m, 2H, 7-ArH and CH=CHCO₂), 6.05 (t, J=8 Hz, 1H, C=CH), 5.72 (d, J=12 Hz, 1H, CH=CHCO₂), 3.89 (s, 3H, ArCO₂CH₃), 3.73 (s, 3H, OCH₃), 3.21 (s, 3H, CO₂CH₃), 2.63 (t, J=8 Hz, 2H, ArCH₂), 2.36 (q, J=8 Hz, 2H, ArCH₂CH₂), 2.04 (br s, 9H, adamantyl), and 1.73 (br s, 6H, adamantyl); $^{13}$C NMR (75 MHz, CDCl₃) δ166.40 (C=O), 166.30 (C=O), 142.20, 139.71,138.19, 137.30, 136.27, 133.62, 130.16, 129.96, 128.23, 128.10, 126.31, 120.22, 119.17, 111.94, 54.89 (OCH₃),52.12 (ArCO₂CH₃), 51.06 (CO₂CH₃), 40.66, 37.13, 36.66, 35.12, 30.94, and 29.10.

For Methyl (2Z),(4Z)-4-(3-carboethoxyphenyl)-7-[3-(1-adamantyl)-4-methoxyphenyl]-2,4-heptadienoate (10j): scale=0.29 mmol, yield=76%; $^1$H NMR (300 MHz, CDCl₃) δ7.92 (dt, J=2, 8 Hz, 1H, 4-ArH), 7.83 (t, J=2 Hz, 1H, 4-ArH), 7.37 (t, J=8 Hz, 1H, 4-ArH), 7.25 (dt, J=2, 8 Hz, 1H, 4-ArH), 6.91 (d, J=2 Hz, 1H, 7-ArH), 6.87 (dd, J=2, 8 Hz, 1H, 7-ArH), 6.73 (d, J=8 Hz, 1H, 7-ArH), 6.57 (d, J=13 Hz, 1H, CH=CHCO₂), 6.06 (t, J=8 Hz, 1H, C=CH), 5.73 (d, J=12 Hz, 1H, CH=CHCO₂), 4.36 (q, J=7 Hz, 2H, CO₂CH₂), 3.77 (s, 3H, OCH₃), 3.20 (s, 3H, CO₂CH₃), 2.62 (t, J=8 Hz, 2H, ArCH₂), 2.34 (q, J=8 Hz, 2H, ArCH₂CH₂), 2.03 (s, 9H, adamantyl), 1.74 (s, 6H, adamantyl), and 1.38 (t, J=7 Hz, 3H, CO₂CH₂CH₃); $^{13}$C NMR (75 MHz, CDCl₃) δ166.83 (C=O), 166.50 (C=O), 157.13, 142.28, 138.67, 138.33, 138.22, 137.28, 133.55, 132.72, 130.28, 130.12, 128.18, 128.07, 126.72, 126.23, 119.01, 111.59, 61.02 (CO₂CH₂),55.06, 51.09, 40.56, 37.13, 36.86, 35.01, 31.44, 29.10, and 14.34 (CO₂CH₂CH₃); IR (film) 2905, 2850, 1720 (C=O), 1495, 1270, and 1235 cm⁻¹; MS (DCI) m/e 529 (MH+), 135 (C₁₀H₁₅+). Anal. Calcd for C₃₄H₄₀O₅: C, 77.24; H, 7.63. Found: C, 77.55; H, 7.56.

For Methyl (2Z),(4Z)-4-(3-carbomethoxyphenyl)-5-(3,4-bispentyloxyphenyl)-2,4-pentadienoate (10k): scale=0.63 mmol, yield=85%; $^1$H NMR (300 MHz, CDCl₃) δ7.91-7.96 (m, 2H, 4-ArH), 7.36-7.45 (m, 2H, 4-ArH), 6.79 (s, 1H, C=CH), 6.56-6.66 (m, 3H, 2×5-ArH and CH=CHCO₂), 6.31 (d, J=2 Hz, 1H, 5-ArH), 5.78 (d, J=12 Hz, 1H, CH=CHCO₂), 3.89 (t, J=6.5 Hz, 2H, ArOCH₂), 3.87 (s, 3H, CO₂CH₃), 3.44 (t, J=6.5 Hz, 2H, ArOCH₂), 3.25 (s, 3H, CO₂CH₃), 1.70-1.80 (m, 2H, ArOCH₂CH₂), 1.54-1.60 (m, 2H, ArOCH₂CH₂), 1.25-1.43 (m, 8H, 4×CH₂), and 0.86-0.94 (m, 6H, 2×CH₃); $^{13}$C NMR (75 MHz, CDCl₃) δ166.92 (C=O), 166.75 (C=O), 149.06, 148.16, 142.76, 139.05, 136.06, 134.93, 134.58, 130.81, 130.59, 128.67, 128.59, 128.34, 123.71, 119.30, 114.00, 112.65, 68.91 (ArOCH₂), 68.52 (ArOCH₂), 52.16 (CO₂CH₃), 51.22 (CO₂CH₃), 28.81, 28.64, 28.13, 27.99, 22.43, 22.35, and 14.02; IR (film) 2955, 2870, 1725 (C=O), 1595, 1510, 1470, 1435, 1265, 1200, 1170, 1140, 1110, and 1000 cm⁻¹; MS (DCI) m/e 495 (MH+), 463 (M+—OCH₃).

Example 10a: General Procedure for Synthesis of 11a–j

A mixture of ester 10 in methanol/tetrahydrofuran/2N sodium hydroxide solution (1:1:1, 0.1M) was heated at reflux for 1–4 h. The reaction mixture was then allowed to cool to room temperature and 10% hydrochloric acid solution was added until the solution reached pH 1. The resulting cloudy mixture was extracted with methylene chloride (2 to 4 portions), and the organic phase was washed with brine, dried over anhydrous magnesium sulfate, filtered, and concentrated. The residue was evaporated from pentane (3 portions) and then dried in vacuo.

For (2Z),(4Z)-4-(3-Carboxyphenyl)-5-phenyl-2,4-pentadienoic acid (11a): scale=2.05 mmol, yield=99%; UV$_{max}$ (CH₃OH) 269 nm (ε=14,700), 222 nm (ε=23,500); $^1$H NMR (300 MHz, CD₃OD) δ7.90-7.95 (m, 1H, 4-ArH), 7.86 (t, J=2 Hz, 1H, 4-ArH), 7.37-7.41 (m, 2H, 4-ArH), 7.06-7.13 (m, 3H, 5-ArH), 6.95-6.98 (m, 2H, 5-ArH), 6.90 (s, 1H, C=CH), 6.71 (d, J=12 Hz, 1H, CH=CHCO₂), and 5.92 (d, J=12 Hz, 1H, CH=CHCO₂); $^{13}$C NMR (75 MHz, CD₃OD) δ170.12 (C=O), 169.54 (C=O), 143.47, 140.11, 138.83, 137.47, 135.51, 135.15, 132.14, 130.66, 129.91, 129.63, 129.09, 128.67, and 122.57; IR (film) 2200–3400 (br, CO₂H), 1695 (C=O), 1625, 1600, 1580, 1435, 1305, 1275, 1250, 1230, 950, 910, 750, and 690 cm⁻¹; MS (DCI) m/e 295 (MH+). Anal. Calcd for C₁₈H₁₄O₄: C, 73.46; H, 4.79. Found: C, 73.40; H, 4.78.

For (2Z),(4Z)-4-(3-Carboxyphenyl)-5-(5,6,7,8-tetrahydro-5,5,8,8-tetramethyl-2-naphthalenyl)-2,4-pentadienoic acid (11b): scale=1.35 mmol, yield=98%; UV$_{max}$ (CH₃OH) 308 nm (ε=15,200), 228 nm (ε=21,100); $^1$H NMR (300 MHz, CD₃OD) δ7.91-7.96 (m, 1H, 4-ArH), 7.89 (t, J=2 Hz, 1H, 4-ArH), 7.42-7.46 (m, 2H, 4-ArH), 7.13 (d, J=8 Hz, 1H, 5-ArH), 6.82 and 6.85 (2 s, 3H, 2×5-ArH and C=CH), 6.68 (d, J=12 Hz, 1H, CH=CHCO₂), 5.86 (d, J=12 Hz, 1H, CH=CHCO₂), 1.52-1.65 (m, 4H, CH₂CH₂), 1.19 (s, 6H, 2'CH₃), and 0.89 (s, 6H, 2×CH₃); $^{13}$C NMR (75 MHz, CD₃OD) δ170.29 (C=O), 169.63 (C=O), 145.89, 145.32, 143.52, 140.66, 137.87, 136.09, 135.52, 134.32, 132.35, 129.81, 128.71, 127.46, 121.76, 36.04, 35.05, 34.82, 32.03, and 31.87; IR (film) 2500–3400 (br, $CO_2H$), 1695 (C=O), 1615, 1585, 1440, 1415, 1365, 1285, 1225, and 910 cm$^{-1}$; MS (DCI) m/e 405 (MH+), 387 (M+—OH). Anal. Calcd for $C_{26}H_{28}O_4 \cdot 0.4$ $H_2O$: C, 75.85; H, 7.05. Found: C, 75.89; H, 6.96.

For (2Z),(4Z)-4-(3-Carboxyphenyl)-5-(5,6,7,8-tetrahydro-5,5,8,8-tetramethyl-2-anthracenyl)-2,4-pentadienoic acid (11c): scale=0.69 mmol, yield=100%; mp 211°–213° C.; UV$_{max}$(CH$_3$OH) 332 nm ($\epsilon$= 21,100), 284 nm ($\epsilon$=21,700); $^1$H NMR (300 MHz, DMSO-d6) $\delta$7.86 (dt, J=2, 8 Hz, 1H, 4-ArH), 7.74 (s, 1H, 4-ArH), 7.69 (d, J=12 Hz, 2H, 5-ArH), 7.56 (s, 1H, ArH), 7.34–7.44 (m, 3H, ArH), 7.00 (s, 1H, C=CH), 6.67–6.74 (m, 2H, ArH and CH=CHCO$_2$), 5.94 (d, J=12 Hz, 1H, CH=CHCO$_2$), 1.67 (s, 4H, CH$_2$CH$_2$), and 1.29 (br s, 12 H, 4×CH$_3$); $^{13}$C NMR (75 MHz, DMSO-d$_6$) $\delta$167.13 (C=O), 167.02 (C=O), 144.56, 144.29, 141.53, 138.47, 136.94, 133.90, 133.36, 132.54, 131.27, 130.80, 130.61, 130.24, 128.72, 128.52, 126.38, 125.29, 124.84, 124.47, 122.48, 34.48, 34.28, 34.21, and 32.18; IR (KBr) 3430 (br, CO$_2$H), 3010, 2960, 2925, 2865, 1690 (C=O), 1615, 1435, 1290, 1260, and 1225 cm$^{-1}$; MS (DCI) m/e 455 (MH+) and 411 (MH+—CO$_2$H). Anal. Calcd for $C_{30}H_{30}O_4 \cdot 0.67$ $H_2O$: C, 77.20; H, 6.77. Found: C, 77.21; H, 6.58.

For (2Z),(4Z)-4-(3-Carboxyphenyl)-5-(4-decyloxyphenyl)-2,4-pentadienoic acid (11d): scale=1.27 mmol, yield=94%; UV$_{max}$ (CH$_3$OH) 314 nm ($\epsilon$=19,700), 228 nm ($\epsilon$=23,000); $^1$H NMR (300 MHz, CD$_3$OD) $\delta$7.93–7.96 (m, 1H, 4-ArH), 7.88 (t, J=2 Hz, 1H, 4-ArH), 7.38–7.41 (m, 2H, 4-ArH), 6.87 (d, J=8 Hz, 2H, 5-ArH), 6.86 (s, 1H, C=CH), 6.63–6.69 (m, 3H, CH=CHCO$_2$ and 2×5-ArH), 5.85 (d, J=12 Hz, 1H, CH=CHCO$_2$), 3.87 (t, J=7 Hz, 2H, ArOCH$_2$), 1.70 (quintet, J=7 Hz, 2H, ArOCH$_2$CH$_2$), 1.21–1.42 (m, 14H, 7×CH$_2$), and 0.88 (t, J=7 Hz, 3H, CH$_3$); $^{13}$C NMR (75 MHz, CD$_3$OD) $\delta$169.25 (C=O), 160.30, 143.78, 140.51, 136.75, 135.62, 132.16, 129.82, 129.71, 121.47, 115.08, 68.92 (ArOCH$_2$), 33.07, 30.69, 30.50, 30.46, 30.34, 27.12, 23.74, and 14.45; IR (KBr) 2400–3500 (br, CO$_2$H), 2950, 2920, 2850, 1695 (C=O), 1605, 1510, 1465, 1440, 1420, 1300, 1255, 1175, 1025, 935, 915, 890, 830, and 750 cm$^{-1}$; MS (DCI) m/e 451 (MH+). Anal. Calcd for $C_{28}H_{34}O_5$: C, 74.64; H, 7.61. Found: C, 74.50; H, 7.56.

For (2Z),(4Z)-4-(3-Carboxyphenyl)-5-(3,4-bisdecyloxyphenyl)-2,4-pentadienoic acid (11e): scale=0.32 mmol, yield=100%; UV$_{max}$ (CH$_2$Cl$_2$) 342 nm ($\epsilon$=20,200); $^1$H NMR (300 MHz, CDCl$_3$) $\delta$8.01 (s, 1H, 4-ArH), 7.92–7.96 (m, 1H, 4-ArH), 7.40–7.45 (m, 2H, 4-ArH), 6.91 (s, 1H, C=CH), 6.75 (d, J=13 Hz, 1H, CH=CHCO$_2$), 6.64 (d, J=8.5 Hz, 1H, 5-ArH), 6.58 (dd, J=2, 8.5 Hz, 1H, 5-ArH), 6.31 (d, J=2 Hz, 1H, 5-ArH), 5.79 (d, J=13 Hz, 1H, CH=CHCO$_2$), 3.89 (t, J=7 Hz, 2H, ArC$^4$OCH$_2$), 3.42 (t, J=7 Hz, 2H, ArC$^3$OCH$_2$), 1.73 (quint, J=7 Hz, 2H, ArC$^4$OCH$_2$CH$_2$), 1.50–1.60 (m, 2H, ArC$^3$OCH$_2$CH$_2$), 1.21–1.38 (m, 28H, 14×CH$_2$), and 0.82–0.87 (m, 6H, 2×CH$_3$); $^{13}$C NMR (75 MHz, CDCl$_3$) $\delta$173.39 (C=O), 171.72 (C=O), 149.30, 149.14, 141.84, 138.74, 138.66, 136.11, 135.36, 130.94, 129.64, 129.39, 129.14, 128.07, 123.97, 117.78, 114.15, 112.58, 68.91, 68.50, 31.90, 29.58, 29.36, 29.33, 29.09, 28.94, 25.94, 24.78, 22.68, and 14.12; IR (KBr) 2955, 2925, 2850, 2665, 1700 (C=O), 1585, 1515, 1435, 1310, 1270, 1240, and 1140 cm$^{-1}$; MS (DCI) m/e 607 (MH+), 563 (M−2×CO$_2$H+2H)+. Anal. Calcd for $C_{38}H_{54}O_6$: C, 75.21; H, 8.97. Found: C, 75.22; H, 8.97.

For (2Z),(4Z)-4-(3-Carboxyphenyl)-7-phenyl-2,4-heptadienoic acid (11f): scale=0.40 mmol, yield=85%; UV$_{max}$ (CH$_3$OH) 262 nm ($\epsilon$=8,800); $^1$H NMR (300 MHz, CD$_3$OD) $\delta$7.90 (dt, J=2, 8 Hz, 1H, 2-ArH), 7.80 (t, J=2 Hz, 1H, 2-ArH), 7.38 (t, J=8 Hz, 1H, 2-ArH), 7.06–7.27 (m, 6H, 1×2-ArH and 5×5-ArH), 6.58 (d, J=12 Hz, 1H, CH=CHCO$_2$), 6.04 (t, J=7.5 Hz, 1H, C=CH), 5.76 (d, J=12 Hz, 1H, CH=CHCO$_2$), 2.68 (t, J=7.5 Hz, 2H, ArCH$_2$), and 2.33 (q, J=7.5 Hz, 2H, ArCH$_2$CH$_2$); $^{13}$C NMR (75 MHz, CD$_3$OD) $\delta$170.10 (C=O), 143.14, 142.60, 139.70, 139.13, 137.78, 134.94, 131.66, 129.49, 129.43, 129.34, 129.14, 126.96, 121.16, 36.41, and 32.43; IR (film) 2400–3500 (br, CO$_2$H), 1695 (C=O), 1620, 1605, 1585, 1440, 1290, 1245, 1170, 915, 885, 755, 725, and 700 cm$^{-1}$; MS (DCI) m/e 323 (MH+), 305 (M+—OH). Anal. Calcd for $C_{20}H_{18}O_4 \cdot 0.1$ $H_2O$: C, 74.11; H, 5.66. Found: C, 74.08; H, 5.61.

For (2Z),(4Z)-4-(3-Carboxyphenyl)-7-(5,6,7,8-tetrahydro-5,5,8,8-tetramethyl-2-naphthalenyl)-2,4-heptadienoic acid (11g): scale=2.21 mmol, yield=75%; $^1$H NMR (300 MHz, CD$_3$OD) $\delta$7.89 (dt, J=2, 8 Hz, 1H, 4-ArH), 7.82 (t, J=2 Hz, 1H, 4-ArH), 7.34 (t, J=8 Hz, 1H, 4-ArH), 7.15 (m, 2H, 4-ArH and 7-ArH), 6.99 (d, J=2 Hz, 1H, 7-ArH), 6.80 (dd, J=2, 8 Hz, 1H, 7-ArH), 6.58 (dd, J=1, 12 Hz, 1H, CH=CHCO$_2$), 6.06 (t, J=8 Hz, 1H, C=CH), 5.75 (d, J=12 Hz, 1H, CH=CHCO$_2$), 2.61 (t, J=8 Hz, 2H, ArCH$_2$), 2.29 (q, J=8 Hz, 2H, ArCH$_2$CH$_2$), 1.65 (s, 4H, CH$_2$CH$_2$), 1.23 (s, 6H, 2×CH$_3$), and 1.20 (s, 6H, 2×CH$_3$); $^{13}$C NMR (75 MHz, CD$_3$OD) $\delta$170.10 (C=O), 169.78 (C=O), 145.62, 143.35, 143.25, 139.75, 139.46, 139.04, 138.28, 134.96, 131.69, 129.37, 129.08, 127.72, 127.52, 127.48, 126.85, 120.99, 36.37, 36.32, 36.19, 35.06, 34.85, 32.67, 32.34, and 31.43; IR (film) 2400–3500 (br, CO$_2$H), 2960, 2925, 2860, 1695 (C=O), and 755 cm$^{-1}$; MS (DCI) m/e 434 (M+2H)+. Anal. Calcd for $C_{28}H_{32}O_4 \cdot 0.1$ $H_2O$: C, 77.43; H, 7.47. Found: C, 77.22; H, 7.47.

For (2Z),(4Z),(6E)-4-(3-Carboxyphenyl)-7-(5,6,7,8-tetrahydro-5,5,8,8-tetramethyl-2-naphthalenyl)-2,4,6-octatrienoic acid (11h): scale=0.30 mmol, yield=67%; UV$_{max}$ (CH$_3$OH) 348 nm ($\epsilon$=33,200); $^1$H NMR (300 MHz, CD$_3$OD) $^1$H NMR (300 MHz, CD$_3$OD) $\delta$7.94–7.98 (m, 2H, 4-ArH), 7.43–7.47 (m, 2H, 4-ArH), 7.05–7.25 (m, 4H, 3×7-ArH and C=CH), 6.73 (d, J=12 Hz, 1H, CH=CHCO$_2$), 6.48 (br d, J=12 Hz, 1H, C=CH), 5.84 (d, J=12 Hz, 1H, CH=CHCO$_2$), 2.25 (d, J=1.5 Hz, 3H, C=CCH$_3$), 1.65 (s, 4H, CH$_2$CH$_2$), 1.22 (s, 6H, 2'CH$_3$), and 1.18 (s, 6H, 2×CH$_3$); $^{13}$C NMR (75 MHz, CD$_3$OD) $\delta$170.56 (C=O), 169.89 (C=O), 145.71, 142.66, 142.46, 141.08, 140.26, 138.66, 135.20, 133.36, 132.39, 131.89, 129.58, 129.21, 127.59, 124.76, 124.07, 123.78, 121.58, 36.24, 36.13, 35.19, 35.03, 32.21, 32.10, and 16.19 (C=CCH$_3$); IR (film) 2400–3600 (br, CO$_2$H), 2960, 2925, 2860, 1690 (C=O), 1585, 1445, 1295, 1255, and 1225 cm$^{-1}$; MS (DCI) m/e 445 (MH+), 399 (M+—CO$_2$H). Anal. Calcd for $C_{29}H_{32}O_4 \cdot 0.33$ $H_2O$: C, 77.30; H, 7.31. Found: C, 77.36; H, 7.20.

For (2Z),(4Z)-4-(3-Carboxyphenyl)-7-[4-(1-adamantyl)-3-methoxyphenyl]-2,4-heptadienoic acid (11i): scale=0.54 mmol, yield=100%; UV$_{max}$ (CH$_3$OH) 280 nm ($\epsilon$=8,600), 270 nm ($\epsilon$=10,500); $^1$H NMR (300 MHz, CD$_3$OD) $\delta$7.90 (dt, J=2, 8 Hz, 1H, 4-ArH), 7.84 (t, J=2 Hz, 1H, 4-ArH), 7.35 (t, J=8 Hz, 1H, 4-ArH), 7.17 (dr, J=2, 8 Hz, 1H, 4-ArH), 7.01 (d, J=8 Hz, 1H, 7-ArH), 6.56–6.61 (m, 3H, 2×7-ArH and CH=CHCO$_2$), 6.05 (t, J=8 Hz, 1H, C=CH), 5.76 (d, J=12 Hz, 1H, CHCO$_2$), 3.72 (s, 3H, OCH$_3$), 2.64 (t, J=8 Hz, 2H, ArCH$_2$), 2.33 (q, J=8 Hz, 2H, ArCH$_2$CH$_2$), 2.06 (br s, 6H, adamantyl), 2.01 (br s, 3H, adamantyl), and 1.73 (br s, 6H, adamantyl); $^{13}$C NMR (75 MHz, CD$_3$OD) δ170.10 (C=O), 169.78 (C=O), 160.11, 143.20, 141.32, 139.76, 139.06, 138.07, 137.13, 134.96, 131.72, 131.59, 129.38, 129.12, 127.15, 121.49, 121.07, 113.16, 55.34 (OCH$_3$), 41.94, 38.28, 37.74, 36.08, 32.42, and 30.63; IR (KBr) 3420 (br, CO$_2$H), 2905, 2850, 1695 (C=O), 1450, 1415, 1290, and 1245 cm$^{-1}$; MS (DCI) m/e 487 (MH+) and 443 (MH+—CO$_2$H). Anal. Calcd for C$_{31}$H$_{34}$O$_5$·0.33 H$_2$O: C, 75.58; H, 7.09. Found: C, 75.59; H, 7.02.

For (2Z),(4Z)-4-(3-Carboxyphenyl)-7-[3-(1-adamantyl)-4-methoxyphenyl]-2,4-heptadienoic acid (11j): scale - 0.21 mmol, yield=87%; $^1$H NMR (300 MHz, CD$_3$OD) δ7.81 (d, J=8 Hz, 1H, 4-ArH), 7.68 (s, 1H, 4-ArH), 7.39 (t, J=8 Hz, 1H, 4-ArH), 7.24 (d, J=8 Hz, 1H, 4-ArH), 6.77-6.88 (m, 3H, 7-ArH), 6.55 (d, J=13 Hz, 1H, CH=CHCO$_2$), 6.00 (t, J=7 Hz, C=CH), 5.76 (d, J=12 Hz, 1H, CH=CHCO$_2$), 3.71 (s, 3H, OCH$_3$), 2.55 (t, J=8 Hz, 2H, ArCH$_2$), 2.22 (q, J=8 Hz, 2H, ArCH$_2$CH$_2$), 1.95 (m, 9H, adamantyl), and 1.68 (s, 6H, adamantyl); $^{13}$C NMR (75 MHz, CDCl$_3$) δ167.29 (C=O), 167.01 (C=O), 156.67, 141.05, 138.05, 137.26, 137.13, 136.19, 133.14, 132.58, 130.54, 129.67, 128.05, 127.83, 126.30, 126.12, 121.06, 111.92, 55.13 (OCH$_3$), 40.12, 36.57, 36.24, 34.34, 31.23, and 28.38; IR (KBr) 2400-3500 (br, CO$_2$H), 2905, 2850, 1695 (C=O), 1495, 1445, 1285, 1260, and 1235 cm$^{-1}$; MS (DCI) m/e 487 (MH+), 135 (C$_{10}$H$_{15}$+). Anal. Calcd for C$_3$H$_{34}$O$_5$: C, 76.52; H, 7.04. Found: C, 76.19; H, 7.14.

Example 10b: Synthesis of 11k

For (2Z),(4Z)-3-Methyl-4-(3-carboxyphenyl)-5-(5,6,7,8-tetrahydro-5,5,8,8-tetramethyl-2-anthracenyl)-2,4-pentadienoic acid (11k). A suspension of potassium t-butylate (1.40 g, 12.5 mmol) in TFIF (40 mL) was cooled under a nitrogen atmosphere to -5° C. A solution of 4-(3-carbomethoxyphenyl)-3-methyl-2-butenoate (Tramposch, K. M. et al. *Biochemical and Biophysical Research Communications* 1992, 189, 272) (1.66 g, 6.00 mmol) in THF (5 mL) was added to the slurry. The mixture was stirred at 0° C. for 30 min. A solution of 5,6,7,8-tetrahydro-5,5,8,8-tetramethyl-2-anthracenaldehyde (3b) (1.33 g, 5.00 mmol) in THF (5 mL) was added slowly to the reaction mixture. After stirring for 30 min at 0° C., 4 mL of water was added. After 3 h of additional stirring, the solution was acidified with 1N HCl to pH 2. This acidic solution was poured into a separatory funnel and shaken with ether. The organic phase was washed with water and brine, dried over anhydrous magnesium sulfate, filtered, and concentrated. The crude product was purified by passage through a silica gel pad using gradient elution (methylene chloride to 5% methanol/methylene chloride). Removal of the solvents gave an oil which was dissolved in acetonitrile to precipitate 11k as a white solid (1.34 g, 55%): mp 186°-7° C.; UV$_{max}$ (CH$_3$CH$_2$OH) 318 nm (ε=16,000), 222 nm (ε=45,000); $^1$H NMR (300 MHz, one drop of DMSO-d$^6$ in CDCl$_3$) δ7.95 (s, 1H, ArH), 7.88 (d, J=8 Hz, 1H, ArH), 7.54 (d, J=13 Hz, 2H, ArH), 7.39-7.42 (m, 2H, ArH), 7.31 (d, J=8.5 Hz, 1H, ArH), 7.20 (t, J=8 Hz, 1H, ArH), 6.85 (dd, J=8.5, 1 Hz, 1H, ArH), 6.64 (s, 1H, ArCH=C), 5.82 (d, J=1 Hz, 1H, C=CHCO$_2$), 1.84 (s, 3H, C=CCH$_3$), 1.68 (s, 4H, CH$_2$CH$_2$), and 1.29 (s, 12H, 4×CH$_3$); $^{13}$C NMR (75 MHz, CDCl$_3$) δ168.96 (C=O), 168.80 (C=O), 156.12, 144.38, 144.25, 140.50, 138.24, 134.70, 133.18, 131.52, 130.85, 130.78, 130.71, 128.86, 128.42, 128.30, 128.15, 126.28, 124.88, 124.41, 119.55, 34.91, 34.40, 34.36, 32.33, and 24.19; IR (KBr) 2965, 2925, 2860, 1690 (C=O), 1650, 1465, 1360, 1300, 1250, 960 cm$^{-1}$; MS (DCI) m/e 469 (MH+), 425. Anal. Calcd for C$_{31}$H$_{32}$O$_4$: C, 79.48; H, 6.84. Found: C, 79.30; H, 7.08.

Example 11: General Procedure for Synthesis of 12

Manganese dioxide (5:1 weight ratio MnO$_2$/alcohol) was added in one portion to a solution of alcohol 5 in methylene chloride (0.1M). The reaction mixture was stirred in a stoppered flask at room temperature for 4–40 h. Additional MnO$_2$ was added if necessary to take the reaction to completion. The brown slurry was filtered through a one-inch pad of Celite and the collected solid was washed with methylene chloride. The filtrate was concentrated in vacuo, and the aldehyde product was used without purification.

For (Z)-2-(3-trifluoromethylphenyl)-3-(4-decyloxyphenyl)-2-propenal (12a): scale=5.9 mmol, yield=90%; lid NMR (300 MHz, CDCl$_3$) a 9.69 (s, 1H, CHO), 7.63 (d, J=8 Hz, 1H, 2-ArH), 7.53 (t, J=8 Hz, 1H, 2-ArH), 7.47 (s, 1H, C=CH), 7.38 (d, J=8 Hz, 1H, 2-ArH), 7.36 (s, 1H, 2-ArH), 7.09 (dt, J=3, 9 Hz, 2H, 3-ArH), 6.73 (dt, J=3, 9 Hz, 2H, 3-ArH), 3.91 (t, J=7 Hz, 2H, ArOCH$_2$), 1.73 (quint, J=7 Hz, 2H, ArOCH$_2$CH$_2$), 1.16-1.40 (m, 14 H, 7×CH$_2$), 0.85 (t, J=7 Hz, 3H, CH$_3$); $^{13}$C NMR (75 MHz, CDCl$_3$) δ193.14 (C=O), 161.31 (3-ArC), 151.30, 138.01, 134.67, 133.10, 132.74 (3-ArC), 129.34, 126.49 (q, $J^3_{c,f}$=4 Hz, 2-ArC), 125.79, 124.98 (q, $J^3_{c,f}$=4 Hz, 2-ArC), 114.69 (3-ArC), 68.19 (ArOCH$_2$), 40.60, 31.87, 29.52, 29.30, 29.04, 25.92, and 14.10; IR (KBr) 2960, 2920, 2870, 2850, 1675 (C=O), 1600, 1570, 1510, 1475, 1425, 1325, 1310, 1260, 1180, and 1165 cm$^{-1}$; MS (DCI) m/e 433 (MH+).

For (Z)-2-(3-trifluoromethylphenyl)-3-(3-decyloxyphenyl)-2-propenal (12b): scale=1.8 mmol, yield=95%; $^1$H NMR (300 MHz, CDCl$_3$) δ9.75 (s, 1H, CHO), 7.62 (d, J=8 Hz, 1H, 2-ArH), 7.56 (t, J=8 Hz, 1H, 2-ArH), 7.48 (s, 1H, 2-ArH), 7.41 (s, 1H, C=CH), 7.38 (d, J=8 Hz, 1H, 2-ArH), 7.15 (t, J=8 Hz, 1H, 3-ArH), 6.85 (dt, J=2, 8 Hz, 1H, 3-ArH), 6.78 (d, J=8 Hz, 1H, 3-ArH), 6.58 (t, J=2 Hz, 1H, 3-ArH), 3.57 (t, J=7 Hz, 2H, ArOCH$_2$), 1.57-1.65 (m, 2H, ArOCH$_2$CH$_2$), 1.21-1.37 (m, 14H, 7×CH$_2$), and 0.87 (t, J=7 Hz, 3H, CH$_3$); $^{13}$C NMR (75 MHz, CDCl$_3$) δ193.16 (C=O), 158.98 (3-ArC), 151.28, 140.32, 134.50, 134.37, 134.00, 129.68, 129.34, 126.50 (q, $J^3_{c,f}$=2 4 Hz, 2-ArC), 125.04 (q, $J^3_{c,f}$=4 Hz, 2-ArC), 123.60, 118.21, 115.02, 67.78 (ArOCH$_2$), 31.89, 29.53, 29.31, 29.27, 28.98, 25.83, 22.68, and 14.11; IR (film) 2925, 2855, 1690 (C=O), 1580, 1325, 1270, and 1165 cm$^{-1}$; MS (DCI) m/e 433 (MH+).

For (Z)-2-(3-trifluoromethylphenyl)-3-(2-decyloxyphenyl)-2-propenal (12c): scale=2.0 mmol, yield=93%; $^1$H NMR (300 MHz, CDCl$_3$) δ9.77 (s, 1H, CHO), 7.87 (s, 1H, C=CH), 7.58 (d, J=8 Hz, 1H, 2-ArH), 7.39-7.47 (m, 2H, 2-ArH), 7.38 (d, J=8 Hz, 1H, 2-ArH), 7.25 (dr, J=2, 8 Hz, 1H, 3-ArH), 6.92 (d, J=8 Hz, 1H, 3-ArH), 6.77 (dd, J=2, 8 Hz, 1H, 3-ArH), 6.61 (t, J=8 Hz, 1H, 3-ArH), 4.03 (t, J=7 Hz, 2H, ArOCH$_2$), 1.85 (quint, J=7 Hz, 2H, ArOCH$_2$CH$_2$), 1.22-1.54 (m, 14H, 7×CH$_2$), and 0.87 (t, J=7 Hz, 3H, CH$_3$); $^{13}$C NMR (75 MHz, CDCl$_3$) δ193.46 (C=O), 157.90 (3-ArC), 146.68, 139.54, 134.30, 133.16, 132.11, 130.30, 129.04, 126.58 (q, $J^3_{c,f}$=4 Hz, 2-ArC), 124.82 (q, $J^3_{c,f}$=4 Hz, 2-ArC), 122.47, 119.97, 111.95, 68.62 (OCH$_2$), 31.89, 29.59, 29.57, 29.37, 29.32, 29.13, 26.12, 22.68, and 14.11; IR (film) 2925, 2855, 1690 (C=O), 1600, 1455, 1325, 1250, and 1165 cm$^{-1}$; MS (DCI) m/e 433 (MH+).

For (Z)-2-(3-trifluoromethylphenyl)-3-[4-(2E),(6E)-3,7-dimethyl-octa-2,6-dienoxy]phenyl-2-propenal (12d): scale=1.35 mmol, yield=92%; $^1$H NMR (300 MHz, CDCl$_3$) δ9.70 (s, 1H, CHO), 7.63 (d, J=8 Hz, 1H, 2-ArH), 7.53 (t, J=8 Hz, 1H, 2-ArH), 7.47 (s, 1H, ArCH=C), 7.39 (d, J=8 Hz, 1H, 2-ArH), 7.36 (s, 1H, 2-ArH), 7.10 (dt, J=3, 9 Hz, 2H, 3-ArH) 6.75 (dt, J=3, 9 Hz, 2H, 3-ArH), 5.41 (dt, J=1, 7 Hz, 1H, C=CHCH$_2$O), 5.03–5.06 (m, 1H, CH=C(CH$_3$)$_2$), 4.51 (d, J=7 Hz, 2H, ArOCH$_2$), 2.03–2.12 (m, 4H, C=CHCH$_2$CH$_2$), and 1.55–1.69 (m, 9H, 3×CH$_3$); $^{13}$C NMR (75 MHz, CDCl$_3$) δ193.11 (C=O), 161.06 (3-ArC), 151.22, 141.89, 138.07, 134.66, 133.10, 132.71 (3-ArC), 131.89, 131.48, 129.34, 126.52 (q, J$^3_{c,f}$=4 Hz, 2-ArC), 125.90, 124.99 (q, J$^3_{c,f}$=4 Hz, 2-ArC), 123.65, 118.74, 114.92 (3-ArC), 65.03 (ArOCH$_2$), 39.48, 26.22, 25.66, 17.67, and 16.67; IR (KBr) 2970, 2915, 2890, 1675, 1600, 1570, 1510, 1425, 1325, 1310, 1255, 1180, 1160, and 1115 cm$^{-1}$; MS (DCI) m/e 429 (MH+).

For (Z)-2-(3-trifluoromethylphenyl)-3-(3,4-bis-decyloxyphenyl)-2-propenal (12e): scale=2.11 mmol, yield=94%; $^1$H NMR (300 MHz, CDCl$_3$) δ9.72 (s, 1H, CHO), 7.40–7.68 (m, 4H, 2-ArH), 7.37 (s, 1H, C=CH), 6.91 (dd, J=2, 8 Hz, 1H, 3-ArH), 6.79 (d, J=8 Hz, 1H, 3-ArH), 6.50 (d, J=2 Hz, 1H, 3-ArH), 4.00 (t, J=7 Hz, 2H, CH$_2$OAr), 3.45 (t, J=7 Hz, 2H, CH$_2$OAr), 1.75–1.88 (m, 2H, CH$_2$CH$_2$OAr), 1.55–1.67 (m, 2H, CH$_2$CH$_2$OAr), 1.20–1.48 (m, 28H, 14×CH$_2$), and 0.83–0.95 (m, 6H, 2×CH$_3$).

For (Z)-2-(3-trifluoromethylphenyl)-3-(5,6,7,8-tetrahydro-5,5,8,8-tetramethyl-2-anthracenyl)-2-propenal (12f): scale=1.6 mmol, yield=78%; $^1$H NMR (300 MHz, CDCl$_3$) δ9.80 (s, 1H, CHO), 7.75 (s, 1H, ArH), 7.64–7.68 (m, 3H, ArH), 7.58 (s, 1H, ArH), 7.45–7.55 (m, 3H, 2×ArH and C=CH), 4.42 (d, J=8 Hz, 1H, ArH), 6.90 (dd, J=2, 9 Hz, 1H, ArH), 1.74 (s, 4H, CH$_2$CH$_2$), and 1.35 (br s, 12 H, 4×CH$_3$); $^{13}$C NMR (75 MHz, CDCl$_3$) δ193.26 (C=O), 151.94, 147.10, 145.58, 139.48, 133.30, 132.41, 132.20, 131.33, 130.22, 129.22, 127.41, 126.73, 125.95, 125.15, 124.91, 34.86 (CH$_2$CH$_2$), 34.81, 34.61, and 32.43 and 32.38 (4×CH$_3$); IR (KBr) 2960, 2930, 1685 (C=O), 1605, 1325, 1165, and 1125 cm$^{-1}$.

For (Z)-2-(3-trifluoromethylphenyl)-5-(5,6,7,8-tetrahydro-5,5,8,8-tetramethyl-2-naphthalenyl)-2-pentenal (12g): scale=1.39 mmol, yield=89%; $^1$H NMR (300 MHz, CDCl$_3$) δ9.80 (s, 1 tt, CHO), 7.50 (br d, J=8 Hz, 1H, 2-ArH), 7.39 (t, J=8 Hz, 1H, 2-ArH), 7.31 (s, 1H, 2-ArH), 7.21 (d, J=8 Hz, 1H, 2-ArH), 7.10 (d, J=8 Hz, 1H, 5-ArH), 7.04 (d, J=2 Hz, 1H, 5-ArH), 6.88 (dd, J=2, 8 Hz, 1H, 5-ArH), 6.82 (t, J=8 Hz, 1H, C=CH), 2.79 (t, J=8 Hz, 2H, ArCH$_2$), 2.65 (q, J=8 Hz, 2H, ArCH$_2$CH$_2$), 1.65 (br s, 4H, CH$_2$CH$_2$), 1.25 (s, 6H, 2×CH$_3$), and 1.22 (s, 6H, 2×CH$_3$).

For (Z)-2-(4-fluorophenyl)-5-(5,6,7,8-tetrahydro-5,5,8,8-tetramethyl-2-naphthalenyl)-2-pentenal (12h): scale=1.94 mmol, yield=95%; $^1$H NMR (300 MHz, CDCl$_3$) δ9.61 (s, 1H, CHO), 7.24 (d, J=8 Hz, 1H, 5-ArH), 6.98–7.08 (m, 3H, ArH), 6.85–6.93 (m, 3H, ArH), 6.76 (t, J=8 Hz, 1H, C=CH), 2.79 (t, J=8 Hz, 2H, ArCH$_2$), 2.65 (q, J=8 Hz, 2H, ArCH$_2$CH$_2$), 1.67 (br s, 4H, CH$_2$CH$_2$), 1.25 (s, 6H, 2'CH$_3$), and 1.23 (s, 6H, 2×CH$_3$).

For (Z)-2-(3-fluorophenyl)-5-(5,6,7,8-tetrahydro-5,5,8,8-tetramethyl-2-naphthalenyl)-2-pentenal (12i): scale=2.73 mmol, yield=94%; $^1$H NMR (300 MHz, CDCl$_3$) δ9.59 (s, 1H, CHO), 7.22–7.31 (m, 2H, 1×2-ArH and 1×5-ArH), 7.03 (d, J=2 Hz, 1H, 5-ArH), 6.98 (apparent tt, J=2, 8Hz, 1H, 2-ArH), 6.88 (dd, J=2, 8 Hz, 1H, 5-ArH), 6.79 (t, J=8 Hz, 1H, C=CH), 6.72 (dd, J=2, 8 Hz, 1H, 2-ArH), 6.63 (apparent dt, J=2, 8 Hz, 1H, 2-ArH), 2.79 (t, J=8 Hz, 2H, ArCH$_2$), 2.64 (q, J=8 Hz, 2H, ArCH$_2$CH$_2$), 1.67 (br s, 4H, CH$_2$CH$_2$), 1.27 (s, 6H, 2×CH$_3$), and 1.24 (s, 6H, 2×CH$_3$).

For (Z)-2-phenyl-5-(5,6,7,8-tetrahydro-5,5,8,8-tetramethyl-2-naphthalenyl)-2-pentenal (12j): scale=0.78 mmol, yield=95%; $^1$H NMR (300 MHz, CDCl$_3$) δ9.61 (s, 1H, CHO), 7.28–7.38 (m, 3H, 2-ArH), 7.22 (d, J=8 Hz, 1H, 5-ArH), 7.05 (d, J=2 Hz, 1H, 5-ArH), 6.92–7.00 (m, 2H, 2-ArH), 6.88 (dd, J=2, 8 Hz, 1H, 5-ArH), 6.75 (t, J=8 Hz, 1H, C=CH), 2.78 (t, J=8 Hz, 2H, ArCH$_2$), 2.66 (q, J=8 Hz, 2H, ArCH$_2$CH$_2$), 1.66 (br s, 4H, CH$_2$CH$_2$), 1.26 (s, 6H, 2×CH$_3$), and 1.24 (s, 6H, 2×CH$_3$).

For (Z)-2-(3-trifluoromethylphenyl)-5-[3-(1-adamantyl)-4-methoxyphenyl]-2-pentenal (12k): scale=0.60 mmol, yield=100%; $^1$H NMR (300 MHz, CDCl$_3$) δ9.63 (s, 1H, CHO), 7.61 (d, J=8 Hz, 1H, 2-ArH), 7.50 (t, J=8 Hz, 1H, 2-ArH), 7.30 (s, 1H, 2-ArH), 7.19 (d, J=8 Hz, 1H, 2-ArH), 6.96 (d, J=2 Hz, 1H, 5-ArH), 6.92 (dd, J=2, 8 Hz, 1H, 5-ArH), 6.85 (t, J=8 Hz, 1H, C=CH), 6.80 (d, J=8 Hz, 1H, 5-ArH), 3.83 (s, 3H, OCH$_3$), 2.80 (t, J=8 Hz, 2H, ArCH$_2$), 2.65 (q, J=8 Hz, 2H, ArCH$_2$CH$_2$), 2.07 (s, 9H, adamantyl), and 1.78 (s, 6H, adamantyl).

For (Z)-2-(3-Phenyl)-5-[3-(1-adamantyl)-4-methoxyphenyl]-2-pentenal (12l): scale=0.96 mmol, yield=89%, ca. 6:1 mixture of Z:E isomers. $^1$H NMR (300 MHz, CDCl$_3$) δ(Z-isomer) 9.60 (s, 1H, CHO), 7.33–7.39 (m, 3H, 2-ArH), 7.03–7.07 (m, 2H, 2-ArH), 6.98 (d, J=2 Hz, 1H, 5-ArH), 6.93 (dd, J=2, 8 Hz, 1H, 5-ArH), 6.78 (d, J=8 Hz, 1H, 5-ArH), 6.75 (t, J=8 Hz, 1H, C=CH), 3.80 (s, 3H, OCH$_3$), 2.79 (t, J=8 Hz, 2H, ArCH$_2$), 2.64 (q, J=8 Hz, 2H, ArCH$_2$CH$_2$), 2.02 (s, 9H, adamantyl), and 1.76 (s, 6H, adamantyl).

For (Z)-2-(3-trifluoromethylphenyl)-5-[4-(1-adamantyl)-3-methoxyphenyl]-2-pentenal (12m): scale=1.06 mmol, yield=87%; $^1$H NMR (300 MHz, CDCl$_3$) δ9.58 (s, 1H, CHO), 7.57 (d, J=8 Hz, 1H, 2-ArH), 7.45 (t, J=8 Hz, 1H, 2-ArH), 7.30 (s, 1H, 2-ArH), 7.09 (m, 2H, 2-ArH and 5-ArH), 6.82 (t, J=7 Hz, 1H, C=CH), 6.65 (dd, J=1, 8 Hz, 1H, 5-ArH), 6.57 (d, J=2 Hz, 1H, 5-ArH), 3.76 (s, 3H, OCH$_3$), 2.79 (t, J=8 Hz, 2H, ArCH$_2$), 2.63 (q, J=8 Hz, 2H, ArCH$_2$CH$_2$), 2.04 (s, 9H, adamantyl), and 1.76 (s, 6H, adamantyl).

For (Z)-2-phenyl-5-[4-(1-adamantyl)-3-methoxyphenyl]-2-pentenal (12n): scale=3.48 mmol, yield=86%; $^1$H NMR (300 MHz, CDCl$_3$) δ9.62 (s, 1H, CHO), 7.30–7.40 (m, 3H, 2-ArH), 7.11 (d, J=8 Hz, 1H, 5-ArH), 6.96–7.03 (m, 2H, 2-ArH), 6.75 (t, J=8 Hz, 1H, C=CH), 6.68 (dd, J=2, 8 Hz, 1H, 5-ArH), 6.58 (d, J=2 Hz, 1H, 5-ArH), 3.77 (s, 3H, OCH$_3$), 2.79 (t, J=8 Hz, 2H, ArCH$_2$), 2.68 (q, J=8 Hz, 2H, ArCH$_2$CH$_2$), 2.07 (br s, 9H, adamantyl), and 1.76 (br s, 6H, adamantyl).

For (Z)-2-(3-trifluoromethylphenyl)-5-[2-(1-adamantyl)-4-methoxyphenyl]-2-pentenal (12o): scale=0.30 mmol, yield=100%; $^1$H NMR (300 MHz, CDCl$_3$) δ9.65 (s, 1H, CHO), 7.60 (d, J=8 Hz, 1H, 2-ArH), 7.49 (t, J=8 Hz, 1H, 2-ArH), 7.33 (s, 1H, 2-ArH), 7.26 (m, 1H, 2-ArH), 6.97 (d, J=8 Hz, 1H, 5-ArH), 6.89 (m, 2H, 5-ArH and C=CH), 6.67 (dd, J=3, 8 Hz, 1H, 5-ArH), 3.77 (s, 3H, OCH$_3$), 3.08 (t, J=8 Hz, 2H, ArCH$_2$), 2.65

(q, J=8 Hz, 2H, ArCH$_2$CH$_2$), 2.04 (s, 3H, adamantyl), 1.94 (s, 6H, adamantyl), and 1.74 (m, 6H, adamantyl).

For (Z)-2-(3-trifluoromethylphenyl)-3-[4-(1-adamantyl)-3-methoxyphenyl]-2-propenal (12p): scale=2.13 mmol, yield=94%; $^1$H NMR (300 MHz, CDCl$_3$) δ9.74 (s, 1H, CHO), 7.65 (d, J=8 Hz, 1H, 2-ArH), 7.57 (t, J=8 Hz, 1H, 2-ArH), 7.51 (s, 1H, 2-ArH), 7.41 (m, 2H, 2-ArH and C=CH), 7.15 (d, J=8 Hz, 1H, 3-ArH), 6.88 (dd, J=2, 8 Hz, 1H, 3-ArH), 6.49 (d, J=2 Hz, 1H, 3-ArH), 3.34 (s, 3H, OCH$_3$), 2.00 (s, 9H, adamantyl), and 1.72 (s, 6H, adamantyl).

For (Z)-2-(3-trifluoromethylphenyl)-5-[4-(1-adamantyl)-3-t-butyldimethylsilyloxyphenyl]-2-pentenal (12q): scale=1.43 mmol, yield=90%; $^1$H NMR (300 MHz, CDCl$_3$) δ9.60 (s, 1H, CHO), 7.59 (d, J=8 Hz, 1H, 2-ArH), 7.46 (t, J=8 Hz, 1H, 2-ArH), 7.31 (s, 1H, 2-ArH), 7.11 (m, 2H, 2-ArH and 5-ArH), 6.82 (t, J=7 Hz, 1H, HC=CCHO), 6.65 (dd, J=1, 8 Hz, 1H, 5-ArH), 6.52 (d, J=2 Hz, 1H, 5-ArH), 2.73 (t, J=7 Hz, 2H, CH$_2$Ar), 2.61 (q, J=7 Hz, 2H, ArCH$_2$CH$_2$), 2.07 (s, 9H, adamantyl), 1.76 (s, 6H, adamantyl), 1.01 (s, 9H, t-butyl), and 0.28 (s, 6H, Si(CH$_3$)$_2$).

Example 12: General Procedure for Synthesis of 13

A solution of 18-crown-6 (5 equivalents) and bis(2,2,2-trifluoroethyl) (methoxycarbonylmethyl)phosphonate (1.1 equivalents) in anhydrous tetrahydrofuran was cooled to −78° C. under argon. A solution of potassium bistrimethylsilylamide (0.5M in toluene, 1.1 equivalents) was added, followed by addition of a solution of the aldehyde 12 (1 equivalent) in tetrahydrofuran (0.05M final concentration). The reaction mixture was allowed to warm to room temperature and then was poured into a separatory funnel containing diethyl ether and saturated ammonium chloride solution. The layers were agitated and separated. The ether layer was washed further with saturated sodium chloride solution, dried over anhydrous magnesium sulfate, filtered, and concentrated. Purification was accomplished by column chromatography (40:1 ratio of silica gel/crude product; elution with 3 to 5% ethyl acetate/hexanes) to provide the target compound.

For Methyl (2Z),(4Z)-4-(3-trifluoromethylphenyl)-5-(4-decyloxyphenyl)-2,4-pentadienoate (13a): scale=2.8 mmol, yield=75%; 7 $^1$H NMR (300 MHz, CDCl$_3$) δ7.36–7.53 (m, 4H, 4-ArH), 6.78–6.86 (m, 3H, 2×5-ArH and C=CH), 6.60–6.66 (m, 3H, 2×5-ArH and CH=CHCO$_2$), 5.81 (d, J=16 Hz, 1H, CH=CHCO$_2$), 3.86 (t, J=6 Hz, 2H, ArOCH$_2$), 3.25 (s, 3H, CO$_2$CH$_3$), 1.71 (quintet, J=6 Hz, 2H, ArOCH$_2$CH$_2$), 1.24–1.50 (m, 14H, 7×CH$_2$), and 0.85 (t, J=6 Hz, 3H, CH$_3$); $^{13}$C NMR (75 MHz, CDCl$_3$) δ166.82 (C=O), 159.02 (5-Ar), 142.64, 139.32, 136.11, 134.47, 133.26, 131.54, 131.03 (5-ArC), 129.01, 127.73, 126.42 (q, J$^3_{c,f}$=4 Hz, 4-ArC), 124.13 (q, J$^3_{c,f}$=4 Hz, 4-ArC), 119.68, 114.18 (5-ArC), 67.96 (ArOCH$_2$), 51.22 (CO$_2$CH$_3$), 31.87, 29.53, 29.35, 29.30, 29.14, 25.97, 22.66, and 14.10; IR (film) 2925, 2855, 1730 (C=O), 1600, 1510, 1325, 1310, 1255, 1175, and 1165 cm$^{-1}$; MS (DCI) m/e 489 (MH+).

For Methyl (2Z),(4Z)-4-(3-trifluoromethylphenyl)-5-(3-decyloxyphenyl)-2,4-pentadienoate (13b): scale=0.90 mmol, yield=95%; $^1$H NMR (300 MHz, CDCl$_3$) δ7.51 (dd, J=2, 7 Hz, 1H, 4-ArH), 7.48 (s, 1H, 4-ArH), 7.36–7.44 (m, 2H, 4-ArH), 7.03 (t, J=8 Hz, 1H, 5-ArH), 6.84 (br s, 1H, C=CH), 6.66–6.70 (m, 1H, 5-ArH), 6.66 (dd, J=2, 12 Hz, 1H, CH=CHCO$_2$), 6.54 (d, J=8 Hz, 1H, 5-ArH), 6.37 (t, J=2 Hz, 1H, 5-ArH), 5.87 (d, J=12 Hz, 1H, CH=CHCO$_2$), 3.56 (t, J=7 Hz, 2H, ArOCH$_2$), 3.28 (s, 3H, CO$_2$CH$_3$), 1.55–1.65 (m, 2H, ArOCH$_2$CH$_2$), 1.21–1.35 (m, 14H, 7×CH$_2$), and 0.87 (t, J=7 Hz, 3H, CH$_3$); $^{13}$C NMR (75 MHz, CDCl$_3$) δ166.65 (C=O), 158.72 (5-ArC), 142.13, 139.06, 136.60, 135.92, 133.26, 131.08, 130.66, 129.13, 129.01, 126.42 (q, f3$_{c,f}$=4 Hz, 4-ArC), 124.18 (q, J$^3_{c,f}$=4 Hz, 4-ArC), 122.30, 120.76, 115.29, 114.42, 67.66 (ArOCH$_2$), 51.28 (CO$_2$CH$_3$), 31.89, 29.55, 29.31, 25.88, 22.68, and 14.11; IR (film) 2925, 1730 (C=O), 1435, 1325, 1265, and 1165 cm$^{-1}$; MS (DCI) m/e 489 (MH+).

For Methyl (2Z),(4Z)-4-(3-trifluoromethylphenyl)-5-(2-decyloxyphenyl)-2,4-pentadienoate (13c): scale=0.92 mmol, yield=72%, 12:1 mixture of Z:E isomers. $^1$H NMR (300 MHz, CDCl$_3$) δ7.42–7.57 (m, 2H, 4-ArH), 7.33–7.37 (m, 2H, 4-ArH), 7.07–7.13 (m, 2H, 5-ArH and C=CH), 6.80 (d, J=8 Hz, 1H, 5-ArH), 6.72 (dd, J=2, 12 Hz, 1H, CH=CHCO$_2$), 6.48–6.70 (m, 2H, 5-ArH), 5.88 (d, J=12 Hz, 1H, CH=CHCO$_2$), 3.95 (t, J=7 Hz, 2H, ArOCH$_2$), 3.28 (s, 3H, CO$_2$CH$_3$), 1.78 (quint, J=7 Hz, 2H, ArOCH$_2$CH$_2$), 1.21–1.47 (m, 14H, 7×CH$_2$), and 0.87 (t, J=7 Hz, 3H, CH$_3$); $^{13}$C NMR (75 MHz, CDCl$_3$) δ166.77 (C=O), 157.29 (5-ArC), 142.93, 139.27, 136.00, 133.11, 131.55, 130.23, 129.21, 128.68, 126.30 (q, J$^3_{c,f}$=4 Hz, 4-ArC), 124.71, 123.89 (q, J$^3_{c,f}$=4 Hz, 4-ArC), 120.43, 119.73, 68.38 (ArOCH$_2$), 51.18 (CO$_2$CH$_3$), 31.90, 29.58, 29.38, 29.33, 29.19, 26.07, 22.67, and 14.11; IR (film) 2925, 2855, 1730 (C=O), 1325, 1250, and 1165 cm$^{-1}$; MS (DCI) m/e 489 (MH+).

For Methyl (2Z),(4Z)-4-(3-trifluoromethylphenyl)-5-[4-(2E),(6E)-3,7-dimethyl-octa-2,6-dien-oxy]phenyl)-2,4-pentadienoate (13d): scale=1.20 mmol, yield=62%; $^1$H NMR (300 MHz, CDCl$_3$) δ7.51–7.53 (m, 1H, 4-ArH), 7.47 (s, 1H, 4-ArH), 7.38–7.42 (m, 2H, 4-ArH), 6.79–6.84 (m, 3H, 2×5-ArH and C=CH), 6.62–6.68 (m, 3H, 2×5-ArH and CH=CHCO$_2$), 5.81 (d, J=12 Hz, 1H, CH=CHCO$_2$), 5.41 (t, J=7 Hz, 1H, C=CHCH$_2$O), 5.03–5.06 (m, 1H, CH=C(CH$_3$)$_2$), 4.45 (d, J=7 Hz, 2H, ArOCH$_2$), 3.26 (s, 3H, CO$_2$CH$_3$), 2.02–2.08 (m, 4H, C=CHCH$_2$CH$_2$), and 1.55–1.68 (m, 9H, 3×CH$_3$); $^{13}$C NMR (75 MHz, CDCl$_3$) δ166.80 (C=O), 158.77 (5-ArC), 142.64, 141.37, 139.30, 136.04, 134.53, 133.26, 131.83, 131.02 (5-ArC), 129.02, 127.86, 126.40 (q, J$^3_{c,f}$=4 Hz, 4-ArC), 124.12 (q, J$^3$c,f=4 Hz, 4-ArC), 123.74, 119.73, 119.16, 114.41 (5-ArC), 64.84 (ArOCH$_2$), 51.22 (CO$_2$CH$_3$), 39.50, 26.26, 25.67, 17.67, and 16.64; IR (film) 2925, 1725 (C=O), 1670, 1600, 1510, 1325, 1310, 1250, 1165, and 1125 cm$^{-1}$; MS (DCI) m/e 485 (MH+).

For Methyl (2Z),(4Z)-4-(3-trifluoromethylphenyl)-5-(3,4-bisdecyloxyphenyl)-2,4-pentadienoate (13e): scale=1.40 mmol, yield=94%; $^1$H NMR (300 MHz, CDCl$_3$) δ7.39–7.53 (m, 4H, 4-ArH), 6.81 (s, 1H, C=CH), 6.57–6.67 (m, 3H, 2×5-ArH and CH=CHCO$_2$), 6.26 (d, J=2 Hz, 1H, 5-ArH), 5.79 (d, J=12 Hz, 1H, CH=CHCO$_2$), 3.91 (t, J=7 Hz, 2H, CH$_2$OAr), 3.43 (t, J=7 Hz, 2H, CH$_2$OAr), 3.24 (s, 3H, CO$_2$CH$_3$), 1.70–1.79 (m, 2H, CH$_2$CH$_2$OAr), 1.54–1.61 (m, 2H, CH$_2$CH$_2$OAr), 1.24–1.45 (m, 28H, 14×CH$_2$), and 0.83–0.89 (m, 6H, 2×CH$_3$); $^{13}$C NMR (75 MHz, CDCl$_3$) δ166.81 (C=O), 149.23, 148.33, 142.31, 139.58, 136.64, 134.49, 133.46, 131.00 (q, J$^2_{c,f}$=38 Hz, 2-ArC), 129.12, 128.08, 126.57 (q, J$^3_{c,f}$=4 Hz, 2-ArC), 124.02 (q, J$^3_{c,f}$=4 Hz, 2-ArC), 124.00 (q, J$^1_{c,f}$=273 Hz, CF$_3$), 123.78, 119.47, 113.82, 112.79, 69.00 (CH$_2$O), 68.50 (CH$_2$O), 51.21 (CO$_2$CH$_3$), 31.90, 29.58, 29.32, 29.12, 29.01, 25.94, 25.80, 22.67, and 14.10; IR (KBr) 2925, 2855, 1730 (C=O), 1595, 1510, 1470, 1435, 1325, 1310, 1270, 1240, 1200, 1165, 1130, 1095, 1070, 1000, 800, and 705 cm$^{-1}$; MS (DCI) m/e 645 (MH+).

For Methyl (2Z), (4Z)-4-(3-trifluoromethylphenyl)-5-(5,6,7,8-tetrahydro-5,5,8,8-tetramethyl-2-anthracenyl)-2,4-pentadienoate (13f): scale=1.3 mmol, yield=82%; $^1$H NMR (300 MHz, CDCl$_3$) δ7.62 (s, 1H, ArH), 7.52–7.57 (m, 3H, ArH), 7.45 (s, 1H, ArH), 7.36–7.39 (m, 3H, ArH), 7.02 (s, 1H, C=CH), 6.74 (dd, J=2, 9 Hz, 1 H, ArH), 6.72 (dd, J=1, 12 Hz, 1H, CH=CHCO$_2$), 5.89 (d, J=12 Hz, 1H, CH=CHCO$_2$), 3.28 (s, 3H, CO$_2$CH$_3$), 1.72 (s, 4H, CH$_2$CH$_2$), and 1.33 (s, 12 H, 4×CH$_3$); IR (KBr) 3010, 2960, 2930, 2865, 1730 (C=O), 1620, 1465, 1435, 1320, 1310, 1240, 1210, 1170, and 1135 cm$^{-1}$; MS (DCI) m/e 492 (MH+).

For Methyl (2Z),(4Z)-4-(3-trifluoromethylphenyl)-7-(5,6,7,8-tetrahydro-5,5,8,8-tetramethyl-2-naphthalenyl)-2,4-heptadienoate (13g): scale=0.74 mmol, yield=90%; $^1$H NMR (300 MHz, CDCl$_3$) δ7.48 (br d, J=8 Hz, 1H, 4-ArH), 7.39 (t, J=8 Hz, 1H, 4-ArH), 7.36 (s, 1H, 4-ArH), 7.18 (d, J=8 Hz, 1H, 4-ArH), 7.17 (d, J=8 Hz, 1H, 7-ArH), 6.98 (d, J=2 Hz, 1H, 7-ArH), 6.82 (dd, J=2, 8 Hz, 1H, 7-ArH), 6.54 (d, J=12 Hz, 1H, CH=CHCO$_2$), 6.07 (t, J=8 Hz, 1H, C=CH), 5.72 (d, J=12 Hz, 1H, CH=CHCO$_2$), 3.18 (s, 3H, CO$_2$CH$_3$), 2.63 (t, J=8 Hz, 2H, ArCH$_2$), 2.32 (q, J=8 Hz, 2H, ArCH$_2$CH$_2$), 1.64 (br s, 4H, CH$_2$CH$_2$), 1.23 (s, 6H, 2×CH$_3$), and 1.21 (s, 6H, 2×CH$_3$); $^{13}$C NMR (75 MHz, CDCl$_3$) δ166.50 (C=O), 144.76, 142.58, 141.77, 139.15, 138.69, 137.73, 136.97, 132.51, 128.50, 126.52, 126.39, 125.79 (q, J$^3_{c,f}$=4 Hz, 4-ArC), 125.61, 123.75 (q, J$^3_{c,f}$=4 Hz, 4-ArC), 119.23, 51.08 (CO$_2$CH$_3$), 35.12, 35.07, 34.13, 33.94, 31.86, 31.80, and 31.07; IR (film) 2960, 2925, 2860, 1730 (C=O), 1495, 1460, 1435, 1385, 1365, 1325, 1310, 1280, 1165, 1125, 1095, 1070, 825, 800, and 760 cm$^{-1}$; MS (DCI) m/e 471 (MH+).

For Methyl (2Z),(4Z)-4-(4-fluorophenyl)-7-(5,6,7,8-tetrahydro-5,5,8,8-tetramethyl-2-naphthalenyl)-2,4-heptadienoate (13h): scale=0.96 mmol, yield=82%; $^1$H NMR (300 MHz, CDCl$_3$) δ7.16 (d, J=8 Hz, 1H, 7-ArH), 6.91–6.98 (m, 5H, 4×4-ArH and 1×7-ArH), 6.82 (dd, J=2, 8 Hz, 1H, 7-ArH), 6.52 (d, J=13 Hz, 1H, CH=CHCO$_2$), 5.99 (t, J=8 Hz, 1H, C=CH), 5.69 (d, J=12 Hz, 1H, CH=CHCO$_2$), 3.24 (s, 3H, CO$_2$CH$_3$), 2.61 (t, J=8 Hz, 2H, ArCH$_2$), 2.32 (q, J=8 Hz, 2H, ArCH$_2$CH$_2$), 1.64 (br s 4H, CH$_2$CH$_2$), 1.24 (s, 6H, 2'CH$_3$), and 1.22 (s, 6H, 2'CH$_3$); $^{13}$C NMR (75 MHz, CDCl$_3$) δ166.97, 166.57 (d, J$^1_{c,f}$=246 Hz, 4-ArC), 144.07, 142.39, 138.09, 137.99, 137.23, 130.71 (d, J$^3_{c,f}$=8 Hz, 4-ArC), 126.44, 125.67, 118.84, 114.79 (J$^2_{c,f}$=21 Hz, 4-ArC), 51.15 (CO$_2$CH$_3$), 35.16, 35.14, 35.09, 34.14, 33.94, 31.89, 31.84 and 31.06; IR (film) 2960, 2925, 2860, 1730 (C=O), 1600, 1510, 1455, 1435, 1360, 1220, 1195, 1170, 1160, 840, and 820 cm$^{-1}$; MS (DCI) m/e 421 (MH+).

For Methyl (2Z),(4Z)-4-(3-fluorophenyl)-7-(5,6,7,8-tetrahydro-5,5,8,8-tetramethyl-2-naphthalenyl)-2,4-heptadienoate (13i): scale=1.35 mmol, yield=91%; $^1$H NMR (300 MHz, CDCl$_3$) δ7.21–7.27 (m, 1H, 4-ArH), 7.17 (d, J=2 Hz, 1H, 7-ArH), 7.00 (d, J=2 Hz, 1H, 7-ArH), 6.80–6.85 (m, 3H, 2×4-ArH and 1×7-ArH), 6.71 (apparent dt, J=2, 8 Hz, 1H, 4-ArH), 6.51 (d, J=12 Hz, 1H, CH=CHCO$_2$), 6.01 (t, J=8 Hz, 1H, C=CH), 5.71 (d, J=12 Hz, 1H, CH=CHCO$_2$), 3.27 (s, 3H, CO$_2$CH$_3$), 2.62 (t, J=8 Hz, 2H, ArCH$_2$), 2.36 (q, J=8 Hz, 2H, ArCH$_2$CH$_2$), 1.64 (br s, 4H, CH$_2$CH$_2$), 1.24 (s, 6H, 2'CH$_3$), and 1.22 (s, 6H, 2'CH$_3$); $^{13}$C NMR (75 MHz, CDCl$_3$) δ166.85 (C=O), 162.47 (d, J$^1_{c,f}$=246 Hz, 4-ArC), 144.74, 142.54, 142.07, 140.11 (d, J$^3_{c,f}$=9 Hz, 4-ArC), 138.36, 137.92, 137.02, 129.38 (d, J$^3_{c,f}$=9 Hz, 4-ArC), 126.45 (d, J$^4_{c,f}$=3 Hz, 4-ArC), 125.67, 124.77, 119.04, 115.98 (J$^2_{c,f}$=21 Hz, 4-ArC), 113.85 (J$^2_{c,f}$=21 Hz, 4-ArC), 51.09 (CO$_2$CH$_3$), 35.15, 35.09, 34.15, 33.94, 31.87, 31.83, and 31.10; IR (film) 2960, 2925, 2860, 1730 (C=O), 1610, 1580, 1490, 1455, 1435, 1265, 1195, 1170, 825, 790, and 700 cm$^{-1}$; MS (DCI) m/e 421 (MH+).

For Methyl (2Z),(4Z)-4-phenyl-7-(5,6,7,8-tetrahydro-5,5,8,8-tetramethyl-2-naphthalenyl)-2,4-heptadienoate (13j): scale=0.69 mmol, yield=72%; $^1$H NMR (300 MHz, CDCl$_3$) δ7.19–7.30 (m, 3H, 4-ArH), 7.16 (d, J=8 Hz, 1H, 7-ArH), 7.03–7.07 (m, 2H, 4-ArH), 7.00 (d, J=2 Hz, 1H, 7-ArH), 6.84 (dd, J=2, 8 Hz, 1H, 7-ArH), 6.55 (d, J=12 Hz, 1H, CH=CHCO$_2$), 6.00 (t, J=8 Hz, 1H, C=CH), 5.69 (d, J=12 Hz, 1H, CH=CHCO$_2$), 3.19 (s, 3H, CO$_2$CH$_3$), 2.62 (t, J=8 Hz, 2H, ArCH$_2$), 2.36 (q, J=8 Hz, 2H, ArCH$_2$CH$_2$), 1.64 (br s, 4H, CH$_2$CH$_2$), 1.24 (s, 6H, 2×CH$_3$), and 1.22 (s, 6H, 2×CH$_3$); $^{13}$C NMR (75 MHz, CDCl$_3$) δ167.15 (C=O), 144.66, 142.55, 142.41, 138.15, 137.83, 129.03, 127.94, 126.97, 126.42, 125.67, 118.74, 51.08 (CO$_2$CH$_3$), 35.27, 35.16, 35.10, 34.15, 33.94, 31.89, 31.84, and 30.04; IR (film) 3020, 2960, 2825, 2860, 1730 (C=O), 1625, 1495, 1455, 1435, 1360, 1275, 1190, 1170, 825, 765, and 700 cm$^{-1}$; MS (DCI) m/e 403 (MH+), 371 (M+—OCH$_3$).

For Methyl (2Z),(4Z)-4-(3-trifluoromethylphenyl)-7-[3-(1-adamantyl)-4-methoxyphenyl]-2,4-heptadienoate (13k): scale=0.30 mmol, yield=82%; $^1$H NMR (300 MHz, CDCl$_3$) δ7.49 (m, 1H, 4-ArH), 7.41 (t, J=8 Hz, 1H, 4-ArH), 7.31 (s, 1H, 4-ArH), 7.23 (m, 1H, 4-ArH), 6.91 (d, J=2 Hz, 1H, 7-ArH), 6.86 (dd, J=2, 8 Hz, 1H, 7-ArH), 6.74 (d, J= 8 Hz, 1H, 7-ArH), 6.55 (dd, J=1, 12 Hz, 1H, CH=CHCO$_2$), 6.07 (br t, J=8 Hz, 1H, C=CH), 5.73 (d, J=12 Hz, 1H, CH=CHCO$_2$), 3.78 (s, 3H, OCH$_3$), 3.18 (s, 3H, CO$_2$CH$_3$), 2.62 (t, J=7 Hz, 2H, ArCH$_2$), 2.32 (q, J=7 Hz, 2H, ArCH$_2$CH$_2$), 2.04 (s, 9H, adamantyl), and 1.74 (s, 6H, adamantyl); $^{13}$C NMR (75 MHz, CDCl$_3$) δ166.71 (C=O), 157.18, 141.77, 139.29, 138.72, 138.36, 137.01, 132.56, 132.49, 128.49, 126.77, 126.21, 125.80, 123.72 (d, J$^3_{c,f}$=3 Hz, 4-ArC), 123.70, 119.17, 111.63, 55.03 (ArOCH$_3$), 51.07 (CO$_2$CH$_3$), 40.55, and 37.12; IR (film) 2905, 2850, 1730 (C=O), 1325, 1235, 1165, and 1125 cm$^{-1}$; MS (DCI) m/e 525 (MH+), 524 (M+), 523 (M—H)+, 135 (C$_{10}$H$_5$+). Anal. Calcd for C$_{32}$H$_{35}$O$_3$F$_3$: C, 73.26; H, 6.72. Found: C, 72.85; H, 6.66.

For Methyl (2Z),(4Z)-4-phenyl-7-[3-(1-adamantyl)-4-methoxyphenyl]-2,4-heptadienoate (13l): scale=0.86 mmol, yield=51%; $^1$H NMR (300 MHz, CDCl$_3$) δ7.19–7.32 (m, 3H, 4-ArH), 7.07–7.10 (m, 2H, 4-ArH), 6.92 (d, J=2 Hz, 1H, 7-ArH), 6.87 (dd, J=2, 8 Hz, 1H, 7-ArH), 6.74 (d, J=8 Hz, 1H, 7-ArH), 6.55 (dd, J=12, 1 Hz, 1H, CH=CHCO$_2$), 5.99 (t, J=8 Hz, 1H, C=CH), 5.70 (d, J=12 Hz, 1H, CH=CHCO$_2$), 3.78 (s, 3H, ArOCH$_3$), 3.19 (s, 3H, CO$_2$CH$_3$), 2.62 (t, J=7 Hz, 2H, ArCH$_2$), 2.37 (q, J=7 Hz, 2H, ArCH$_2$CH$_2$), 2.04 (s, 9H, adamantyl), and 1.75 (s, 6H, adamantyl); $^{13}$C NMR (75 MHz, CDCl$_3$) δ167.14 (C=O), 157.11, 142.57, 138.33, 138.12, 137.96, 137.87, 132.92, 129.06, 127.96, 126.95, 126.75, 126.23, 118.71, 111.59, 55.08 (OCH$_3$), 51.08 (CO$_2$CH$_3$), 40.57, 37.14, 36.87, 35.06, 31.34, and 29.11; IR (film) 2905, 2850, 1730 (C=O), 1495, and 1235 cm$^{-1}$; MS (DCI) m/e 457 (MH+), 425 (M—OCH$_3$)+, 255, 135 (C$_{10}$H$_{15}$+). Anal. Calcd for C$_{31}$H$_{36}$O$_3$: C, 81.54; H, 7.95. Found: C, 81.33; H, 7.81.

For Methyl (2Z),(4Z)-4-(3-trifluoromethylphenyl)-7-[4-(1-adamantyl)-3-methoxyphenyl]-2,4-heptadienoate (13m): scale=0.46 mmol, yield=96%; $^1$H NMR (300

MHz, CDCl$_3$) δ7.51 (d, J=8 Hz, 1H, 4-ArH), 7.42 (d, J=8 Hz, 1H, 4-ArH), 7.38 (s, 1H, 4-ArH), 7.21 (d, J=8 Hz, 1H, 4-ArH), 7.08 (d, J=8 Hz, 1H, 7-ArH), 6.64 (d, J=8 Hz, 1H, 7-ArH), 6.56 (m, 2H, CH=CHCO$_2$ and 7-ArH), 6.08 (t, J=8 Hz, 1H, C=CH), 5.74 (d, J=12 Hz, 1H, CH=CHCO$_2$), 3.75 (s, 3H, OCH$_3$), 3.20 (s, 3H, CO$_2$CH$_3$), 2.66 (t, J=8 Hz, 2H, ArH$_2$), 2.36 (q, J=8 Hz, 2H, ArCH$_2$CH$_2$), 2.06 (s, 9H, adamantyl), and 1.75 (s, 6H, adamantyl); $^{13}$C NMR (75 MHz, CDCl$_3$) δ166.69 (C=O), 158.75, 141.74, 139.54, 138.86, 138.70, 137.09, 136.35, 132.55, 132.55, 130.34 (d, $J^2_{c,f}$=32 Hz, 4-ArC), 128.54, 126.41, 125.80 (d, $J^3_{c,f}$=4 Hz, 4-ArC), 124.13 (d, $J^1_{c,f}$=270 Hz, CF$_3$), 123.77, 120.24, 119.35, 111.88, 54.86 (OCH$_3$), 51.09 (CO$_2$CH$_3$), 40.65, 37.14, 36.68, 35.08, 30.98, and 29.12; IR (film) 2905, 2850, 1730 (C=O), 1325, 1250, 1200, 1165, 1125, and 1070 cm$^{-1}$; MS (DCI) m/e 525 (MH$^+$), 523 (M—H)$^+$, 135 (C$_{10}$H$_{15}$$^+$); Exact mass spectrum Calcd for C$_{32}$H$_{35}$O$_3$F$_3$Na (MNa$^+$): 547.2436. Found: 547.2424.

For Methyl (2Z),(4Z)-4-phenyl-7-[4-(1-adamantyl)-3-methoxyphenyl]-2,4-heptadienoate (13n): scale=2.95 mmol, yield=96%; $^1$H NMR (300 MHz, CDCl$_3$) δ7.18–7.31 (m, 3H, 4-ArH), 7.04–7.08 (m, 3H, 2×4-ArH and 1×7-ArH), 6.63 (dd, J=2, 8 Hz, 1H, 7-ArH), 6.52–6.57 (m, 2H, 1×7-ArH and CH=CHCO$_2$), 6.00 (t, J=8 Hz, 1H, C=CH), 5.69 (d, J=12 Hz, 1H, CH=CHCO$_2$), 3.74 (s, 3H, OCH$_3$), 3.19 (CO$_2$CH$_3$), 2.63 (t, J=8 Hz, 2H, ArCH$_2$), 2.38 (q, J=8 Hz, 2H, ArCH$_2$CH$_2$), 2.04 (br s, 9H, adamantyl), and 1.73 (br s, 6H, adamantyl); $^{13}$C NMR (75 MHz, CDCl$_3$) δ167.13 (C=O), 158.69, 142.50, 139.92, 138.23, 137.80, 137.58, 136.18, 129.05, 127.95, 126.99, 126.28, 120.23, 118.81, 111.95, 54.90 (OCH$_3$), 52.00 (CO$_2$CH$_3$), 40.65, 37.14, 36.65, 35.19, 30.90, and 29.10; IR (film) 2905, 2850, 1730 (C=O), 1610, 1495, 1450, 1435, 1410, 1250, 1200, 1170, 1140, 1040, 1025, 760, and 700 cm$^{-1}$; MS (DCI) m/e 457 (MH$^+$).

For Methyl (2Z),(4Z)-4-(3-trifluoromethylphenyl)-7-[2-(1-adamantyl)-4-methoxyphenyl]-2,4-heptadienoate (13o): scale=0.31 mmol, yield=80%; $^1$H NMR (300 MHz, CDCl$_3$) δ7.49 (d, J=8 Hz, 1H, 4-ArH), 7.41 (t, J=8 Hz, 1H, 4-ArH), 7.37 (s, 1H, 4-ArH), 7.31 (d, J=7 Hz, 1H, 4-ArH), 6.92 (d, J=8 Hz, 1H, 7-ArH), 6.82 (d, J=3 Hz, 1H, 7-ArH), 6.62 (dd, J=3, 8 Hz, 1H, 7-ArH), 6.58 (d, J=13 Hz, 1H, CH=CHCO$_2$), 6.11 (t, J=8 Hz, 1H, C=CH), 5.75 (d, J=12 Hz, 1H, CH=CHCO$_2$), 3.74 (s, 3H, OCH$_3$), 3.20 (s, 3H, CO$_2$CH$_3$), 2.92 (m, 2H, ArCH$_2$), 2.34 (m, 2H, ArCH$_2$CH$_2$), 2.01 (br s, 3H, adamantyl), 1.90 (m, 6H, adamantyl), and 1.71 (m, 6H, adamantyl); $^{13}$C NMR (75 MHz, CDCl$_3$) δ166.68 (C=O), 157.58, 149.01, 141.68, 138.98, 138.67, 136.95, 132.62, 131.74, 128.53, 125.69 (d, $J^3_{c,f}$=4 Hz, 4-ArC), 123.84 (d, $J^3_{c,f}$=4 Hz, 4-ArC), 119.44, 113.08, 109.94, 55.07 (OCH$_3$), 51.12 (CO$_2$CH$_3$), 42.07, 37.84, 36.74, 33.19, 32.90, and 29.08; IR (film) 2910, 2850, 1730 (C=O), 1325, 1165, and 1130 cm$^{-1}$; MS (DCI) m/e 525 (MH$^+$), 135 (C$_{10}$H$_{15}$$^+$). Anal. Calcd for C$_{32}$H$_{35}$O$_3$F$_3$·0.20CH$_3$CO$_2$CH$_2$CH$_3$: C, 72.67; H, 6.80. Found: C, 72.65; H, 6.68.

For Methyl (2Z),(4Z)-4-(3-trifluoromethylphenyl)-5-[4-(1-adamantyl)-3-methoxyphenyl]-2,4-pentadienoate (13p): scale=0.55 mmol, yield=86%; $^1$H NMR (300 MHz, CDCl$_3$) δ7.41–7.55 (m, 4H, 4-ArH), 7.02 (d, J=8 Hz, 1H, 5-ArH), 6.83 (s, 1H, C=CH), 6.60–6.67 (m, 2H, CH=CHCO$_2$ and 5-ArH), 6.25 (d, J=2 Hz, 1H, 5-ArH), 5.83 (d, J=12 Hz, 1H, CH-CHCO$_2$), 3.32 (s, 3H, OCH$_3$), 3.26 (s, 3H, CO$_2$CH$_3$), 1.98 (s, 9H, adamantyl), and 1.71 (s, 6H, adamantyl); $^{13}$C NMR (75 MHz, CDCl$_3$) δ166.74 (C=O), 158.21, 142.10, 139.42, 139.13, 136.35, 135.84, 133.80, 133.38, 130.95 (d, $J^2_{c,f}$=32 Hz, 4-ArC), 129.15, 126.58 (d, $J^3_{c,f}$=4 Hz, 4-ArC), 126.36, 124.13 (d, $J^3_{c,f}$=4 Hz, 4-ArC), 123.99 (q, $J^1_{c,f}$=271 Hz, CF$_3$), 122.96, 120.08, 112.03, 54.23 (ArOCH$_3$), 51.26 (CO$_2$CH$_3$), 40.36, 37.03, 36.96, and 28.98; IR (film) 2905, 2850, 1730 (C=O), 1325, 1255, 1205, 1165, and 1130 cm$^{-1}$; MS (DCI) m/e 497 (MH$^+$), 135 (C$_{10}$H$_{15}$$^+$). Anal. Calcd for C$_{30}$H$_{31}$O$_3$F$_3$: C, 72.56; H, 6.29. Found: C, 72.43; H, 6.32.

For Methyl (2Z),(4Z)-4-(3-trifluoromethylphenyl)-7-[4-(1adamantyl)-3-t-butyldimethylsilyloxyphenyl]-2,4-heptadienoate (13q): scale=1.29 mmol, yield=79%; $^1$H NMR (300 MHz, CDCl$_3$) δ7.50 (d, J=8 Hz, 1H, 4-ArH), 7.40 (t, J=8 Hz, 1H, 4-ArH), 7.36 (s, 1H, 4-ArH), 7.22 (d, J=8 Hz, 1H, 4-ArH), 7.07 (d, J=8 Hz, 1H, 7-ArH), 6.61 (dd, J=8, 2 Hz, 1H, 7-ArH), 6.54 (d, J=13 Hz, HC=CHCO$_2$), 6.48 (d, J=2 Hz, 1H, 7-ArH), 6.06 (t, J=8 Hz, 1H, C=CH), 5.73 (d, J=12 Hz, 1H, HC=CHCO$_2$), 3.73 (s, 3H, ArOCH$_3$), 3.19 (s, 3H, CO$_2$CH$_3$), 2.58 (t, J=8 Hz, 2H, CH$_2$Ar), 2.31 (q, J=7 Hz, 2H, ArCH$_2$CH$_2$), 2.05 (s, 9H, adamantyl), 1.73 (s, 6H, adamantyl), 0.99 (s, 9H, t-butyl), and 0.26 (s, 6H, Si(CH$_3$)$_2$); $^{13}$C NMR (75 MHz, CDCl$_3$) δ166.69 (C=O), 154.55, 141.67, 139.11, 138.85, 138.65, 137.28, 137.13, 132.55, 130.38 (d, $J^2_{c,f}$=32 Hz), 130.16, 128.53, 126.97, 125.75 (d, $J^3_{c,f}$=4 Hz), 123.80 (d, $J^3_{c,f}$=4 Hz), 120.33, 119.30, 119.05, 51.10 (CO$_2$CH$_3$), 40.44, 37.06, 36.53, 34.75, 30.89, 29.03, 26.40, 18.90 (C(CH$_3$)$_3$), and −3.39 (Si(CH$_3$)$_2$); IR (film) 2930, 2906, 2854, 1730 (C=O), 1324, 1264, 1254, 1166, 1128, 856, and 836 cm$^{-1}$; MS (DCI) m/e 625(MH$^+$), 623 (M—H)$^+$, 567 (M-t-butyl)$^+$, 135 (C$_{10}$H$_{15}$$^+$). Anal. Calcd for C$_{37}$H$_{47}$O$_3$F$_3$: C, 71.12; H, 7.58. Found: C, 70.80; H, 7.30.

Example 13: General Procedure for Synthesis of 14

A mixture of ester 13 in methanol/tetrahydrofuran/2N sodium hydroxide solution (1:1:1, 0.1M) was heated at reflux for 1–4 h. The reaction mixture was then allowed to cool to room temperature and 10% hydrochloric acid solution was added until the solution reached pH 1. The resulting cloudy mixture was extracted with methylene chloride (2 to 4 portions), and the organic phase was washed with brine, dried over anhydrous magnesium sulfate, filtered, and concentrated. The residue was evaporated from pentane (3 portions) and then dried in vacuo.

For (2Z),(4Z)-4-(3-Trifluoromethylphenyl)-5-(4-decyloxyphenyl)-2,4-pentadienoic acid (14a): scale=0.49 mmol, yield=100%, 15:1 mixture of 2Z;2E isomers. mp 86°–88° C.; UV$_{max}$ (CH$_3$OH) 300 nm (ε=20,700), 224 nm (ε=10,900), 324 nm (ε=14,800); $^1$H NMR (300 MHz, CD$_3$OD) δ7.41–7.57 (m, 4H, 4-ArH), 6.84–6.90 (m, 3H, 2×5-ArH and C=CH), 6.64–6.70 (m, 3H, 2×5-ArH and CH=CHCO$_2$), 5.88 (d, J=12 Hz, 1H, CH=CHCO$_2$), 3.89 (t, J=6 Hz, 2H, ArOCH$_2$), 1.70 (quint, J=6 Hz, 2H, ArOCH$_2$CH$_2$), 1.28–1.50 (m, 14H, 7×CH$_2$), and 0.85 (t, J=6 Hz, 3H, CH$_3$); $^{13}$C NMR (75 MHz, CD$_3$OD) δ169.90 (C=O), 160.40 (5-ArC), 143.42, 141.17, 136.29, 135.98, 134.69, 132.11 (5-ArC), 129.49, 127.69 (q, $J^3_{c,f}$=4 Hz, 4-ArC), 125.00 (q, $J^3_{c,f}$=4 Hz, 4-ArC), 121.90, 115.17 (5-ArC), 68.97 (ArOCH$_2$), 33.05, 30.68, 30.47, 30.44, 30.30, 23.72, and 14.43; IR (KBr) 2500–3500 (br, CO$_2$H), 2955, 2940, 2920, 2870, 2850, 1700 (C=O), 1600, 1510, 1470, 1450, 1420, 1325, 1310, 1255, 1180, and 1160 cm$^{-1}$; MS (DCI) m/e 475 (MH$^+$). Anal. Calcd for C$_{28}$H$_{33}$O$_3$: C, 70.87; H, 7.01. Found: C, 70.83; H, 7.03.

For (2Z),(4Z)-4-(3-Trifluoromethylphenyl)-5-(3-decyloxyphenyl)-2,4-pentadienoic acid (14b): scale=0.80 mmol, yield=99%, 18:1 mixture of 2Z:2E isomers. UV$_{max}$ (CH$_3$OH) 322 nm ($\epsilon$=19,000), 234 nm ($\epsilon$=12,300); $^1$H NMR (300 MHz, CDCl$_3$) $\delta$7.56 (d, J=7 Hz, 1H, 4-ArH), 7.41–7.51 (m, 3H, 4-ArH), 7.06 (t, J=8 Hz, 1H, 5-ArH), 6.90 (s, 1H, C=CH), 6.64–6.74 (m, 2H, 5-ArH and CH=CHCO$_2$), 6.61 (d, J=8 Hz, 1H, 5-ArH), 6.38 (t, J=2 Hz, 1H, 5-ArH), 5.94 (d, J=12 Hz, 1H, CH=CHCO$_2$), 3.56 (t, J= 7 Hz, 2H, ArOCH$_2$), 1.54–1.64 (m, 2H, ArOCH$_2$CH$_2$), 1.21–1.35 (m, 14H, 7×CH$_2$), and 0.88 (t, J=7 Hz, 3H, CH$_3$); $^{13}$C NMR (75 MHz, CDCl$_3$) $\delta$169.95 (C=O), 160.10 (5-ArC), 142.97, 140.95, 138.38, 135.78, 134.66, 130.34, 130.20, 127.78 (q, $J^3_{c,f}$2 4 Hz, 4-ArC), 125.17 (q, $J^3$c,f=4 Hz, 4-ArC), 123.49, 122.87, 116.19, 115.38, 68.66 (ArOCH$_2$), 33.07, 30.70, 30.66, 30.46, 30.39, 30.18, 27.00, 23.74, and 14.44; IR (film) 2500–3400 (br, CO$_2$H), 3060, 2925, 2855, 1695 (C=O), 1600, 1575, 1490, 1470, 1435, 1325, 1265, 1230, and 1165 cm$^{-1}$; MS (DCI) m/e 475 (MH+). Anal. Calcd for C$_{28}$H$_{33}$O$_3$F$_3$: C, 70.87; H, 7.01. Found: C, 70.68; H, 6.99.

For (2Z),(4Z)-4-(3-Trifluoromethylphenyl)-5-(2-decyloxyphenyl)-2,4-pentadienoic acid (14c): scale=0.61 mmol, yield=100%, 3.5:1 mixture of 2Z:2E isomers. UV$_{max}$ (CH$_3$OH) 320 nm ($\epsilon$=2,900), 245 nm ($\epsilon$=3,000); $^1$H NMR (300 MHz, CD$_3$OD) $\delta$7.37–7.68 (m, 3H, 4-ArH), 7.23–7.30 (m, 1H, 4-ArH), 7.09–7.15 (m, 1H, 5-ArH), 7.07 (br s, 1H, C=CH), 6.74–6.99 (m, 1H, 5-ArH), 6.72 (dd, J=1, 12 Hz, 1H, CH=CHCO$_2$), 6.62 (dd, J=2, 8 Hz, 1H, 5-ArH), 6.55 (t, J=8 Hz, 1H, 5-ArH), 5.97 (d, J=12 Hz, 1H, CH=CHCO$_2$, 2Z isomer), 5.38 (d, J=15 Hz, 1H, CH=CHCO$_2$, 2E isomer), 3.97–4.05 (m, 2H, ArOCH$_2$), 1.73–1.87 (m, 2H, ArOCH$_2$CH$_2$), 1.22–1.58 (m, 14H, 7×CH$_2$), and 0.86–0.89 (m, 3H, CH$_3$); $^{13}$C NMR (75 MHz, CD$_3$OD) $\delta$169.80 (C=O), 158.72 (5-ArC), 143.43, 141.02, 137.68, 134.48, 132.10, 131.51, 131.44, 131.15, 130.93, 130.32, 129.94, 127.57 (q, $J^3_{c,f}$=4 Hz, 4-ArC), 126.41, 124.92 (q, $J^3$c,f=4 Hz, 4-ArC), 123.07, 122.14, 120.77, 113.43, 112.94, 69.45 (ArOCH$_2$), 33.08, 31.34, 30.75, 30.70, 30.50, 30.34, 27.27, 23.75, and 14.45; IR (film) 2500–3500 (br, CO$_2$H), 2925, 2855, 1695 (C=O), 1595, 1455, 1325, 1290, 1250, 1165, and 1130 cm$^{-1}$; MS (DCI) m/e 475 (MH+). Anal. Calcd for C$_{28}$H$_{33}$O$_3$: C, 70.87; H, 7.01. Found: C, 70.83; H, 6.91.

For (2Z),(4Z)-4-(3-Trifluoromethylphenyl)-5-[4-(2E),(6E)-3,7-dimethyl-octa-2,6-dien-oxy]phenyl)-2,4-pentadienoic acid (14d): scale=0.74 mmol, yield=98%, 11:1 mixture of 2Z:2E isomers. UV$_{max}$ (CH$_3$OH) 324 nm ($\epsilon$=12,600), 234 nm ($\epsilon$=9,200); $^1$H NMR (300 MHz, CD$_3$OD) $\delta$7.56 (d, J=7 Hz, 1H, 4-ArH), 7.41–7.50 (m, 3H, 4-ArH), 6.84–6.88 (m, 3H, 2×5-ArH and ArCH=C), 6.65–6.70 (m, 3H, 2×5-ArH and CH=CHCO$_2$), 5.88 (d, J=12 Hz, 1H, CH=CHCO$_2$), 5.37 (dt, J=1, 7 Hz, 1H, C=CHCH$_2$O), 5.04–5.07 (m, 1H, CH=C(CH$_3$)$_2$), 4.48 (d, J=7 Hz, 2H, ArOCH$_2$), 2.04–2.11 (m, 4H, C=CHCH$_2$CH$_2$), and 1.58–1.69 (m, 9H, 3×CH$_3$); $^{13}$C NMR (75 MHz, CD$_3$OD) $\delta$170.15 (C=O), 160.10 (5-ArC), 143.43, 141.93, 141.15, 136.33, 135.98, 134.70, 132.58, 132.07 (5-ArC), 130.33, 129.56, 127.68 (q, $J^3$c,f=4 Hz, 4-ArC), 125.12 (q, f3c,f=4 Hz, 4-ArC), 124.94, 121.88, 121.03, 115.49 (5-ArC), 65.81 (ArOCH$_2$), 40.54, 27.34, 25.87, 17.73, and 16.61; IR (KBr) 2500–3500 (br, CO$_2$H), 3035, 2975, 2930, 2890, 1700 (C=O), 1595, 1510, 1440, 1420, 1330, 1310, 1300, 1255, 1180, 1135, and 1095 cm$^{-1}$; MS (DCI) m/e 471 (MH+). Anal. Calcd for C$_{28}$H$_{29}$O$_3$F$_3$: C, 71.47; H, 6.21. Found: C, 71.29; H, 6.16.

For (2Z),(4Z)-4-(3-Trifluoromethylphenyl)-5-(3,4-bisdecyloxyphenyl)-2,4-pentadienoic acid/(2E),(4Z)-4-(3-Trifluoromethylphenyl)-5-(3,4-bisdecyloxyphenyl)-2,4-pentadienoic acid (14e): scale=1.09 mmol, yield=73%, 3:2 mixture of 2Z:2E isomers; UV$_{max}$ (CH$_3$OH) 350 nm (sh, e=21,200), 242 ($\epsilon$=13,100); $^1$H NMR (300 MHz, CDCl$_3$) $\delta$7.36–7.72 (m, 4H, 4-ArH), 6.91 (s, 1H, C=CH from E-isomer), 6.83 (s, 1H, C=CH from Z-isomer), 6.59–6.71 (m, 3H, 2×5-ArH and CH=CHCO$_2$), 6.31 (d, J=2 Hz, 1H, 5-ArH from Z-isomer), 6.20 (d, J=2 Hz, 1H, 5-ArH from E-isomer), 5.78 (d, J=12 Hz, 1H, CH=CHCO$_2$ from Z-isomer), 5.26 (d, J=15 Hz, 1H, CH=CHCO$_2$ from E-isomer), 3.89–3.94 (m, 2H, CH$_2$OAr), 3.43 (t, J=7 Hz, 2H, CH$_2$OAr from Z-isomer), 3.36 (t, J=7 Hz, 2H, CH$_2$OAr from E-isomer), 1.70–1.79 (m, 2H, CH$_2$CH$_2$OAr), 1.51–1.63 (m, 2 H, CH$_2$CH$_2$OAr), 1.21–1.47 (m, 28H, 14×CH$_2$), and 0.83–0.88 (m, 6H, 2×CH$_3$); $^{13}$C NMR (75 MHz, CDCl$_3$) $\delta$171.80 (C=O from E-isomer), 166.81 (C=O from Z-isomer), 112.56–151.52 (27 peaks from ArC and C=C, both isomers), 68.99 (CH$_2$OAr), 68.51 (CH$_2$OAr), 68.31 (CH$_2$OAr), 31.90, 29.57, 29.35, 29.12, 28.99, 25.94, 25.79, 22.68, and 14.10; IR (KBr) 2300–3300 (br, CO$_2$H), 2955, 2920, 2850, 1690 (C=O from Z-isomer), 1675 (C=O from E-isomer), 1615, 1590, 1510, 1470, 1430, 1330, 1275, 1235, 1205, 1165, 1140, 1130, 1070, and 1015 cm$^{-1}$; MS (FAB) m/e 630 (M+). Anal. Calcd for C$_{38}$H$_{53}$O$_4$F$_3$: C, 72.35; H, 8.47. Found: C, 72.45; H, 8.48.

For (2Z), (4Z)-4-(3-trifluoromethylphenyl)-5-(5,6,7,8-tetrahydro-5,5,8,8-tetramethyl-2-anthracenyl)-2,4-pentadienoic acid (14f): scale=1.0, yield=100%; UV$_{max}$ (CH$_3$OH) 332 nm ($\epsilon$=23,800), 282 nm ($\epsilon$=23,100), and 279 nm ($\epsilon$=22,800); $^1$H NMR (300 MHz, CD$_3$OD) $\delta$7.68 (s, 1 H, ArH), 7.58 (s, 1H, ArH), 7.52 (s, 1H, ArH), 7.42–7.47 (m, 2H, ArH), 7.41 (d, J=9 Hz, 1H, ArH), 7.08 (br s, 1H, C=CH), 6.80 (dd, J=2, 9 Hz, 1H, ArH), 6.76 (dd, J=1, 12 Hz, 1H, CH=CHCO$_2$), 5.96 (d, J=12 Hz, 1H, CH=CHCO$_2$), 1.76 (s, 4H, CH$_2$CH$_2$), and 1.35 (br s, 12 H, 4×CH$_3$); $^{13}$C NMR (75 MHz, CD$_3$OD/CDCl$_3$) $\delta$167.92 (C=O), 144.06, 143.62, 141.45, 138.70, 135.56, 134.22, 132.60, 131.61, 130.84, 130.48, 129.50, 128.09, 128.06, 125.53, 124.70, 124.44, 124.17, 123.63, 123.10, 120.44, 34.02 (CH$_2$CH$_2$), 33.46, 33.36, and 30.86 (4×CH$_3$); IR (KBr) 2400–3300 (br, CO$_2$H), 3050, 3010, 2960, 2930, 2985, 1695 (C=O), 1610, 1430, 1325, 1310, 1280, 1250, 1225, 1180, and 1135 cm$^{-1}$; MS (DCI) m/e 479 (MH+). Anal. Calcd. for C$_{30}$H$_{29}$O$_2$F$_3$.0.25 H$_2$O: C, 74.59; H, 6.15. Found: C, 74.56; H, 6.14.

For (2Z),(4Z)-4-(3-Trifluoromethylphenyl)-7-(5,6,7,8-tetrahydro-5,5,8,8-tetramethyl-2-naphthalenyl)-2,4-heptadienoic acid (14g): scale=0.62 mmol, yield=40%; UV$_{max}$ (CH$_3$OH) 252 nm ($\epsilon$=9,800); $^1$H NMR (300 MHz, CD$_3$OD) $\delta$7.51 (br d, J=8 Hz, 1H, 4-ArH), 7.41 (t, J=8 Hz, 1H, 4-ArH), 7.33 (s, 1H, 4-ArH), 7.16 (d, J=8 Hz, 1H, 7-ArH), 7.13 (d, J=8 Hz, 1H, 4-ArH), 6.99 (d, J=2 Hz, 1H, 7-ArH), 6.79 (dd, J=2, 8 Hz, 1H, 7-ArH), 6.57 (d, J=12 Hz, 1H, CH=CHCO$_2$), 6.08 (t, J=8 Hz, 1H, C=CH), 5.76 (d, J=12 Hz, 1H, CH=CHCO$_2$), 2.62 (t, J=8 Hz, 2H, ArCH$_2$), 2.27 (q, J=8 Hz, 2H, ArCH$_2$CH$_2$), 1.66 (br s, 4H, CH$_2$CH$_2$), 1.24 (s, 6H, 2×CH$_3$), and 1.21 (s, 6H, 2×CH$_3$); $^{13}$C NMR (75 MHz, CD$_3$OD) $\delta$169.97 (C=O), 145.64, 143.43, 142.79, 140.42, 139.31, 138.88, 138.66, 134.11, 129.70, 127.53 (q, $J^3_{c,f}$=4 Hz, 4-ArC), 126.92 (q, $J^3_{c,f}$=4 Hz, 4-ArC), 124.67, 121.24, 36.31, 36.05, 35.06, 34.86, 32.54, and 32.31; IR (film) 2500–3500 (br, $CO_2H$), 3020, 2960, 2930, 2860, 1700 (C=O), 1615, 1455, 1435, 1355, 1325, 1310, 1280, 1250, 1220, 1165, 1130, 1100, 1070, 760, and 705 cm$^{-1}$; MS (DCI) m/e 457 (MH+). Anal. Calcd for $C_{28}H_{31}O_2F_3$.0.15 $H_2O$: C, 73.22; H, 6.87. Found: C, 73.25; H, 6.90.

For (2Z),(4Z)-4-(4-Fluorophenyl)-7-(5,6,7,8-tetrahydro-5,5,8,8-tetramethyl-2-naphthalenyl)-2,4-heptadienoic acid (14h): scale=0.77 mmol, yield=61%; UV$_{max}$ (CH$_3$OH) 252 nm ($\epsilon$=12,000); $^1$H NMR (300 MHz, CD$_3$OD) δ7.16 (d, J=8 Hz, 1H, 7-ArH), 6.99 (d, J=2 Hz, 1H, 7-ArH), 6.91–6.97 (m, 4H, 4-ArH), 6.79 (dd, J=2, 8 Hz, 1H, 7-ArH), 6.50 (d, J=12 Hz, 1H, CH=CHCO$_2$), 5.99 (t, J=8 Hz, 1H, C=CH), 5.72 (d, J=12 Hz, 1H, CH=CHCO$_2$), 2.60 (t, J=8 Hz, 2H, ArCH$_2$), 2.27 (q, J=8 Hz, 2H, ArCH$_2$CH$_2$), 1.67 (br s, 4H, CH$_2$CH$_2$), 1.24 (s, 6H, 2'CH$_3$), and 1.22 (s, 6H, 2×CH$_3$); $^{13}$C NMR (75 MHz, CD$_3$OD) δ170.43, 163.23 (d, $J^1_{c,f}$=246 Hz, 4-ArC), 145.59, 143.36, 143.07, 139.52, 138.92, 137.71, 132.19 (d, $J^3_{c,f}$=8 Hz, 4-ArC), 127.62, 127.47, 126.95, 120.84, 115.54 (d, $J^2_{c,f}$=21 Hz, 4-ArC), 36.32, 36.10, 35.06, 34.85, 32.59, and 32.34; IR (film) 2400–3500 (br, $CO_2H$), 2960, 2925, 2860, 1695 (C=O), 1605, 1510, 1455, 1435, 1360, 1280, 1220, 1160, 840, 825, and 760 cm$^{-1}$; MS (DCI) m/e 407 (MH+), 389 (M+—OH). Anal. Calcd for $C_{27}H_{31}O_2F$: C, 79.77; H, 7.69. Found: C, 79.40; H, 7.51.

For (2Z),(4Z)-4-(3-Fluorophenyl)-7-(5,6,7,8-tetrahydro-5,5,8,8-tetramethyl-2-naphthalenyl)-2,4-heptadienoic acid (14i): scale=1.13 mmol, yield=74%; UV$_{max}$ (CH$_3$OH) 270 nm (sh, $\epsilon$=7,700), 242 ($\epsilon$=9,700); $^1$H NMR (300 MHz, CDCl$_3$) δ7.16–7.26 (m, 2H, 1×4-ArH and 1×7-ArH), 7.00 (d, J=2 Hz, 1H, 7-ArH), 6.80–6.91 (m, 3H, 2×4-ArH and 1×7-ArH), 6.71 (apparent dt, J=2, 8 Hz, 1H, 4-ArH), 6.59 (d, J=12 Hz, 1H, CH=CHCO$_2$), 6.03 (t, J=8 Hz, 1H, C=CH), 5.71 (d, J=12 Hz, 1H, CH=CHCO$_2$), 2.62 (t, J=8 Hz, 2H, ArCH$_2$), 2.37 (q, J=8 Hz, 2H, ArCH$_2$CH$_2$), 1.64 (br s, 4H, CH$_2$CH$_2$), 1.23 (s, 6H, 2×CH$_3$), and 1.21 (s, 6H, 2×CH$_3$); $^{13}$C NMR (75 MHz, CDCl$_3$) δ165.20 (C=O), 162.47 (d, $J^1_{c,f}$=246 Hz, 4-ArC), 145.14, 144.74, 142.52, 140.01 (d, $J^3_{c,f}$=8 Hz, 4-ArC), 137.98, 137.93, 136.49, 129.41 (d, $J^3_{c,f}$=8 Hz, 4-ArC), 126.45, 125.71, 124.77, 115.97 (d, $J^2_{c,f}$=21 Hz, 4-ArC), 113.91 (d, $J^2_{c,f}$=21 Hz, 4-ArC), 35.14, 35.09, 34.14, 33.94, 31.87, 31.83, and 31.19; IR (film) 2400–3500 (br, $CO_2H$), 2960, 2925, 2860, 1700 (C=O), 1610, 1580, 1490, 1455, 1440, 1360, 1250, 1220, 1190, 885, 825, 785, and 760 cm$^{-1}$; MS (DCI) m/e 407 (MH+). Anal. Calcd for $C_{27}H_{31}O_2F$: C, 79.77; H, 7.69. Found: C, 79.21; H, 7.76.

For (2Z),(4Z)-4-Phenyl-7-(5,6,7,8-tetrahydro-5,5,8,8-tetramethyl-2-naphthalenyl)-2,4-heptadienoic acid (14j): scale=0.45 mmol, yield=81%; UV$_{max}$ (CH$_3$OH) 247 nm (sh, $\epsilon$=11,700), 220 ($\epsilon$=19,000); $^1$H NMR (300 MHz, CD$_3$OD) δ7.19–7.27 (m, 3H, 4-ArH), 7.15 (d, J=8 Hz, 1H, 7-ArH), 6.95–7.00 (m, 3H, 2×4-ArH and 1×7-ArH), 6.80 (dd, J=2, 8 Hz, 1H, 7-ArH), 6.52 (d, J=12 Hz, 1H, CH=CHCO$_2$), 5.99 (t, J=8 Hz, 1H, C=CH), 5.73 (d, J=12 Hz, 1H, CH=CHCO$_2$), 2.60 (t, J=8 Hz, 2H, ArCH$_2$), 2.29 (q, J=8 Hz, 2H, ArCH$_2$CH$_2$), 1.66 (br s, 4H, CH$_2$CH$_2$), 1.24 (s, 6H, 2×CH$_3$), and 1.21 (s, 6H, 2×CH$_3$); $^{13}$C NMR (75 MHz, CD$_3$OD) δ145.56, 143.67, 143.30, 139.63, 139.44, 136.82, 130.27, 128.91, 128.02, 127.56, 127.45, 126.91, 120.71, 36.36, 36.33, 36.21, 35.06, 34.85, 32.62, and 32.34; IR (film) 2400–3500 (br, $CO_2H$), 3020, 2960, 2925, 2860, 1695 (C=O), 1620, 1495, 1455, 1440, 1360, 1285, 1245, 825, 760, and 700 cm$^{-1}$; MS (DCI) m/e 389 (MH+), 371 (M+—OH). Anal. Calcd for $C_{27}H_{32}O_2$.0.2 $H_2O$: C, 82.69; H, 8.32. Found: C, 82.76; H, 8.27.

For (2Z),(4Z)-4-(3-Trifluoromethylphenyl)-7-[3-(1-adamantyl]-4-methoxyphenyl]-2,4-heptadienoic acid (14k): scale=0.19 mmol, yield=75%; $^1$H NMR (300 MHz, CDCl$_3$) δ7.46 (d, J=8 Hz, 1H, 4-ArH), 7.37 (d, J=8 Hz, 1H, 4-ArH), 7.32 (m, 1H, 4-ArH), 7.21 (d, J=8 Hz, 1H, 4-ArH), 6.91 (d, ]=2 Hz, 1H, 7-ArH), 6.86 (dd, J=2, 8 Hz, 1H, 7-ArH), 6.73 (d, J=8 Hz, 1H, 7-ArH), 6.63 (d, J=12 Hz, 1H, CH=CHCO$_2$), 6.08 (t, J=8 Hz, 1H, C=CH), 5.72 (d, J=12 Hz, 1H, CH=CHCO$_2$), 3.78 (s, 3H, OCH$_3$), 2.62 (t, J=8 Hz, 2H, ArCH$_2$), 2.33 (q, J=8 Hz, 2H, ArCH$_2$CH$_2$), 2.04 (s, 9H, adamantyl), and 1.74 (s, 6H, adamantyl); $^{13}$C NMR (75 MHz, CDCl$_3$) δ170.89 (C=O), 157.17, 145.10, 138.98, 138.66, 138.36, 136.50, 132.48, 130.35 (d, $J^2_{c,f}$=32 Hz, 4-ArC), 128.43, 126.77, 126.24, 125.75 (d, $J^3_{c,f}$=4 Hz, 4-ArC), 124.47, 123.79 (d, $J^3_{c,f}$=4 Hz, 4-ArC), 120.48 (d, $J^1_{c,f}$=271 Hz, CF$_3$), 118.41, 111.63, 55.03 (OCH$_3$), 40.56, 37.13, 36.86, 34.77, 31.50, and 29.10; IR (film) 2400–3500 (br, $CO_2H$), 2905, 2850, 1700 (C=O), 1325, 1235, 1165, and 1130 cm$^{-1}$; MS (DCI) m/e 511 (MH+), 135 ($C_{10}H_{15}$+). Anal. Calcd for $C_{31}H_{33}O_3F_3$: C, 72.92; H, 6.51. Found: C, 72.93; H, 6.58.

For (2Z),(4Z)-4-Phenyl-7-[3-(1-adamantyl)-4-methoxyphenyl]-2,4-heptadienoic acid (14l): scale=0.37 mmol, yield=60%; $^1$H NMR (300 MHz, CDCl$_3$) δ7.19–7.33 (m, 3H, 4-ArH), 7.12 (m, 2H, 4-ArH), 6.95 (d, J=2 Hz, 1H, 7-ArH), 6.90 (d, J=8 Hz, 1H, 7-ArH), 6.75 (d, J=8 Hz, 1H, 7-ArH), 6.66 (d, J=12 Hz, 1H, CH=CHCO$_2$), 6.03 (t, J=8 Hz, 1H, C=CH), 5.72 (d, ]=12 Hz, 1H, CH=CHCO$_2$), 3.79 (s, 3H, ArOCH$_3$), 2.64 (t, J=7 Hz, 2H, ArCH$_2$), 2.41 (q, J=7 Hz, 2H, ArCH$_2$CH$_2$), 2.07 (s, 9H, adamantyl), and 1.77 (s, 6H, adamantyl); $^{13}$C NMR (75 MHz, CDCl$_3$) δ171.65 (C=O), 157.12, 145.98, 138.33, 137.85, 137.44, 137.15, 133.01, 128.02, 127.08, 126.79, 126.31, 118.19, 111.62, 55.10 (OCH$_3$), 40.60, 37.17, 36.90, 34.93, 31.49, and 29.14; IR (KBr) 2400–3600 (br, $CO_2H$), 2905, 2850, 1695 (C=O), 1495, 1445, 1235, and 700 cm$^{-1}$; MS (DCI) m/e 443 (MH+), 255, 135 ($C_{10}H_{15}$+). Anal. Calcd for $C_{30}H_{34}O_3$.0.11 $H_2O$: C, 81.05; H, 7.76. Found: C, 80.68; H, 7.78.

For (2Z),(4Z)-4-(3-Trifluoromethylphenyl)-7-[4-(1-adamantyl)-3-methoxyphenyl]-2,4-heptadienoic acid (14m): scale=0.75 mmol, yield=77%; $^1$H NMR (300 MHz, CDCl$_3$) δ7.46 (d, J=8 Hz, 1H, 4-ArH), 7.35 (m, 2H, 4-ArH), 7.17 (d, J=8 Hz, 1H, 4-ArH), 7.07 (d, J=8 Hz, 1H, 7-ArH 6.60–6.60 (m, 2H, 7-ArH and CH=CHCO$_2$), 6.55 (d, J=2 Hz, 1H, 7-ArH), 6.08 (t, J=7 Hz, 1H, C=CH), 5.72 (d, J=12 Hz, 1H, CH=CHCO$_2$), 3.74 (s, 3H, OCH$_3$), 2.64 (t, J=7 Hz, 2H, ArCH$_2$), 2.36 (q, J=7 Hz, 2H, ArCH$_2$CH$_2$), 2.05 (s, 9H, adamantyl), and 1.74 (s, 6H, adamantyl); $^{13}$C NMR (75 MHz, CDCl$_3$) δ170.95 (C=O), 158.74, 145.01, 139.59, 138.63, 138.54, 136.56, 136.35, 132.46, 130.36 (d, $J^2_{c,f}$=32 Hz, 4-ArC), 128.47, 126.39, 125.78, (d, $J^3_{c,f}$=4 Hz, 4-ArC), 123.84 (d, $J^3_{c,f}$=4 Hz, 4-ArC), 122.28, 120.25, 118.59, 111.92, 54.87 (OCH$_3$), 40.64, 37.14, 36.67, 34.92, 31.06, and 29.10; IR (KBr) 2400–3600 (br, $CO_2H$), 2905, 2850, 1700 (C=O), 1325, 1250, 1165, and 1130 cm$^{-1}$; MS (DCI) m/e 511 (MH+), 135 ($C_{10}H_{15}$+). Anal. Calcd for $C_{31}H_{33}O_3F_3$: C, 72.92; H, 6.51. Found: C, 72.90; H, 6.65.

For (2Z),(4Z)-4-Phenyl-7-[4-(1-adamantyl)-3-methoxyphenyl]-2,4-heptadienoic acid (14n): scale=1.93 mmol, yield=65%; UV$_{max}$ (CH$_3$OH) 284 nm (sh, ε=8,000), 276 (ε=9,200), 242 (ε=14,500); $^1$H NMR (300 MHz, CDCl$_3$) δ7.17–7.29 (m, 3H, 4-ArH), 7.04–7.08 (m, 3H, 2×4-ArH and 1×7-ArH), 6.60–6.65 (m, 2H, 1×7-ArH and CH=CHCO$_2$), 6.56 (d, J=2 Hz, 1H, 7-ArH), 6.01 (t, J=8 Hz, 1H, C=CH), 5.71 (d, J=12 Hz, 1H, CH=CHCO$_2$), 3.73 (s, 3H, OCH$_3$), 2.63 (t, J=8 Hz, 2H, ArCH$_2$), 2.41 (q, J=8 Hz, 2H, ArCH$_2$CH$_2$), 2.04 (br s, 9H, adamantyl), and 1.74 (br s, 6H, adamantyl); $^{13}$C NMR (75 MHz, CDCl$_3$) δ170.48 (C=O), 158.71, 145.81, 139.97, 137.76, 137.58, 136.69, 136.20, 129.03, 127.99, 127.11, 126.28, 120.31, 118.07, 112.06, 54.92 (OCH$_3$), 40.68, 37.15, 36.66, 35.02, 30.98, and 29.12; IR (KBr) 2400–3600 (br, CO$_2$H), 3055, 3030, 2905, 2850, 1695 (C=O), 1610, 1570, 1495, 1450, 1410, 1290, 1245, 1180, 1160, 1140, 1040, 1025, 810, and 700 cm$^{-1}$; MS (DCI) m/e 443 (MH+). Anal. Calcd for C$_{30}$H$_{34}$O$_3$: C, 81.41; H, 7.74. Found: C, 81.03; H, 7.78.

For (2Z),(4Z)-4-(3-Trifluoromethylphenyl)-7-[2-(1-adamantyl)-4-methoxyphenyl]-2,4-heptadienoic acid (14o): scale=0.21 mmol, yield=77%; $^1$H NMR (300 MHz, CDCl$_3$) δ7.45 (m, 1H, 4-ArH), 7.36 (m, 2H, 4-ArH), 7.28 (d, J=8 Hz, 1H, 4-ArH), 6.92 (d, J=8 Hz, 1H, 7-ArH), 6.82 (d, J=3 Hz, 1H, 7-ArH), 6.60–6.67 (m, 2H, 7-ArH and CH=CHCO$_2$), 6.12 (t, J=8 Hz, 1H, C=CH), 5.74 (d, J=12 Hz, 1H, CH=CHCO$_2$), 3.74 (s, 3H, OCH$_3$), 2.90 (m, 2H, ArCH$_2$), 2.35 (m, 2H, ArCH$_2$CH$_2$), 1.89–2.08 (s, 9H, adamantyl), and 1.62–1.75 (m, 6H, adamantyl); $^{13}$C NMR (75 MHz, CDCl$_3$) δ170.74 (C=O), 157.57, 149.02, 145.04, 138.58, 136.42, 132.65, 132.53, 131.79, 130.22, 128.47, 125.67 (d, $J^3_{c,f}$=4 Hz, 4-ArC), 123.91 (d, $J^3_{c,f}$=3 Hz, 4-ArC), 118.63, 113.08, 109.93, 55.07 (OCH$_3$), 42.18, 42.05, 37.83, 36.74, 32.99, and 29.07; IR (KBr) 2400–3600 (br, CO$_2$H), 2905, 2850, 1700 (C=O), 1610, 1325, 1250, 1165, and 1125 cm$^{-1}$; MS (DCI) m/e 511 (MH+), 135 (C$_{10}$H$_{15}$+). Anal. Calcd for C$_3$H$_{33}$O$_3$F$_3$: C, 72.92; H, 6.51. Found: C, 72.55; H, 6.47.

For (2Z),(4Z)-4-(3-Trifluoromethylphenyl)-5-[-4-(1-adamantyl)-3-methoxyphenyl]-2,4-pentadienoic acid (14p): scale=0.37 mmol, yield=84%; $^1$H NMR (300 MHz, CDCl$_3$) δ7.50 (s, 1H, 4-ArH), 7.34–7.46 (m, 3H, 4-ArH), 7.03 (d, J=8 Hz, 1H, 5-ArH), 6.84 (s, 1H, C=CH), 6.70 (dd, J=1, 12 Hz, 1H, CH=CHCO$_2$), 6.64 (dd, J=2, 8 Hz, 1H, 5-ArH), 6.30 (d, J=2 Hz, 1H, 5-ArH), 5.80 (d, J=12 Hz, 1H, CH=CHCO$_2$), 3.32 (s, 3H, OCH$_3$), 1.98 (s, 9H, adamantyl), and 1.71 (s, 6H, adamantyl); $^{13}$C NMR (75 MHz, CDCl$_3$) δ171.15 (C=O), 158.21, 145.28, 139.42, 139.24, 136.25, 135.48, 133.80, 133.22, 130.95 (d, $J^2_{c,f}$=32 Hz, 4-ArC), 129.09, 126.47 (d, $J^3_{c,f}$=3 Hz, 4-ArC), 126.37, 124.21 (d, $J^3_{c,f}$=3 Hz, 4-ArC), 123.06, 120.42 (q, $J^1_{c,f}$=271 Hz, CF$_3$), 112.16, 54.22 (OCH$_3$), 40.36, 37.04, 36.98, and 28.98; IR (KBr) 2400–3600 (br, CO$_2$H), 2910, 2880, 2850, 1690 (C=O), 1330, 1250, 1240, 1165, and 1120 cm$^{-1}$; MS (DCI) m/e 483 (MH+), 135 (C$_{10}$H$_{15}$+). Anal. Calcd for C$_{29}$H$_{29}$O$_3$F$_3$: C, 72.18; H, 6.06. Found: C, 72.19; H, 6.09.

For (2Z),(4Z)-4-(3-Trifluoromethylphenyl)-7-[4-(1-adamantyl)-3-hydroxyphenyl]-2,4-heptadienoic acid (14q): prepared from 15 using the general procedure above (example 12). The crude product was purified by column chromatography (20:1 silica gel/crude product; elution with 5% methanol/methylene chloride), scale=0.33 mmol, yield=55%; $^1$H NMR (300 MHz, CDCl$_3$) δ7.48 (d, J=8 Hz, 1H, 4-ArH), 7.35–7.39 (m, 2H, 4-ArH), 7.19 (d, J=8 Hz, 1H, 4-ArH), 7.06 (d, J=8 Hz, 1H, 7-ArH), 6.59–6.65 (m, 2H, CH=CHCO$_2$ and 7-ArH), 6.34 (d, J=2 Hz, 1H, 7-ArH), 6.04 (t, J=7 Hz, 1H, C=CH), 5.75 (d, J=12 Hz, 1H, H=CHCO$_2$), 2.58 (t, J=7 Hz, 2H, CH$_2$Ar), 2.34 (q, J=7 Hz, 2H, ArCH$_2$CH$_2$), 2.04–2.07 (m, 9H, adamantyl), and 1.74 (s, 6H, adamantyl); $^{13}$C NMR (75 MHz, CDCl$_3$) δ171.18 (C=O), 154.28, 145.48, 139.66, 138.58, 137.84, 136.34, 134.21, 132.46, 130.43 (d, $J^2_{c,f}$=32 Hz, 4-ArC), 128.58, 126.95, 125.69 (d, f3$_{c,f}$=4 Hz, 4-ArC), 124.07 (d, $J^1_{c,f}$=271 Hz, CF$_3$), 123.96 (d, $J^3_{c,f}$=3 Hz, 4-ArC), 120.58, 118.51, 116.97, 40.59, 37.05, 36.38, 34.27, 30.82, and 29.02; IR (KBr) 2500–3600 (br, CO$_2$H), 2905, 2850, 1680 (C=O), 1615, 1420, 1325, 1270, 1260, 1225, 1165, 1125, and 1075 cm$^{-1}$; MS (DCI) m/e 497 (MH+), 496 (M+), 495 (M—H)+, 135 (C$_{10}$H$_{15}$+). Anal. Calcd for C$_{30}$H$_{31}$O$_3$F$_3$: C, 72.56; H, 6.29. Found: C, 72.56; H, 6.37.

For (2Z),(4Z)-4-(3-Trifluoromethylphenyl)-7-[4-(1-adamantyl)-3-pentyloxyphenyl]-2,4-heptadienoic acid (14r): prepared from 16r; purified by column chromatography (40:1 silica gel/crude product; elution with 3% methanol/methylene chloride); scale=0.55 mmol, yield=74%; $^1$H NMR (300 MHz, CDCl$_3$) δ7.45 (d, J=7 Hz, 1H, 4-ArH), 7.33–7.38 (m, 2H, 4-ArH), 7.17 (d, J=8 Hz, 1H, 4-ArH), 7.06 (d, J=8 Hz 1H, 7-ArH), 6.57–6.65 (m, 2H, 7-ArH and HC=CHCO$_2$), 6.54 (d, J=2 Hz, 1H, 7-ArH), 6.08 (t, J=8 Hz, 1H, C=CH), 5.73 (d, J=12 Hz, 1H, HC=CHCO$_2$), 3.86 (t, J=6.5 Hz, 2H, OCH$_2$), 2.63 (t, J=8 Hz, 2H, CH$_2$Ar), 2.36 (q, J=8 Hz, 2H, ArCH$_2$CH$_2$), 2.04–2.07 (m, 9H, adamantyl), 1.83 (quint, J=7 Hz, 2H, OCH$_2$CH$_2$), 1.74 (s, 6H, adamantyl), 1.45–1.56 (m, 2H, O(CH$_2$)$_2$CH$_2$), 1.33–1.42 (m, 2H, O(CH$_2$)$_3$CH$_2$), and 0.93 (t, J=7 Hz, 3H, O(CH$_2$)$_4$CH$_3$); $^{13}$C NMR (75 MHz, CDCl$_3$) δ170.84 (C=O), 158.09, 145.00, 139.49, 138.73, 138.61, 136.57, 136.04, 132.48, 130.36 (d, $J^2_{c,f}$=32 Hz, 4-ArC), 128.46, 126.35, 125.76, 123.80, 119.92, 119.59, 118.49, 112.08, 67.52 (OCH$_2$), 40.59, 37.17, 36.70, 35.12, 31.09, 30.27, 29.12, 28.65, 22.43, and 14.08; IR (film) 2400–3300 (br, CO$_2$H), 2905, 2850, 1700 (C=O), 1325, 1165, and 1130 cm$^{-1}$; MS (DCI) m/e 567 (MH+), 549 (M—OH)+, 431 (M—C$_{10}$H$_{15}$)+, 135 (C$_{10}$H$_{15}$+). Anal. Calcd for C$_{35}$H$_{41}$O$_3$F$_3$: C, 74.18; H, 7.29. Found: C, 73.99; H, 7.39.

For (2Z),(4Z)-4-(3-Trifluoromethylphenyl)-7-[4-(1-adamantyl)-3-(3,5-difluorobenzyloxy)phenyl]-2,4-heptadienoic acid (14s): prepared from 16s; purified by column chromatography (20:1 silica gel/crude product; elution with 3% methanol/methylene chloride); scale=0.48 mmol, yield=86%; $^1$H NMR (300 MHz, CDCl$_3$) δ7.46 (d, J=8 Hz, 1H, 4-ArH), 7.32–7.38 (m, 2H, 4-ArH), 7.17 (d, J=8 Hz, 1H, 4-ArH), 7.13 (d, J=8 Hz, 1H, 7-ArH), 7.00 (d, J=6 Hz, 2H, HArCH$_2$), 6.67–6.78 (m, 2H, HArCH$_2$ and 7-ArH), 6.62 (d, J=13 Hz, 1H, HC=CHCO$_2$), 6.56 (d, J=1.5 Hz, 1H, 7-ArH), 6.05 (t, J=8 Hz, 1H, C=CH), 5.73 (d, J=12 Hz, 1H, HC=CHCO$_2$), 4.98 (s, 2H, OCH$_2$), 2.63 (t, J=8 Hz, 2H, CH$_2$Ar), 2.35 (q, J=8 Hz, 2H, ArCH$_2$CH$_2$), 2.04–2.08 (m, 9H, adamantyl), and 1.72 (s, 6H, adamantyl); $^{13}$C NMR (75 MHz, CDCl$_3$) δ170.71 (C=O), 163.22 (d, $J^1_{c,f}$=247 Hz, 3,5-difluorobenzyl), 157.23, 145.02, 139.73, 138.58, 138.34, 136.64, 136.47, 132.43, 128.49, 126.88, 125.76, 123.89, 121.08, 118.57, 112.79, 109.68 (d, $J^2_{c,f}$=25 Hz, 3,5-difluorobenzyl), 102.98 (t, $J^2_{c,f}$=25 Hz, 3,5-difluorobenzyl), 68.89 (CH$_2$O), 40.68, 37.04, 36.77, 34.85, 31.02, and 29.02; IR (KBr) 2400–3600 (br, CO$_2$H), 2905, 2850, 1700 (C=O), 1630, 1600, 1325, 1245, 1165, 1120, 1070 cm$^{-1}$; MS (DCI) m/e 623 (MH+), 622 (M+), 621 (M—H)+, 135 (C10H$_{15}$+). Anal. Calcd for C$_{37}$H$_{35}$O$_3$F$_5$: C, 71.37; H, 5.67. Found: C, 70.93; H, 5.62.

For (2Z),(4Z)-4-(3-Trifluoromethylphenyl)-7-[4-(1-adamantyl)-3-(4-methoxybenzyloxy)phenyl]-2,4-heptadienoic acid (14t): prepared from 16t; purified by column chromatography (20:1 silica gel/crude product; elution with 3% methanol/methylene chloride); scale=0.55 mmol, yield=73%; $^1$H NMR (300 MHz, CDCl$_3$) δ7.46 (d, J=8 Hz, 1H, 4-ArH), 7.32–7.40 (m, 4H, 2×4-ArH and 2×HArCH$_2$), 7.17 (d, J=7.5 Hz, 1H, 4-ArH), 7.10 (d, J=8 Hz, 1H, 7-ArH), 6.91 (dt, J=9, 2 Hz, 2H, HArCH$_2$), 6.59–6.66 (m, 3H, 2×7-ArH and HC=CHCO$_2$), 6.06 (t, J=7 Hz, 1H, C=CH), 5.73 (d, J=12 Hz, 1H, HC=CHCO$_2$), 4.93 (s, 2H, OCH$_2$), 3.82 (s, 3H, OCH$_3$), 2.64 (t, J=8 Hz, 2H, CH$_2$Ar), 2.36 (q, J=8 Hz, 2H, ArCH$_2$CH$_2$), 2.07–2.08 (m, 6H, adamantyl), 1.99 (s, 3H, adamantyl), and 1.68 (s, 6H, adamantyl); $^{13}$C NMR (75 MHz, CDCl$_3$) δ170.60 (C=O), 159.14, 157.80, 144.99, 139.57, 138.61, 138.56, 136.59, 136.39, 132.47, 130.57, 130.14, 129.71,129.46, 128.88, 128.48, 126.57, 125.79 (d, $J^3_{c,f}$=4 Hz, 4-ArC), 123.85 (d, $J^3_{c,f}$=4 Hz, 4-ArC), 122.29, 120.44, 118.50, 113.81, 112.75, 69.73 (OCH$_2$), 55.29 (OCH$_3$), 40.56, 37.08, 36.73, 34.91, 31.04, and 29.06; IR (KBr) 2500–3600 (br, CO$_2$H), 2905, 2850, 1700 (C=O), 1610, 1515, 1325, 1245, 1165, 1130, 1070, 1030, and 805 cmA; MS (DCI) m/e 617 (MH$^+$), 616 (M$^+$), 615 (M—H)$^+$, 135 (C$_{10}$H$_{15}$$^+$), 121. Anal. Calcd for C$_{38}$H$_{39}$O$_4$F$_3$: C, 74.01; H, 6.37. Found: C, 73.77; H, 6.35.

For (2Z),(4Z)-4-(3-Trifluoromethylphenyl)-7-[4-(1-adamantyl)-3-benzyloxyphenyl]-2,4-heptadienoic acid (14u): prepared from 16u; purified by column chromatography (20:1 silica gel/crude product; elution with 3% methanol/methylene chloride), scale=0.47 mmol, yield=98%; $^1$H NMR (300 MHz, CDCl$_3$) δ7.31–7.48 (m, 8 H, 5×HArCH$_2$ and 3×4-ArH), 7.17 (d, J=8 Hz, 1H, 4-ArH), 7.12 (d, J=8 Hz, 1H, 7-ArH), 6.60–6.67 (m, 3H, 2×7-ArH and HC=CHCO$_2$), 6.07 (t, J=7 Hz, 1H, C=CH), 5.73 (d, J=12 Hz, 1H, HC=CHCO$_2$), 5.01 (s, 2H, OCH$_2$), 2.64 (t, J=8 Hz, 2H, CH$_2$Ar), 2.36 (q, J=8 Hz, 2H, ArCH$_2$CH$_2$), 2.01–(m, 9H, adamantyl), and 1.70 (s, 6H, adamantyl); $^{13}$C NMR (75 MHz, CDCl$_3$) δ170.86 (C=O), 157.74, 145.07, 139.62, 138.61, 137.40, 136.60, 136.42, 130.37 (d, $J^2_{c,f}$=32 Hz, 4-ArC), 132.46, 128.46, 127.65, 127.25, 126.63, 125.82, 123.83, 120.55, 118.50, 112.76, 70.00 (OCH$_2$), 40.58, 37.07, 36.75, 34.91, 31.05, and 29.06; IR (KBr) 2400–3600 (CO$_2$H), 2905, 2850, 1700 (C=O), 1325, 1245, 1165, and 1130 cm$^{-1}$; MS (DCI) m/e 587 (MH$^+$), 135 (C$_{10}$H$_{15}$$^+$), 91 (C$_7$H$_7$$^+$). Anal. Calcd for C$_{37}$H$_{37}$O$_3$F$_3$: C, 75.75; H, 6.36. Found: C, 75.58; H, 6.53.

For (2Z),(4Z)-4-(3-Trifluoromethylphenyl)-7-[4-(1-adamantyl)-3-(carboxymethoxy)phenyl]-2,4-heptadienoic acid (14v): prepared from methyl (2Z),(4Z)-4-(3-trifluoromethylphenyl)-7-[4-(1-adamantyl)-3-(carbot-butoxymethoxy)-phenyl]-2,4-heptadienoate (16v) according to the general procedure except that the reflux time was increased to 48 h, scale=0.16 mmol, yield=90%; $^1$H NMR (300 MHz, CDCl$_3$) δ10.19 (br s, 2H, CO$_2$H), 7.46 (d, J=8 Hz, 1H, 4-ArH), 7.32–7.37 (m, 2H, 4-ArH), 7.11–7.15 (m, 2H, 4-ArH and 7-ArH), 6.70 (d, J=8 Hz, 1H, 7-ArH), 6.64 (d, J=12 Hz, 1H, HC=CHCO$_2$), 6.43 (s, 1H, 7-ArH), 6.07 (t, J=7 Hz, 1H, C=CH), 5.75 (d, J=12 Hz, 1H, HC=CHCO$_2$), 4.58 (s, 2H, OCH$_2$), 2.64 (t, J=7 Hz, 2H, ArCH$_2$), 2.37 (q, J=7 Hz, 2H, ArCH$_2$CH$_2$), 2.04–2.08 (m, 9H, adamantyl), and 1.75 (s, 6H, adamantyl); $^{13}$C NMR (75 MHz, CDCl$_3$) δ174.87 (C=O), 171.77 (C=O), 156.53, 145.33, 139.61, 138.51, 138.29, 136.77, 136.54, 132.47, 130.41 (d, $J^2_{c,f}$=32 Hz, 4-ArC), 128.56, 127.04, 125.70, 123.90, 122.25, 121.53, 118.49, 112.49, 64.77 (OCH$_2$), 40.60, 37.01, 36.74, 34.63, 30.88, and 29.08; IR (KBr) 2400–3600 (br, CO$_2$H), 2905, 2850, 1730 (C=O), 1705 (C=O), 1435, 1420, 1325, 1245, 1165, 1130, and 1070 cm$^{-1}$; MS (DCI) m/e 555 (MH$^+$), 135 (C$_{10}$H$_{15}$$^+$). Anal. Calcd for C$_{32}$H$_{33}$F$_3$O$_5$: C, 69.30; H, 6.00. Found: C, 69.12; H, 5.98.

Example 14: Procedure for Synthesis of Methyl (2Z),(4Z)-4-(3-trifluoromethylphenyl)-7-[4-(1-adamantyl)-3-hydroxyphenyl]-2,4-heptadienoate (15)

A colorless solution of 13q (2.50 g, 4.00 mmol) in THF (100 mL) was treated dropwise with a 1.1M solution of tetrabutylammonium fluoride (3.64 mL, 4.00 mmol). After 5 rain, the yellow reaction mixture was partitioned between ether and a saturated ammonium chloride solution. The organic phase was washed with brine, dried with anhydrous magnesium sulfate, filtered, and concentrated. The residue was purified by column chromatography (40:1 silica gel/crude product; elution with hexane and then 2:1 methylene chloride/hexane) to give 1.99 g of a yellow oil. The oil was dissolved in pentane (150 mL) and cooled at −30° C. The precipitate which formed over the course of 18 h was collected by filtration, and dried in vacuo to give 1.57 g (77%) of 15 as a yellow solid; mp 72°–4° C.; $^1$H NMR (300 MHz, CDCl$_3$) δ7.52 (d, J=8 Hz, 1H, 4-ArH), 7.42 (t, J=8 Hz, 1H, 4-ArH), 7.38 (s, 1H, 4-ArH), 7.24 (d, J=8 Hz, 1H, 4-ArH), 7.08 (d, J=8 Hz, 1H, 7-ArH), 6.62 (dd, J=8, 2 Hz, 1H, 7-ArH), 6.57 (d, J=12 Hz, HC=CHCO$_2$), 6.41 (d, J=2 Hz, 1H, 7-ArH), 6.03 (t, J=8 Hz, 1H, C=CH), 5.77 (d, J=12 Hz, 1H, HC=CHCO$_2$), 4.95 (s, 1H, OH), 3.27 (s, 3H, CO$_2$CH$_3$), 2.62 (t, J=7 Hz, 2H, CH$_2$Ar), 2.35 (q, J=7 Hz, 2H, ArCH$_2$CH$_2$), 2.06–2.09 (m, 9H, adamantyl), and 1.77 (s, 6H, adamantyl); $^{13}$C NMR (75 MHz, CDCl$_3$) δ166.86 (C=O), 154.38, 142.16, 139.60, 138.63, 138.21, 136.93, 134.21, 132.52, 130.34 (d, $J^2_{c,f}$=32 Hz, 4-ArC), 128.59, 126.89, 125.73 (d, $J^3_{c,f}$=4 Hz, 4-ArC), 123.84 (d, $J^3_{c,f}$=4 Hz, 4-ArC), 120.55, 119.38, 116.81, 51.25 (CO$_2$CH$_3$), 40.59, 37.05, 36.37, 34.36, 30.58, and 29.01; IR (KBr) 3385 (OH), 2905, 2850, 1700 (C=O), 1325, 1315, 1230, 1155, 1125, 1075 cm$^{-1}$; MS (DCI) m/e 511 (MH$^+$), 509 (M—H)$^+$, 135 (C$_{10}$H$_{15}$$^+$). Anal. Calcd for C$_{31}$H$_{33}$O$_3$F$_3$·C$_5$H$_{12}$: C, 73.60; H, 7.19. Found: C, 73.62; H, 7.04.

Example 15: General Procedure for Synthesis of 16

Procedure A: A solution of phenol 15 (1 equivalent) in acetone (0.2–0.3M) was treated with the alkyl halide (1–2 equivalents), potassium iodide (0 to 0.1 equivalents), and powdered, anhydrous potassium carbonate (1 equivalent). The heterogeneous reaction mixture was stirred and heated at reflux for 24 h. The resulting slurry was cooled slightly, and then the acetone was removed under reduced pressure. The residue was partitioned between ether and water. The organic phase was washed with brine, dried over anhydrous magnesium sulfate, filtered, and concentrated. The crude product was purified by column chromatography (20:1 to 40:1 ratio silica gel/crude product; elution with 5% ethyl acetate/hexane).

Procedure B: A solution of the phenol 15 (1 equivalent) and the alkyl halide (1–1.5 equivalents) in dimethylformamide (ca. 0.12M) under a nitrogen atmosphere was treated wih sodium hydride (60% dispersion in oil, 0.98 equivalents). The mixture was stirred for 1–18 h. The reaction mixture was partitioned between water and 2:1 hexane/ethyl acetate. The organic phase was washed with water (5×), dried over anhydrous magnesium sulfate, filtered, and concentrated. The crude product was purified by column chromatography (20:1 to 40:1 ratio silica gel/crude product; elution with 5–10% ethyl acetate/hexane).

For Methyl (2Z),(4Z)-4-(3-trifluoromethylphenyl)-7-[4-(1-adamantyl)-3-pentyloxyphenyl]-2,4-heptadienoate (16r): via procedure B using pentyl iodide, scale=0.59 mmol, yield=58%; $^1$H NMR (300 MHz, CDCl$_3$) δ7.51 (d, J=8 Hz, 1H, 4-ArH), 7.39–7.44 (m, 2H, 4-ArH), 7.21 (d, J=8 Hz, 1H, 4-ArH), 7.09 (d, J=8 Hz, 1H, 7-ArH), 6.63 (d, J=8 Hz, 1H, 7-ArH), 6.55–6.59 (m, 7-ArH and HC=CHCO$_2$), 6.09 (t, J=8 Hz, 1H, C=CH), 5.75 (d, J=12 Hz, 1H, HC=CHCO$_2$), 3.89 (t, J=6.5 Hz, 2H, OCH$_2$), 3.21 (s, 3H, CO$_2$CH$_3$), 2.66 (t, J=8 Hz, 2H, CH$_2$Ar), 2.37 (q, J=8 Hz, 2H, ArCH$_2$CH$_2$), 2.06–2.10 (m, 9H, adamantyl), 1.76–1.90 (m, 8 H, OCH$_2$CH$_2$ and 6×adamantyl), 1.54 (quint, J=7 Hz, 2H, O(CH$_2$)$_2$CH$_2$), 1.43 (quint, J=7 Hz, 2H, O(CH$_2$)$_3$CH$_2$), and 0.96 (t, J=7 Hz, 3H, O(CH$_2$)$_4$CH$_3$); $^{13}$C NMR (75 MHz, CDCl$_3$) δ166.71 (C=O), 158.13, 141.76, 139.45, 138.97, 138.72, 137.08, 136.06, 132.57, 130.34 (d, $J^2_{c,f}$=32 Hz, 4-ArC), 128.55, 126.38, 125.82 (d, $J^3_{c,f}$=4 Hz, 4-ArC), 123.75 (d, $J^3_{c,f}$=4 Hz, 4-ArC), 120.63 (d, $J^1_{c,f}$=257 Hz, CF$_3$), 119.92, 119.31, 112.07, 67.52 (OCH$_2$), 51.10 (CO$_2$CH$_3$), 40.64, 37.20, 36.73, 35.12, 31.02, 29.20, 29.16, 28.68, 22.45, and 14.10; IR (film) 2905, 2850, 1730 (C=O), 1325, 1165, and 1125 cm$^{-1}$; MS (DCI) m/e 581 (MH$^+$), 549 (M—OCH$_3$)$^+$, 445 (M—C$_{10}$H$_{15}$)$^+$, 135 (C$_{10}$H$_{15}^+$). Anal. Calcd for C$_{36}$H$_{43}$O$_3$F$_3$: C, 74.46; H, 7.46. Found: C, 74.40; H, 7.33.

For Methyl (2Z),(4Z)-4-(3-trifluoromethylphenyl)-7-[4-(1-adamantyl)-3-(3,5-difluorobenzyloxy)phenyl]-2,4-heptadienoate (16s): via procedure B using 3,5-difluorobenzyl bromide, scale=0.65 mmol, yield=82%; $^1$H NMR (300 MHz, CDCl$_3$) δ7.49 (d, J=8 Hz, 1H, 4-ArH), 7.40 (t, J=8 Hz, 1H, 4-ArH), 7.35 (s, 1H, 4-ArH), 7.19 (d, J=8 Hz, 1H, 4-ArH), 7.13 (d, J=8 Hz, 1H, 7-ArH), 6.97–7.00 (m, 2H, HArCH$_2$), 6.75 (tt, J=9, 2 Hz, 1H, HArCH$_2$), 6.69 (dd, J=8, 2 Hz, 1H, 7-ArH), 6.52–6.56 (m, 2H, 7-ArH and HC=CHCO$_2$), 6.05 (t, J=7.5 Hz, 1H, C=CH), 5.74 (d, J=12 Hz, 1H, HC=CHCO$_2$), 4.99 (s, 2H, OCH$_2$Ar), 3.19 (s, 3H, OCH$_3$), 2.64 (t, J=8 Hz, 2H, CH$_2$Ar), 2.33 (q, J=8 Hz, 2H, ArCH$_2$CH$_2$), 2.04–2.09 (m, 9 adamantyl), and 1.72 (s, 6H, adamantyl); $^{13}$C NMR (75 MHz, CDCl$_3$) δ166.67 (C=O), 168.33 (d, $J^1_{c,f}$=248 Hz, 3,5-difluorobenzyl), 157.23, 141.69, 141.49, 139.69, 138.64, 138.59, 137.13, 136.47, 132.50, 128.55, 126.88, 125.79 (d, $J^3_{c,f}$=4 Hz, 4-ArC), 123.81 (d, $J^3_{c,f}$=4 Hz, 4-ArC), 121.06, 119.42, 112.78, 109.60, 109.66 (d, $J^2_{c,f}$=25 Hz, 3,5-difluorobenzyl), 102.99 (t, $J^2_{c,f}$=25 Hz, 3,5-difluorobenzyl), 68.88 (CH$_2$O), 51.12 (OCH$_3$), 40.68, 37.03, 36.77, 35.01, 30.94, and 29.01; IR (film) 2905, 2850, 1725 (C=O), 1600, 1325, 1165, 1120, and 1070 cm$^{-1}$; MS (DCI) m/e 637 (MH$^+$), 636 (M$^+$), 635 (M—H)$^+$, 605 (M—OCH$_3$)$^+$, 135 (C$_{10}$H$_{15}^+$). Anal. Calcd for C$_{38}$H$_{37}$O$_3$F$_5$: C, 71.69; H, 5.86. Found: C, 71.53; H, 5.82.

For Methyl (2Z),(4Z)-4-(3-trifluoromethylphenyl)-7-[4-(1-adamantyl)-3-(4-methoxybenzyloxy)phenyl]-2,4-heptadienoate (16t): via procedure A using 4-methoxybenzyl chloride, scale=0.65 mmol, yield=84%; $^1$H NMR (300 MHz, CDCl$_3$) δ7.52 (d, J=8 Hz, 1H, 4-ArH), 7.38–7.45 (m, 4H, 2×4-ArH and 2×HArCH$_2$), 7.21 (d, J=7.5 Hz, 1H, 4-ArH), 7.11 (d, J=8 Hz, 1H, 7-ArH), 6.93 (d, J=9 Hz, 2H, HArCH$_2$), 6.65–6.69 (m, 2H, 2×7-ArH), 6.56 (d, J=12 Hz, 1H, HC=CHCO$_2$), 6.09 (t, J=7 Hz, 1H, C=CH), 5.67 (d, J=12 Hz, 1H, HC=CHCO$_2$), 4.94 (s, 2H, OCH$_2$), 3.83 (s, 3H, ArOCH$_3$), 3.20 (s, 3H, CO$_2$CH$_3$), 2.67 (t, J=8 Hz, 2H, CH$_2$Ar), 2.38 (q, J=8 Hz, 2H, ArCH$_2$CH$_2$), 2.09 (s, 6H, adamantyl), 2.01 (s, 3H, adamantyl), and 1.60 (s, 6H, adamantyl).

For Methyl (2Z),(4Z)-4-(3-trifluoromethylphenyl)-7-[4-(1-adamantyl)-3-benzyloxyphenyl]-2,4-heptadienoate (16u): via procedure A using benzyl bromide, scale=0.59 mmol, yield=92%; via procedure B, scale=0.08 mmol, yield=79%; $^1$H NMR (300 MHz, CDCl$_3$) δ7.30–7.52 (m, 8H, 5×HArCH$_2$ and 3×4-ArH), 7.20 (d, J=8 Hz, 1H, 4-ArH), 7.13 (d, J=8 Hz, 1H, 7-ArH), 6.66–6.68 (m, 2H, 2×7-ArH), 6.55 (d, J=13 Hz, 1H, HC=CHCO$_2$), 6.07 (t, J=7 Hz, 1H, C=CH), 5.75 (d, J=12 Hz, 1H, HC=CHCO$_2$), 5.03 (s, 2H, OCH$_2$), 3.19 (s, 3H, OCH$_3$), 2.66 (t, J=8 Hz, 2H, CH$_2$Ar), 2.35 (q, J=8 Hz, 2H, ArCH$_2$CH$_2$), 2.02–2.11 (m, 9H, adamantyl), and 1.71 (s, 6H, adamantyl); IR (film) 2905, 2850, 1700 (C=O), 1325, 1245, 1165, 1130, 1070, 1025, 805, and 695 cm$^{-1}$; MS (DCI) m/e 601 (MH$^+$), 600 (M), 599 (M—H)$^+$, 509 (M—CH$_2$Ph)$^+$, 135 (C$_{10}$H$_{15}^+$).

For Methyl (2Z),(4Z)-4-(3-trifluoromethylphenyl)-7-[4-(1-adamantyl)-3-(carbo-t-butoxymethoxy)phenyl]-2,4-heptadienoate (16v): prepared via procedure B using t-butyl bromoacetate, scale=1.30 mmol, yield=62%. $^1$H NMR (300 MHz, CDCl$_3$) δ7.51 (d, J=8 Hz, 1H, 4-ArH), 7.42 (t, J=8 Hz, 1H, 4-ArH), 7.37 (s, 1H, 4-ArH), 7.22 (d, J=8 Hz, 1H, 4-ArH), 7.11 (d, J=8 Hz, 1H, 7-ArH), 6.68 (dd, J=8, 2 Hz, 1H, 7-ArH), 6.57 (d, J=12 Hz, 1H, HC=CHCO$_2$), 6.41 (d, J=2 Hz, 1H, 7-ArH), 6.07 (t, J=7 Hz, 1H, C=CH), 5.77 (d, J=12 Hz, 1H, HC=CHCO$_2$), 4.43 (s, 2H, OCH$_2$), 3.20 (s, 3H, OCH$_3$), 2.63 (t, J=7 Hz, 2H, ArCH$_2$), 2.35 (q, J=7 Hz, 2H, ArCH$_2$CH$_2$), 2.06–2.11 (m, 9H, adamantyl), 1.72–1.82 (m, 6H, adamantyl), and 1.48 (s, 9H, t-butyl).

Example 16: General Procedure for Synthesis of 17

A solution of aldehyde 9 (1 equivalent) in anhydrous toluene (0.1M) at room temperature under argon was treated sequentially with methyl diethylphosphonoacetate (1.5 equivalents) and sodium methoxide (25 wt % in methanol, 1.4 equivalents). The reaction mixture was stirred at room temperature for 12–16 h, and then treated with additional sodium methoxide (25 wt % in methanol, 1 equivalent). The mixture was stirred for 0.5 h and then partitioned between diethyl ether and saturated ammonium chloride solution. The organic layer was washed with saturated sodium chloride solution, dried over anhydrous magnesium sulfate, filtered, and concentrated. Purification by column chromatography (40:1 ratio of silica gel/crude product; elution with 5% ethyl acetate in hexanes) gave the desired product.

For Methyl (2E),(4Z)-4-(3-carbomethoxyphenyl)-5-(5,6,7,8-tetrahydro-5,5,8,8-tetramethyl-2-naphthalenyl)-2,4-pentadienoate (17a): scale=0.81 mmol, yield=75%; UV$_{max}$ (CH$_3$OH) 326 nm (ε=36,800), 232 nm (ε=20,900); $^1$H NMR (300 MHz, CDCl$_3$) δ8.06 (dt, J=2, 8 Hz, 1H, 4-ArH), 7.87 (t, J=2 Hz, 1H, 4-ArH), 7.67 (d, J=16 Hz, 1H, CH=CHCO$_2$), 7.52 (t, J=8 Hz, 1H, 4-ArH), 7.36 (dt, J=2, 8 Hz, 1H, 4-ArH), 7.07 (d, J=8 Hz, 1H, 5-ArH), 6.90 (s, 1H, C=CH), 6.82 (d, J=2 Hz, 1H, 5-ArH), 6.72 (dd, J=2, 8 Hz, 1H, 5-ArH), 5.80 (d, J=16 Hz, 1H, CH=CHCO$_2$), 3.88 (s, 3H, CO$_2$CH$_3$), 3.70 (s, 3H, CO$_2$CH$_3$), 1.51–1.60 (m, 4H, CH$_2$CH$_2$), 1.17 (s, 6H, 2×CH$_3$), and 0.92 (s, 6H, 2×CH$_3$); $^{13}$C NMR (75 MHz, CDCl$_3$) δ167.60 (C=O), 166.71 (C=O), 149.80, 146.02, 144.79, 139.69, 137.88, 137.23, 134.05, 132.34, 131.28, 130.51, 129.48, 129.04, 128.40, 127.73, 126.63, 119.11, 52.20 (CO$_2$CH$_3$), 51.52 (CO$_2$CH$_3$), 34.79, 34.22, 33.92, 31.54, and 31.38; IR (film) 2955, 2860, 1720 (C=O), 1615, 1590, 1435, 1310, 1280, 1265, 1205, 1190, 1170, 1120, 1095, 1080, and 980 cm$^{-1}$; MS (DCI) m/e 433 (MH+), 401 (M+—OCH$_3$).

For Methyl (2E),(4Z)-4-(3-carbomethoxyphenyl)-5-(5,6,7,8-tetrahydro-5,5,8,8-tetramethyl-2-anthracenyl)-2,4-pentadienoate (17b): scale=1.80 mmol, yield=99%; $^1$H NMR (300 MHz, CDCl$_3$) δ8.08 (dt, J=2, 8 Hz, 1H, 4-ArH), 7.88 (t, J=2 Hz, 1H, 4-ArH), 7.72 (d, J=15 Hz, 1H, CH=CHCO$_2$), 7.53 (d, J=12 Hz, 2H, ArH), 7.45–7.51 (m, 2H, ArH), 7.32–7.37 (m, 2H, ArH), 7.01 (s, 1H, C=CH), 6.67 (dd, J=2, 9 Hz, 1H, ArH), 5.43 (d, J=15 Hz, 1H, CH=CHCO$_2$), 3.89 (s, 2H, CO$_2$CH$_3$), 3.72 (s, 3H, CO$_2$CH$_3$), 1.71 (s, 4H, CH$_2$CH$_2$), and 1.17–1.23 (m, 15 H, 4×CH$_3$ and CO$_2$CH$_2$CH$_3$); $^{13}$C NMR (75 MHz, CDCl$_3$) δ167.64 (C=O), 166.77 (C=O), 149.50, 145.74, 144.99, 142.30, 139.97, 138.77, 137.86, 137.49, 134.28, 133.62, 132.13, 131.35, 131.12, 130.62, 129.37, 129.19, 126.91, 125.44, 124.66, 123.01, 119.41, 52.25 (CO$_2$CH$_3$), 51.60 (CO$_2$CH$_3$), 34.96, 34.67, 32.44 (4×CH$_3$), and 29.73; IR (film) 2955, 2925, 2860, 1720 (C=O), 1615, 1595, 1460, 1435, 1365, 1305, 1295, 1265, 1210, 1195, 1170, 1120, and 1110 cm$^{-1}$; MS (DCI) m/e 483 (MH+), 451 (MH+—CH$_3$OH).

For Methyl (2E),(4Z)-4-(3-carbomethoxyphenyl)-5-(3,4-bispentyloxyphenyl)-2,4-pentadienoate (17c): scale=0.32 mmol, yield=95%; $^1$H NMR (300 MHz, CDCl$_3$) δ8.03 (dt, J=2, 8 Hz, 1H, 4-ArH), 7.87 (t, J=2 Hz, 1H, 4-ArH), 7.65 (dd, J=1, 15.5 Hz, 1H, CH=CHCO$_2$), 7.51 (t, J=8 Hz, 1H, 4-ArH), 7.36 (dt, J=2, 8 Hz, 1H, 4-ArH), 6.86 (d, J=1 Hz, 1H, C=CH), 6.60–6.67 (m, 2H, 2×5-ArH), 6.28 (d, J=2 Hz, 1H, 5-ArH), 5.32 (d, J=15 Hz, 1H, CH=CHCO$_2$), 3.91 (t, J=6.5 Hz, 2H, ArOCH$_2$), 3.88 (s, 3H, CO$_2$CH$_3$), 3.63 (s, 3H, CO$_2$CH$_3$), 3.40 (t, J=6.5 Hz, 2H, ArOCH$_2$) 1.70–1.79 (m, 2H, ArOCH$_2$CH$_2$), 1.54–1.59 (m, 2H, ArOCH$_2$CH$_2$), 1.24–1.42 (m, 8H, 2×CH$_2$), and 0.85–0.95 (m, 6H, 2×CH$_3$ ); $^{13}$C NMR (75 MHz, CDCl$_3$) δ167.65 (C=O), 166.57 (C=O), 148.72, 148.23, 139.38, 137.94, 136.04, 134.21, 131.31, 130.69, 129.46, 128.95, 128.05, 124.54, 118.53, 113.91, 112.59, 68.91 (ArOCH$_2$), 68.41 (ArOCH$_2$), 52.21 (CO$_2$CH$_3$), 51.49 (CO$_2$CH$_3$), 28.75, 28.59, 28.10, 27.95, 22.40, 22.34, and 14.00; IR (film) 2950, 2935, 2870, 1730 (C=O), 1715 (C=O), 1615, 1590, 1510, 1470, 1435, 1395, 1310, 1275, 1260, 1240, 1210, 1190, 1160, 1140, 1120, 1095, 1075, 1015, 985, and 740 cm$^{-1}$; MS (DCI) m/e 495 (MH+), 463 (M+—OCH$_3$).

For Methyl (2E),(4Z)-4-(3-carbomethoxyphenyl)-5-(3,4-bisdecyloxyphenyl)-2,4-pentadienoate (17d): scale=0.32 mmol, yield=75%; $^1$H NMR (300 MHz, CDCl$_3$) δ8.04 (dr, J=2, 8 Hz, 1H, 4-ArH), 7.87 (t, J=2 Hz, 1H, 4-ArH), 7.65 (d, J=15 Hz, 1H, CH=CHCO$_2$), 7.51 (t, J=8 Hz, 1H, 4-ArH), 7.36 (dt, J=2, 8 Hz, 1H, 4-ArH), 6.86 (s, 1H, C=CH), 6.59–6.66 (m, 2H, 2×5-ArH), 6.28 (d, J=2 Hz, 1H, 5-ArH), 5.32 (d, J=15 Hz, 1H, CH=CHCO$_2$), 3.90 (t, J=6.5 Hz, 2H, 5-ArOCH$_2$), 3.88 (s, 3H, CO$_2$CH$_3$), 3.70 (s, 3H, CO$_2$CH$_3$), 3.40 (t, J=6.5 Hz, 2H, 5-ArOCH$_2$), 1.73 (quintet, 2H, 5-ArOCH$_2$CH$_2$), 1.50–1.65 (m, 2H, 5-ArOCH$_2$CH$_2$), 1.18–1.43 (m, 28H, 14×CH$_2$), and 0.83–0.89 (m, 6H, 2×CH$_3$ ); $^{13}$C NMR (75 MHz, CDCl$_3$) δ167.67 (C=O), 166.57 (C=O), 149.74, 149.64, 148.21, 139.40, 137.94, 136.02, 134.21, 131.30, 130.69, 129.46, 128.95, 128.02, 124.49, 118.51, 113.91, 112.57, 68.91 (ArOCH$_2$), 68.44 (ArOCH$_2$), 52.22 (CO$_2$CH$_3$), 51.50 (CO$_2$CH$_3$), 31.92, 31.89, 29.58, 29.33, 29.06, 28.92, 25.92, 25.79, 22.68, and 14.12; IR (film) 2950, 2920, 2870, 2850, 1720 (C=O), 1615, 1585, 1515, 1470, 1435, 1310, 1280, 1245, 1210, 1195, 1170, 1145, 1120, 1090, 1020, 980, and 740 cm$^{-1}$; MS (DCI) m/e 635 (MH+), 603 (M+—OCH$_3$).

For Ethyl (2E),(4Z)-4-(3-carboethoxyphenyl)-7-(5,6,7,8-tetrahydro-5,5,8,8-tetramethyl-2-naphthalenyl)-2,4-heptadienoate (17e): scale=0.98 mmol, yield=82%; prepared as described in the general procedure except that sodium ethoxide (21 wt % in ethanol) was used in place of sodium methoxide. $^1$H NMR (300 MHz, CDCl$_3$) δ7.99 (d, J=8 Hz, 1H, 4-ArH), 7.77 (s, 1H, 4-ArH), 7.51 (d, J=16 Hz, 1H, CH=CHCO$_2$), 7.38 (t, J=8 Hz, 1H, 4-ArH), 7.17 (d, J=8 Hz, 1H, 4-ArH), 6.97 (m, 2H, 7-ArH), 6.81 (d, J=8 Hz, 1H, 7-ArH), 6.21 (t, J=8 Hz, 1H, C=CH), 5.28 (d, J=16 Hz, 1H, CH=CHCO$_2$), 4.37 (q, J=7 Hz, 2H, CO$_2$CH$_2$CH$_3$), 4.15 (q, J=7 Hz, 2H, CO$_2$CH$_2$CH$_3$), 2.63 (t, J=7 Hz, 2H, ArCH$_2$), 2.27 (q, J=7 Hz, 2H, ArCH$_2$CH$_2$), 1.65 (s, 4H, CH$_2$CH$_2$), 1.39 (t, J=7 Hz, 3H, CO$_2$CH$_2$CH$_3$), and 1.18–1.25 (m, 15H, 4×CH$_3$ and CO$_2$CH$_2$CH$_3$); $^{13}$C NMR (75 MHz, CDCl$_3$) δ167.24 (C=O), 166.34 (C=O), 148.02, 144.74, 142.59, 142.21, 139.63, 137.71, 136.77, 133.66, 130.82, 130.25, 128.65, 128.56, 126.50, 126.45, 125.70, 119.24, 61.09 (CO$_2$CH$_2$CH$_3$), 60.27 (CO$_2$CH$_2$CH$_3$), 35.16, 35.10, 34.15, 33.95, 31.91, 31.87, 31.67, 14.35 (CO$_2$CH$_2$CH$_3$), and 14.28 (CO$_2$CH$_2$CH$_3$); IR (film) 2960, 2930, 1720 (C=O), 1625, 1305, 1280, 1260, and 1175 cm$^{-1}$; MS (DCI) m/e 489 (MH+), 443 (M—OCH$_2$CH$_3$)+.

Example 17: General Procedure for Synthesis of 18

A mixture of ester 17 in methanol/tetrahydrofuran/2N sodium hydroxide solution (1:1:1, 0.1M) was heated at reflux for 1–4 h. The reaction mixture was then allowed to cool to room temperature and 10% hydrochloric acid solution was added until the solution reached pH 1. The resulting cloudy mixture was extracted with methylene chloride (2 portions), and the organic phase was washed with brine, dried over anhydrous magnesium sulfate, filtered, and concentrated. The residue was evaporated from pentane (3 portions) and then dried in vacuo.

For (2E),(4Z)-4-(3-Carboxyphenyl)-5-(5,6,7,8-tetrahydro-5,5,8,8-tetramethyl-2-naphthalenyl)-2,4-pentadienoic acid (18a): scale=0.50 mmol, yield=75%; mp 279°–282° C.; UV$_{max}$ (CH$_3$OH) 324 nm (ε=34,400), 232 nm (ε=19,100); $^1$H NMR (300 MHz, CD$_3$OD) δ8.08 (dt, J=2, 8 Hz, 1H, 4-ArH), 7.84 (t, J=2 Hz, 1H, 4-ArH), 7.71 (d, J=16 Hz, 1H, CH=CHCO$_2$), 7.62 (t, J=8 Hz, 1H, 4-ArH), 7.41 (dr, J=2, 8 Hz, 1H, 4 -ArH), 7.15 (d, J=8 Hz, 1H, 5-ArH), 7.03 (s, 1H, C=CH), 6.87 (dd, J=2, 8 Hz, 1H, 5-ArH), 6.81 (d, J=2 Hz, 1H, 5-ArH), 5.28 (d, J=16 Hz, 1H, CH=CHCO$_2$), 1.54–1.60 (m, 4H, CH$_2$CH$_2$), 1.18 (s, 6H, 2×CH$_3$), and 0.98 (s, 6H, 2×CH$_3$); $^{13}$C NMR (75 MHz, CD$_3$OD) δ170.47 (C=O), 169.37 (C=O), 151.21, 147.03, 145.66, 140.98, 139.51, 138.91, 135.24, 133.85, 133.35, 131.89, 130.78, 130.28, 129.44, 129.09, 127.68, 120.49, 35.94, 35.15, 34.87, 31.95, and 31.86; IR (film) 3400 (br, CO$_2$H), 2960, 2925, 2860, 1685 (C=O), 1615, 1590, 1450, 1410, 1280, and 1215 cm$^{-1}$; MS (DCI) m/e 405 (MH+), 387 (M+—OH). Anal. Calcd. for C$_{26}$H$_{28}$O$_4$.0.25 H$_2$O: C, 76.34; H, 7.02. Found: C, 76.21; H, 6.85.

For (2E),(4Z)-4-(3-Carboxyphenyl)-5-(5,6,7,8-tetrahydro-5,5,8,8-tetramethyl-2-anthracenyl)-2,4-pentadienoic acid (18b): scale=1.60 mmol, yield=99%; UV$_{max}$ (CH$_3$OH) 342 nm (ε=36,700), 294 nm (ε=27,500), 284 nm (ε=25,900); $^1$H NMR (300 MHz, DMSO-d$_6$) δ7.86 (br t, J=8 Hz, 1H, 4-ArH), 7.60–7.73 (m, 7H, 6×ArH and CH=CHCO$_2$), 7.42–7.46 (m, 2H, ArH), 7.37 (s, 1H, C=CH), 5.23 (d, J=15 Hz, 1H, CH=CHCO$_2$), 1.67 (s, 4H, CH$_2$CH$_2$), and 1.28 (br s, 12H, 4×CH$_3$); $^{13}$C NMR (75 MHz, DMSO-d$_6$) δ167.29 (C=O), 166.91 (C=O), 148.78, 145.20, 144.56, 139.34, 137.76, 137.21, 133.88, 132.07, 131.65, 131.11, 130.91, 130.17, 129.88, 129.75, 128.95, 126.70, 125.084, 124.81, 124.52, 120.14, 34.41, 34.34, 34.22, and 32.17; IR (KBr) 2400–3400 (br, CO$_2$H), 3010, 2960, 2920, 2860, 1685 (C=O), 1610, 1575, 1450, 1410, 1365, 1295, and 1215 cm$^{-1}$; MS (DCI) m/e 455 (MH+) and 411 (MH+—CO$_2$H); Anal. Calcd for C$_{30}$H$_{30}$O$_4$.0.6H$_2$O: C, 77.42; H, 6.76. Found: C, 77.37; H, 6.93.

For (2E),(4Z)-4-(3-Carboxyphenyl)-5-(3,4-bispentyloxyphenyl)-2,4-pentadienoic acid (18c): scale=0.16 mmol, yield=95%; UV$_{max}$ (CH$_3$OH) 346 nm (ε=28,500), 230 nm (ε=18,400); $^1$H NMR (300 MHz, CD$_3$OD) δ8.09 (dt, J=2, 8 Hz, 1H, 4-ArH), 7.86 (t, J=2 Hz, 1H, 4-ArH), 7.70 (d, J=15.5 Hz, CH=CHCO$_2$), 7.63 (t, J=8 Hz, 1H, 4-ArH), 7.42 (dr, J=2, 8 Hz, 1H, 4-ArH), 6.99 (s, 1H, C=CH), 6.73–6.80 (m, 2H, 5-ArH), 6.30 (d, J=2 Hz, 1H, 5-ArH), 5.26 (d, J=15 Hz, 1H, CH=CHCO$_2$), 3.92 (t, J=6.5 Hz, 2H, ArOCH$_2$), 3.37 (t, J=6.5 Hz, 2H, ArOCH$_2$), 1.68–1.77 (m, 2H, ArOCH$_2$CH$_2$), 1.50–1.56 (m, 2H, ArOCH$_2$CH$_2$), 1.27–1.46 (m, 8H, 4×CH$_2$), and 0.84–0.98 (m, 6H, 2×CH$_3$ ); $^{13}$C NMR (75 MHz, CD$_3$OD) δ170.50 (C=O), 169.00 (C=O), 151.33, 151.12, 149.50, 140.68, 139.52, 137.65, 135.39, 132.01, 130.84, 130.28, 129.69, 126.35, 119.86, 115.07, 114.06, 70.02 (ArOCH$_2$), 69.60 (ArOCH$_2$), 29.99, 29.78, 29.37, 29.19, 23.48, 23.41, and 14.39; IR (film) 2000–3400 (br, CO$_2$H), 1695 (C=O), 1680 (C=O), 1615, 1580, 1510, 1465, 1430, 1315, 1270, 1240, 1210, and 1140 cm$^{-1}$; MS (DCI) m/e 467 (MH+), 449 (M+—OH). Anal. Calcd. for C$_{28}$H$_{34}$O$_6$: C, 72.08; H, 7.34. Found: C, 72.84; H, 7.84.

For (2E),(4Z)-4-(3-Carboxyphenyl)-5-(3,4-bisdecyloxyphenyl)-2,4-pentadienoic acid (18d): scale=0.21 mmol, yield=96%; mp 151°–154° C.; UV$_{max}$ (CH$_3$OH) 354 nm (ε=30,700), 242 nm (ε=15,200); $^1$H NMR (300 MHz, CDCl$_3$) δ8.12 (dt, J=2, 8 Hz, 1H, 4-ArH), 7.96 (t, J=2 Hz, 1H, 4-ArH), 7.75 (d, J=15 Hz, CH=CHCO$_2$), 7.55 (t, J=8 Hz, 1H, 4-ArH), 7.42 (dt, J=2, 8 Hz, 1H, 4-ArH), 6.92 (s, 1H, C=CH), 6.61–6.68 (m, 2H, 5-ArH), 6.30 (d, J=2 Hz, 1H, 5-ArH), 5.31 (d, J=15 Hz, 1H, CH=CHCO$_2$), 3.91 (t, J=6.5 Hz, 2H, ArOCH$_2$), 3.42 (t, J=6.5 Hz, 2H, ArOCH$_2$), 1.74 (quintet, 2H, ArOCH$_2$CH$_2$), 1.50–1.65 (m, 2H, ArOCH$_2$CH$_2$), 1.20–1.45 (m, 28H, 14×CH$_2$), and 0.82–0.88 (m, 6H, 2×CH$_3$ ); $^{13}$C NMR (75 MHz, CDCl$_3$) δ172.58 (C=O), 171.44 (C=O), 149.92, 148.25, 137.91, 135.69, 135.00, 131.35, 130.60, 129.62, 127.81, 124.76, 118.00, 114.06, 112.58, 68.91 (ArOCH$_2$), 68.44 (ArOCH$_2$), 31.92, 31.89, 29.58, 29.33, 29.06, 28.92, 25.92, 25.79, 22.68, and 14.12; IR (film) 2300–3600 (br, CO$_2$H), 2925, 2855, 1685 (C=O), 1615, 1585, 1510, 1470, 1450, 1415, 1310, 1270, 1240, 1205, and 1140 cm$^{-1}$; MS (DCI) m/e 607 (MH+), 589 (M+—OCH$_3$). Anal. Calcd. for C$_{38}$H$_{54}$O$_6$: C, 75.21; H, 8.97. Found: C, 75.30; H, 8.96.

For (2E),(4Z)-4-(3-Carboxyphenyl)-7-(5,6,7,8-tetrahydro-5,5,8,8-tetramethyl-2-naphthalenyl)-2,4-heptadienoic acid (18e): scale=0.53 mmol, yield=39%; $^1$H NMR (300 MHz, DMSO-d$_6$) δ12.63 (br s, 2H, CO$_2$H), 7.90 (d, J=7 Hz, 1H, 4-ArH), 7.57 (s, 1H, 4-ArH), 7.44 (m, 2H, CH=CHCO$_2$ and 4-ArH), 7.13 (d, J=8 Hz, 1H, 4-ArH), 6.96 (m, 2H, 7-ArH), 6.76 (d, J=8 Hz, 1H, 7-ArH), 6.36 (t, J=8 Hz, 1H, C=CH), 5.05 (d, J=16 Hz, 1H, CH=CHCO$_2$), 2.57 (m, 2H, ArCH$_2$), 2.15 (m, 2H, ArCH$_2$CH$_2$), 1.57 (s, 4H, CH$_2$CH$_2$), 1.17 (s, 6H, 2×CH$_3$), and 1.13 (s, 6H, 2×CH$_3$); $^{13}$C NMR (75 MHz, DMSO-d$^6$) δ167.36 (C=O), 167.34 (C=O), 147.60, 143.97, 142.24, 141.82, 138.91, 137.67, 136.39, 133.32, 131.03, 129.60, 128.84, 128.42, 126.14, 125.58, 119.21, 34.65, 34.33, 33.72, 33.55, 31.64, and 31.59; IR (KBr) 2400–3600 (br, CO$_2$H), 2960, 2930, 1690 (C=O), 1620, 1450, 1310, and 1290 cm$^{-1}$; MS (DCI) m/e 432 (MH+), 417 (M—CH$_2$)+, 415 (M—OH)+, 387; Anal. Calcd for C$_{28}$H$_{32}$O$_4$.0.2 H$_2$O: C, 77.12; H, 7.49. Found: C, 76.76; H, 7.43.

Example 18: General Procedure for Synthesis of 19

A solution of aldehyde 12 (1 equivalent) in anhydrous toluene (0.1M) at room temperature under argon was treated sequentially with methyl diethylphosphonoacetate (1.5 equivalents) and sodium methoxide (25 wt % in methanol, 1.4 equivalents). The reaction mixture was stirred at room temperature for 12–16 h, and then treated with additional sodium methoxide (25 wt % in methanol, 1 equivalent). The mixture was stirred for 0.5 h and then partitioned between diethyl ether and saturated ammonium chloride solution. The organic layer was washed with saturated sodium chloride solution, dried over anhydrous magnesium sulfate, filtered, and concentrated. Purification by column chromatography on silica gel (40:1 ratio of silica gel/crude product; elution with 5% ethyl acetate in hexanes) gave the desired product.

For Methyl (2E),(4Z)-4-(3-trifluoromethylphenyl)-7-(5,6,7,8-tetrahydro-5,5,8,8-tetramethyl-2-naphthalenyl)-2,4-heptadienoate (19a): scale=0.49 mmol, yield=86%; $^1$H NMR (300 MHz, CDCl$_3$) δ7.54 (br d, J=8 Hz, 1H, 4-ArH), 7.48 (d, J=15 Hz, 1H, CH=CHCO$_2$), 7.41 (t, J=8 Hz, 1H, 4-ArH), 7.24 (s, 1H, 4-ArH), 7.16 (d, J=8 Hz, 1H, 4-ArH), 6.94–6.96 (m, 2H, 7-ArH), 6.78 (dd, J=2, 8 Hz, 1H, 7-ArH), 6.21 (t, J=8 Hz, 1H, C=CH), 5.23 (d, J=15 Hz, 1H, CH=CHCO$_2$), 3.68 (s, 3H, CO$_2$CH$_3$), 2.61 (t, J=8 Hz, 2H, ArCH$_2$), 2.24 (q, J=8 Hz, 2H, ArCH$_2$CH$_2$), 1.63 (br s, 4H, CH$_2$CH$_2$), 1.24 (s, 6H, 2'CH$_3$), and 1.20 (s, 6H, 2'CH$_3$); $^{13}$C NMR (75 MHz, CDCl$_3$) δ167.55 (C=O), 147.98, 144.79, 142.73, 139.12, 137.49, 137.20, 132.63, 128.97, 126.56, 126.48, 125.86 (q, J$^3_{c,f}$=4 Hz, 4-ArC), 125.67, 124.37 (q, J$^3_{c,f}$=4 Hz, 4-ArC), 118.81, 51.54 (CO$_2$CH$_3$), 35.10, 35.06, 34.13, 33.95, 31.87, 31.83, and 31.69; IR (film) 2960, 2926, 2860, 1720 (C=O), 1625, 1435, 1325, 1310, 1295, 1270, 1170, 1130, 1110, 1070, and 705cm$^{-1}$; MS (DCI) m/e 471 (MH+).

For Methyl (2E,(4Z)-4-(4-fluorophenyl)-7-(5,6,7,8-tetrahydro-5,5,8,8-tetramethyl-2-naphthalenyl)-2,4-heptadienoate (19b): scale=0.85 mmol, yield=84%; $^1$H NMR (300 MHz, CDCl$_3$) δ7.46 (d, J=16 Hz, 1H, CH=CHCO$_2$), 7.16 (d, J=8 Hz, 1H, 7-ArH), 6.72–7.00 (m, 6H, 4×4-ArH and 2×7-ArH), 6.15 (t, J=8 Hz, 1H, C=CH), 5.27 (d, J=16 Hz, 1H, CH=CHCO$_2$), 3.68 (s, 3H, CO$_2$CH$_3$), 2.61 (t, J=8 Hz, 2H, ArCH$_2$), 2.25 (q, J=8 Hz, 2H, ArCH$_2$CH$_2$), 1.64 (br s, 4H, CH$_2$CH$_2$), 1.24 (s, 6H, 2×CH$_3$), and 1.22 (s, 6H, 2×CH$_3$); $^{13}$C NMR (75 MHz, CDCl$_3$) δ167.74, 148.66, 144.72, 142.61, 142.29, 139.54, 137.69, 130.78 (d, J$^3_{c,f}$=8 Hz, 4-ArC), 126.50, 125.78, 118.56, 115.31 (d, J$^2_{c,f}$=21 Hz, 4-ArC), 51.47 (CO$_2$CH$_3$), 35.11, 35.08, 35.00, 34.13, 33.94, 31.90, 31.85 and 31.66; IR (film) 2960, 2925, 2860, 1720

(C=O), 1625, 1510, 1460, 1435, 1305, 1270, 1225, 1190, 1170, 845, and 825 cm$^{-1}$; MS (DCI) m/e 421 (MH+).

For Methyl (2E),(4Z)-4-(3-fluorophenyl)-7-(5,6,7,8-tetrahydro-5,5,8,8-tetramethyl-2-naphthalenyl)-2,4-heptadienoate (19c): scale=1.09 mmol, yield=81%; $^1$H NMR (300 MHz, CDCl$_3$) δ7.45 (d, J=15 Hz, 1H, CH=CHCO$_2$), 7.21–7.28 (m, 1H, 4-ArH), 7.17 (d, J=2 Hz, 1H, 7-ArH), 6.92–6.99 (m, 2H, 1×4-ArH and 1×7-ArH), 6.79 (dd, J=2, 8 Hz, 1H, 7-ArH), 6.61 (dt, J=2, 8 Hz, 1H, 4-ArH), 6.49 (dq, J=2, 8 Hz, 1H, 4-ArH), 6.15 (t, J=8 Hz, 1H, C=CH), 5.29 (d, J=15 Hz, 1H, CH=CHCO$_2$), 3.71 (s, 3H, CO$_2$CH$_3$), 2.62 (t, J=8 Hz, 2H, ArCH$_2$), 2.26 (q, J=8 Hz, 2H, ArCH$_2$CH$_2$), 1.64 (br s, 4H, CH$_2$CH$_2$), 1.24 (s, 6H, 2'CH$_3$), and 1.20 (s, 6H, 2×CH$_3$); $^{13}$C NMR (75 MHz, CDCl$_3$) δ167.69 (C=O), 148.09, 144.76, 142.66, 142.22, 139.35, 138.56 (d, $J^3_{c,f}$=9 Hz, 4-ArC), 137.59, 129.90 (d, $J^3_{c,f}$=9 Hz, 4-ArC), 126.49, 125.75, 124.86, 118.66, 116.13 (d, $J^2_{c,f}$=21 Hz, 4-ArC), 114.33 (d, $J^2_{c,f}$=21 Hz, 4-ArC), 51.49 (CO$_2$CH$_3$), 35.08, 34.98, 34.13, 33.95, 31.84, and 31.68; IR (film) 2960, 2925, 2860, 1720 (C=O), 1625, 1610, 1580, 1435, 1305, 1265, 1190, and 1170 cm$^{-1}$; MS (DCI) m/e 421 (MH+).

For Methyl (2E),(4Z)-4-phenyl-7-(5,6,7,8-tetrahydro-5,5,8,8-tetramethyl-2-naphthalenyl)-2,4-heptadienoate (19d): scale=0.63 mmol, yield=91%; $^1$H NMR (300 MHz, CDCl$_3$) δ7.48 (d, J=15 Hz, 1H, CH=CHCO$_2$), 7.23–7.32 (m, 3H, 4-ArH), 7.16 (d, J=8 Hz, 1H, 7-ArH), 6.96 (d, J=2 Hz, 1H, 7-ArH), 6.84–6.88 (m, 2H, 4-ArH), 6.79 (dd, J=2, 8 Hz, 1H, 7-ArH), 6.15 (t, J=8 Hz, 1H, C=CH), 5.33 (d, J=15 Hz, 1H, CH=CHCO$_2$), 3.69 (s, 3H, CO$_2$CH$_3$), 2.61 (t, J=8 Hz, 2H, ArCH$_2$), 2.27 (q, J=8 Hz, 2H, ArCH$_2$CH$_2$), 1.64 (br s, 4H, CH$_2$CH$_2$), 1.24 (s, 6H, 2×CH$_3$), and 1.21 (s, 6H, 2×CH$_3$); $^{13}$C NMR (75 MHz, CDCl$_3$) δ167.87 (C=O), 148.78, 144.68, 142.51, 141.87, 140.53, 137.83, 136.32, 129.11, 128.34, 127.32, 126.46, 125.74, 118.51, 51.40 (CO$_2$CH$_3$), 35.15, 35.10, 34.13, 33.93, 31.90, 31.85, and 31.59; IR (film) 2960, 2925, 2860, 1720 (C=O), 1620, 1495, 1455, 1435, 1305, 1265, 1190, 1170, 1105, 980, 825, and 700 cmA; MS (DCI) m/e 403 (MH+).

For Methyl (2E),(4Z)-4-(3-trifluoromethylphenyl)-7-[3-(1-adamantyl)-4-methoxyphenyl]-2,4-heptadienoate (19e): scale=0.30 mmol, yield=81%; $^1$H NMR (300 MHz, CDCl$_3$) δ7.55 (d, J=8 Hz, 1H, 4-ArH), 7.50 (d, J=16 Hz, 1H, CH=CHCO$_2$), 7.43 (t, J=8 Hz, 1H, 4-ArH), 7.14 (s, 1H, 4-ArH), 7.04 (d, J=8 Hz, 1H, 4-ArH), 6.87 (d, J=2 Hz, 1H, 7-ArH), 6.82 (dd, J=2, 8 Hz, 1H, 7-ArH), 6.73 (d, J=8 Hz, 1H, 7-ArH), 6.21 (t, J=8Hz, 1H, C=CH), 5.23 (d, J=16Hz, 1H, CH=CHCO$_2$), 3.78 (s, 3H, ArOCH$_3$), 3.69 (s, 3H, CO$_2$CH$_3$), 2.62 (t, J=7 Hz, 2H, ArCH$_2$), 2.23 (q, J=7 Hz, 2H, ArCH$_2$CH$_2$), 2.02 (s, 9H, adamantyl), and 1.73 (s, 6H, adamantyl); $^{13}$C NMR (75 MHz, CDCl$_3$) δ167.54 (C=O), 157.24, 148.05, 142.85, 139.13, 138.32, 137.24, 132.66, 132.16, 130.91 (d, f$2_{c,f}$=32 Hz, 4-ArC), 128.94, 126.89, 126.29, 125.79 (d, $J^3_{c,f}$=4 Hz, 4-ArC), 124.32 (d, $J^3_{c,f}$=4 Hz, 4-ArC), 118.76, 111.62, 55.01 (ArOCH$_3$), 51.52 (CO$_2$CH$_3$), 40.57, 37.09, 36.86, 34.76, 32.00, and 29.07; IR (film) 2905, 2850, 1720 (C=O), 1325, 1235, 1170, and 1130 cm$^{-1}$; MS (DCI) m/e 525 (MH+), 255, 135 (C$_{10}$H$_{15}$+); Anal. Calcd for C$_{32}$H$_{35}$O$_3$F$_3$: C, 73.26; H, 6.72. Found: C, 73.58; H, 6.70.

For Methyl (2E),(4Z)-4-(3-trifluoromethylphenyl)-7-[4-(1-adamantyl)-3-methoxyphenyl]-2,4-heptadienoate (19f): scale=0.46 mmol, yield=66%; $^1$H NMR (300 MHz, CDCl$_3$) δ7.55 (d, J=8 Hz, 1H, 4-ArH), 7.49 (d, J=16 Hz, 1H, CH=CHCO$_2$), 7.42 (t, J=8 Hz, 1H, 4-ArH), 7.24 (s, 1H, 4-ArH), 7.07 (d, J=8 Hz, 1H, 4-ArH), 6.95 (d, J=8 Hz, 1H, 7-ArH), 6.59 (dd, J=8, 2 Hz, 1H, 7-ArH), 6.50 (d, J=1 Hz, 1H, 7-ArH), 6.21 (t, J=8 Hz, 1H, C=CH), 5.24 (d, J=16 Hz, 1H, CH=CHCO$_2$), 3.73 (s, 3H, ArOCH$_3$), 3.69 (s, 3H, CO$_2$CH$_3$), 2.64 (t, J=7 Hz, 2H, ArCH$_2$), 2.26 (q, J=7 Hz, 2H, ArCH$_2$CH$_2$), 2.05 (s, 9H, adamantyl), and 1.74 (s, 6H, adamantyl); $^{13}$C NMR (75 MHz, CDCl$_3$) δ167.53 (C=O), 158.75, 147.90, 142.48, 139.23, 137.20, 136.45, 132.72, 130.90 (d, $J^2_{c,f}$=32 Hz, 4-ArC), 128.97, 126.42, 125.84 (d, $J^3_{c,f}$=4 Hz, 4-ArC), 124.35 (d, f3$_{c,f}$=4 Hz, 4-ArC), 120.31, 118.93, 111.89, 54.84 (ArOCH$_3$), 51.54 (CO$_2$CH$_3$), 40.63, 37.13, 36.68, 34.92, 31.58, and 29.10; IR (film) 2905, 2850, 1720 (C=O), 1325, 1310, 1170, 1130, and 1070 cm$^{-1}$; MS (DCI) m/e 525 (MH+), 493 (M—OCH$_3$)+, 135 (C$_{10}$H$_{15}$)+; Anal. Calcd for C$_{32}$H$_{35}$O$_3$F$_3$: C, 73.26; H, 6.72. Found: C, 73.09; H, 6.50.

Example 19: General Procedure for Synthesis of 20

A mixture of ester 19 in methanol/tetrahydrofuran/2N sodium hydroxide solution (1:1:1, 0.1M) was heated at reflux for 1–4 h. The reaction mixture was then allowed to cool to room temperature and 10% hydrochloric acid solution was added until the solution reached pH 1. The resulting cloudy mixture was extracted with methylene chloride (2 portions), and the organic phase was washed with brine, dried over anhydrous magnesium sulfate, filtered, and concentrated. The residue was evaporated from pentane (3 portions) and then dried in vacuo.

For (2E),(4Z)-4-(3-Trifluoromethylphenyl)-7-(5,6,7,8-tetrahydro-5,5,8,8-tetramethyl-2-naphthalenyl)-2,4-heptadienoic acid (20a): scale=0.39 mmol, yield=94%; UV$_{max}$ (CH$_3$OH) 260 nm (ε=23,200); $^1$H NMR (300 MHz, CD$_3$OD) δ7.61 (br d, J=8 Hz, 1H, 4-ArH), 7.51 (d, J=15 Hz, 1H, CH—CHCO$_2$), 7.48 (t, J=8 Hz, 1H, 4-ArH), 7.18 (d, J=8 Hz, 1H, 4-ArH), 7.16 (s, 1H, 4-ArH), 6.97 (d, J=2 Hz, 1H, 7-ArH), 6.83 (d, J=8 Hz, 1H, 7-ArH), 6.76 (dd, J=2, 8 Hz, 1H, 7-ArH), 6.31 (t, J=8 Hz, 1H, C=CH), 5.08 (d, J=15 Hz, 1H, CH=CHCO$_2$), 2.65 (t, J=8 Hz, 2H, ArCH$_2$), 2.20 (q, J=8 Hz, 2H, ArCH$_2$CH$_2$), 1.67 (br s, 4H, CH$_2$CH$_2$), 125 (s, 6H, 2×CH$_3$), and 1.20 (s, 6H, 2×CH$_3$); $^{13}$C NMR (75 MHz, CD$_3$OD) δ170.45 (C=O), 149.55, 145.61, 144.14, 143.58, 140.63, 139.03, 138.89, 134.26, 130.40, 127.84, 127.61, 126.97 (q, $J^3_{c,f}$=4 Hz, 2-ArC), 125.28 (q, $J^3_{c,f}$=4 Hz, 2-ArC), 120.23, 36.30, 35.87, 35.06, 34.88, 33.17, and 32.33; IR (film) 2400–3600 (br, CO$_2$H), 2960, 2930, 2860, 1690 (C=O), 1620, 1460, 1415, 1365, 1325, 1310, 1275, 1205, 1165, 1130, and 1070 cm$^{-1}$; MS (DCI) m/e 457 (MH+). Anal. Calcd. for C$_{28}$H$_{31}$O$_2$F$_3$: C, 73.66; H, 6.84. Found: C, 73.41; H, 6.84.

For (2E,(4Z)-4-(4-Fluorophenyl)-7-(5,6,7,8-tetrahydro-5,5,8,8tetramethyl-2-naphthalenyl)-2,4-heptadienoic acid (20b): scale=0.66 mmol, yield=88%; UV$_{max}$ (CH$_3$OH) 264 nm (ε=24,300); $^1$H NMR (300 MHz, CD$_3$OD) δ7.47 (d, J=16 Hz, 1H, CH=CHCO$_2$), 7.18 (d, J=8 Hz, 1H, 7-ArH), 6.96–7.08 (m, 3H, ArH), 6.76 (dd, J=2, 8 Hz, 1H, 7-ArH), 6.62–6.69 (m, 2H, ArH), 6.22 (t, J=8 Hz, 1H, C=CH), 5.13 (d, J=16 Hz, 1H, CH=CHCO$_2$), 2.63 (t, J=8 Hz, 2H, ArCH$_2$), 2.21 (q, J=8 Hz, 2H, ArCH$_2$CH$_2$), 1.67 (br s, 4H, CH$_2$CH$_2$), 1.26 (s, 6H, 2'CH$_3$), and 1.20 (s, 6H, 2×CH$_3$); $^{13}$C NMR (75 MHz, CD$_3$OD) δ170.69, 163.45 (d, $J^1_{c,f}$=246 Hz, 4-ArC), 150.22, 145.58, 143.59, 141.13, 139.21, 133.76, 132.19 (d, $J^3_{c,f}$=8 Hz, 4-ArC), 127.88, 127.55, 126.85, 120.84, 116.14 (d, $J^2_{c,f}$=21 Hz, 4-ArC), 36.32, 35.92, 35.06, 34.88, 33.19, 32.38, and 32.36; IR (film) 2400–3600 (br, $CO_2H$), 2960, 2925, 2860, 1690 (C=O), 1615, 1510, 1495, 1460, 1415, 1155, 985, 840, and 825 cm$^{-1}$; MS (DCI) m/e 407 (MH+). Anal. Calcd. for $C_{27}H_{31}O_2F \cdot 0.1 H_2O$: C, 79.41; H, 7.70. Found: C, 79.27; H, 7.67.

For (2E),(4Z)-4-(3-Fluorophenyl)-7-(5,6,7,8-tetrahydro-5,5,8,8-tetramethyl-2-naphthalenyl)-2,4-heptadienoic acid (20c): scale=0.65 mmol, yield=48%; $UV_{max}$ ($CH_3OH$) 262 nm ($\epsilon$=24,900); $^1H$ NMR (300 MHz, $CD_3OD$) $\delta$7.47 (d, J=15 Hz, 1H, CH=$CHCO_2$), 7.25–7.33 (m, 1H, 4-ArH), 7.18 (d, J=2 Hz, 1H, 7-ArH), 6.97–7.04 (m, 2H, 1×4-ArH and 1×7-ArH), 6.76 (dd, J=2, 8 Hz, 1H, 7-ArH), 6.51 (dt, J=2, 8 Hz, 1H, 4-ArH), 6.30 (dq, J=2, 8 Hz, 1H, 4-ArH), 6.24 (t, J=8 Hz, 1H, C=CH), 5.12 (d, J=15 Hz, 1H, CH=$CHCO_2$), 2.64 (t, J=8 Hz, 2H, $ArCH_2$), 2.22 (q, J=8 Hz, 2H, $ArCH_2CH_2$), 1.67 (br s, 4H, $CH_2CH_2$), 1.26 (s, 6H, 2×$CH_3$), and 1.20 (s, 6H, 2×$CH_3$); $^{13}C$ NMR (75 MHz, $CD_3OD$) $\delta$170.53 (C=O), 148.75, 145.00, 143.58, 141.00, 140.15, 139.09 (d, $J^3_{c,f}$=9 Hz, 4-ArC), 131.18 (d, $J^3_{c,f}$=9 Hz, 4-ArC), 127.87, 127.52, 127.10, 126.25, 120.01, 117.05 (d, $J^2_{c,f}$=21 Hz, 4-ArC), 115.17 (d, $J^2_{c,f}$=21 Hz, 4-ArC), 36.31, 35.88, 35.06, 34.89, 33.22, and 32.34; IR (film) 2300–3600 (br, $CO_2H$), 2960, 2925, 2860, 1685 (C=O), 1605, 1580, 1490, 1455, 1425, 1385, 1360, 1320, 1310, 1265, 1250, 1200, 915, 880, 825, 795, and 695 cm$^{-1}$; MS (DCI) m/e 407 (MH+). Anal. Calcd. for $C_{27}H_{31}O_2F$: C, 79.77; H, 7.69. Found: C, 79.74; H, 7.63.

For (2E),(4Z)-4-Phenyl-7-(5,6,7,8-tetrahydro-5,5,8,8-tetramethyl-2-naphthalenyl)-2,4-heptadienoic acid (20d): scale=0.63 mmol, yield=91%; $UV_{max}$ ($CH_3OH$) 264 nm ($\epsilon$=22,000); $^1H$ NMR (300 MHz, $CD_3OD$) $\delta$7.48 (d, J=15 Hz, 1H, CH=$CHCO_2$), 7.27–7.33 (m, 3H, 4-ArH), 7.17 (d, J=8 Hz, 1H, 7-ArH), 6.96 (d, J=2 Hz, 1H, 7-ArH), 6.70–6.78 (m, 3H, 2×4-ArH and 1×7-ArH), 6.20 (t, J=8 Hz, 1H, C=CH), 5.15 (d, J=15 Hz, 1H, CH=$CHCO_2$), 2.62 (t, J=8 Hz, 2H, $ArCH_2$), 2.22 (q, J=8 Hz, 2H, $ArCH_2CH_2$), 1.67 (br s, 4H, $CH_2CH_2$), 1.25 (s, 6H, 2'$CH_3$), and 1.20 (s, 6H, 2×$CH_3$); $^{13}C$ NMR (75 MHz, $CD_3OD$) $\delta$150.42, 145.54, 145.46, 143.46, 143.13, 142.17, 139.26, 137.77, 130.27, 129.40, 128.41, 127.78, 127.50, 127.06, 119.93, 36.34, 36.02, 35.06, 34.87, 33.14, and 32.36; IR (KBr) 2400–3300 (br, $CO_2H$), 3020, 2955, 2925, 2865, 1690 (C=O), 1615, 1600, 1495, 1460, 1440, 1415, 1385, 1360, 1310, 1300, 1285, 1275, 1250, 1235, 1200, 990, 820, and 695 cm$^{-1}$; MS (DCI) m/e 389 (MH+), 371 (M+—OH). Anal. Calcd. for $C_{27}H_{32}O_2$: C, 83.46; H, 8.30. Found: C, 83.51; H, 8.58.

For (2Z),(4Z)-4-(3-Trifluoromethylphenyl)-7-[3-(1-adamantyl)-4-methoxyphenyl]-2,4-heptadienoic acid (20e): scale=0.19 mmol, yield=87%; $^1H$ NMR (300 MHz, $CDCl_3$) $\delta$7.57 (m, 2H, 4-ArH and CH=$CHCO_2$), 7.44 (t, J=8 Hz, 1H, 4-ArH), 7.15 (s, 1H, 4-ArH), 7.05 (d, J=8 Hz, 1H, 4-ArH), 6.87 (d, J=2 Hz, 1H, 7-ArH), 6.82 (dd, J=2, 8 Hz, 1H, 7-ArH), 6.73 (d, J=8 Hz, 1H, 7-ArH), 6.27 (t, J=8 Hz, 1H, C=CH), 5.23 (d, J=16 Hz, 1H, CH=$CHCO_2$), 3.79 (s, 3H, $ArOCH_3$), 2.63 (t, J=7 Hz, 2H, $ArCH_2$), 2.25 (q, J=7 Hz, 2H, $ArCH_2CH_2$), 2.03 (s, 9H, adamantyl), and 1.73 (s, 6H, adamantyl); $^{13}C$ NMR (75 MHz, $CDCl_3$) $\delta$172.20 (C=O), 157.27, 150.14, 144.20, 139.11, 138.36, 136.95, 132.63, 132.05, 130.97 (d, $J^2_{c,f}$=32 Hz, 4-ArC), 129.02, 126.87, 126.28, 125.80, 124.42, 118.14, 111.64, 55.01 ($OCH_3$), 40.57, 37.10, 36.87, 34.69, 32.08, and 20.07; IR (KBr) 2400–3700 (br, $CO_2H$), 2905, 2850, 1690, 1615, 1325, 1235, 1165, and 1130 cm$^{-1}$; MS (DCI) m/e 511 (MH+), 493 (M-OH)+, 465, 255, 135 ($C_{10}H_{15}$)+; Anal. Calcd for $C_{31}H_{33}O_3F_3$: C, 72.92; .H, 6.51. Found: C, 72.50; H, 6.68.

For (2Z),(4Z)-4-(3-Trifluoromethylphenyl)-7-[4-(1-adamantyl)-3-methoxyphenyl]-2,4-heptadienoic acid (20f): scale=0.24 mmol, yield=69%; $^1H$ NMR (300 MHz, $CDCl_3$) $\delta$7.55 (m, 2H, 4-ArH and CH=$CHCO_2$), 7.43 (t, J=8 Hz, 1H, 4-ArH), 7.24 (d, J=1 Hz, 1H, 4-ArH), 7.07 (d, J=8 Hz, 1H, 4-ArH), 6.95 (d, J=8 Hz, 1H, 7-ArH), 6.59 (dd, J=8, 2 Hz, 1H, 7-ArH), 6.50 (d, J=2 Hz, 1H, 7-ArH), 6.26 (t, J=8 Hz, 1H, C=CH), 5.23 (d, J=16 Hz, 1H, CH=$CHCO_2$), 3.73 (s, 3H, $ArOCH_3$), 2.64 (t, J=7 Hz, 2H, $ArCH_2$), 2.28 (q, J=8 Hz, 2H, $ArCH_2CH_2$), 2.05 (s, 9H, adamantyl), and 1.74 (s, 6H, adamantyl); $^{13}C$ NMR (75 MHz, $CDCl_3$) $\delta$172.34 (C=O), 158.77, 150.00, 143.82, 139.22, 139.18, 136.89, 136.51, 132.69, 130.98 (d, $J^2_{c,f}$=32 Hz, 4-ArC), 129.04, 126.45, 125.80, 124.46, 122.14, 120.29, 118.35, 111.88, 54.85 ($OCH_3$), 40.63, 37.13, 36.69, 34.84, 31.66, and 29.10; IR (KBr) 2400–3600 (br, $CO_2H$), 2905, 2850, 1690 (C=O), 1615, 1325, 1165, and 1130 cm$^{-1}$; MS (DCI) m/e 511 (MH+), 493 (M-OH)+, 135 ($C_{10}H_{15}$)+; Anal. Calcd for $C_{31}H_{33}O_3F_3$: C, 72.92; H, 6.51. Found: C, 72.79; H, 6.60.

Example 20: Synthesis of 3-(t-Butyldiphenylsiloxymethyl)bromobenzene 22

A stirred solution of 3-bromobenzyl alcohol (21) (10.0 g, 53.5 mmol), 4-dimethylaminopyridine (0.33 g, 2.7 mmol), and t-butylchlorodiphenylsilane (17.6 g, 64.2 mmol) in anhydrous $CH_2Cl_2$ (240 mL) was cooled to 0° C. under argon. Triethylamine (8.1 g, 80.2 mmol) was added dropwise via syringe and the reaction mixture was allowed to warm to room temperature over 3.5 h. The reaction solution was washed with water, and the aqueous portion was extracted again with $CH_2Cl_2$. The organic layers were combined, washed sequentially with 1N HCl solution, water, and saturated sodium chloride solution, dried over anhydrous magnesium sulfate, filtered, and concentrated to afford 25.3 g of 22 as a clear, pale yellow oil. Purification by column chromatography (20:1 ratio silica gel/crude product; elution with 5% to 7.5% ethyl acetate/hexanes) yielded 21.2 g (93%) of 22 as a pale yellow oil. $^1H$ NMR (300 MHz, $CDCl_3$) $\delta$7.63–7.65 (m, 4H, ArH), 7.35–7.48 (m, 8 H, ArH), 7.18–7.28 (m, 2H, ArH), 4.72 (s, 2H, $CH_2OSi$), and 1.05 (s, 9H, $SiC(CH_3)_3$).

Example 21: Synthesis of 3-(t-Butyldiphenylsiloxymethyl)benzyl alcohol 23

Magnesium turnings (1.45 g, 59.5 mmol) were weighed into a flask which was then flame-dried under vacuum. An argon atmosphere was introduced, and anhydrous THF (30 mL) and dibromoethane (approx. 0.1 mL) were added. The mixture was stirred at room temperature. Approximately 25 mL of a solution of 22 (21.1 g, 49.6 mmol) in anhydrous THF (120 mL) was added via cannula. Within 10 min, the solution became dark yellow-brown. The remainder of the solution of 22 was then added via cannula, and the entire reaction solution was heated at reflux for 2 h. The solution was allowed to cool to room temperature, and p-formaldehyde (2.98 g, 99.2 mmol) was added. The reaction mixture was stirred at room temperature for 19 h and then poured into a separatory funnel containing saturated ammonium chloride solution. The aqueous mixture was extracted twice with diethyl ether. The organic layers were combined, washed with saturated sodium chloride solution, dried over anhydrous magnesium sulfate, filtered, and concentrated to give 19.1 g of a clear, yellow liquid. Purification by column chromatography (10:1 ratio silica gel/crude product; gradient elution with 10% to 30% ethyl acetate/hexanes) provided 11.9 g (64%) of 23 as a pale yellow oil. $^1$H NMR (300 MHz, CDCl$_3$) δ7.69–7.73 (m, 4H, ArH), 7.25–7.46 (m, 10 H, ArH), 4.79 (s, 2H, CH$_2$OSi), 4.68 (s, 2H, CH$_2$OH), and 1.11 (s, 9H, SiC(CH$_3$)$_3$); $^{13}$C NMR (75 MHz, CDCl$_3$) δ141.32, 140.67, 135.48, 133.35, 129.61, 128.41, 127.62, 125.46, 125.29, 124.54, 65.32 (CH$_2$OSi, CH$_2$OH), 26.75 (SiC(CH$_3$)$_3$), and 19.22 (SiC(CH$_3$)$_3$); IR (film) 3340 (br, OH), 2940, 2860, 1475, 1430, 1150, and 1110 cm$^{-1}$; MS (FAB) m/e 399 (M+Na)$^+$.

Example 22: Synthesis of 3-(t-Butyldiphenylsiloxymethy)benzyl chloride 24

Methanesulfonyl chloride (3.96 g, 34.6 mmol) was added dropwise to a stirred solution of 23 (11.8 g, 31.4 mmol), LiCl (1.33 g, 31.4 mmol), and s-collidine (4.19 g, 34.6 mmol) in anhydrous DMF (120 mL) at 0° C. under argon. The reaction mixture was allowed to warm to room temperature over 2 h, and was then poured into water and extracted twice with diethyl ether. The organic layers were combined and washed with saturated sodium chloride solution, dried over anhydrous magnesium sulfate, filtered, and concentrated to give 11.8 g (95%) of 24 as a clear, dark yellow liquid. The chloride was used without purification in the next reaction. $^1$H NMR (300 MHz, CDCl$_3$) δ7.72–7.76 (m, 4H, ArH), 7.31–7.48 (m, 10H, ArH), 4.82 (s, 2H, CH$_2$OSi), 4.62 (s, 2H, CH$_2$Cl), and 1.15 (s, 9H, SiC(CH$_3$)$_3$); $^{13}$C NMR (75 MHz, CDCl$_3$) δ141.71, 137.35, 135.58, 135.51, 133.39, 129.74, 129.60, 128.64, 127.74, 127.08, 126.20, 126.06, 65.24 (CH$_2$OSi), 46.34 (CH$_2$Cl), 26.84 (SiC(CH$_3$)$_3$), and 19.32 (SiC(CH$_3$)$_3$); MS (DCI) m/e 395 (MH+).

Example 23: Synthesis of [3-(t-Butyldiphenylsiloxymethyl)phenyl]acetonitrile 25

Sodium cyanide (1.57 g, 32.0 mmol) and tetrabutylammonium iodide (0.11 g, 0.30 mmol) were added to a stirred solution of 24 (11.8 g, 29.9 mmol) in anhydrous DMF (90 mL) at room temperature under argon. The reaction mixture was heated to 80° C. for 2 h. The solution was allowed to cool to room temperature and was poured into saturated ammonium chloride solution and extracted twice with diethyl ether. The organic layers were combined, washed with saturated sodium chloride, dried over anhydrous magnesium sulfate, filtered, and concentrated to give 11.0 g of a clear, brown oil. Purification by column chromatography (20:1 ratio silica gel/crude product; gradient elution with 1% to 10% ethyl acetate/hexanes) provided 8.39 g (73%) of 25 as a pale yellow, clear oil. $^1$H NMR (300 MHz, CDCl$_3$) δ7.64–7.67 (m, 4H, ArH), 7.19–7.41 (m, 10H, ArH), 4.74 (s, 2H, CH$_2$OSi), 3.70 (s, 2H, CH$_2$CN), and 1.08 (s, 9H, SiC(CH$_3$)$_3$); $^{13}$C NMR (75 MHz, CDCl$_3$) δ142.24, 135.57, 133.31, 129.81, 129.04, 127.78, 126.41, 125.69, 125.54, 117.87 (CN), 65.13 (CH$_2$OSi), 26.85 (SiC(CH$_3$)$_3$), 23.65 (CH$_2$CN), and 19.31 (SiC(CH$_3$)$_3$); IR (film) 2960, 2930, 2890, 2860, 2250 (CN), 1470, 1430, 1150, 1110, and 1080 cm$^{-1}$; MS (DCI) m/e 386 (MH+).

Example 24: Synthesis of (4E)-2-[3-(t-Butyldiphenylsiloxymethyl)phenyl]-5-(5,6,7,8-tetrahydro-5,5,8,8-tetramethyl-2-naphthalenyl)-4-hexenonitrile 26

A solution of diisopropylamine (0.23 g, 2.25 mmol) in anhydrous THF (2 mL) was cooled to 0° C. under argon, and treated with n-BuLi (1.4M in hexanes, 1.46 mL, 2.05 mmol) dropwise via syringe. The solution was stirred for 30 min, and was cooled to −78° C. A solution of 25 (0.73 g, 2.05 mmol) in anhydrous THF (4 mL) was added via cannula. The resulting orange solution was stirred for 30 min, and then added via cannula to a solution of 36 (0.92 g, 2.86 mmol) in anhydrous THF (1.5 mL) cooled to −78° C. The flask was rinsed with anhydrous THF (1 mL). The reaction mixture was allowed to warm to room temperature over 4 h, and was poured into a separatory funnel containing saturated ammonium chloride solution and diethyl ether. The layers were agitated and separated, and the organic layer was washed with saturated sodium chloride solution, dried over anhydrous magnesium sulfate, filtered, and concentrated to afford 1.55 g of a clear, yellow oil. Purification by column chromatography (30:1 ratio silica gel/crude product; gradient elution with 1% to 5% ethyl acetate/hexanes) provided 0.77 g (60%) of 26 as a clear, dark yellow oil. $^1$H NMR (300 MHz, CDCl$_3$) δ7.66–7.69 (m, 4H, ArH), 7.07–7.44 (m, 13H, ArH), 5.71 (t, J=6 Hz, 1H, CH=C), 4.77 (s, 2H, CH$_2$OSi), 3.86 (t, J=6 Hz, 1H, CHCN), 2.71–2.86 (m, 2H, CH$_2$CHCN), 1.92 (s, 3H, C=CCH$_3$), 1.67 (s, 4H, CH$_2$CH$_2$), 1.27 (s, 6H, 2×CH$_3$), 1.27 (s, 6H, 2'CH$_3$), and 109 (s, 9H, SiC(CH$_3$)$_3$); $^{13}$C NMR (75 MHz, CDCl$_3$) δ143.88, 142.03, 135.44, 135.30, 133.20, 129.66, 128.80, 127.65, 126.27, 125.87, 125.60, 124.80, 123.67, 123.09, 120.74, 120.53 (CN), 65.07 (CH$_2$OSi), 37.55 (CHCN), 35.03, 34.92, 34.17, 33.95, 31.75, 31.69, 27.82 (SiC(CH$_3$)$_3$), 19.20 (SiC(CH$_3$)$_3$), and 16.01; IR (film) 2960, 2930, 2860, 2240 (CN), 1460, 1430, 1110, and 1080 cm$^{-1}$; MS (DCI) m/e 626 (MH+).

Example 25: Synthesis of (4E)-2-[3-(t-Butyldiphenylsiloxymethyl)phenyl]-5-(5,6,7,8-tetrahydro-5,5,8,8-tetramethyl-2-naphthalenyl)-4-hexenal 27

Diisobutylaluminum hydride (1.0M in hexanes, 1.54 mL, 1.54 mmol) was added dropwise to a solution of 26 (0.74 g, 1.18 mmol) in anhydrous diethyl ether (22 mL) at 0° C. under argon. The reaction mixture was allowed to warm to room temperature over 2.5 h. The reaction was quenched with ethyl acetate (2.5 mL) and 1N H$_2$SO$_4$ solution (5 mL) and stirring was continued for 10 min. The mixture was poured into a separatory funnel and the layers were separated. The aqueous layer was extracted again with diethyl ether. The organic layers were combined, washed sequentially with 1N NaOH solution and saturated sodium chloride solution, and concentrated in vacuo to give 0.72 g (97%) of 27 as a dark yellow oil. $^1$H NMR showed the presence of trace impurities, but the compound decomposed on silica gel. The material was used without purification in the next reaction. $^1$H NMR (300 MHz, CDCl$_3$) δ9.73 (s, 1H, CHO), 7.61–7.77 (m, 4H, ArH), 7.03–7.42 (m, 13H, ArH), 5.62 (t, J=9 Hz, 1H, CH=C), 4.78 (s, 2H, CH$_2$OSi), 3.66 (t, J=6 Hz, 1H, CHCHO), 2.92–3.01 (m, 1H, 1×CH$_2$CH), 2.55–2.67 (m, 1H, 1×CH$_2$CH), 1.95

(s, 3H, C=CCH₃), 1.66 (s, 4H, CH₂CH₂), 1.28 (s, 12H, 4×CH₃), and 1.07 (s, 9H, SiC(CH₃)₃).

Example 26: Synthesis of Methyl (2Z),(6E)-4-[3-(t-butyldiphenylsiloxymethyl)phenyl]-7-(5,6,7,8-tetrahydro-5,5,8,8-tetramethyl-2-naphthalenyl)-2,6-octadienoate 28

Potassium bis(trimethylsilyl) amide (0.5M in toluene, 2.28 mL, 1.14 mmol) was added to a stirred solution of 18-crown-6 (1.51 g, 5.72 mmol), bis(2,2,2-trifluoroethyl) (methoxycarbonylmethyl)phosphonate (0.36 g, 1.14 mmol), and 27 (0.72 g, 1.14 mmol) in anhydrous THF (16.5 mL) at −78° C. under argon. The reaction mixture was maintained at −78° C. for 1 h, and was then allowed to warm to room temperature over 3 h. The solution was poured into a separatory funnel containing saturated ammonium chloride solution and was extracted twice with diethyl ether. The organic layers were combined, washed with saturated sodium chloride solution, dried over anhydrous magnesium sulfate, filtered, and concentrated to afford 0.85 g of a bright yellow oil. Purification by column chromatography (40:1 ratio silica gel/crude product; gradient elution from 1% to 5% ethyl acetate/hexanes) yielded 0.42 g (53%) of 28 as a dark yellow oil. $^1$H NMR (300 MHz, CDCl₃) δ7.67-7.72 (m, 4H, ArH), 7.18-7.42 (m, 12H, ArH), 7.06 (dd, J=2, 8 Hz, 1H, ArH), 6.33 (t, J=12 Hz, 1H, CH=CHCO₂), 5.80 (d, J=12 Hz, 1H, CH=CHCO₂), 5.67 (t, J=9 Hz, 1H, CH=CCH₃), 4.90-4.98 (m, 1H, CHCH=CH), 4.78 (s, 2H, CH₂OSi), 3.70 (s, 3H, CO₂CH₃), 2.58-2.64 (m, 2H, CH₂CH), 1.98 (s, 3H, CH=CCH₃), 1.68 (s, 4H, CH₂CH₂), 1.27 (s, 12H, 4×CH₃), and 1.10 (s, 9H, SiC(CH₃)₃).

Example 27: Synthesis of Methyl(2Z),(6E)-4-[3-hydroxymethyl)phenyl]-7-(5,6,7,8-tetrahydro-5,5,8,8-tetramethyl-2-naphthalenyl)-2,6-octadienoate 29

A solution of 28 (0.70 g, 1.02 mmol) in 3% concentrated HC₁ in methanol was heated slightly to dissolve the starting material and then was stirred at room temperature for 4.5 h. The reaction mixture was poured into water and extracted twice with diethyl ether. The organic layers were combined, washed with saturated sodium chloride solution, dried over anhydrous magnesium sulfate, filtered, and concentrated to provide 0.73 g of a yellow liquid. Purification by column chromatography (30:1 ratio silica gel/crude product; gradient elution with 5% to 20% ethyl acetate /hexanes) yielded 0.34 g (74%) of 29 as a clear yellow oil. $^1$H NMR (300 MHz, CDCl₃) δ7.20-7.34 (m, 6H, ArH), 7.04 (dd, J=2, 8 Hz, 1H, 7-ArH), 6.38 (t, J=12 Hz, 1H, CH=CHCO₂), 5.81 (d, J=12 Hz, 1H, CH=CHCO₂), 5.64 (t, J=9 Hz, 1H, CH=CCH₃), 4.90-4.99 (m, 1H, CHCH=CH), 4.68 (d, J=6 Hz, 2H, CH₂OH), 3.71 (s, 3H, CO₂CH₃), 2.64 (t, J=6 Hz, 2H, CH₂CH), 1.97 (s, 3H, CH=CCH₃), 1.66 (s, 4H, CH₂CH₂), and 1.26 (s, 12H, 4×CH₃).

Example 28: Synthesis of Methyl (2Z),(6E)-4-[3-formylphenyl]-7-(5,6,7,8-tetrahydro-5,5,8,8-tetramethyl-2naphthalenyl)-2,6-octadienoate 30

MnO₂ (0.40 g, 4.6 mmol) was added to a solution of 29 (0.41 g, 0.92 mmol) in CH₂C₁₂ (4 mL) and the slurry was stirred in a stoppered flask at room temperature. Additional portions of MnO₂ (0.40 g, 4.6 mmol each time) were added to the reaction mixture after 15 h, 17 h, 21.5 h, and 23.5 h. Additional CH₂C₁₂ (5 mL) was added to the mixture after 15 h. After 39 h, the slurry was filtered through a 1 inch pad of Celite and the filtrate was concentrated to give 0.33 g (83%) of 30 as a clear yellow oil. $^1$H NMR (300 MHz, CDCl₃) δ9.98 (s, 1H, CHO), 7.82 (s, 1H, 4-ArH), 7.72 (d, J=9 Hz, 1H, 4-ArH), 7.58 (d, J=9 Hz, 1H, 4-ArH), 7.46 (t, J=8 Hz, 1H, 4-ArH), 7.18 (d, J=6 Hz, 1H, 7-ArH), 7.19 (s, 1H, 7-ArH), 7.02 (dd, J=2, 8 Hz, 1H, 7-ArH), 6.37 (t, J=10.5 Hz, 1H, CH=CHCO₂), 5.84 (d, J=12 Hz, 1H, CH=CHCO₂), 5.59 (t, J=7.5 Hz, 1H, CH=CH₃), 5.00 (q, J=7.5 Hz, 1H, CHCH=CH), 3.69 (s, 3H, CO₂CH₃), 2.65 (t, J=9 Hz, 2H, CH₂CH), 1.94 (s, 3H, CH=CCH₃), 1.64 (s, 4H, CH₂CH₂), and 1.23 (s, 12H, 4×CH₃); $^{13}$C NMR (75 MHz, CDCl₃) δ192.36 (C=O), 151.29, 144.44, 134.24, 129.26, 128.42, 128.32, 126.23, 123.74, 123.47, 123.07, 119.43, 51.25 (CO₂CH₃), 43.45, 35.15 and 35.03 (CH₂CH₂), 34.25, 34.01, 31.81, 30.94, and 16.11; IR (film) 2960, 2925, 2860, 1720 (ester C=O), 1700 (CH=O), 1455, 1435, 1215, 1195, and 1175 cm⁻¹; MS (DCI) m/e 445 (MH +).

Example 29: Synthesis of Methyl (2Z),(6E)-4-[3-carbomethoxyphenyl]-7-(5,6,7,8-tetrahydro-5,5,8,8-tetramethyl-7-naphthalenyl)-2,6-octadienoate 31

MnO₂ (0.64 g, 7.4 mmol) was added to a solution of 30 (0.33 g, 0.74 mmol), sodium cyanide (0.20 g, 4.0 mmol), and glacial acetic acid (approx. 0.02 mL) in anhydrous methanol (12 mL) and the slurry was stirred in a stoppered flask at room temperature. Additional MnO₂ (0.64 g, 7.4 mmol) was added to the mixture after 4 h. After 20 h, the reaction mixture was filtered through a 1 inch pad of Celite and the filtrate was concentrated to give a beige solid. The solid was diluted with water and diethyl ether and poured into a separatory funnel. The layers were agitated and separated, and the aqueous portion was extracted again with diethyl ether. The organic layers were combined, washed with saturated sodium chloride solution, dried over anhydrous magnesium sulfate, and concentrated to yield 0.32 g (91%) of 31 as a yellow oil. The diester was used in the next reaction without purification. $^1$H NMR (300 MHz, CDCl₃) δ7.98 (s, 1H, 4-ArH), 7.88 (d, J=8 Hz, 1H, 4-ArH), 7.50 (d, J=8 Hz, 11H, 4-ArH), 7.36 (t, J=7.5 Hz, 1 H, 4-ArH), 7.18 (d, J=6 Hz, 1H, 7-ArH), 7.17 (s, 1H, 7-ArH), 7.02 (dd, J=2, 8 Hz, 1H, 7-ArH), 6.38 (t, J=11 Hz, 1H, CH=CHCO₂), 5.82 (d, J=12 Hz, 1H, CH=CHCO₂), 5.60 (t, J=6 Hz, 1H, CH=CCH₃), 4.96 (q, J=10.5 Hz, 1H, CHCH=CH), 3.89 (s, 3H, ArCO₂CH₃), 3.69 (s, 3H, CO₂CH₃), 2.64 (t, J=7.5 Hz, 2H, CH₂CH), 1.95 (s, 3H, CH=CCH₃), 1.64 (s, 4H, CH₂CH₂), and 1.24 (s, 12H, 4×CH₃); $^{13}$C NMR (75 MHz, CDCl₃) δ167.10 (C=O), 166.46 (C=O), 151.61, 144.40, 143.55, 143.43, 140.75, 136.83, 132.70, 130.43, 128.62, 128.45, 127.86, 126.18, 123.76, 123.72, 123.08, 119.17, 52.11 (CO₂CH₃), 51.21 (CO₂CH₃), 43.60, 35.21 and 35.18 (CH₂CH₂), 35.05, 34.24, 34.00, 31.80 (4×CH₃), 31.93, 29.71, 16.10, and 15.27; IR (film) 2955, 2925, 2860, 1725 (C=O), 1435, 1280, 1230, 1195, and 1175 cm⁻¹; MS (DCI) m/e 475 (MH+).

Example 30: Synthesis of (2Z),(6E)-4-[3-Carboxyphenyl]-7-(5,6,7,8-tetrahydro-5,5,8,8-tetramethyl-2-naphthalenyl)-2,6-octadienoic acid 32

A solution of 31 (0.32 g, 0.67 mmol) and bis(tributyltin) oxide (1.61 g, 2.7 mmol) in anhydrous toluene (18 mL) was stirred at reflux under argon for 111 h. The reaction mixture was allowed to cool to room temperature and was concentrated to remove toluene. The remaining solution was treated with 0.5N HCl solution (30 mL) and was extracted with ethyl acetate (3×40 mL). The organic layers were combined and extracted with 1N NaOH solution (3×65 mL). The aqueous layers were combined and acidified with 1N HCl solution to pH 3. The acidified aqueous solution was then extracted with $CH_2Cl_2$ (3×250 mL). The organic layers were combined and concentrated to give 0.24 g of a yellow solid. Purification by reverse-phase column chromatography on $C_{18}$ silica gel (100:1 ratio of silica gel/crude product; elution with 10% $H_2O$/methanol to 100% methanol) yielded 0.12 g (40%) of 32 as an off-white solid. mp 145°–148° C.; $UV_{max}$ ($CH_3OH$) 249 nm ($\epsilon$=16,500), 237 nm ($\epsilon$=22,500); $^1$H NMR (300 MHz, $CD_3OD$) $\delta$8.00 (s, 1H, 4-ArH), 7.88 (d, J=8 Hz, 1H, 4-ArH), 7.58 (d, J=8 Hz, 1H, 4-ArH), 7.42 (t, J=7 Hz, 1H, 4-ArH), 7.11–7.18 (m, 2H, 7-ArH 6.99 (dd, J=2, 8 Hz, 1H, 7-ArH), 6.47 (t, J=11 Hz, 1H, CH=CHCO$_2$), 5.86 (d, J=12 Hz, 1H, CH=CHCO$_2$), 5.56 (t, J=6 Hz, 1H, CH=CCH$_3$), 4.97 (m, 1H, CHCH=CH, obscured under $CH_3OH$), 2.65 (t, J=8 Hz, 2H, CH$_2$CH), 1.94 (s, 3H, CH=CCH$_3$), 1.66 (s, 4H, CH$_2$CH$_2$), and 1.23 (s, 12H, 4×CH$_3$); $^{13}$C NMR (75 MHz, $CD_3OD$) $\delta$169.58 (C=O), 152.51, 145.36, 145.19, 144.33, 142.38, 138.29, 133.72, 133.60, 133.50, 130.02, 129.88, 129.73, 129.00, 127.24, 127.18, 124.96, 124.84, 124.80, 124.12, 120.74, 45.08, 36.36, 36.24, 36.05, 35.31, 35.15, 34.91, 32.30, 32.21, 16.31, and 14.09; IR (KBr) 3600–2400 (br, CO$_2$H), 2960, 2925, 2860, 1695 (C=O), 1640, 1455, 1420, 1280, and 1245 cm$^{-1}$; MS (DCI) m/e 447 (MH$^+$); Anal. Calcd for $C_{29}H_{34}O_4 \cdot 0.5\ H_2O$: C, 76.42; H, 7.74. Found: C, 76.52; H, 7.76.

Example 31: Synthesis of Ethyl (2E)-3-(5,6,7,8-tetrahydro-5,5,8,8tetramethyl-2-naphthalenyl)-2-butenoate 34

A solution of 2-acetyl-5,6,7,8-tetrahydro-5,5,8,8-tetramethylnaphthalene (33, 4.60 g, 20.0 mmol) and methyl diethylphosphonoacetate (7.33 g, 34.9 mmol) in anhydrous toluene (80 mL) was treated dropwise via syringe with sodium methoxide (25 wt % in methanol, 5.5 mL, 24.0 mmol) at room temperature under argon. The reaction mixture was stirred for 14 h and then poured into a separatory funnel containing diethyl ether and saturated ammonium chloride solution. The layers were agitated and separated, and the organic layer was washed with saturated sodium chloride solution, dried over anhydrous magnesium sulfate, filtered, and concentrated to afford 6.5 g of a pale yellow oil. Purification by column chromatography (20:1 ratio silica gel/crude product; elution with 10% ethyl acetate/hexanes) gave 4.10 g (72%) of 34 as a clear, colorless oil. $^1$H NMR (300 MHz, CDCl$_3$) $\delta$7.40 (d, J=2 Hz, 1H, ArH), 7.30 (d, J=7 Hz, 1H, ArH), 7.25 (dd, J=2, 8 Hz, 1H, ArH), 6.15 (br s, 1H, C=CH), 3.75 (s, 3H, CO$_2$CH$_3$), 2.58 (s, 3H, CH$_3$C=C), 1.67 (s, 4H, CH$_2$CH$_2$), 1.26 (s, 6H, 2×CH$_3$), and 1.28 (s, 6H, 2×CH$_3$).

Example 32: Synthesis of (2E)-3-(5,6,7,8-Tetrahydro-5,5,8,8-tetramethyl-2-naphthalenyl)-2-butenol 35

A solution of ester 34 (4.10 g, 14.3 mmol) in anhydrous diethyl ether (40 mL) was added via cannula over 10 min to a slurry of lithium aluminum hydride (0.33 g, 8.6 mmol) in diethyl ether (100 mL) at 0° C. under argon. After 2 h, additional lithium aluminum hydride (0.13 g, 3.4 mmol) was added, and the mixture was stirred for 5 h. The reaction was quenched by sequential addition of H$_2$O (0.46 mL), 15% aqueous sodium hydroxide (0.46 mL), and H$_2$O (1.38 mL). The resulting slurry was filtered and the filtrate was concentrated in vacuo to give 3.8 g of a colorless oil. Purification by column chromatography (30:1 ratio silica gel/crude product; elution with 10% to 15% ethyl acetate/hexanes) provided 3.51 g (95%) of 35 as a colorless oil. $^1$H NMR (300 MHz, CDCl$_3$) $\delta$7.35 (d, J=2 Hz, 1H, ArH), 7.28 (d, J=8 Hz, 1H, ArH), 7.18 (dd, J=2, 8 Hz, 1H, ArH), 5.95 (t, J=5 Hz, 1H, C=CH), 435 (t, J=5 Hz, 2H, CH$_2$OH), 2.10 (s, 3H, CH$_3$C=C), 1.65 (s, 4H, CH$_2$CH$_2$), 1.30 (s, 6H, 2×CH$_3$), and 1.28 (s, 6H, 2×CH$_3$).

Example 33: Synthesis of (2E)-3-(5,6,7,8-Tetrahydro-5,5,8,8-tetramethyl-2-naphthalenyl)-2-butenyl bromide 36

A stirred solution of phosphorous tribromide (0.31 g, 1.16 mmol) and pyridine (0.057 g, 0.72 mmol) in petroleum ether (18 mL) was cooled to −10° C. under argon. The mixture was treated with a solution of 35 (0.94 g, 3.62 mmol) in anhydrous diethyl ether (18 mL). The reaction mixture was allowed to warm to room temperature over 2.5 h. The solution was then diluted with diethyl ether and washed twice with water. The aqueous layers were combined and back-extracted with another portion of diethyl ether. The organic layers were combined, washed with saturated sodium chloride solution, dried over anhydrous magnesium sulfate, filtered, and concentrated to give 1.00 g (86%) of 36 as an off-white solid. The bromide was used without purification in the next reaction. $^1$H NMR (300 MHz, CDCl$_3$) $\delta$7.33 (d, 1H, ArH), 7.28 (d, 1H, ArH), 7.18 (dd, J=12 Hz, 1H, ArH), 6.05 (t, J=9 Hz, 1H, C=CH), 4.12 (d, J=9 Hz, 2H, CH$_2$Br), 2.13 (s, 3H, CH=CCH$_3$), 1.68 (s, 4H, CH$_2$CH$_2$), 1.26 (s, 6H, 2'CH$_3$), and 1.24 (s, 6H, 2×CH$_3$).

Example 34: Synthesis of (Z)-2-(3-Trifluoromethylphenyl)-5-(5,6,7,8-tetrahydro-5,5,8,8-tetramethyl-2-naphthalenyl)-2-pentenyl acetate 37

A solution of (Z)-2-(3-trifluoromethylphenyl)-5-(5,6,7,8-tetrahydro-5,5,8,8-tetramethyl-2-naphthalenyl)-2-pentenol 5r (0.99 g, 2.4 mmol) in anhydrous pyridine (25 mL) at room temperature under argon was treated with 4-dimethylaminopyridine (0.01 g) and acetic anhydride (0.32 g, 3.1 mmol). The reaction mixture was stirred for 2 h and then partitioned between diethyl ether (100 mL) and 1N HCl solution (50 mL). The ether layer was washed further with saturated sodium chloride solution, dried over anhydrous magnesium sulfate, filtered, and concentrated to give 1.09 g (100%) of the product as a colorless oil. The acetate was used without purification in the next reaction. $^1$H NMR (300 MHz, CDCl$_3$) $\delta$7.50 (d, J=8 Hz, 1H, 2-ArH), 7.36–7.41 (m, 2H, 2-ArH), 7.17 (d, J=8 Hz, 1H, 2-ArH), 7.11 (d, J=8 Hz, 1H, 5-ArH), 6.98 (d, J=2 Hz, 1H, 5-ArH), 6.82 (dd, J=2, 8 Hz, 1 Hz, 5-ArH), 5.89 (t, J=7.5 Hz, 1H, C=CH), 4.73 (s, 2H, CH$_2$OAc), 2.61 (t, J=7 Hz, 2H, ArCH$_2$), 2.24 (q, J=7 Hz, 2H, ArCH$_2$CH$_2$), 1.99 (s, 3H, CH$_3$C=O), 1.64 (s, 4H, CH$_2$CH$_2$), 1.24 (s, 6H, 2'CH$_3$), and 1.22 (s, 6H, 2×CH$_3$); $^{13}$C NMR (75 MHz, CDCl$_3$) $\delta$170.66 (C=O), 144.70, 142.52, 138.81, 137.91, 134.89, 133.09, 131.95, 128.67, 126.48, 126.45, 125.73, 125.36, 125.31, 124.02, 68.68 (CH$_2$OAc), 35.33, 35.14, 35.09, 34.12, 31.87, 31.81, 30.67, and 20.89; IR (film) 2960, 2925, 2860, 1745 (C=O), 1325, 1225, 1165, and 1130 cm$^{-1}$; MS (DCI) m/e 399 (M+—OAc).

Example 35: Synthesis of Methyl (Z)-2-carbomethoxy-4-(3trifluoromethylphenyl)-7-(5,6,7,8-tetrahydro-5,5,8,8-tetramethyl-2-naphthalenyl)-4-heptenoate 38

Dimethyl malonate (1.44 g, 10.9 mmol) was added dropwise to a slurry of sodium hydride (80% dispersion in oil, 0.31 g, 10.5 mmol) in anhydrous THF (20 mL) at room temperature under argon. The reaction mixture was stirred for 15 min and then treated with a solution of (Z)-2-(3-trifluoromethylphenyl)-5-(5,6,7,8-tetrahydro-5,5,8,8-tetramethyl-2-naphthalenyl)-2-pentenyl acetate (37) (1.09 g, 2.38 mmol), triphenylphosphine (0.062 g, 0.24 mmol), and tetrakis(triphenylphosphine)palladium(0) (0.137 g, 0.12 mmol) in THF (4 mL). The resulting mixture was heated at reflux for 4 h. The yellow solution was allowed to cool to room temperature and was partitioned between diethyl ether and saturated ammonium chloride solution. The organic phase was washed with saturated sodium chloride solution, dried over anhydrous magnesium sulfate, filtered, and concentrated to afford 1.68 g of crude product. Purification was achieved by column chromatography (30:1 ratio of silica gel/crude product; elution with 2% to 4% ethyl acetate in hexanes, 25 mL fractions). Fractions 8–21 ($R_f$=0.25, 10% ethyl acetate/hexanes) were pooled and concentrated to give 0.65 g of a colorless oil. NMR showed the presence of 10% other isomers. Fractions 22–30 ($R_f$=0.25, 10% ethyl acetate/hexanes) were pooled and concentrated to provide 0.41 g of a colorless oil. NMR showed >98% of one isomer, methyl (Z)-2-carbomethoxy-4-(3-trifluoromethylphenyl)-7-(5,6,7,8-tetrahydro-5,5,8,8-tetramethyl-2-naphthalenyl)-4-heptenoate 38. The combined yield of the reaction was 84%. $^1$H NMR (300 MHz, CDCl$_3$) δ7.33–7.51 (m, 3H, 4-ArH), 7.10–7.23 (m, 2H, 1×4-ArH and 1×7-ArH), 6.95 (d, J=2 Hz, 1H, 7-ArH), 6.79 (dd, J=2, 8 Hz, 1H, 7-ArH), 5.65 (t, J=7 Hz, 1H, C=CH), 3.64 (s, 6H, 2'CO$_2$CH$_3$), 3.31 (t, J=8 Hz, 1H, HC(CO$_2$Me)$_2$), 2.92 (d, J=8 Hz, 2H, CH$_2$CH(CO$_2$Me)2), 2.53 (t, J=7 Hz, 2H, ArCH$_2$), 2.13 (q, J=7 Hz, 2H, ArCH$_2$CH$_2$), 1.63 (s, 4H, CH$_2$CH$_2$), 1.23 (s, 6H, 2×CH$_3$), and 1.21 (s, 6H, 2×CH$_3$); $^{13}$C NMR (75 MHz, CDCl$_3$) δ169.17 (C=O), 144.69, 142.41, 140.17, 138.07, 136.01, 132.02, 131.17, 128.76, 126.41, 126.32, 125.60, 125.25, 123.86, 52.45 (CO$_2$CH$_3$), 50.60 (C(CO$_2$Me)$_2$), 38.16, 35.65, 35.15, 35.09, 34.12, 33.92, 31.87, 31.80, and 30.80; IR (film) 2960, 2925, 2860, 1755 (C=O), 1740 (C=O), 1435, 1325, 1310, 1275, 1235, 1160, 1130, and 1070 cm$^{-1}$; MS (DCI) m/e 531(MH+), 499 (M+−CH$_3$O).

Example 36: Synthesis of (Z)-2-Carboxy-4-(3-trifluoromethylphenyl)-7-(5,6,7,8-tetrahydro-5,5,8,8-tetramethyl-2-naphthalenyl)-4-heptenoic acid 39

A solution of methyl (Z)-2-carbomethoxy-4-(3-trifluoromethylphenyl)-7-(5,6,7,8-tetrahydro-5,5,8,8-tetramethyl-2-naphthalenyl)-4-heptenoate (38) (0.15 g, 0.28 mmol) in 1:1:1 methanol/THF/2N sodium hydroxide solution (4.5 mL) was heated at reflux for 4 h. The reaction mixture was allowed to cool to room temperature and was treated with 10% hydrochloric acid solution (10 mL). The aqueous solution was extracted with diethyl ether (2×50 mL), and the organic layers were washed with saturated sodium chloride solution, dried over anhydrous magnesium sulfate, filtered, and concentrated to give 0.13 g (92%) of a white foam. $^1$H NMR (300 MHz, CDCl$_3$) δ7.48 (d, J=8 Hz, 1H, 4-ArH), 7.37 (d, J=8 Hz, 1H, 4-ArH), 7.32 (br s, 1H, 4-ArH), 7.09–7.20 (m, 2H, 1×4-ArH and 1×7-ArH), 6.94 (d, J=2 Hz, 1H, 7-ArH), 6.77 (dd, J=2, 8 Hz, 1H, 7-ArH), 5.68 (t, J=7.5 Hz, 1H, C=CH), 3.36 (t, J=8 Hz, 1H, CH(CO$_2$Me)$_2$), 2.94 (d, J=8 Hz, 2H, CH$_2$CH(CO$_2$Me)$_2$), 2.53 (t, J=7 Hz, 2H, ArCH$_2$), 2.14 (q, J=7 Hz, 2H, ArCH$_2$CH$_2$), 1.63 (s, 4H, CH$_2$CH$_2$), 1.22 (s, 6H, 2×CH$_3$), and 1.20 (s, 6H, 2×CH$_3$); $^{13}$C NMR (75 MHz, CDCl$_3$) δ173.50 (C=O), 144.72, 142.46, 139.80, 138.06, 135.35, 132.10, 131.72, 128.83, 126.37, 125.73, 125.22, 124.06, 50.14 (C(CO$_2$Me)$_2$), 37.97, 35.49, 35.15, 35.09, 34.10, 33.92, 31.86, 31.80, and 30.86; IR (KBr) 2400–3600 (br), 1720 (C=O), 1460, 1440, 1410, 1325, 1310, 1165, 1130, and 1070 cm$^{-1}$; MS (FAB) m/e 525 (M++Na); Anal. Calcd for C$_{29}$H$_{33}$O$_4$F$_3$.0.25H$_2$O: C, 68.69; H, 6.66. Found: C, 68.73; H, 6.68.

Example 37: Synthesis of (Z)-4-(3-trifluoromethylphenyl)-7-(5,6,7,8-tetrahydro-5,5,8,8-tetramethyl-2-naphthalenyl)-4-heptenoic acid 40

A solution of (Z)-2-carboxy-4-(3-trifluoromethylphenyl)-7-(5,6,7,8-tetrahydro-5,5,8,8-tetramethyl-2-naphthalenyl)-4-heptenoic acid 39 (0.108 g, 0.21 mmol) in anhydrous acetonitrile (2 mL) was treated with copper(I) oxide (0.003 g, 0.02 mmol). The mixture was heated at reflux for 7 h, and then additional copper(I) oxide (0.003 g, 0.02 mmol) was added and heating was continued for 14 h further. The reaction mixture was then allowed to cool to room temperature and was concentrated in vacuo. The residue was treated with water (5 mL) and 10% aqueous hydrochloric acid solution (5 mL). The aqueous mixture was extracted with diethyl ether (2×50 mL), and then organic layers were washed with saturated sodium chloride solution, dried over anhydrous magnesium sulfate, filtered, and concentrated to give 0.10 g of crude product. Column chromatography (60:1 ratio silica gel/crude product; elution with 30% ethyl acetate/hexanes) gave 0.057 g (58%) of the product as a colorless oil. $^1$H NMR (300 MHz, CDCl$_3$) δ7.47 (d, J=8 Hz, 1H, 4-ArH), 7.37 (d, J=8 Hz, 1H, 4-ArH), 7.32 (br s, 1H, 4-ArH), 7.16 (d, J=8 Hz, 1H, 4-ArH), 7.08 (d, J=8 Hz, 1H, 7-ArH), 6.97 (d, J=2 Hz, 1H, 7-ArH), 6.80 (dd, J=2, 8 Hz, 1H, 7-Axil), 5.61 (t, J=7.5 Hz, 1H, C=CH), 2.64 (t, J=7.5 Hz, 2H, CH$_2$CO$_2$), 2.56 (t, J=7.5 Hz, 2H, ArCH$_2$), 2.33 (t, J=7.5 Hz, 2H, C=CCH$_2$CH$_2$CO$_2$), 2.15 (q, J=7.5 Hz, 2H, ArCH$_2$CH$_2$), 1.65 (s, 4H, CH$_2$CH$_2$), 1.24 (s, 6H, 2'CH$_3$), and 1.22 (s, 6H, 2×CH$_3$); $^{13}$C NMR (75 MHz, CDCl$_3$) δ178.61 (C=O), 144.63, 142.39, 140.94, 138.24, 138.13, 131.86, 129.01, 128.68, 126.54, 126.40, 125.85, 125.73, 125.05, 123.63, 35.73, 35.17, 35.11, 34.12, 33.93, 33.85, 32.80, 31.88, 31.82, and 30.85; IR (film) 3600–2400 (br), 2960, 2925, 2860, 1710 (C=O), 1495, 1455, 1440, 1410, 1325, 1310, 1275, 1165, 1130, and 1070 cm$^{-1}$; MS (FAB) m/e 481 (MH+); Anal. Calcd for C$_{28}$H$_{33}$O$_2$F$_3$.0.25 H$_2$O: C, 72.62; H, 7.29. Found: C, 72.51; H, 7.16.

Reasonable variations, such as those which would occur to a skilled artisan can be made herein without departing from the scope of the invention.

We claim:

1. A compound of Formula I:

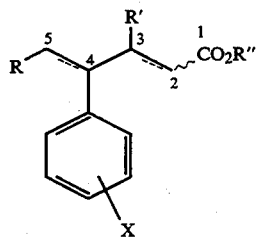 (I)

wherein the bonds between $C_2$ and $C_3$ and/or between $C_4$ and $C_5$ are unsaturated;

X=COOH, H, F, $C_1$, Br, I, COOR", CONH$_2$, COR''', CHO, CH$_2$OH, CH$_2$OR''', OH, OR''', CF$_3$, $C_{1-6}$ alkyl, $C_{1-6}$ alkenyl, $C_{1-6}$ haloalkyl, NO$_2$, P(O)(OH)$_2$, SO$_2$H, or SO$_3$H;

R=substituted or unsubstituted alkyl, aryl, arylalkyl, alkenyl, or arylalkenyl groups, with the proviso that each of these groups must have 6 or more carbons and R cannot be

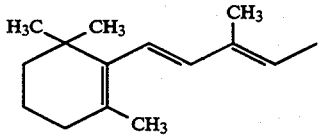

R'=H or $C_{1-6}$ alkyl;

R"=H, $C_{1-6}$ alkyl, C(R$^3$)$_2$OC(O)R$^4$, CH$_2$CH$_2$NR$^5$R$^6$, CH$_2$CH$_2$CH$_2$NR$^5$R$^6$, CH$_2$C(O)N(R$^6$)$_2$, or other groups yielding physiologically hydrolyzable esters;

R'''=$C_{1-6}$ alkyl;

R$^3$=H, CH$_3$, C$_2$H$_5$, CH$_3$CH$_2$CH$_2$ (with R$^3$'s being the same or different);

R$^4$=C$_{6-12}$ aryl, C$_{1-7}$ linear, branched or cyclic alkyl, or C$_{1-7}$ linear, branched or cyclic alkoxy;

R$^5$=R$^6$, or when linked with R$^6$, is a C$_3$-C$_6$ cycloalkyl or a —CH$_2$CH$_2$OCH$_2$CH$_2$-group; and R$^6$=C$_{1-3}$ alkyl.

2. The compounds of claim 1 having a structure selected from the group consisting of structure types IA, IB, IC, and ID:

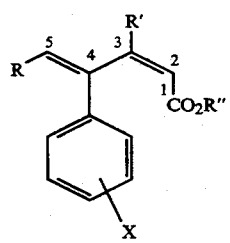 (IA)

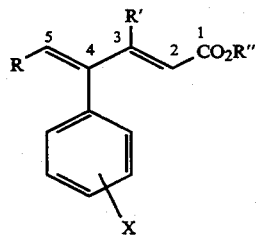 (IB)

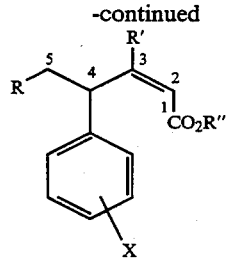 (IC)

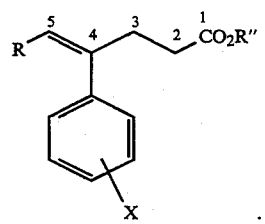 (ID)

3. The compound of claim 2 conforming to structure IA.

4. The compound of claim 3 selected from the group consisting of:

(2Z), (4Z)-4-(3-carboxyphenyl)-5-(5,6,7,8-tetrahydro-5,5,8,8-tetramethyl-2-naphthalenyl)-2,4-pentadienoic acid;

(2Z), (4Z)-4-(3-carboxyphenyl)-5-(5,6,7,8-tetrahydro-5,5,8,8-tetramethyl-2-anthracenyl)-2,4-pentadienoic acid;

(2Z), (4Z)-4-(3-carboxyphenyl)-5-(4-decyloxyphenyl)-2,4-pentadienoic acid;

(2Z), (4Z)-4-(3-carboxyphenyl)-5-(3,4-bisdecyloxyphenyl)-2,4-pentadienoic acid;

(2Z), (4Z)-4-(3-carboxyphenyl)-7-(5,6,7,8-tetrahydro-5,5,8,8-tetramethyl-2-naphthalenyl)-2,4-heptadienoic acid;

(2Z), (4Z), (6E)-4-(3-carboxyphenyl)-7-(5,6,7,8-tetrahydro-5,5,8,8-tetramethyl-2-naphthalenyl)-2,4,6-octatrienoic acid;

(2Z), (4Z)-4-(3-carboxyphenyl)-7-[4-(1-adamantyl)-3-methoxyphenyl]-2,4-heptadienoic acid;

(2Z), (4Z)-4-(3-carboxyphenyl)-7-[3-(1-adamantyl)-4-methoxyphenyl]-2,4-heptadienoic acid;

(2Z), (4Z)-4-(3-trifluoromethylphenyl)-5-(4-decyloxyphenyl]-2,4-pentadienoic acid;

(2Z), (4Z)-4-(3-trifluoromethylphenyl)-5-(3-decyloxyphenyl]-2,4-pentadienoic acid;

(2Z), (4Z)-4-(3-trifluoromethylphenyl)-5-(2-decyloxyphenyl]-2,4-pentadienoic acid;

(2Z), (4Z)-4-(3-trifluoromethylphenyl)-5-[4-(2E), (6E)-3,7-dimethylocta-2,6-dienoxy]phenyl-2,4-pentadienoic acid;

(2Z), (4Z)-4-(3-trifluoromethylphenyl)-5-(3,4-bisdecyloxyphenyl)-2,4-pentadienoic acid;

(2E), (4Z)-4-(3-trifluoromethylphenyl)-5-(3,4-bisdecyloxyphenyl)-2,4-pentadienoic acid;

(2Z), (4Z)-4-(3-trifluoromethylphenyl)-5-(5,6,7,8-tetrahydro-5,5,8,8-tetramethyl-2-anthracenyl)-2,4-pentadienoic acid;

(2Z), (4Z)-4-(3-trifluoromethylphenyl)-7-(5,6,7,8-tetrahydro-5,5,8,8-tetramethyl-2-naphthalenyl)-2,4-heptadienoic acid;

(2Z), (4Z)-4-(4-fluorophenyl)-7-(5,6,7,8-tetrahydro-5,5,8,8-tetramethyl-2-naphthalenyl)-2,4-heptadienoic acid;

(2Z), (4Z)-4-(3-fluorophenyl)-7-(5,6,7,8-tetrahydro-5,5,8,8-tetramethyl-2-naphthalenyl)-2,4-heptadienoic acid;

(2Z), (4Z)-4-phenyl-7-(5,6,7,8-tetrahydro-5,5,8,8-tetramethyl-2-naphthalenyl)-2,4-heptadienoic acid;

(2Z), (4Z)-4-(3-trifluoromethylphenyl)-7-[3-(1-adamantyl)-4-methoxyphenyl]-2,4-heptadienoic acid;

(2Z), (4Z)-4-phenyl-7-[3-(1-adamantyl)-4-methoxyphenyl]-2,4-heptadienoic acid;

(2Z), (4Z)-4-(3-trifluoromethylphenyl)-7-[4-(1-adamantyl)-3methoxyphenyl]-2,4-heptadienoic acid;

(2Z), (4Z)-4-phenyl-7-[4-(1-adamantyl)-3-methoxyphenyl]-2,4-heptadienoic acid;

(2Z), (4Z)-4-(3-trifluoromethylphenyl)-7-[2-(1-adamantyl)-4-methoxyphenyl]-2,4-heptadienoic acid;

(2Z), (4Z)-4-(3-trifluoromethylphenyl)-5-[4-(1-adamantyl)-3-methoxyphenyl]-2,4-pentadienoic acid;

(2Z), (4Z)-4-(3-trifluoromethylphenyl)-7-[4-(1-adamantyl)-3-hydroxyphenyl]-2,4-heptadienoic acid;

(2Z), (4Z)-4-(3-trifluoromethylphenyl)-7-[4-(1-adamantyl)-3-pentyloxyphenyl]-2,4-heptadienoic acid;

(2Z), (4Z)-4-(3-trifluoromethylphenyl)-7-[4-(1-adamantyl)-3-(4-methoxybenzyloxy)phenyl]-2,4-heptadienoic acid;

(2Z), (4Z)-4-(3-trifluoromethylphenyl)-7-[4-(1-adamantyl)-3-benzyloxy)phenyl]-2,4-heptadienoic acid;

(2Z), (4Z)-4-(3-trifluoromethylphenyl)-7-[4-(1-adamantyl)-3-(carboxymethoxy)phenyl]-2,4-heptadienoic acid; and (2Z), (4Z)-3-methyl-4-(3-carboxyphenyl)-5-(5,6,7,8-tetrahydro-5,5,8,8-tetramethyl-2-anthracenyl)-2,4-pentadienoic acid;

5. The compound of claim 2 conforming to structure IB.

6. The compound of claim 5 selected from the group consisting of:

(2E), (4Z)-4-(3-carboxyphenyl)-5-(5,6,7,8-tetrahydro-5,5,8,8-tetramethyl-2-anthracenyl)-2,4-pentadienoic acid;

(2E), (4Z)-4-(3-carboxyphenyl)-5-(3,4-bispentyloxyphenyl)-2,4-pentadienoic acid;

(2E), (4Z)-4-(3-carboxyphenyl)-5-(3,4-bisdecyloxyphenyl)-2,4-pentadienoic acid;

(2E), (4Z)-4-(3-carboxyphenyl)-7-(5,6,7,8-tetrahydro-5,5,8,8-tetramethyl-2-naphthalenyl)-2,4-heptadienoic acid;

(2E), (4Z)-4-(3-trifluoromethylphenyl)-7-(5,6,7,8-tetrahydro-5,5,8,8-tetramethyl-2-naphthalenyl)-2,4-heptadienoic acid;

(2E), (4Z)-4-(4-fluorophenyl)-7-(5,6,7,8-tetrahydro-5,5,8,8tetramethyl-2-naphthalenyl)-2,4-heptadienoic acid;

(2E), (4Z)-4-(3-fluorophenyl)-7-(5,6,7,8-tetrahydro-5,5,8,8-tetramethyl-2-naphthalenyl)-2,4-heptadienoic acid;

(2E), (4Z)-4-phenyl-7-(5,6,7,8-tetrahydro-5,5,8,8-tetramethyl-2-naphthalenyl)-2,4-heptadienoic acid;

(2E), (4Z)-4-(3-trifluoromethylphenyl)-7-[3-(1-adamantyl)-4-methoxyphenyl]-2,4-heptadienoic acid; and (2E), (4Z)-4-(3-trifluoromethylphenyl)-7-[4-(1-adamantyl)-3-methoxyphenyl]-2,4-heptadienoic acid;

7. The compound of claim 2 conforming to structure IC.

8. The compound of claim 7 selected from the group consisting of:

(2E), (6E)-4-(3-carboxyphenyl)-7-(5,6,7,8-tetrahydro-5,5,8,8-tetramethyl-2-naphthalenyl)-2,6-octadienoic acid, and (2E)-4-[3-carboxyphenyl]-7-(5,6,7,8-tetrahydro-5,5,8,8-tetramethyl-2-naphthalenyl)-hepta-2-enoic acid.

9. The compound of claim 2 conforming to structure ID.

10. (Z)-4-(3-trifluoromethylphenyl)-7-(5,6,7,8-tetrahydro-5,5,8,8-tetramethyl-2-naphthalenyl)-4-heptenoic acid.

11. A potassium, sodium, triethanolamine, tris(hydroxymethyl)aminomethane, N-methylglucamine, or L-lysine monosalt of a compound of claim 1 in which R″=H.

12. A potassium, sodium, triethanolamine, tris(hydroxymethyl)aminomethane, N-methylglucamine, or L-lysine bissalt of a compound of claim 1 in which R″=H and X=COOH.

13. The dipotassium salt of (2Z), (4Z)-3-methyl-4-(3carboxyphenyl)-5-(5,6,7,8-tetrahydro-5,5,8,8-tetramethyl-2-anthracenyl)-2,4-pentadienoic acid.

14. The disodium salt of (2Z), (4Z)-3-methyl-4-(3-carboxyphenyl)-5-(5,6,7,8-tetrahydro-5,5,8,8-tetramethyl-2-anthracenyl)-2,4-pentadienoic acid.

15. The bis(triethanolamine) salt of (2Z), (4Z)-3-methyl-4-(3-carboxyphenyl)-5-(5,6,7,8-tetrahydro-5,5,8,8-tetramethyl-2-anthracenyl)-2,4-pentadienoic acid.

16. The bis-[tris(hydroxymethyl)aminomethane] salt of (2Z), (4Z)-3-methyl-4-(3-carboxyphenyl)-5-(5,6,7,8-tetrahydro-5,5,8,8-tetramethyl-2-anthracenyl)-2,4-pentadienoic acid.

17. The bis-(N-methylglucamine) salt of (2Z), (4Z)-3-methyl-4-(3carboxyphenyl)-5-(5,6,7,8-tetramethyl-2-anthracenyl)-2,4-pentadienoic acid.

18. The bis-(L-lysine) salt of (2Z), (4Z)-3-methyl-4-(3-carboxyphenyl)-5-(5,6,7,8-tetrahydro-5,5,8,8-tetramethyl-2-anthracenyl)-2,4-pentadienoic acid.

19. The method of making a compound of structure type IA comprising the step:

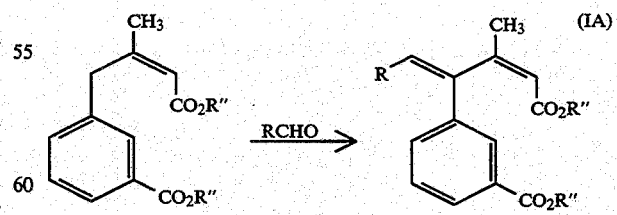

wherein reaction takes place at about 0° C. in the presence of an organic diluent.

20. A pharmaceutical composition containing an anti-inflammatory effective amount of at least one compound of claim 1 and a suitable amount of at least one pharmaceutically acceptable carrier.

21. The composition of claim 20 wherein the compound of claim 1 is present in an amount of about 0.005 to about 10.0 wt %.

22. The composition of claim 21 in a topical dosage form.

23. The composition of claim 21 in an oral dosage form.

24. A method of treating inflammation comprising the step of administering to a subject an anti-inflammatory effective amount of a compound of claim 1.

25. A method of treating inflammation comprising the step of administering to a subject an anti-inflammatory effective amount of a compound of claim 2.

26. The method of claim 25 wherein the compound is administered via a topical formulation.

27. The method of claim 25 wherein the compound is administered via an oral formulation.

28. The method of claim 19 wherein the reaction takes place in the presence of tetrahydrofuran.

* * * * *

UNITED STATES PATENT AND TRADEMARK OFFICE
CERTIFICATE OF CORRECTION

PATENT NO: 5,436,369

DATED : July 25, 1995

INVENTOR(S): Bronson, et al.

It is certified that error appears in the above-identified patent and that said Letters Patent is hereby corrected as shown below:

In claim 1, column 105, line 14, replace "$C_1$" with -- Cl --.

Signed and Sealed this

Thirty-first Day of October 1995

Attest:

BRUCE LEHMAN

*Attesting Officer*  *Commissioner of Patents and Trademarks*